US007928139B2

(12) United States Patent
Allen et al.

(10) Patent No.: US 7,928,139 B2
(45) Date of Patent: *Apr. 19, 2011

(54) NAPHTHALENONE COMPOUNDS EXHIBITING PROLYL HYDROXYLASE INHIBITORY ACTIVITY, COMPOSITIONS, AND USES THEREOF

(75) Inventors: Jennifer R. Allen, Newbury Park, CA (US); Kaustav Biswas, Calabasas, CA (US); Marian C. Bryan, Agoura Hills, CA (US); Roland Burli, Bishop's Stortford (GB); Guo-Qiang Cao, Thousand Oaks, CA (US); Michael J. Frohn, Thousand Oaks, CA (US); Jennifer E. Golden, Olathe, KS (US); Stephanie Mercede, Thousand Oaks, CA (US); Susana Neira, Naperville, IL (US); Tanya Peterkin, Gordon Town (JM); Alexander J. Pickrell, Westlake Village, CA (US); Anthony Reed, Oxnard, CA (US); Christopher M. Tegley, Thousand Oaks, CA (US); Xiang Wang, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 12/612,465

(22) Filed: Nov. 4, 2009

(65) Prior Publication Data

US 2010/0048572 A1    Feb. 25, 2010

Related U.S. Application Data

(63) Continuation of application No. 12/002,537, filed on Dec. 17, 2007, now Pat. No. 7,635,715.

(60) Provisional application No. 60/875,693, filed on Dec. 18, 2006, provisional application No. 60/963,152, filed on Aug. 1, 2007.

(51) Int. Cl.
*A61K 31/352* (2006.01)
*A61K 31/195* (2006.01)

(52) U.S. Cl. ........ 514/451; 514/563; 514/462; 514/357; 514/311; 514/278

(58) Field of Classification Search .................. 514/563, 514/462, 451, 357, 311, 278, 258
See application file for complete search history.

(56) References Cited

U.S. PATENT DOCUMENTS

| 3,954,733 | A | 5/1976 | Tobiki et al. |
| 3,992,371 | A | 11/1976 | Tobiki et al. |
| 4,215,123 | A | 7/1980 | Scotese et al. |
| 4,374,138 | A | 2/1983 | Haskell et al. |
| 4,382,089 | A | 5/1983 | Haskell et al. |
| 4,404,201 | A | 9/1983 | Haskell et al. |
| 4,468,394 | A | 8/1984 | Machida et al. |
| 4,710,473 | A | 12/1987 | Morris |
| 5,037,826 | A | 8/1991 | Blythin et al. |
| 5,126,341 | A | 6/1992 | Suzuki et al. |
| 5,502,035 | A | 3/1996 | Haviv et al. |
| 5,719,164 | A | 2/1998 | Weidmann et al. |
| 5,798,451 | A | 8/1998 | von Deyn et al. |
| 5,972,841 | A | 10/1999 | von Deyn et al. |
| 6,093,730 | A | 7/2000 | Weidmann et al. |
| 6,593,343 | B2 | 7/2003 | Björk et al. |
| 6,787,326 | B1 | 9/2004 | Ratcliffe et al. |
| 7,635,715 | B2 * | 12/2009 | Allen et al. ............ 514/451 |
| 2003/0153503 | A1 | 8/2003 | Klaus et al. |
| 2004/0235082 | A1 | 11/2004 | Fourney et al. |
| 2004/0254215 | A1 | 12/2004 | Arend et al. |
| 2005/0020487 | A1 | 1/2005 | Klaus et al. |
| 2005/0107364 | A1 | 5/2005 | Hutchinson et al. |

(Continued)

FOREIGN PATENT DOCUMENTS

| AT | 328085 | 3/1976 |
| EP | 0 500 297 A1 | 8/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |

(Continued)

OTHER PUBLICATIONS

He, L. et al., "Probabilistic Neural Network Multiple Classifier System for Predicting the Genotoxicity of Quinolones and Quinoline Derivatives," Chem. Res. Toxicol. 18, pp. 428-440 (2005).
Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).

(Continued)

*Primary Examiner* — Charanjit S Aulakh
(74) *Attorney, Agent, or Firm* — Bernard P. Friedrichsen

(57) ABSTRACT

Compounds of Formula I and Formula II are useful as inhibitors of HIF prolyl hydroxylases. Compounds of Formula I and Formula II have the following structures:

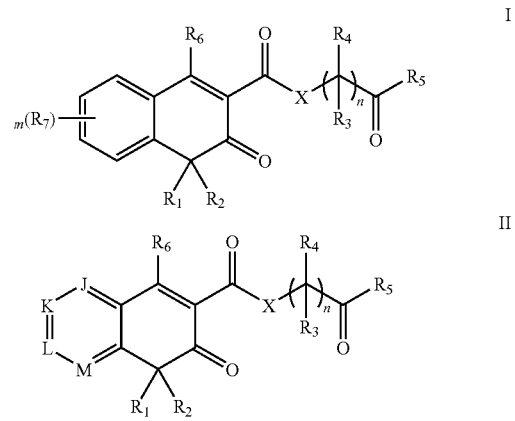

where the definitions of the variables are provided herein.

30 Claims, 3 Drawing Sheets

U.S. PATENT DOCUMENTS

| | | |
|---|---|---|
| 2006/0216295 A1 | 9/2006 | Crabtree et al. |
| 2006/0251638 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0203174 A1 | 8/2007 | Klimko et al. |
| 2007/0249605 A1 | 10/2007 | Allen et al. |
| 2008/0171756 A1 | 7/2008 | Shaw et al. |
| 2009/0088475 A1 | 4/2009 | Allen et al. |
| 2009/0093483 A1 | 4/2009 | Allen et al. |
| 2009/0099171 A1 | 4/2009 | Allen et al. |
| 2009/0111806 A1 | 4/2009 | Allen et al. |
| 2009/0156605 A1 | 6/2009 | Allen et al. |
| 2009/0156633 A1 | 6/2009 | Allen et al. |

FOREIGN PATENT DOCUMENTS

| | | |
|---|---|---|
| GB | 1 449 256 | 9/1976 |
| JP | 493592 A | 4/1974 |
| JP | 7224040 A2 | 8/1995 |
| SU | 1735288 | 5/1992 |
| WO | WO 01/85732 A1 | 11/2001 |
| WO | WO 02/076396 A2 | 10/2002 |
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990).

Schofield, C.J. et al., "Oxygen Sensing by HIF Hydroxylases", Nature Reviews, Molecular Cell Biology, 5(5), pp. 243-254 (2004).

McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).

Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987).

Kath, J.C. et al., Potent Small Molecule CCR1 Antagonists, Bioorg & Med. Chem. Letters, 14(9), pp. 2169-2173 (2004).

Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).

Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).

Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).

Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).

McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).

Jöonssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).

Buckle, D.R. et al., "Synthesis and Antiallergic Activity of 2-Hydroxy-3-nitro-1,4-naphthoquinones," J. Med. Chem. 20(8), pp. 1059-1064 (1977).

Invitation to Pay Additional Fees and Communication Relating to the Results of the Partial International Search from co-pending PCT Application No. PCT/US2007/025819 mailed on Dec. 19, 2008.

* cited by examiner

NAPHTHALENONE COMPOUNDS EXHIBITING PROLYL HYDROXYLASE INHIBITORY ACTIVITY, COMPOSITIONS, AND USES THEREOF

CROSS REFERENCES TO RELATED APPLICATIONS

This application is a continuation of, and claims priority to, U.S. patent application Ser. No. 12/002,537, filed on Dec. 17, 2007, pending which claims the benefit of U.S. Provisional Application No. 60/875,693, filed on Dec. 18, 2006, and U.S. Provisional Application No. 60/963,152, filed on Aug. 1, 2007, each of which is hereby incorporated by reference in its entirety and for all purposes as if fully set forth herein.

REFERENCE TO THE SEQUENCE LISTING

The present application is being filed along with a Sequence Listing in electronic format. The Sequence Listing is provided as a file entitled A-1222-US-CNT_SeqList_from_A-1222-US-NP.txt, created Dec. 14, 2007, which is 6 KB in size. The information in the electronic format of the Sequence Listing is incorporated herein by reference in its entirety.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

In one aspect, the invention provides at least one compound of Formula I:

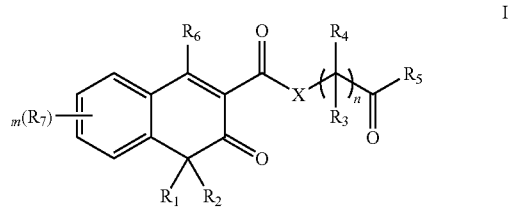

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

m is 0 to 4;

n is 1 to 6;

$R_1$ and $R_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents;

X is selected from $-NR_a-$, $-O-$, $-S-$, or $-(CR_bR_c)-$ wherein $R_a$ is selected from H or lower alkyl;

$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is chosen from H, OH, SH $NH_2$, $NHSO_2R_8$, or sulfonyl;

each $R_7$, if present, is independently selected from alkyl, substituted alkyl, alkenyl, substituted alkenyl, alkynyl, substituted alkynyl, $NR_dR_e$, $C(O)OR_8$, $OR_8$, $SR_8$, $SO_2R_8$, CN, $NO_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_9$, wherein:

Y is selected from $-N(R_{10})-Z-$ or $-Z-N(R_{10})-$;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, or substituted alkynyl;

$R_9$ is selected from H, heterocyclyl, substituted heterocyclyl, aryl, substituted aryl, heteroaryl, or substituted heteroaryl;

$R_{10}$ is selected from H, lower alkyl, or substituted lower alkyl;

$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments of the compound of Formula I, $R_5$ is OH

In some embodiments of the compound of Formula I, $R_6$ is selected from OH, SH, $NH_2$, $NHSO_2R_8$, or sulfonyl. In some such embodiments, $R_6$ is OH.

In some embodiments of the compound of Formula I, m is 1 to 4 and at least one instance of $R_7$ is a substituted or unsubstituted aryl, substituted or unsubstituted heteroaryl, substituted or unsubstituted cycloalkyl, or a substituted or unsubstituted heterocyclyl group. In some such embodiments, m is 1 to 4 and at least one instance of $R_7$ is a heterocyclyl group. In other such embodiments, m is 1 to 4 and at least one instance of $R_7$ is a heteroaryl group. In other such embodiments, m is 1 to 4 and at least one instance of $R_7$ is a phenyl or substituted phenyl group.

In some embodiments of the compound of Formula I, m is 1 to 4 and at least one instance of $R_7$ is independently selected from halo or a moiety substituted with at least one halo.

In some embodiments of the compound of Formula I, m is 0. In other embodiments, m is 1.

In some embodiments of the compound of Formula I, n is 1. In some such embodiments, one of $R_3$ or $R_4$ is a substituted lower alkyl. In some such embodiments, one of $R_3$ or $R_4$ is a perhaloalkyl such as a $CF_3$ group.

In some embodiments of the compound of Formula I, $R_1$ and $R_2$ are independently selected from CN, lower alkyl, aryl, or substituted aryl. In some such embodiments, $R_1$ and $R_2$ are both lower alkyl. In some such embodiments, $R_1$ and $R_2$ are both methyl groups. In other embodiments, $R_1$ and $R_2$ join to form a spirocyclic ring system. In some such embodiments, $R_1$ and $R_2$ join to form a 3 to 7 membered ring. In some such embodiments, $R_1$ and $R_2$ join to form a 3 to 7 membered cycloalkyl ring such as a cyclopropyl, cyclobutyl, cyclopentyl, cyclohexyl, or cycloheptyl ring. In some such embodiments, the cycloalkyl ring may be substituted. For example, the cycloalkyl ring may include an oxo (=O) group or other substituent. In some such embodiments, $R_1$ and $R_2$ join to form a heterocyclic spirocyclic ring system. In some such embodiments, the heterocyclic spirocyclic ring system includes one O, N, or S atom and in some cases includes one O atom. In some embodiments, $R_1$ and $R_2$ join to form a 5-7 or 5-6 membered ring. In some embodiments, $R_1$ and $R_2$ join to form a 5-7 or 5-6 membered ring that comprises one N atom. In some such embodiments, $R_1$ and $R_2$ join to form a piperidine ring that is optionally substituted. In some embodiments, $R_1$ and $R_2$ join to form a 5 or 6 membered ring comprising one O atom. In still other such embodiments, $R_1$ and $R_2$ join to form a six membered ring comprising one O atom. In some such embodiments, $R_1$ and $R_2$ join to form a 6 membered ring. In some embodiments, $R_1$ and $R_2$ join to form a tetrahydrofuran ring whereas in other embodiments they join to form a pyran ring.

In some embodiments of the compound of Formula I, $R_1$ and $R_2$ join to form the group $-CH_2-CH_2-O-CH_2-CH_2-$. In other embodiments, $R_1$ and $R_2$ join to form the group $-CH_2-O-CH_2-CH_2-$, $-O-CH_2-CH_2-CH_2-$, or $CH_2-O-CH_2-CH_2-CH_2-$.

In some embodiments of the compound of Formula I, $R_1$ is CN. In some embodiments $R_1$ is CN and $R_2$ is a $C_1$-$C_4$ alkyl group. In some such embodiments, $R_1$ is CN and $R_2$ is a methyl group.

In some embodiments of the compound of Formula I, X is NH, n is 1, $R_3$ and $R_4$ are independently selected from H, lower alkyl or substituted lower alkyl, and $R_6$ is OH. In some such embodiments $R_5$ is OH. In some such embodiments, one of $R_3$ and $R_4$ is a methyl group. In other such embodiments, one of $R_3$ or $R_4$ is a substituted lower alkyl. In some such embodiments, one of $R_3$ or $R_4$ is a perhaloalkyl such as a $CF_3$ group.

In some embodiments of the compound of Formula I, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ join together to form a 3 to 6 membered ring or a substituted 3 to 6 membered ring. In some such embodiments, one of $R_3$ or $R_4$ is a $C_1$-$C_4$ alkyl or a substituted $C_1$-$C_4$ alkyl. In some such embodiments, one of $R_3$ or $R_4$ is a methyl group. In some such embodiments, n is 1. In still other such embodiments, X is $-NH-$.

In some embodiments of the compound of Formula I, X is $-(CR_bR_c)-$. In some such embodiments, X is $-CH_2-$. In other embodiments, X is $-O-$. In still other embodiments, X is $-NR_a-$. In some such embodiments, X is $-NH-$.

In another aspect, the invention provides at least one compound of Formula II:

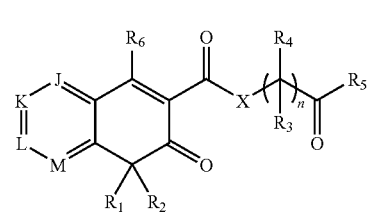

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are independently selected from $CR_7$ or N, wherein 0, 1, or 2 of J, K, L, and M are N;

n is 1 to 6;

$R_1$ and $R_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents;

X is selected from $-NR_a-$, $-O-$, $-S-$, or $-(CR_bR_c)-$, wherein $R_a$ is selected from H or lower alkyl;

$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is selected from H, OH, SH NH$_2$, NHSO$_2$R$_8$, or sulfonyl;

each $R_7$ is independently selected from H, alkyl, substituted alkyl, alkenyl, substituted alkenyl, alkynyl, substituted alkynyl, NR$_d$R$_e$, C(O)R$_8$, C(O)OR$_9$, OR$_9$, SR$_9$, SO$_2$R$_9$, CN, NO$_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, haloalkyl, perhaloalkyl, or —Y—R$_{10}$, wherein:

Y is selected from —N(R$_{11}$)—Z— or —Z—N(R$_{11}$)—;

Z is selected from C(O), SO$_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl;

$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_c$ can join together to form a 3 to 6 membered ring or a substituted 3 to 6 membered ring.

In some embodiments of the compound of Formula II, each of J, K, L, and M is CR$_7$.

In some embodiments of the compound of Formula II, one of J, K, L, and M is N, and the other three of J, K, L, and M are CR$_7$. In some such embodiments, J is N and K, L, and M are CR$_7$. In other such embodiments, K is N and J, L, and M are CR$_7$. In still other such embodiments, L is N and J, K, and M are CR$_7$. In still further such embodiments, M is N and J, K, and L are CR$_7$.

In some embodiments of any embodiments of the compound of Formula II, $R_5$ is OH.

In some embodiments of any embodiments of the compound of Formula II, $R_6$ is OH.

In some embodiments of the compound of Formula II, at least one instance of $R_7$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_7$ is a heterocyclyl group. In some embodiments, at least one instance of $R_7$ is a heteroaryl group. In some embodiments, at least one instance of $R_7$ is a phenyl or substituted phenyl group.

In some embodiments of the compound of Formula II, at least one instance of $R_7$ is chosen from a halo or a moiety substituted with at least one halo.

In some embodiments of the compound of Formula II, n is 1. In some such embodiments, one of $R_3$ or $R_4$ is a substituted lower alkyl. In some such embodiments, one of $R_3$ or $R_4$ is a perhaloalkyl such as a CF$_3$ group.

In some embodiments of the compound of Formula II, $R_1$ and $R_2$ are independently selected from CN, lower alkyl, aryl, or substituted aryl. In some embodiments, $R_1$ and $R_2$ are both lower alkyl. In some embodiments, $R_1$ and $R_2$ are both methyl groups. In other embodiments, $R_1$ and $R_2$ join to form a spirocyclic ring system. In some such embodiments, $R_1$ and $R_2$ join to form a 3 to 7 membered ring. In some such embodiments, $R_1$ and $R_2$ join to form a 3 to 7 membered cycloalkyl ring such as a cyclopropyl, cyclobutyl, cyclopentyl, cyclohexyl, or cycloheptyl ring. In some such embodiments, the cycloalkyl ring may be substituted. For example, the cycloalkyl ring may include an oxo (═O) group or other substituent. In some such embodiments, $R_1$ and $R_2$ join to form a heterocyclic spirocyclic ring system. In some such embodiments, the heterocyclic spirocyclic ring system includes one O, N, or S atom and in some cases includes one O atom. In some embodiments, $R_1$ and $R_2$ join to form a 5-7 or 5-6 membered ring. In some embodiments, $R_1$ and $R_2$ join to form a 5-7 or 5-6 membered ring that comprises one N atom. In some such embodiments, $R_1$ and $R_2$ join to form a piperidine ring that is optionally substituted. In some embodiments, $R_1$ and $R_2$ join to form a 5 or 6 membered ring comprising one O atom. In still other such embodiments, $R_1$ and $R_2$ join to form a six membered ring comprising one O atom. In some such embodiments, $R_1$ and $R_2$ join to form a 6 membered ring. In some embodiments, $R_1$ and $R_2$ join to form a tetrahydrofuran ring whereas in other embodiments they join to form a pyran ring.

In some embodiments of the compound of Formula II, $R_1$ and $R_2$ join to form the group —CH$_2$—CH$_2$—O—CH$_2$—CH$_2$—. In other embodiments, $R_1$ and $R_2$ join to form the group —CH$_2$—O—CH$_2$—CH$_2$—, —O—CH$_2$—CH$_2$—CH$_2$—, or —CH$_2$—O—CH$_2$—CH$_2$—CH$_2$—.

In some embodiments of the compound of Formula II, $R_1$ is CN. In some embodiments $R_1$ is CN and $R_2$ is a C$_1$-C$_4$ alkyl group. In some such embodiments, $R_1$ is CN and $R_2$ is a methyl group.

In some embodiments of the compound of Formula II, X is NH, n is 1, $R_3$ and $R_4$ are independently selected from H, lower alkyl or substituted lower alkyl, and $R_6$ is OH. In some such embodiments $R_5$ is OH. In some such embodiments, one of $R_3$ and $R_4$ is a methyl group. In other such embodiments, one of $R_3$ or $R_4$ is a substituted lower alkyl. In some such embodiments, one of $R_3$ or $R_4$ is a perhaloalkyl such as a CF$_3$ group.

In some embodiments of the compound of Formula II, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ join together to form a 3 to 6 membered ring or a substituted 3 to 6 membered ring. In some such embodiments, one of $R_3$ or $R_4$ is a C$_1$-C$_4$ alkyl or a substituted C$_1$-C$_4$ alkyl. In some such embodiments, one of $R_3$ or $R_4$ is a methyl group. In some such embodiments, n is 1. In still other such embodiments, X is —NH—.

In some embodiments of the compound of Formula II, X is —(CR$_b$R$_c$)—. In some such embodiments, X is —CH$_2$—. In other embodiments, X is —O—. In still other embodiments, X is —NR$_a$—. In some such embodiments, X is —NH—.

In some embodiments, the at least one compound is a salt. Such salts may be anhydrous or associated with water as a hydrate.

In some embodiments, the compound is a prodrug. In some such embodiments, the compound is a (C$_1$-C$_6$)alkyl ester such as a methyl, ethyl, propyl, butyl, pentyl, or hexyl ester.

Also provided herein are pharmaceutical compositions that include at least one pharmaceutically acceptable carrier, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Further provided is a method of modulating the amount of HIF in a cell. Such methods include contacting the cell with at least one compound of any of the embodiments described herein.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 µM or less. In other embodiments, the HIF PHD inhibitory activity $IC_{50}$ value of the compound is 10 µM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

Other objects, features and advantages of the invention will become apparent to those skilled in the art from the following description and claims.

BRIEF DESCRIPTION OF THE DRAWINGS

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 1:
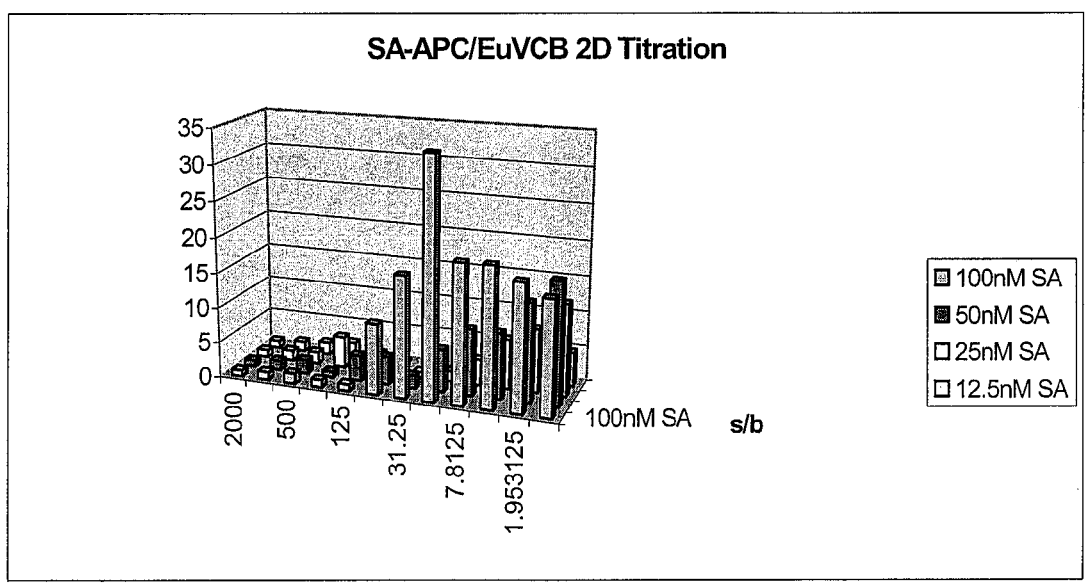
FIG. 1 is a graph illustrating the ratio of fluorescence signal to background generated by the interaction of Eu-VCB with streptavidin-APC-hydroxyprolyl HIF1α peptide.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I and Formula II include, but are not limited to, optical isomers of compounds of Formula I and Formula II, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I and Formula II include Z- and E-forms (or cis- and trans-forms) of compounds with double bonds.

Compounds of the invention may exist in multiple tautomeric forms. These forms are illustrated below as "Tautomer A", "Tautomer B", and "Tautomer C":

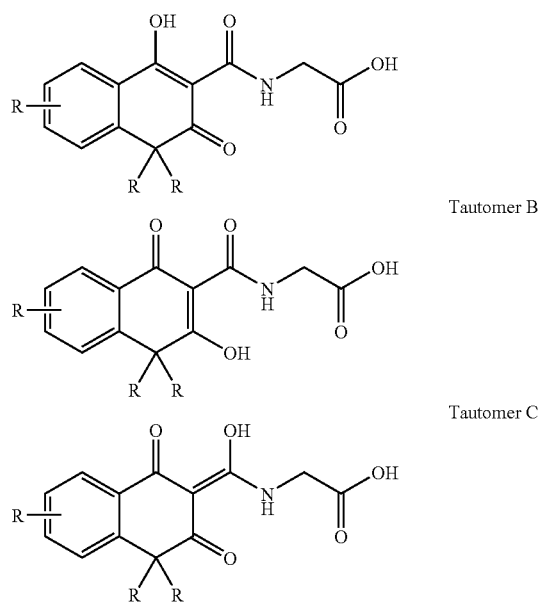

Tautomer A

Tautomer B

Tautomer C

Compounds of the invention are depicted structurally and named as compounds in the "Tautomer A" form. However, it is specifically contemplated that the compounds may also exist in "Tautomer B" or "Tautomer C" form and compounds in "Tautomer B" form or "Tautomer C" form or another tautomeric form are expressly considered to be part of the invention.

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I or Formula II. The term "prodrugs" includes any compounds that become compounds of Formula I or Formula II when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I or Formula II. In some embodiments, the prodrugs of the compounds of Formula I and Formula II are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemi-hydrates.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl group as defined herein. Representative examples include, but are not limited to, methoxy, ethoxy, propoxy, butoxy, cyclohexyloxy, and the like.

"Alkoxycarbonyl" refers to a radical —C(O)—OR where R is as defined above.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkylene" refers to a divalent saturated hydrocarbon group derived from a parent alkane by removal of two hydrogen atoms. Examples of alkylene group include, but are not limited to, —CH$_2$—, —CH$_2$CH$_2$—, —CH(CH$_3$)—, —CH$_2$CH$_2$CH$_2$—, —CH$_2$C(CH$_3$)(H)—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH=CH—, —CH=C(H)CH$_2$—, —CH$_2$C(H)=C(H)CH$_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —CH$_2$C≡C—, —CH$_2$C≡CCH$_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocyclic ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically, but not necessarily, a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. In certain embodiments, an arylalkyl group can be (C$_{6-30}$) arylalkyl, e.g., the alkyl group of the arylalkyl group can be (C$_{1-10}$) and the aryl moiety can be (C$_{5-20}$).

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be C$_{3-10}$ cycloalkyl, such as, for example, C$_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocyclylalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic ring systems containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkyl moiety of the heteroarylalkyl can include 1 to 10 members and the heteroaryl moiety of the heteroarylalkyl can include from 5 to 20-members.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

Spirocyclic ring systems found in compounds of the invention contain from 3 to 7, from 4 to 7, from 5 to 6, 5, or 6 ring members. Spirocyclic ring systems may be carbocyclic and thus contain only carbon atoms as ring members. Examples of carbocyclic spirocyclic ring systems include cycloalkyl groups such as, but not limited to, cyclopropyl, cyclobutyl, cyclopentyl, cyclohexyl, and cycloheptyl rings. Spirocyclic ring systems found in compounds of the invention may contain 1 or 2 hetero atoms chosen from —O—, —S—, and —NR—, a "heterocyclic spirocyclic ring system". Spirocyclic ring systems may be unsubstituted or may be substituted. For example, spirocyclic ring systems may include substituents such as, but not limited to, an oxo (═O) group, an optionally substituted alkyl group, an optionally substituted arylalkyl group, an optionally substituted heteroarylalkyl group, an optionally substituted heterocyclylalkyl group, a halogen, a group of formula —C(═O)-alkyl, a group of formula —C(═O)-aryl, a group of formula —C(═O)-heteroaryl, a group of formula —C(═O)-heterocyclyl, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —R$_{11}$, —OH, ═O, —OR$_{11}$, —SR$_{11}$, —SH, ═S, —NR$_{11}$R$_{12}$, ═NR$_{11}$, —CX$_3$, —CF$_3$, —CN, —NO$_2$, —S(O)$_2$R$_{11}$, —OS(O$_2$)OH, —OS(O)$_2$R$_{11}$, —OP(O)(OR$_{11}$)(OR$_{12}$), —C(O)R$_{11}$, —C(S)R$_{11}$, —C(O)OR$_{11}$, —C(O)NR$_{11}$R$_{12}$, —C(O)OH, —C(S)OR$_{11}$, —NR$_{13}$C(O)NR$_{11}$R$_{12}$, —NR$_{13}$C(S)NR$_{11}$R$_{12}$, —NR$_{13}$C(NR$_{11}$)NR$_{11}$R$_{12}$, —C(NR$_{11}$)NR$_{11}$R$_{12}$, —S(O)$_2$NR$_{11}$R$_{12}$, —NR$_{13}$S(O)$_2$R$_{11}$, —NR$_{13}$C(O)R$_{11}$, and —S(O)R$_{11}$ where each X is independently a halo; each R$_{11}$ and R$_{12}$ are independently hydrogen, alkyl, substituted alkyl, alkyl interrupted by one or more —O— or —S— groups, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl, substituted heteroarylalkyl, —NR$_{13}$R$_{14}$, —C(O)R$_{13}$ or —S(O)$_2$R$_{13}$ or optionally R$_{11}$ and R$_{12}$ together with the atom to which R$_{11}$ and R$_{12}$ are attached form one or more heterocyclyl, substituted heterocyclyl, heteroaryl, or substituted heteroaryl rings; and R$_{13}$ and R$_{14}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl or substituted heteroarylalkyl, or optionally R$_{13}$ and R$_{14}$ together with the nitrogen atom to which R$_{13}$ and R$_{14}$ are attached form one or more heterocyclyl, substituted heterocyclyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides at least one compound of Formula I:

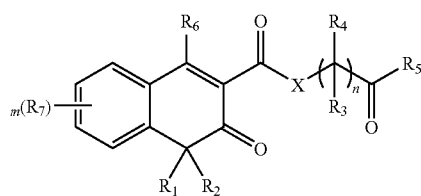

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

m is 0 to 4;

n is 1 to 6;

$R_1$ and $R_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents;

X is selected from $-NR_a-$, $-O-$, $-S-$, or $-(CR_bR_c)-$ wherein $R_a$ is selected from H or lower alkyl;

$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is chosen from H, OH, SH $NH_2$, $NHSO_2R_8$, or sulfonyl;

each $R_7$, if present, is independently selected from alkyl, substituted alkyl, alkenyl, substituted alkenyl, alkynyl, substituted alkynyl, $NR_dR_e$, $C(O)OR_8$, $OR_8$, $SR_8$, $SO_2R_8$, CN, $NO_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_9$, wherein:

Y is selected from $-N(R_{10})-Z-$ or $-Z-N(R_{10})-$;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, or substituted alkynyl;

$R_9$ is selected from H, heterocyclyl, substituted heterocyclyl, aryl, substituted aryl, heteroaryl, or substituted heteroaryl;

$R_{10}$ is selected from H, lower alkyl, or substituted lower alkyl;

$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments of the compound of Formula I, $R_5$ is OH.

In some embodiments of the compound of Formula I, $R_6$ is selected from OH, SH, $NH_2$, $NHSO_2R_8$, or sulfonyl. In some such embodiments, $R_6$ is OH.

In some embodiments of the compound of Formula I, m is 1 to 4 and at least one instance of $R_7$ is a substituted or unsubstituted aryl, substituted or unsubstituted heteroaryl, substituted or unsubstituted cycloalkyl, or a substituted or unsubstituted heterocyclyl group. In some such embodiments, m is 1 to 4 and at least one instance of $R_7$ is a heterocyclyl group. In other such embodiments, m is 1 to 4 and at least one instance of $R_7$ is a heteroaryl group. For example, in some embodiments, at least one instance of $R_7$ is a heteroaryl group such as a substituted or unsubstituted pyridine group. In some embodiments, at least one instance of $R_7$ is selected from an optionally substituted 2-, 3-, or 4-pyridyl group. In some such embodiments, at least one instance of $R_7$ is a pyridine group substituted with one or more substituents selected from lower alkyl, halo, hydroxy, alkoxy, or the like. In other such embodiments, m is 1 to 4 and at least one instance of $R_7$ is a phenyl or substituted phenyl group. For example, in some embodiments, at least one instance of $R_7$ is selected from a phenyl or a phenyl substituted with at least one substituent selected from lower alkyl, halo, alkoxy, a dialkylamino group such as a dimethylamino group, and the like.

In some embodiments, at least one instance of $R_7$ is selected from a lower alkyl group such as a methyl group. In other embodiments, at least one instance of $R_7$ is selected from an alkyl group, a substituted alkyl group, an alkenyl group, a substituted alkenyl group, an alkynyl group, or a substituted alkynyl group. For example, in some embodiments, at least one instance of $R_7$ is selected from a group of formula methyl, ethyl, propyl, butyl, pentyl, hexyl, heptyl, octyl, $-CH=CH-CH_2-O-CH_3$, $-CH_2-CH_2-CH_2-O-CH_3$, $-CH=CH-phenyl$, $-CH_2-CH_2-phenyl$, $-C\equiv C-phenyl$, $-C\equiv C-pyridyl$, $-C\equiv C-CH_2-O-CH_3$, or the like.

In some embodiments of the compound of Formula I, m is 1 to 4 and at least one instance of $R_7$ is independently selected from halo or a moiety substituted with at least one halo. In some embodiments, at least one instance of $R_7$ is a perhaloalkyl group such as a perfluoroalkyl such as a $CF_3$. In some embodiments, at least one instance of $R_7$ is a halo group selected from F, Cl, or Br. In some embodiments, at least two instances of $R_7$ are halo groups independently selected from F, Cl, and Br.

In some embodiments, at least one instance of $R_7$ is an $OR_8$ group where $R_8$ is H, a lower alkyl, or a substituted lower alkyl. For example, in some embodiments, at least one instance of $R_8$ is selected from an $-OH$, a methoxy group, an ethoxy group, a benzyloxy group, a group of formula —OCH$_2$—CH(CH$_3$)$_2$, or the like.

In some embodiments of the compound of Formula I, m is 0. In other embodiments, m is 1.

In some embodiments of the compound of Formula I, n is 1. In some such embodiments, one of R$_3$ or R$_4$ is a substituted lower alkyl. In some such embodiments, one of R$_3$ or R$_4$ is a perhaloalkyl such as a CF$_3$ group. In other such embodiments where n is 1, both of R$_3$ and R$_4$ are H. In some embodiments where n is 1, one of R$_3$ and R$_4$ is a lower alkyl group or a substituted lower alkyl group such as, but not limited to, a methyl, ethyl, propyl, —CH$_2$—OH group, or the like. In some such embodiments, one of R$_3$ and R$_4$ is H and the other of R$_3$ and R$_4$ is a lower alkyl groups.

In some embodiments of the compound of Formula I, R$_1$ and R$_2$ are independently selected from CN, lower alkyl, aryl, or substituted aryl. In some such embodiments, R$_1$ and R$_2$ are both lower alkyl. In some such embodiments, R$_1$ and R$_2$ are both methyl groups. In other embodiments, R$_1$ and R$_2$ join to form a spirocyclic ring system. In some such embodiments, R$_1$ and R$_2$ join to form a 3 to 7 membered ring. In some such embodiments, R$_1$ and R$_2$ join to form a 3 to 7 membered cycloalkyl ring such as a cyclopropyl, cyclobutyl, cyclopentyl, cyclohexyl, or cycloheptyl ring. In some such embodiments, the cycloalkyl ring may be substituted. For example, the cycloalkyl ring may include an oxo (=O) group or other substituent. In some such embodiments, R$_1$ and R$_2$ join to form a heterocyclic spirocyclic ring system. In some such embodiments, the heterocyclic spirocyclic ring system includes one O, N, or S atom and in some cases includes one O atom. In some embodiments, R$_1$ and R$_2$ join to form a 5-7 or 5-6 membered ring. In some embodiments, R$_1$ and R$_2$ join to form a 5-7 or 5-6 membered ring that comprises one N atom. In some such embodiments, R$_1$ and R$_2$ join to form a piperidine ring that is optionally substituted. For example, in some embodiments, R$_1$ and R$_2$ join to form a piperidine in which the N atom of the piperidine is bonded to a benzyl group, a group of formula —C(=O)-phenyl, or a lower alkyl group such as a methyl group, whereas in other embodiments, the piperidine ring is not substituted. In some embodiments, R$_1$ and R$_2$ join to form a 5 or 6 membered ring comprising one O atom. In still other such embodiments, R$_1$ and R$_2$ join to form a six membered ring comprising one O atom. In some such embodiments, R$_1$ and R$_2$ join to form a 6 membered ring. In some embodiments, R$_1$ and R$_2$ join to form a tetrahydrofuran ring whereas in other embodiments they join to form a pyran ring.

In some embodiments of the compound of Formula I, R$_1$ and R$_2$ join to form the group —CH$_2$—CH$_2$—O—CH$_2$—CH$_2$—. In other embodiments, R$_1$ and R$_2$ join to form the group —CH$_2$—O—CH$_2$—CH$_2$—, —O—CH$_2$—CH$_2$—CH$_2$—, or —CH$_2$—O—CH$_2$—CH$_2$—CH$_2$—.

In some embodiments of the compound of Formula I, R$_1$ is CN. In some embodiments R$_1$ is CN and R$_2$ is a C$_1$-C$_4$ alkyl group. In some such embodiments, R$_1$ is CN and R$_2$ is a methyl group.

In some embodiments of the compound of Formula I, at least one of R$_1$ and R$_2$ is selected from aryl or substituted aryl. For example, in some embodiments, at least one of R$_1$ and R$_2$ is phenyl or a phenyl substituted with one or more of F, Cl, Br, lower alkyl, OH, or lower alkoxy. In some such embodiments, the other of R$_1$ and R$_2$ is a lower alkyl group such as, but not limited to a methyl or ethyl group.

In some embodiments of the compound of Formula I, X is NH, n is 1, R$_3$ and R$_4$ are independently selected from H, lower alkyl or substituted lower alkyl, and R$_6$ is OH. In some such embodiments R$_5$ is OH. In some such embodiments, at least one of R$_3$ and R$_4$ is a methyl group. In other such embodiments, one of R$_3$ or R$_4$ is a substituted lower alkyl. In some such embodiments, one of R$_3$ or R$_4$ is a perhaloalkyl such as a CF$_3$ group.

In some embodiments of the compound of Formula I, R$_3$ is selected from H, lower alkyl, substituted lower alkyl, lower haloalkyl, or substituted lower haloalkyl and R$_4$ is selected from lower alkyl, substituted lower alkyl, lower haloalkyl, or substituted lower haloalkyl, or R$_3$ and R$_4$ join together to form a 3 to 6 membered ring or a substituted 3 to 6 membered ring. In some such embodiments, R$_4$ is a C$_1$-C$_4$ alkyl or a substituted C$_1$-C$_4$ alkyl. In some such embodiments, R$_4$ is a C$_1$-C$_4$ alkyl or a substituted C$_1$-C$_4$ alkyl and R$_3$ or is H. In some embodiments, one of R$_3$ or R$_4$ is a methyl group. In some such embodiments, n is 1. In still other such embodiments, X is —NH—.

In some embodiments of the compound of Formula I, X is —(CR$_b$R$_c$)—. In some such embodiments, X is —CH$_2$—. In other embodiments, X is —O—. In still other embodiments, X is —NR$_a$—. In some such embodiments, X is —NH—.

In another aspect, the invention provides at least one compound of Formula II:

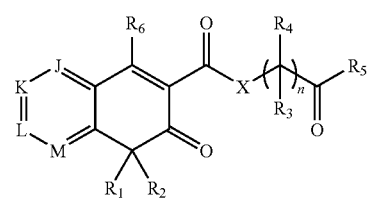

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are independently selected from CR$_7$ or N, wherein 0, 1, or 2 of J, K, L, and M are N;

n is 1 to 6;

R$_1$ and R$_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or R$_1$ and R$_2$ can join to form a spirocyclic ring system that may be substituted with one or more substituents;

X is selected from —NR$_a$—, —O—, —S—, or —(CR$_b$R$_c$)—, wherein R$_a$ is selected from H or lower alkyl;

R$_3$ and R$_4$ are independently selected from H, lower alkyl, substituted lower alkyl, lower haloalkyl, or substituted lower haloalkyl, or R$_3$ and R$_4$ can join together to form a 3 to 6 membered ring or a substituted 3 to 6 membered ring;

R$_5$ is selected from OH, SH, NH$_2$, lower alkyl, substituted lower alkyl, lower alkoxy, substituted lower alkoxy, or sulfanyl;

R$_6$ is selected from H, OH, SH NH$_2$, NHSO$_2$R$_8$, or sulfonyl;

each R$_7$ is independently selected from H, alkyl, substituted alkyl, alkenyl, substituted alkenyl, alkynyl, substituted alkynyl, NR$_d$R$_e$, C(O)R$_8$, C(O)OR$_9$, OR$_9$, SR$_9$, SO$_2$R$_9$, CN, NO$_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, haloalkyl, perhaloalkyl, or —Y—$R_{10}$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl;

$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments of the compound of Formula II, each of J, K, L, and M is $CR_7$.

In some embodiments of the compound of Formula II, one of J, K, L, and M is N, and the other three of J, K, L, and M are $CR_7$. In some such embodiments, J is N and K, L, and M are $CR_7$. In other such embodiments, K is N and J, L, and M are $CR_7$. In still other such embodiments, L is N and J, K, and M are $CR_7$. In still further such embodiments, M is N and J, K, and L are $CR_7$.

In some embodiments of any embodiments of the compound of Formula II, $R_5$ is OH.

In some embodiments of any embodiments of the compound of Formula II, $R_6$ is OH.

In some embodiments of the compound of Formula II, at least one instance of $R_7$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_7$ is a heterocyclyl group. In some embodiments, at least one instance of $R_7$ is a heteroaryl group. For example, in some embodiments, at least one instance of $R_7$ is a heteroaryl group such as a substituted or unsubstituted pyridine group. In some embodiments, at least one instance of $R_7$ is selected from an optionally substituted 2-, 3-, or 4-pyridyl group. In some such embodiments, at least one instance of $R_7$ is a pyridine group substituted with one or more substituents selected from lower alkyl, halo, hydroxy, alkoxy, or the like. In some embodiments, at least one instance of $R_7$ is a phenyl or substituted phenyl group. For example, in some embodiments, at least one instance of $R_7$ is selected from a phenyl or a phenyl substituted with at least one substituent selected from lower alkyl, halo, alkoxy, a dialkylamino group such as a dimethylamino group, and the like.

In some embodiments, at least one instance of $R_7$ is selected from a lower alkyl group such as a methyl group. In other embodiments, at least one instance of $R_7$ is selected from an alkyl group, a substituted alkyl group, an alkenyl group, a substituted alkenyl group, an alkynyl group, or a substituted alkynyl group. For example, in some embodiments, at least one instance of $R_7$ is selected from a group of formula methyl, ethyl, propyl, butyl, pentyl, hexyl, heptyl, octyl, —CH=CH—$CH_2$—O—$CH_3$, —$CH_2$—$CH_2$—$CH_2$—O—$CH_3$, —CH=CH-phenyl, —$CH_2$—$CH_2$-phenyl, —C≡C-phenyl, —C≡C-pyridyl, —C≡C—$CH_2$—O—$CH_3$, or the like.

In some embodiments of the compound of Formula II, at least one instance of $R_7$ is chosen from a halo or a moiety substituted with at least one halo. In some embodiments, at least one instance of $R_7$ is a perhaloalkyl group such as a perfluoroalkyl such as a $CF_3$. In some embodiments, at least one instance of $R_7$ is a halo group selected from F, Cl, or Br. In some embodiments, at least two instances of $R_7$ are halo groups independently selected from F, Cl, and Br.

In some embodiments, at least one instance of $R_7$ is an $OR_8$ group where $R_8$ is H, a lower alkyl, or a substituted lower alkyl. For example, in some embodiments, at least one instance of $R_8$ is selected from an —OH, a methoxy group, an ethoxy group, a benzyloxy group, a group of formula —$OCH_2$—CH($CH_3$)$_2$, or the like.

In some embodiments of the compound of Formula II, n is 1. In some such embodiments, one of $R_3$ or $R_4$ is a substituted lower alkyl. In some such embodiments, one of $R_3$ or $R_4$ is a perhaloalkyl such as a $CF_3$ group. In other such embodiments where n is 1, both of $R_3$ and $R_4$ are H. In some embodiments where n is 1, at least one of $R_3$ and $R_4$ is a lower alkyl group or a substituted lower alkyl group such as, but not limited to, a methyl, ethyl, propyl, —$CH_2$—OH group, or the like. In some embodiments where n is 1, at least one of $R_3$ and $R_4$ is a lower alkyl group or a substituted lower alkyl group and the other of $R_3$ and $R_4$ is H. In some embodiments, both of $R_3$ and $R_4$ are lower alkyl groups In some embodiments of the compound of Formula II, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ join together to form a 3 to 6 membered ring or a substituted 3 to 6 membered ring. In some such embodiments, $R_4$ is a $C_1$-$C_4$ alkyl or a substituted $C_1$-$C_4$ alkyl. In some embodiments, $R_4$ is a $C_1$-$C_4$ alkyl or a substituted $C_1$-$C_4$ alkyl and $R_3$ is H. In some such embodiments, one of $R_3$ or $R_4$ is a methyl group. In some such embodiments, n is 1. In still other such embodiments, X is —NH—.

In some embodiments of the compound of Formula II, $R_1$ and $R_2$ are independently selected from CN, lower alkyl, aryl, or substituted aryl. In some such embodiments, $R_1$ and $R_2$ are both lower alkyl. In some such embodiments, $R_1$ and $R_2$ are both methyl groups. In other embodiments, $R_1$ and $R_2$ join to form a spirocyclic ring system. In some such embodiments, $R_1$ and $R_2$ join to form a 3 to 7 membered ring. In some such embodiments, $R_1$ and $R_2$ join to form a 3 to 7 membered cycloalkyl ring such as a cyclopropyl, cyclobutyl, cyclopentyl, cyclohexyl, or cycloheptyl ring. In some such embodiments, the cycloalkyl ring may be substituted. For example, the cycloalkyl ring may include an oxo (=O) group or other substituent. In some such embodiments, $R_1$ and $R_2$ join to form a heterocyclic spirocyclic ring system. In some such embodiments, the heterocyclic spirocyclic ring system includes one O, N, or S atom and in some cases includes one O atom. In some embodiments, $R_1$ and $R_2$ join to form a 5-7 or 5-6 membered ring. In some embodiments, $R_1$ and $R_2$ join to form a 5-7 or 5-6 membered ring that comprises one N atom. In some such embodiments, $R_1$ and $R_2$ join to form a piperidine ring that is optionally substituted. For example, in some embodiments, $R_1$ and $R_2$ join to form a piperidine in which the N atom of the piperidine is bonded to a benzyl group, a group of formula —C(=O)-phenyl, or a lower alkyl group such as a methyl group, whereas in other embodiments, the piperidine ring is not substituted. In some embodiments, $R_1$ and $R_2$ join to form a 5 or 6 membered ring comprising one O atom. In still other such embodiments, $R_1$ and $R_2$ join to form a six membered ring comprising one O atom. In some such embodiments, $R_1$ and $R_2$ join to form a 6 membered ring. In some embodiments, $R_1$ and $R_2$ join to form a tetrahydrofuran ring whereas in other embodiments they join to form a pyran ring.

In some embodiments of the compound of Formula II, $R_1$ and $R_2$ join to form the group —$CH_2$—$CH_2$—O—$CH_2$—$CH_2$—. In other embodiments, $R_1$ and $R_2$ join to form the group —$CH_2$—O—$CH_2$—$CH_2$—, —O—$CH_2$—$CH_2$—$CH_2$—, or —$CH_2$—O—$CH_2$—$CH_2$—$CH_2$—.

In some embodiments of the compound of Formula II, $R_1$ is CN. In some embodiments $R_1$ is CN and $R_2$ is a $C_1$-$C_4$ alkyl group. In some such embodiments, $R_1$ is CN and $R_2$ is a methyl group.

In some embodiments of the compound of Formula II, at least one of $R_1$ and $R_2$ is selected from aryl or substituted aryl. For example, in some embodiments, at least one of $R_1$ and $R_2$ is phenyl or a phenyl substituted with one or more of F, Cl, Br, lower alkyl, OH, or lower alkoxy. In some such embodiments, the other of $R_1$ and $R_2$ is a lower alkyl group such as, but not limited to a methyl or ethyl group.

In some embodiments of the compound of Formula II, X is NH, n is 1, $R_3$ and $R_4$ are independently selected from H, lower alkyl or substituted lower alkyl, and $R_6$ is OH. In some such embodiments $R_5$ is OH. In some such embodiments, one of $R_3$ or $R_4$ is a substituted lower alkyl. In some such embodiments, one of $R_3$ or $R_4$ is a perhaloalkyl such as a $CF_3$ group.

In some embodiments of the compound of Formula II, X is —($CR_bR_c$)—. In some such embodiments, X is —$CH_2$—. In other embodiments, X is —O—. In still other embodiments, X is —$NR_a$—. In some such embodiments, X is —NH—.

In some embodiments, the compound of Formula II has the Formula IIA, and the variables $R_1$, $R_2$, $R_3$, $R_4$, $R_5$, and $R_7$ have the definitions provided in any of the aspects and embodiments described above.

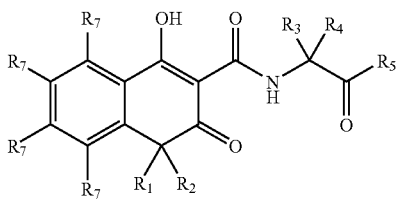

IIA

In some embodiments of the compound of Formula IIA, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ join together to form a 3 to 6 membered ring or a substituted 3 to 6 membered ring. In some such embodiments, $R_4$ is a $C_1$-$C_4$ alkyl or a substituted $C_1$-$C_4$ alkyl. In some embodiments, $R_4$ is a $C_1$-$C_4$ alkyl or a substituted $C_1$-$C_4$ alkyl and $R_3$ is H. In some such embodiments, $R_4$ is a methyl group.

In some embodiments, the compound of Formula II has the Formula IIB, and the variables $R_1$, $R_2$, $R_3$, $R_4$, $R_5$, and $R_7$ have the definitions provided in any of the aspects and embodiments described above

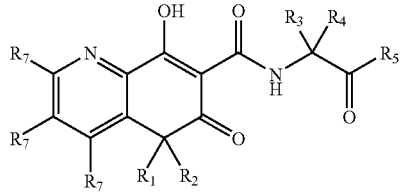

IIB

In some embodiments, the compound of Formula II has the Formula IIC, and the variables $R_1$, $R_2$, $R_3$, $R_4$, $R_5$, and $R_7$ have the definitions provided in any of the aspects and embodiments described above.

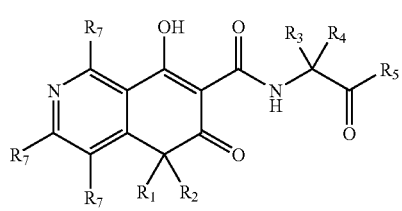

IIC

In some embodiments, the compound of Formula II has the Formula IID, and the variables $R_1$, $R_2$, $R_3$, $R_4$, $R_5$, and $R_7$ have the definitions provided in any of the aspects and embodiments described above.

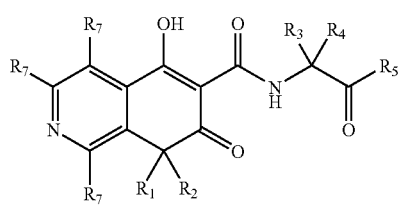

IID

In some embodiments, the compound of Formula II has the Formula IIE, and the variables $R_1$, $R_2$, $R_3$, $R_4$, $R_5$, and $R_7$ have the definitions provided in any of the aspects and embodiments described above.

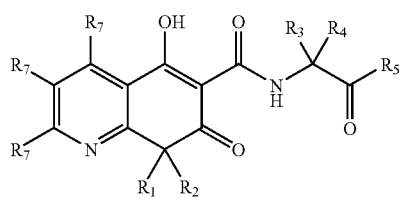

IIE

In certain embodiments the compound of the present invention can be
N-((6-chloro-4-hydroxy-1,1-dimethyl-2-oxo-naphthalen-3-yl)carbonyl)glycine
N-((4-hydroxy-2-oxo-6-(trifluoromethyl)-2',3',5',6'-tetrahydro-2H-spiro[naphthalene-1,4'-pyran]-3-yl)carbonyl)glycine N-((6-fluoro-4-hydroxy-2-oxo-2',3',5',6'-tetrahydro-spiro[naphthalene-1,4'-pyran]-3-yl)carbonyl)glycine
N-((7,8-difluoro-4-hydroxy-1,1-dimethyl-2-oxo-naphthalen-3-yl)carbonyl)glycine
N((1-cyano-4-hydroxy-1-methyl-2-oxo-naphthalen-3-yl)carbonyl)glycine
N-((7-chloro-4-hydroxy-2-oxo-2',3',5',6'-tetrahydro-spiro[naphthalene-1,4'-pyran]-3-yl)carbonyl)glycine
N-((6-chloro-8-fluoro-4-hydroxy-1,1-dimethyl-2-oxo-naphthalen-3-yl)carbonyl)glycine
N-((6,7-difluoro-4-hydroxy-2-oxo-2',3',5',6'-tetrahydro-spiro[naphthalene-1,4'-pyran]-3-yl)carbonyl)glycine
N-((6,7-difluoro-4-hydroxy-1,1-dimethyl-2-oxo-naphthalen-3-yl)carbonyl)glycine
N-((6,7-dichloro-4-hydroxy-2-oxo-2',3',5',6'-tetrahydro-spiro[naphthalene-1,4'-pyran]-3-yl)carbonyl)glycine
N-((6,7-dichloro-4-hydroxy-1,1-dimethyl-2-oxo-naphthalen-3-yl)carbonyl)glycine
N-(((1R)-6-chloro-1-cyano-4-hydroxy-1-methyl-2-oxo-naphthalen-3-yl)carbonyl)glycine
N-(((1S)-1-cyano-4-hydroxy-1-methyl-2-oxo-naphthalen-3-yl)carbonyl)glycine
N-(((1R)-1-cyano-4-hydroxy-1-methyl-2-oxo-naphthalen-3-yl)carbonyl)glycine
N-(((1S)-1-cyano-4-hydroxy-1-methyl-2-oxo-naphthalen-3-yl)carbonyl)glycine
N-((7-chloro-6-fluoro-4-hydroxy-1,1-dimethyl-2-oxo-naphthalen-3-yl)carbonyl)glycine
or a pharmaceutically acceptable salt thereof.

In some embodiments, the compound is selected from any one of the Example compounds or is a salt or ($C_1$-$C_6$) alkyl ester thereof.

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

In some embodiments, the at least one compound is a salt. Such salts may be anhydrous or associated with one or more molecules of water as a hydrate.

In some embodiments, the compound is a prodrug. In some such embodiments, the compound is a ($C_1$-$C_6$)alkyl ester such as a methyl, ethyl, propyl, butyl, pentyl, or hexyl ester.

Also provided herein are pharmaceutical compositions that include at least one pharmaceutically acceptable carrier, excipient, or diluent, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Further provided is a method of modulating the amount of HIF in a cell comprising contacting the cell with at least one compound of any of the embodiments described herein.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 µM or less. In other embodiments, the HIF PHD inhibitory activity $IC_{50}$ value of the compound is 10 µM or less. In still other embodiments, the HIF PHD inhibitory activity $IC_{50}$ value of the compound is 100 nM or less, whereas in others it is 10 nM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be prepared using the general synthetic route shown below in Scheme 1 and described more fully in the Examples.

reaction by reduction of the diazonium ion by Cu(I) and halide transfer from copper. Iodo compound C can selectively be reacted with an appropriately substituted alkyne under Sonogashira or Stephens-Castro reaction conditions to give compound D. Sonogashira reactions typically involve palladium catalysis, whereas the Stephens-Castro reactions involve copper arylacetylenes. Conversion of bromide D to compound E can be accomplished by palladium mediated cross-coupling of an appropriate metal enolate or silyl enolether derivative. Compound F can be generated by acidic deprotection of an appropriate orthoester derivative E or by deprotection of an appropriate trialkyl silane E followed by deprotonation and quenching with various electrophiles such as ethylchloroformate or ethyl cyanoformate. Compound F can be cyclized to compound G by reaction of a nucleophilic benzaldoxime derivative and subsequent elimination of aryl cyanide. Alternatively, compound F could be cyclized to

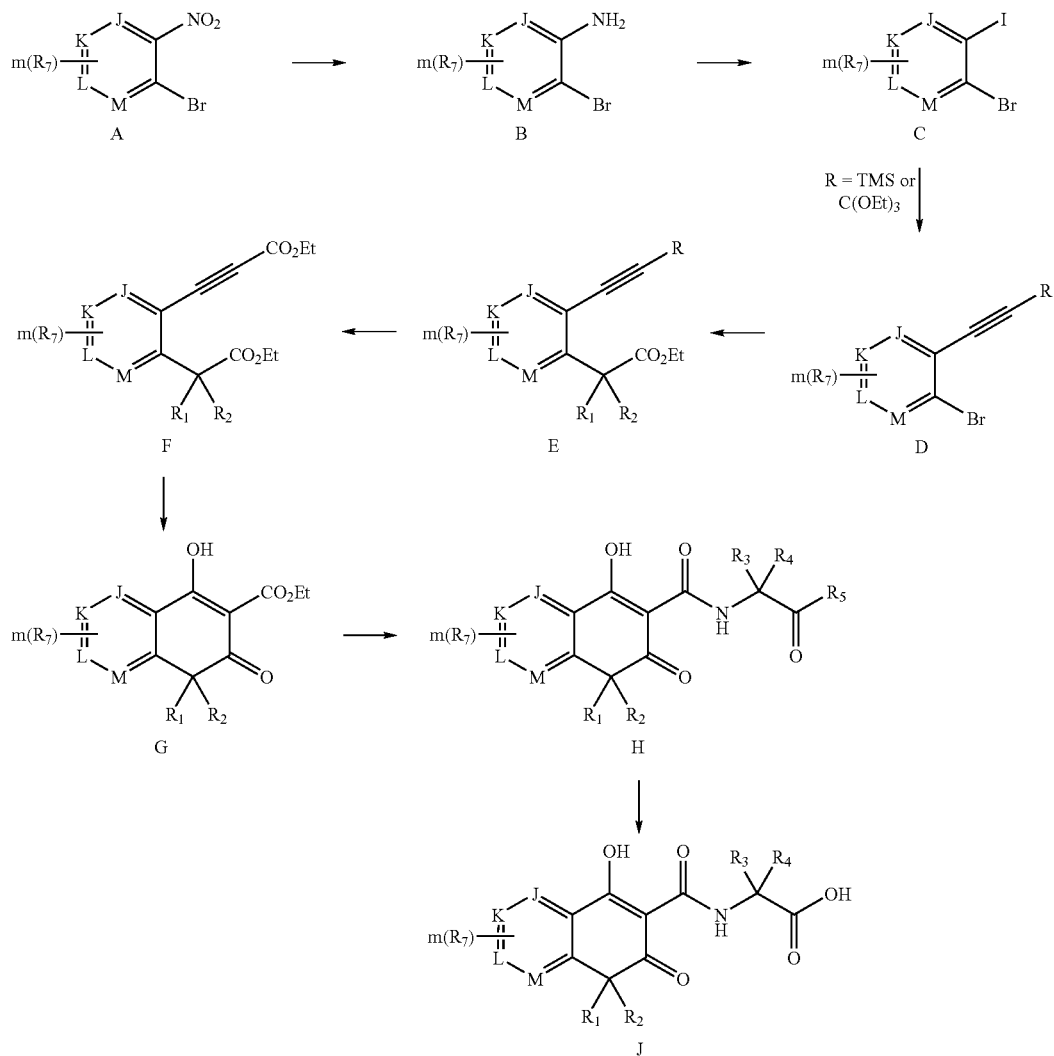

As shown in Scheme 1, the nitro bromo compound A is reduced to the amino bromo compound B by standard reducing agents like $SnCl_4$ or Fe/HCl. Compound B can be converted to iodo compound C by reaction with nitrous acid to form the appropriate diazonium ion, followed by Sandmeyer compound G with additional oxygen nucleophiles such as allylic alcohol, benzylic alcohol or other protected alcohols. Compound H can generated by heating ester G in the presence of an amine. Specifically, compound H can be formed by heating compound G with a glycine alkyl ester derivative.

Compound J can be formed by deprotecting an appropriate ester under basic saponification conditions. Alternatively, compound J can be formed by deprotecting an appropriate ester by acidic hydrolysis conditions.

The compounds of the invention can also be prepared using the general synthetic route shown below in Scheme 2 and described more fully in the Examples.

As shown in Scheme 2, iodo compound L can be prepared from amino compound K by diazotization with nitrous acid followed by Sandmeyer reaction with copper iodide. Compound L can be converted to compound M by deprotonation with reagents such as sodium hydride or potassium tert-butoxide followed by alkylation with alkyl halides or sulfonates such as methyl iodide or methyl sulfate. Compound N can be

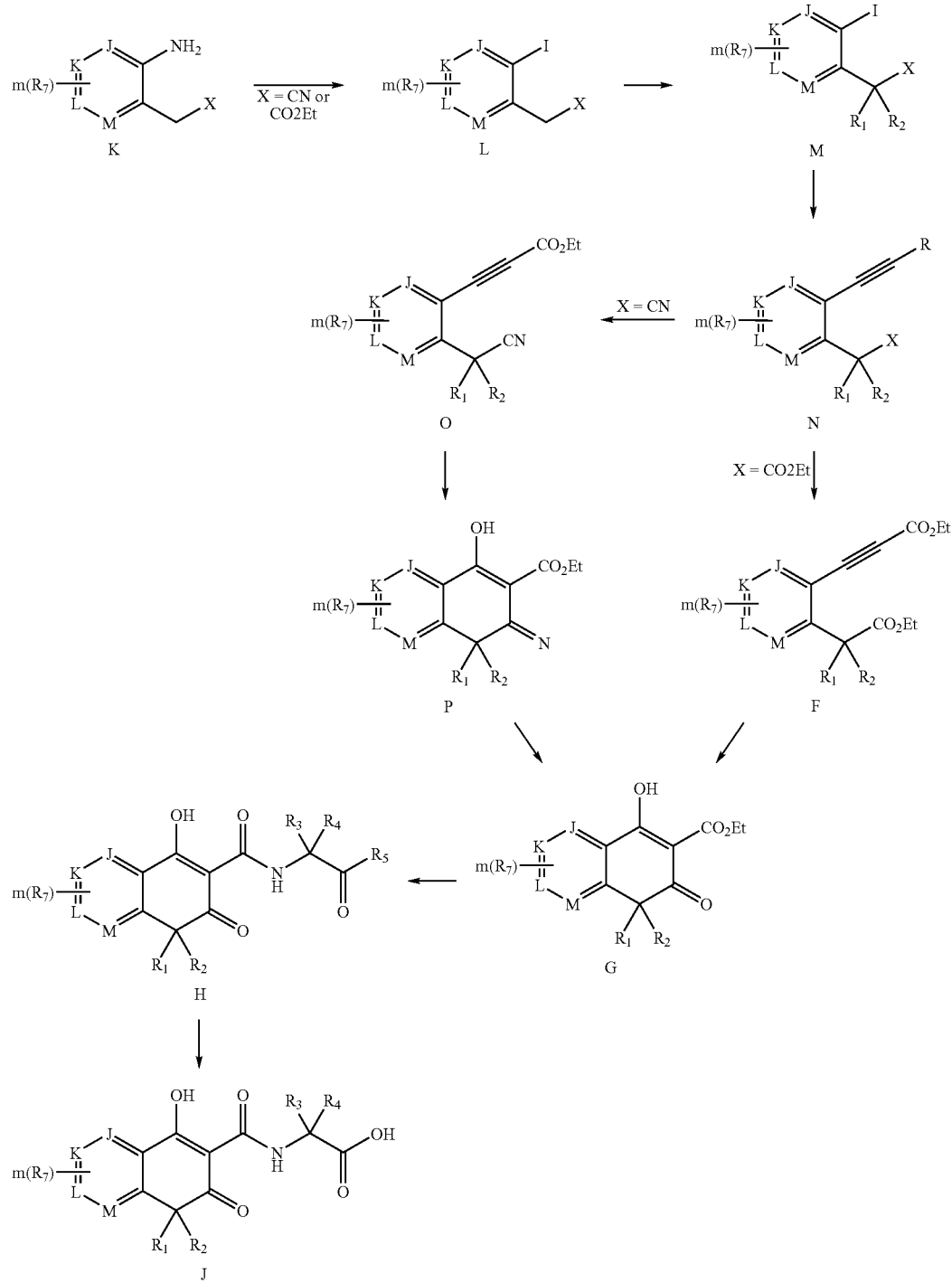

Scheme 2 prepared from compound M by reaction with an appropriate alkyne under Sonogashira or Castro-Stevens reaction conditions as described in Scheme 1. Compound N can be converted to either compound O or compound F by acidic deprotection of an appropriate orthoester derivative N or by deprotection of an appropriate trialkyl silane N followed by deprotonation and quenching with various electrophiles as described in Scheme 1. Compound O can be converted to compound P or compound F can be converted to compound G utilizing the cyclization conditions described with respect to Scheme 1. Furthermore, compound G can be generated by reaction of compound P with acidic hydrolysis conditions such as refluxing hydrochloric acid. The conversion of compound G to compounds H and compounds J are as described in Scheme 1.

The compounds of the invention can also be prepared using the general synthetic route shown below in Scheme 3 and described more fully in the Examples.

As shown in Scheme 3, compound Q can be alkylated to give compound R using the methodology described with respect to Scheme 2. Compound S can be prepared by acidic hydrolysis of an appropriate cyano derivative under conditions of refluxing hydrochloric acid. Alternatively, compound S can be prepared by an appropriate ester derivative under typical saponification deprotection conditions. Carboxylic acid S can be converted to the corresponding acid chloride by reaction with thionyl chloride or oxalyl chloride following typical protocols. Acid chloride T can be converted to compound U by reaction of an appropriate malonate anion, such as, but not limited to, the magnesium anion of diethylmalonate. Compound G is formed by a Friedel-Crafts acylation using reagents such as aluminum chloride, polyphosphoric acid or $P_2O_5$. Compound G is converted to compound H and compound J by conditions described with respect to Scheme 1.

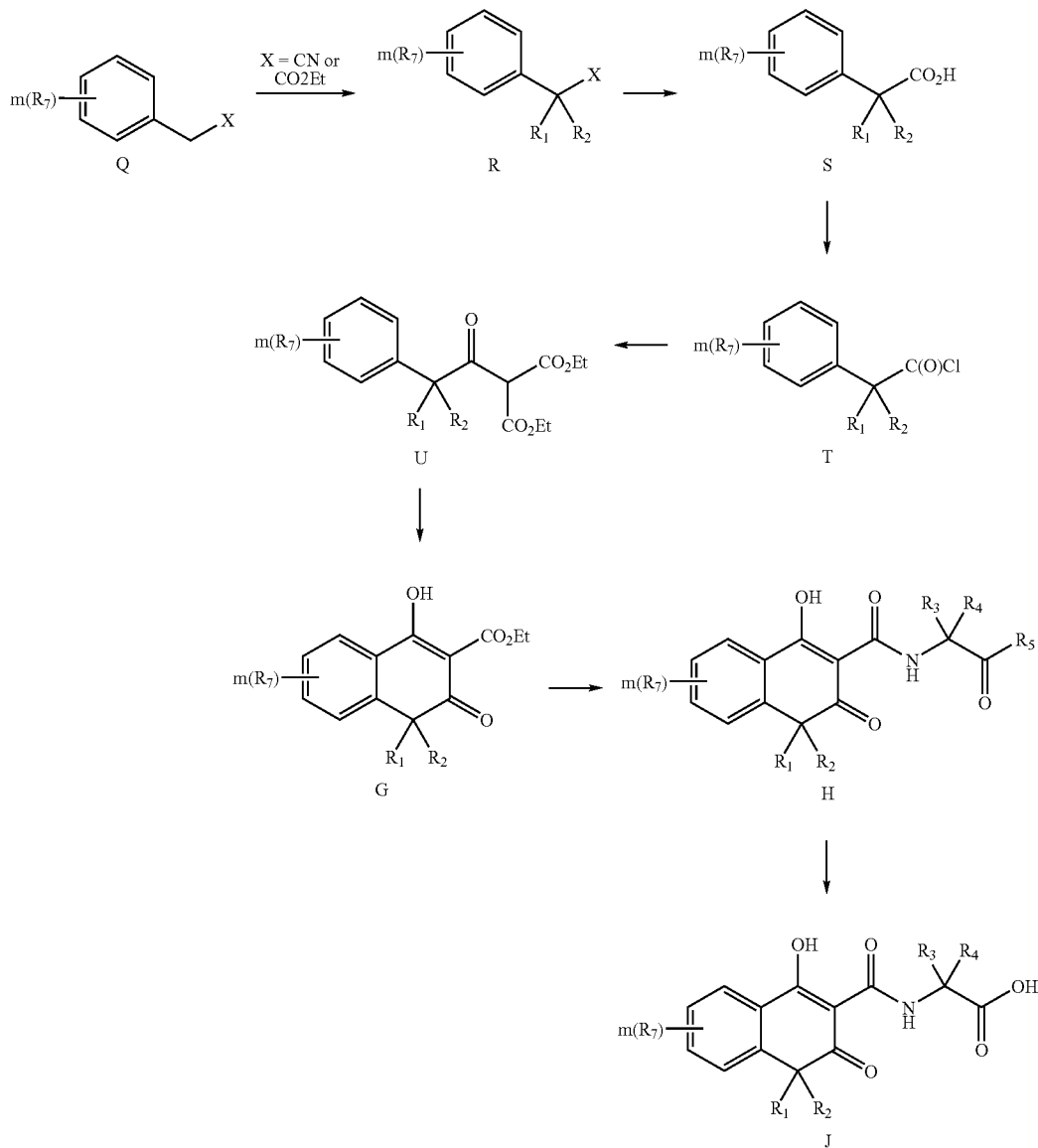

The compounds of the invention can further be prepared using the general synthetic route shown below in Scheme 4 and described more fully in the Examples.

Scheme 4

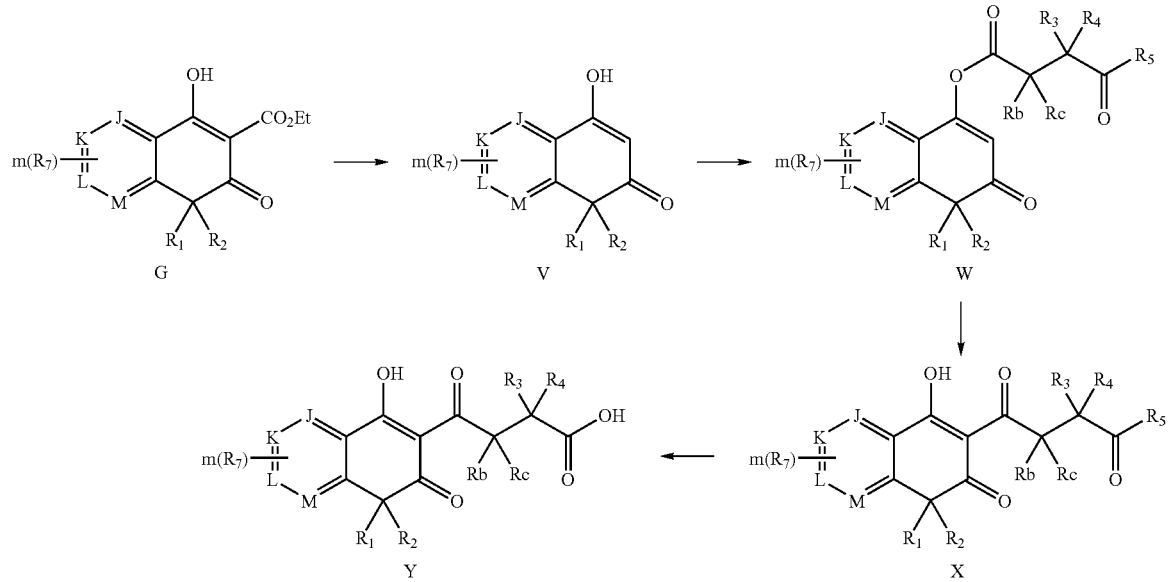

As shown in Scheme 4, Compound V can be prepared from ester compound G by decarboxylation under typical acidic conditions analogous to refluxing concentrated hydrochloric acid. Acylation of compound V by reaction with an appropriate acid chloride with compound V is accomplished by general base catalysis using triethylamine and analogous bases. Compound W can be rearranged via a Fries rearrangement to give compound X. Typical reagents for this include aluminum trichloride and sodium acetate. Compound Y can be prepared from an appropriate ester X by conditions analogous to those described with respect to Scheme 1.

In one aspect, the invention provides a method for synthesizing a compound of Formula IV or a tautomer thereof.

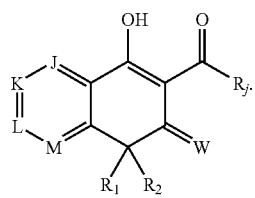

IV

Typically, such methods include cyclizing a compound of Formula III to form a compound of Formula IV

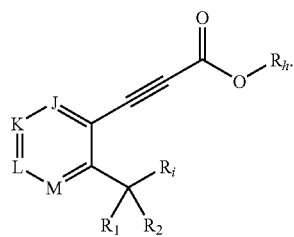

III

Generally, the cyclization is carried out in the presence of a nucleophile and a base in a polar aprotic solvent or solvent system. In such methods, a compound of the formula Ar—C(H)=N—OH where Ar is substituted or unsubstituted aryl, or a salt thereof, is typically included or present in the reaction as the nucleophile. In some embodiments, the nucleophile has the following formula:

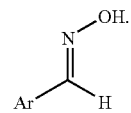

Typically, an aryl cyanide is eliminated from the reaction. In some embodiments Ar is phenyl. Examples of other Ar groups that may be utilized include, but are not limited to, nitro substituted phenyls such as 2-nitrophenyl, 3-nitrophenyl, or 4-nitrophenyl; methyl substituted phenyls such as 2-methylphenyl, 3-methylphenyl, 4-methylphenyl, and xylyl; cyanophenyls such as 2-cyanophenyl, 3, cyanophenyl, and 4-cyanophenyl; trifluoromethyl substituted phenyls such as 2-trifluoromethylphenyl, 3-trifluoromethylphenyl, and 4-trifluoromethylphenyl; various halophenyls such as fluoro, chloro, and bromophenyls, and the like. In some embodiments, a nucleophile such as allyl alcohol or benzyl alcohol may be utilized that may require deprotecting to provide the compound of Formula IV. Typically, a base such as a metal hydride is also included in the reaction mixture during cyclization of the compound of Formula III.

In compounds of Formula III and Formula IV,

J, K, L, and M are selected from $CR_7$ or N, wherein 0, 1, or 2 of J, K, L, and M are N;

$R_h$ is a $C_1$-$C_6$ alkyl group;

$R_j$ is a —O—$C_1$-$C_6$ alkyl group;

$R_1$ and $R_2$ are independently selected from alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents and may include 0, 1, or 2 heteroatom ring members selected from S, N, and O, or one of $R_1$ and $R_2$ may be a $CO_2R_z$ wherein $R_z$ is $C_1$-$C_6$ alkyl if $R_i$ is $CO_2R_k$;

$R_i$ is selected from —CN or $CO_2R_k$, wherein k is a $C_1$-$C_6$ alkyl group;

W is O when $R_i$ is $CO_2R_k$, and W is NH when $R_i$ is —CN;

each $R_7$ is independently selected from H, alkyl, substituted alkyl, alkenyl, substituted alkenyl, alkynyl, substituted alkynyl, $NR_dR_e$, $C(O)R_8$, $C(O)OR_9$, $OR_9$, $SR_9$, $SO_2R_9$, CN, $NO_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, haloalkyl, perhaloalkyl, or —Y—$R_{10}$;

Y is selected from —$N(R_{11})$—Z— or —Z—$N(R_{11})$—;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In certain embodiments of the method for synthesizing compounds of Formula IV, each of J, K, L, and M is a $CR_7$. In some embodiments, one of J, K, L, and M is N and the other three of J, K, L, and M is a $CR_7$.

In certain embodiments of the method for synthesizing compounds of Formula IV, $R_h$ is selected from methyl, ethyl, or propyl. In some such embodiments, $R_h$ and is ethyl. In other embodiments, $R_h$ is a branched $C_1$-$C_6$ alkyl such as an isopropyl or t-butyl group.

In certain embodiments of the method for synthesizing compounds of Formula IV, $R_j$ is selected from —O-methyl, —O-ethyl, or —O-propyl. In some such embodiments, $R_j$ and is —O-ethyl. In still other such embodiments, $R_h$ is methyl, ethyl, or propyl.

In certain embodiments of the method for synthesizing compounds of Formula IV, $R_i$ is —CN.

In certain embodiments of the method for synthesizing compounds of Formula IV, $R_i$ is a $CO_2R_k$. In some such embodiments, $R_k$ is selected from methyl, ethyl, or propyl. In some such embodiments, $R_k$ is ethyl.

In some embodiments when $R_i$ is —CN, the method may further include reacting the compound of Formula IV with water under aqueous acidic conditions to convert W from —NH to O. In some such embodiments, where W is —NH, W is converted to O by reacting the compound with aqueous hydrochloric acid or aqueous sulfuric acid.

In some embodiments, $R_i$ is $CO_2R_k$ and W is O.

In one embodiment of the method of synthesizing compounds of Formula IV, $R_1$ and $R_2$ are independently selected from alkyl, substituted alkyl, alkenyl, substituted alkenyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents and may include 0, 1, or 2 heteroatom ring members selected from S, N, and O. In some such embodiments, $R_1$ and $R_2$ are independently selected from alkyl, substituted alkyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl. In some embodiments, $R_1$ and $R_2$ join to form a spirocyclic ring system that may be substituted with one or more substituents and may include 0, 1, or 2 heteroatom ring members selected from S, N, and O. In some embodiments at least one of $R_1$ and $R_2$ is selected from methyl, ethyl, propyl or butyl. In some such embodiments, at least one of $R_1$ and $R_2$ is a methyl group. In still other embodiments, $R_1$ and $R_2$ are independently selected from $C_1$-$C_4$ alkyl groups. In some such embodiments, both $R_1$ and $R_2$ are methyl groups. In some embodiments, one or both of $R_1$ and $R_2$ is a substituted alkyl group. In some such embodiments, one or both of $R_1$ and $R_2$ is a $CF_3$ group.

In other embodiments of the method of synthesizing compounds of Formula IV, each $R_7$ is independently selected from H, alkyl, substituted alkyl, alkenyl, substituted alkenyl, alkynyl, substituted alkynyl, $NR_dR_e$, $OR_9$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, haloalkyl, or perhaloalkyl.

Various protecting groups may be used for the various substituents as will be readily contemplated by those skilled in the art to form a protected group for the reaction. The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The cyclization of a compound of Formula III to form a compound of Formula IV is typically accomplished by reacting the compound of Formula III with a nucleophiles as described above and a base in a polar aprotic solvent or in a polar aprotic solvent system. The reaction typically does not require heating, but may be heated if so desired. The reaction may be carried out at various temperatures, but is typically conducted at temperatures ranging from −20° C. to 40° C. Various bases may be used to carry out the reaction. Examples of some suitable bases include, but are not limited to non-nucleophilic bases such as metal hydrides such as, but not limited to NaH, LiH, and KH. In some embodiments, the base is NaH. Examples of other suitable bases include lithium hexamethyldisilazide (LiHMDS) or analogous potassium or sodium analogs. Other suitable bases may include potassium, lithium, or sodium t-butoxide. In an alternative procedure anion of the nucleophile is preformed and then added to the compound of Formula III.

Various aprotic solvents and solvent systems may be used in conjunction with the reaction to convert compounds of Formula III to compounds of Formula IV. Examples of suitable solvents and solvent systems include ethereal solvents such as diethyl ether, dimethoxyethane, tetrahydrofuran, dioxane, and the like. Other suitable solvents include, but are not limited to, DMF, DMSO, N-methylpyrrolidone, and the like. In some embodiments, an ethereal solvent is used in conjunction with DMF, DMSO, or N-methylpyrrolidone. In some such embodiments, an ethereal solvent is used in conjunction with DMF. In some embodiments, a cyclic ethereal solvent such as THF or dioxane is used in conjunction with DMF.

In some embodiments where W is O, the method may further include reacting a compound of Formula IV where $R_j$ is an —O—$C_1$-$C_6$ alkyl group with an amine of Formula V to form an amide compound of Formula VI. In alternative embodiments, $R_j$ is first converted to —OH or a halogen such as Cl or Br. Therefore, in some embodiments where the compound of Formula IV is reacted with amine of Formula V, $R_j$ is selected from a halogen, —OH, or a —O—$C_1$-$C_6$ alkyl group The amine of Formula V has the following structure:

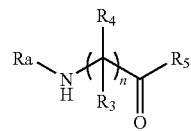

V wherein n is 1 to 6;

$R_a$ is selected from H or lower alkyl;

$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring; and $R_5$ is selected from OH, SH, $NH_2$, lower alkyl, substituted lower alkyl, lower alkoxy, substituted lower alkoxy, or sulfanyl.

In some embodiments, n is 1. In still other embodiments $R_5$ is OH or alkoxy. In still other embodiments, $R_3$ and $R_4$ are both H. In still other embodiments, at least one of $R_3$ and $R_4$ is a lower alkyl such as a methyl, ethyl, or propyl group. In other embodiments, $R_a$ is H.

The compound of Formula VI has the following formula

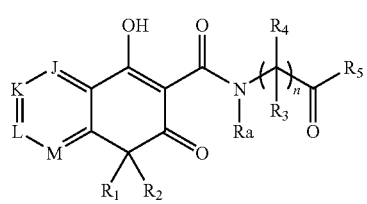

VI where the variables have the same values as described for the compounds of Formula IV and the amines of Formula V.

Typically, an amine of Formula V is reacted with a compound of Formula IV where W is O, by treating the compound of Formula IV with the amine in a polar aprotic solvent or solvent system such as those described above. Suitable solvents include ethereal solvent such as THF, dioxane, and the like. If desired, a non-nucleophilic base such as DIPEA, TEA, or the like may be used. If $R_5$ is an alkoxy group such that the compound includes an ester, the reaction of the amine with the compound of Formula V may be followed by a saponification to produce the carboxylic acid or salt thereof.

As noted above, in some embodiments, the method may include converting the —C(=O)$R_j$ group of the compound of Formula IV (where $R_j$ is an —O—$C_1$-$C_6$ alkyl) to a carboxylic acid (—C(=O)OH) or an acyl halide (—C(=O)($R_{j'}$)) where $R_{j'}$ is a halide such as Cl or Br. In some such embodiments, the carboxylic acid or the acyl halide of the compound of Formula IV is then reacted with an amine of Formula V under standard amide forming conditions to produce the compound of Formula VI.

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following Abbreviations are used to refer to various reagents and solvents:

| | |
|---|---|
| AcOH | Acetic Acid |
| ACN | Acetonitrile |
| dba | dibenzylidene acetone |
| DCM | Dichloromethane |
| DIPEA | Diisopropylethylamine |
| DMF | N,N-Dimethyl Formamide |
| DMSO | Dimethylsulfoxide |
| dppf | 1,1'-bis(diphenylphosphino)ferrocene |
| EtOAc | Ethyl Acetate |
| EtOH | Ethanol |
| GC | Gas Chromatography |
| HMPA | Hexamethylphosphoramide |
| IPAc | Isopropyl acetate |
| LDA | Lithium Diisopropylamide |
| MeI | Methyl Iodide |
| MeOH | Methanol |
| NMP | N-methyl-2-pyrrolidone |
| $PPh_3$ | Triphenylphosphine |
| p-TSA | para-toluenesulfonic acid |
| tBu | tert-butyl |
| TEA | Triethylamine |
| TFA | Trifluoroacetic acid |
| THF | Tetrahydrofuran |
| TLC | Thin Layer Chromatography |
| TMS | Trimethylsilyl |
| TR-FRET | Time Resolved-Fluorescence Resonance Energy Transfer |

Example 1

N-((6-Chloro-4-hydroxy-2-oxo-2',3',5',6'-tetrahydro-2H-spiro[naphthalene-1,4'-pyran]-3-yl)carbonyl)glycine

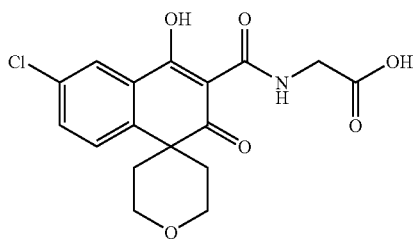

Step A: Preparation of 4-(4-Chlorophenyl)tetrahydro-2H-pyran-4-carboxylic acid To a solution of (4-chlorophenyl)acetonitrile (1.15 g, 7.59 mmol) in DMF (11.5 mL) at 10° C., was added sodium tert-butoxide (0.80 g, 8.34 mmol). The resulting mixture was aged for 10 minutes and then treated with bis(2-chloroethyl) ether (1.19 g, 8.34 mmol). The mixture was aged at 10° C. for 1 hour, warmed to ambient temperature and treated with a second portion of sodium tert-butoxide (0.80 g, 8.34 mmol). After 10 minutes, the mixture was quenched with a 1.0M $H_3PO_4$ solution and extracted with EtOAc (2×25 mL). The combined extracts were washed with saturated brine, dried ($MgSO_4$), and concentrated in vacuo to give a brown solid. The product was dissolved in 1,4-dioxane (5 mL) and treated with a 9.0M $H_2SO_4$ solution at 100° C. for 48 hours. The cooled mixture was then brought to pH=10 and extracted with diethyl ether (2×25 mL). The aqueous phase was acidified to pH=2 with 5N HCl, and the resulting precipitate was collected by vacuum filtration. The solid was dried under vacuum at 50° C. overnight. MS m/e=241.2 $(M+H)^+$.

Step B: Preparation of Diethyl 2-(4-(4-chlorophenyl)-tetrahydro-2H-pyran-4-carbonyl)malonate To a solution of 4-(4-chlorophenyl)tetrahydro-2H-pyran-4-carboxylic acid (0.500 g, 2.08 mmol) in IPAc (2.5 mL) was added DMF (0.050 mL). Oxalyl chloride (0.277 g, 0.19 mL, 2.18 mmol) was then added at ambient temperature over a period of 20 minutes. The resulting solution was stirred at room temperature for a period of 2 hours. In a separate flask, a solution of diethyl malonate (0.420 g, 0.40 mL, 2.60 mmol) in IPAc (3.5 mL) was treated with $MgCl_2$ (0.247 g, 2.60 mmol). The resulting slurry was aged at room temperature for 30 minutes and subsequently treated with TEA (0.704 g, 0.97 mL, 2.60 mmol). After a further 2 hours at ambient temperature, the malonate slurry was cooled to 5° C. and treated with the acyl chloride solution. The resulting mixture was aged at room temperature for 2 hours then treated with a 5N HCl solution (2.5 mL). The organic layer was separated, and the aqueous layer was extracted 3 times with IPAc (2.5 mL). The organic phases were combined, dried ($MgSO_4$), and concentrated under reduced pressure to afford the title compound as an orange oil. MS m/e=383.2 $(M+H)^+$.

Step C: Preparation of Ethyl 6-chloro-4-hydroxy-2-oxo-2',3',5',6'-tetrahydro-spiro[naphthalene-1,4'-pyran]-3-carboxylate Concentrated $H_2SO_4$ (9.5 mL, 18.0M) was treated with $P_2O_5$ (4.25 g, 29.9 mmol). The resulting slurry was stirred at room temperature for 2 hours. The mixture was cooled in an ice bath and treated with a solution of diethyl 2-(4-(4-chlorophenyl)-tetrahydro-2H-pyran-4-carbonyl)malonate (1.70 g, 4.44 mmol) in IPAc (3.0 mL). The resulting green solution was aged for 15 minutes and subsequently poured into ice water. The resulting mixture was extracted with IPAc (3×20 mL), and the combined organic extracts were dried ($MgSO_4$). The organic solution was concentrated in vacuo to furnish a brown solid. The crude product was recrystallized from hot heptane to give the title compound as a pale yellow solid (0.81 g). MS m/e=337.2 $(M+H)^+$.

Step D: Preparation of Methyl N-((6-chloro-4-hydroxy-2-oxo-2',3',5',6'-tetrahydro-2H-spiro[naphthalene-1,4'-pyran]-3-yl)carbonyl)glycinate A mixture of ethyl 6-chloro-4-hydroxy-2-oxo-2',3',5',6'-tetrahydro-spiro[naphthalene-1,4'-pyran]-3-carboxylate (0.810 g, 2.41 mmol), glycine methyl ester hydrochloride (0.39 g, 3.11 mmol, 1.3 eq.), 1,4-dioxane (7.0 mL) and DIPEA (1.3 mL, 7.46 mmol) was heated at 80° C. for 6 hours. The mixture was then cooled to room temperature and extracted with EtOAc (3×25 mL). The combined organic extracts were washed with 2N HCl and brine. The solution was dried ($MgSO_4$) and concentrated under reduced pressure to give a pale yellow solid. The product was recrystallized from EtOAc to give a colorless solid (0.68 g). MS m/e=380.0 $(M+H)^+$.

Step E: Preparation of N-((6-Chloro-4-hydroxy-2-oxo-2',3',5',6'-tetrahydro-spiro[naphthalene-1,4'-pyran]-3-yl)carbonyl)glycine Methyl N-((6-chloro-4-hydroxy-2-oxo-2',3',5',6'-tetrahydro-2H-spiro[naphthalene-1,4'-pyran]-3-yl)carbonyl)glycinate (0.684 g, 1.79 mmol, 1.0 eq.) was suspended in water (10.0 mL) and treated with lithium hydroxide monohydrate (0.227 g, 5.40 mmol). After 30 minutes at ambient temperature, the resulting homogeneous mixture was quenched with 1N HCl solution to pH=2. The white solid that precipitated upon acidification was collected by vacuum filtration and washed with 1:1 $H_2O$/acetone (2×2.0 mL). The product was dried under vacuum at 80° C. for 24 hours to give the title compound in quantitative yield. MS m/e=366.0 $(M+H)^+$. Calculated for $C_{17}H_{16}ClNO_6$ 365.07.

Example 2

N-((6-Chloro-4-hydroxy-1,1-dimethyl-2-oxo-naphthalen-3-yl)carbonyl)glycine

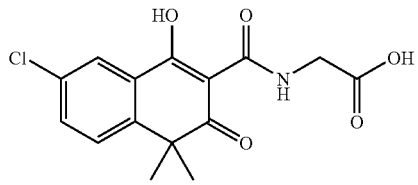

Step A: Preparation of Diethyl 2-(2-(4-chlorophenyl)-2-methylpropanoyl)malonate A solution of 2-(4-chlorophenyl)-2-methylpropionic acid (1.99 g, 10.0 mmol, 1.0 eq.) in IPAc (10 mL) was treated with DMF (0.02 mL) and oxalyl chloride (0.92 mL, 10.5 mmol). The resulting solution was stirred at room temperature for 2 hours. In a separate vessel, was charged diethyl malonate (1.91 mL, 12.5 mmol), IPAc (14 mL), and $MgCl_2$ (11.9 g, 12.5 mmol). The resulting malonate slurry was stirred at room temperature for 30 minutes and subsequently treated with TEA (4.7 mL, 33.5 mmol). The resulting suspension was aged at room temperature for 2 hours, cooled to 5° C. and treated with the above acyl chloride solution. The resulting mixture was warmed to ambient temperature and aged for 1 hour. The slurry was quenched with a 5N HCl solution (10 mL) and the phases were split. The organic phase was washed with saturated NaHCO$_3$ solution (2×10 mL) and water (1×10 mL). The organic phase was dried (MgSO$_4$) and concentrated in vacuo to afford an orange oil. MS m/e=341.2 (M+H)$^+$.

Step B: Preparation of Ethyl 6-chloro-4-hydroxy-1,1-dimethyl-2-oxo-naphthalene-3-carboxylate Concentrated H$_2$SO$_4$ (5.0 mL, 18.0M) was cooled to −4° C. and treated with diethyl 2-(2-(4-chlorophenyl)-2-methylpropanoyl)malonate (1.00 g, 2.93 mmol). The resulting green solution was warmed to room temperature and allowed to stir for 1 hour. The solution was then poured into a 0° C. chilled mixture of water (10 mL) and heptane (5 mL). The resulting precipitate was collected by vacuum filtration, washed with cold water (10 mL) and heptane (1 mL). The product was dried at 40° C. overnight under vacuum to give 0.69 g of the title compound. MS m/e=295.2 (M+H)$^+$.

Step C: Preparation of Methyl N-((6-chloro-4-hydroxy-1,1-dimethyl-2-oxo-naphthalene-3-yl)carbonyl)glycinate A mixture of ethyl 6-chloro-4-hydroxy-1,1-dimethyl-2-oxo-naphthalene-3-carboxylate (0.224 g, 0.761 mmol), glycine methyl ester hydrochloride (0.115 g, 0.914 mmol, 99% Aldrich), 1-methyl-2-pyrrolidinone (1.5 mL), and TEA (0.32 mL, 2.28 mmol) was heated at 80° C. for 4 hours. The resulting mixture was cooled to room temperature and treated with water (10 mL) causing a white solid to precipitate. The product was collected by vacuum filtration and rinsed with water. MS m/e=338.0 (M+H)$^+$.

Step D: Preparation of N-((6-Chloro-4-hydroxy-1,1-dimethyl-2-oxo-naphthalen-3-yl)carbonyl)glycine Methyl N-((6-chloro-4-hydroxy-1,1-dimethyl-2-oxo-naphthalene-3-yl)carbonyl)glycinate (0.256 g, 0.760 mmol) was suspended in water (3.0 mL) and treated with a 5N NaOH solution (0.38 mL, 1.90 mmol). After 20 minutes at ambient temperature, the resulting homogeneous mixture was quenched with a 1N HCl solution to pH=2. The white solid that precipitated upon acidification was collected by vacuum filtration and washed with 1:1 H$_2$O/acetone (2×2.0 mL). The product was subsequently dried at 80° C. under vacuum for 24 hours. MS m/e=324.0 (M+H)$^+$. Calculated for C$_{15}$H$_{14}$ClNO$_5$ 323.06.

Example 3

N-((4-Hydroxy-2-oxo-6-(trifluoromethyl)-2',3',5',6'-tetrahydro-2H-spiro[naphthalene-1,4'-pyran]-3-yl)carbonyl)glycine

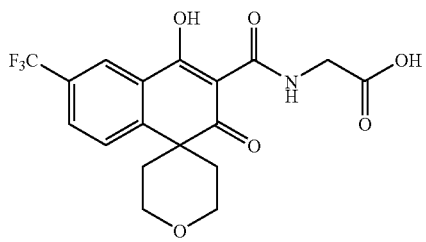

Step A: Preparation of Ethyl 2-(4-(trifluoromethyl)phenyl)acetate

A solution of (trifluoro-p-tolyl)-acetic acid (19.85 g, 97.2 mmol) in EtOH (200 mL) was treated with H$_2$SO$_4$, 36N (16.4 mL, 194 mmol). The reaction was heated at reflux. After 48 hours, the reaction was cooled to 23° C., diluted with EtOAc (750 mL), washed with saturated NaHCO$_3$ solution (2×400 mL) and brine (400 mL), dried over MgSO$_4$, and concentrated in vacuo affording 20.98 g of ethyl 2-(4-(trifluoromethyl)phenyl)acetate.

Step B: Preparation of 4-(4-(Trifluoromethyl)phenyl)-tetrahydro-2H-pyran-4-carboxylic acid A suspension of NaH (60% dispersion in mineral oil (2.3 g, 60 mmol)) in NMP (80 mL) was cooled to 0° C. under nitrogen. The reaction mixture was treated with a solution of ethyl 2-(4-(trifluoromethyl)phenyl)acetate (4.672 g, 20 mmol) in NMP (20 mL) in a dropwise fashion over 10 minutes (effervescence occurred), followed by bis(2-bromoethyl)ether (2.8 mL, 22 mmol). After 15 minutes, the reaction was warmed to 23° C. After 20 hours, the reaction was diluted with a 10% HCl solution (300 mL; slowly, a lot of effervescence was observed) and extracted with diethyl ether (2×300 mL). The combined organic layers were washed with brine (200 mL), dried over MgSO$_4$, concentrated in vacuo and purified by silica gel chromatography (eluant: 25-50% EtOAc/hexane) affording 3.76 g of 4-(4-(trifluoromethyl)phenyl)-tetrahydro-2H-pyran-4-carboxylic acid. MS m/e=275.1 (M+H)$^+$.

Step C: Preparation of Diethyl 2-(4-(4-(trifluoromethyl)phenyl)-tetrahydro-2H-pyran-4-carbonyl)malonate A suspension of 4-(4-(trifluoromethyl)phenyl)-tetrahydro-2H-pyran-4-carboxylic acid (3.749 g, 13.7 mmol) and thionyl chloride (9.97 mL, 137 mmol) was heated at reflux. After 2 hours, the reaction was cooled to 23° C. and concentrated in vacuo, azeotroped with toluene (2×20 mL) and further dried on the vacuum line for 90 minutes. A solution of diethyl malonate (2.17 mL, 14.4 mmol) in ACN (50 mL) in an oven-dried round-bottomed flask, was cooled to 0° C. and treated with MgCl$_2$ (1.30 g, 13.7 mmol), followed by TEA (3.99 mL, 28.7 mmol). The reaction was warmed to 23° C. After 2 hours and 30 minutes, a solution of the crude acid chloride in ACN (10 mL) was added, and the reaction was heated to 50° C. After 15 hours, the reaction was cooled to 23° C., diluted with EtOAc (400 mL), and washed with a 10% HCl solution (300 mL). The aqueous layer was extracted with EtOAc (300 mL). The combined organic layers were washed with brine (200 mL), dried over MgSO$_4$, and concentrated in vacuo affording 5.50 g of diethyl 2-(4-(4-(trifluoromethyl)phenyl)-tetrahydro-2H-pyran-4-carbonyl)malonate. MS m/e=417.2 (M+H)$^+$.

Step D: Preparation of 1,1-Dimethylethyl N-((4-hydroxy-2-oxo-6-(trifluoromethyl)-2',3',5',6'-tetrahydro-spiro[naphthalene-1,4'-pyran]-3-yl)carbonyl)glycinate H$_2$SO$_4$ (4897 μL, 88139 μmol) was cooled to 0° C. and treated with P$_2$O$_5$ (1501 mg, 10577 μmol). The reaction was warmed to 23° C. and treated with diethyl 2-(4-(4-(trifluoromethyl)phenyl)-tetrahydro-2H-pyran-4-carbonyl)malonate (734 mg, 1763 μmol) after 10 minutes. After 75 minutes, the reaction was diluted with EtOAc (10 mL) and poured into an ice-water mixture (~50 mL). The suspension was extracted with EtOAc (3×50 mL). The organic layers were combined, washed with brine (50 mL), dried over MgSO$_4$, and concentrated in vacuo affording 650 mg of the crude cyclized product. MS m/e=371.2 (M+H)$^+$.

A solution of the crude product from the previous step (797 mg, 2152 µmol), glycine tert-butyl ester hydrochloride (433 mg, 2583 µmol) and DIPEA (937 µL, 5380 µmol) in 1,4-dioxane (20 mL) was heated to 120° C. in a sealed vessel. After 4 hours, the reaction was cooled to 23° C., diluted with EtOAc (300 mL), washed with a 10% HCl solution (150 mL), water (150 mL), and brine (150 mL), dried over MgSO$_4$, concentrated in vacuo, and purified by silica gel chromatography (eluant: 10-25% EtOAc/hexane) affording 502 mg of the title compound. MS m/e=456.2 (M+H)$^+$.

Step E: Preparation of N-((4-Hydroxy-2-oxo-6-(trifluoromethyl)-2',3',5',6'-tetrahydro-spiro[naphthalene-1,4'-pyran]-3-yl)carbonyl)glycine A solution of 1,1-dimethylethyl N-((4-hydroxy-2-oxo-6-(trifluoromethyl)-2',3',5',6'-tetrahydro-spiro[naphthalene-1,4'-pyran]-3-yl)carbonyl)glycinate (500 mg, 1098 µmol) in TFA (4 mL) was stirred at 23° C. After 25 minutes, the reaction was concentrated in vacuo and azeotroped with DCM (2×10 mL). The crude solid was washed with diethyl ether affording 356 mg of N-((4-hydroxy-2-oxo-6-(trifluoromethyl)-2',3',5',6'-tetrahydro-2H-spiro[naphthalene-1,4'-pyran]-3-yl)carbonyl)glycine. MS m/e=400.1 (M+H)$^+$. Calculated for $C_{18}H_{16}F_3NO_6$ 399.09.

Example 4

N-((4-Hydroxy-1,1-dimethyl-2-oxo-6-(trifluoromethyl)-naphthalen-3-yl)carbonyl)glycine

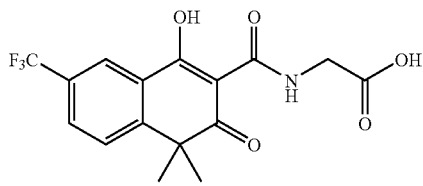

Step A: Preparation of Methyl 2-methyl-2-(4-(trifluoromethyl)phenyl)propanoate

A suspension of NaH (60% dispersion in mineral oil (1805 mg, 45123 µmol)) in DMF (100 mL) was cooled to 0° C. in an oven-dried round bottomed flask. A solution of ethyl 2-(4-(trifluoromethyl)phenyl)acetate (4191 mg, 18049 µmol) and MeI (3372 µL, 54148 µmol) in DMF (10 mL) was cooled to 0° C., and was added to the reaction mixture in a dropwise fashion over 15 minutes. The flask was rinsed with DMF (2×5 mL), and the rinse was added to the reaction mixture. After 15 minutes, the reaction was warmed to 23° C. After 48 hours, the reaction was diluted with EtOAc (250 mL) and washed with a 10% HCl solution (200 mL), water (200 mL), and brine (100 mL), dried over MgSO$_4$, concentrated in vacuo, and purified by silica gel chromatography (eluant: 3% EtOAc/hexane) affording 2580 mg of the title compound. MS m/e=261.2 (M+H)$^+$.

Step B: Preparation of 2-Methyl-2-(4-(trifluoromethyl)phenyl)propanoic acid

A solution of methyl 2-methyl-2-(4-(trifluoromethyl)phenyl)propanoate (1528 mg, 6206 µmol) in MeOH (60 mL) and water (15 mL), was treated with KOH (1741 mg, 31028 µmol). The reaction was heated to reflux. After 18 hours, the reaction was cooled to 23° C. and concentrated in vacuo. The crude mixture was partitioned between water/diethyl ether (100 mL each). The aqueous layer was separated and washed with diethyl ether (100 mL). The combined ether layers were extracted with a 1N NaOH solution (25 mL). The combined aqueous washes were acidified with concentrated HCl to pH=2 and were then extracted with EtOAc (3×100 mL). The combined EtOAc layers were dried over MgSO$_4$ and concentrated in vacuo to afford 1323 mg of the title compound. MS m/e=233.1 (M+H)$^+$.

Step C: Preparation of Diethyl 2-(2-methyl-2-(4-(trifluoromethyl)phenyl)propanoyl)malonate A solution of 2-methyl-2-(4-(trifluoromethyl)phenyl)propanoic acid (1325 mg, 5706 µmol) in thionyl chloride (4162 µL, 57063 µmol) was heated at reflux under nitrogen. After 2 hours, the reaction was cooled to 23° C. and concentrated in vacuo to afford the crude acid chloride. In an oven-dried round-bottomed flask, magnesium (208 mg, 8559 µmol) and diethyl malonate (1293 µL, 8559 µmol) were added to EtOH (15 mL) and CCl$_4$ (0.2 mL). The reaction was stirred at 23° C. for 30 minutes followed by the addition of THF (15 mL). The reaction was heated to reflux under nitrogen. After 1 hour, a solution of the crude acid chloride in THF (10 mL) was added in a drop wise fashion. After 30 minutes, the reaction was cooled to 23° C., diluted with diethyl ether (150 mL), and washed with water (150 mL). The aqueous layer was extracted with diethyl ether (150 mL). The combined ether layers were washed with brine (100 mL), dried over MgSO$_4$, concentrated in vacuo, and purified on silica gel (eluant: 5-20% EtOAc/hexane) affording 1115 mg of the title compound. MS m/e=375.2 (M+H)$^+$.

Step D: Preparation of 1,1-Dimethylethyl N-((4-hydroxy-1,1-dimethyl-2-oxo-6-(trifluoromethyl)-naphthalen-3-yl)carbonyl)glycinate Diethyl 2-(2-methyl-2-(4-(trifluoromethyl)phenyl)propanoyl)malonate (1000 mg, 2671 µmol) was cooled to 0° C. in a round-bottomed flask and was then treated with concentrated H$_2$SO$_4$ (10 mL). The ice-bath was removed, and the reaction was stirred at 23° C. After 2 hours, the reaction was poured into an ice-water mixture (100 mL) and extracted with EtOAc (3×150 mL). The combined organic layers were washed with brine (100 mL), dried over MgSO$_4$, and concentrated in vacuo affording 861 mg crude product of ethyl 4-hydroxy-1,1-dimethyl-2-oxo-6-(trifluoromethyl)-naphthalene-3-carboxylate. MS m/e=329.1 (M+H)$^+$.

A solution of crude ethyl 4-hydroxy-1,1-dimethyl-2-oxo-6-(trifluoromethyl)-naphthalene-3-carboxylate (562 mg, 1712 µmol), glycine tert-butyl ester hydrochloride (316 mg, 1883 µmol) and DIPEA (447 µL, 2568 µmol) in 1,4-dioxane (20 mL) was heated to 120° C. in a sealed vessel. After 14 hours, the reaction was cooled to 23° C., and the solvent was removed under vacuum. The residue was diluted with EtOAc (100 mL), washed with water (75 mL) and brine (75 mL), dried over MgSO$_4$, concentrated in vacuo, and purified by silica gel chromatography (eluant: 4-8% EtOAc/hexane) affording 435 mg of the title compound. MS m/e=358.1 (M-C$_4$H$_8$+H)$^+$.

Step E: Preparation of N-((4-Hydroxy-1,1-dimethyl-2-oxo-6-(trifluoromethyl)-naphthalen-3-yl)carbonyl) glycine A solution of 1,1-dimethylethyl N-((4-hydroxy-1,1-dimethyl-2-oxo-6-(trifluoromethyl)-naphthalen-3-yl)carbonyl) glycinate (432 mg, 1045 µmol) in toluene (5 mL), was treated with silica gel (314 mg, 5225 µmol). The reaction was heated at 110° C. After 4 hours, the reaction was cooled to 23° C. and filtered. The residue was washed with DCM (150 mL), and the filtrates were discarded. The residue was subsequently washed with a 10% MeOH/DCM solution (1000 mL). The filtrate was concentrated in vacuo, affording 312 mg of the title compound. MS m/e=358.1 (M+H)+. Calculated for $C_{16}H_{14}F_3NO_5$ 357.08.

Example 5

N-((4-Hydroxy-1,1-dimethyl-2-oxo-6-(3-pyridinyl)-naphthalen-3-yl)carbonyl)glycine

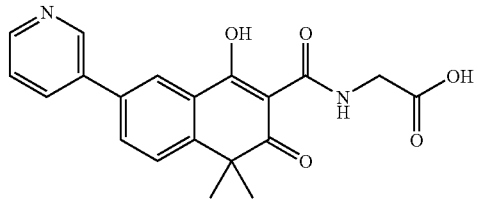

Step A: Preparation of 1,1-Dimethylethyl N-((4-hydroxy-1,1-dimethyl-2-oxo-6-(3-pyridinyl)-naphthalen-3-yl)carbonyl)glycinate A suspension of 1,1-dimethylethyl N-((6-bromo-4-hydroxy-1,1-dimethyl-2-oxo-naphthalen-3-yl)carbonyl)glycinate (284 mg, 669 μmol, see Example 39), pyridin-3-ylboronic acid (165 mg, 1339 μmol), and $Na_2CO_3$ (2.0M aqueous solution (669 μL, 1339 μmol)) in 1,4-dioxane (5 mL) was treated with $Pd(PPh_3)_4$ (77 mg, 67 μmol) in a microwave vial. The vessel was capped, degassed, backfilled with argon (2×), and heated at 150° C. in a microwave for 1200 sec. The reaction was diluted with EtOAc (50 mL), washed with water (50 mL) and brine (50 mL), dried over $MgSO_4$, concentrated in vacuo, and purified by silica gel chromatography (eluant: 20-28-40% EtOAc/hexane) affording 113 mg of the title compound. MS m/e=423.2 (M+H)+.

Step B: Preparation of N-((4-Hydroxy-1,1-dimethyl-2-oxo-6-(3-pyridinyl)-naphthalen-3-yl)carbonyl) glycine A suspension of 1,1-dimethylethyl N-((4-hydroxy-1,1-dimethyl-2-oxo-6-(pyridin-3-yl)-naphthalen-3-yl)carbonyl) glycinate (109 mg, 258 μmol) and silica gel (230-400 mesh, EMD Chemicals) (78 mg, 1290 μmol) in toluene (5 mL) was heated to 110° C. After 2 hours, the reaction was cooled to 23° C., filtered and washed with DCM (25 mL). The washings were discarded. The residue was subsequently washed with a 10% MeOH/DCM solution (1000 mL). The filtrate was then concentrated in vacuo affording 91 mg of the title compound. MS m/e=367.2 (M+H)+. Calculated for $C_{20}H_{18}N_2O_5$ 366.12.

Example 6

N-((6-(2-Fluoro-6-methyl-3-pyridinyl)-4-hydroxy-1,1-dimethyl-2-oxo-naphthalen-3-yl)carbonyl)glycine

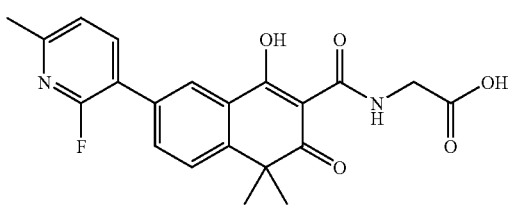

The title compound was prepared using a procedure similar to that outlined in Example 5. MS m/e=399.0 (M+H)+. Calculated for $C_{21}H_{19}FN_2O_5$ 398.13.

Example 7

N-((4-Hydroxy-1,1-dimethyl-6-(2-methyl-4-pyridinyl)-2-oxo-naphthalen-3-yl)carbonyl)glycine

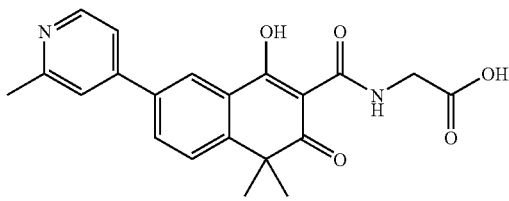

The title compound was prepared using a procedure similar to that outlined in Example 5. MS m/e=381.0 (M+H)+. Calculated for $C_{21}H_{20}N_2O_5$ 380.14.

Example 8

N-((4-Hydroxy-1,1-dimethyl-6-(2-methyl-3-pyridinyl)-2-oxo-naphthalen-3-yl)carbonyl)glycine

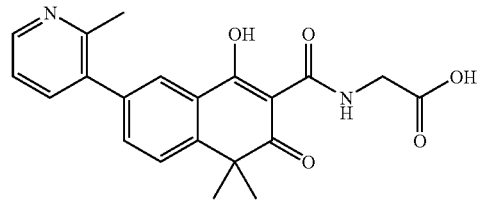

The title compound was prepared using a procedure similar to that outlined in Example 5. MS m/e=381.2 (M+H)+. Calculated for $C_{21}H_{20}N_2O_5$ 380.14.

Example 9

N-((6-(5-Fluoro-3-pyridinyl)-4-hydroxy-1,1-dimethyl-2-oxo-naphthalen-3-yl)carbonyl)glycine

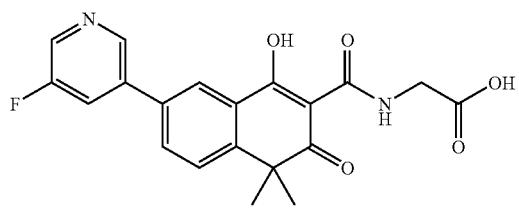

The title compound was prepared using a procedure similar to that outlined in Example 5. MS m/e=385.0 (M+H)+. Calculated for $C_{20}H_{17}FN_2O_5$ 384.11.

Examples 10 and 11

N-(((3R)-6'-Chloro-4'-hydroxy-2'-oxo-4,5-dihydro-spiro[furan-3,1'-naphthalen]-3'-yl)carbonyl)glycine and N-(((3S)-6'-Chloro-4'-hydroxy-2'-oxo-4,5-dihydro-spiro[furan-3,1'-naphthalen]-3'-yl)carbonyl)glycine

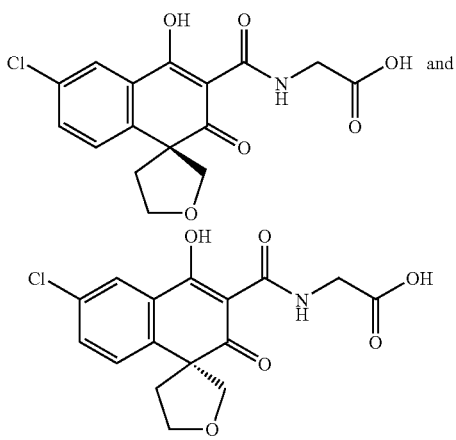

The title compounds were obtained as separate enantiomers by chiral separation of N-((6'-chloro-4'-hydroxy-2'-oxo-4,5-dihydro-2'H-spiro[furan-3,1'-naphthalen]-3'-yl)carbonyl)glycine (Example 12) using chiral HPLC. MS m/e=352.0 (M+H)$^+$. Calculated for $C_{16}H_{14}ClNO_6$ 351.05.

Example 12

N-((6'-Chloro-4'-hydroxy-2'-oxo-4,5-dihydro-2'H-spiro[furan-3,1'-naphthalen]-3'-yl)carbonyl)glycine

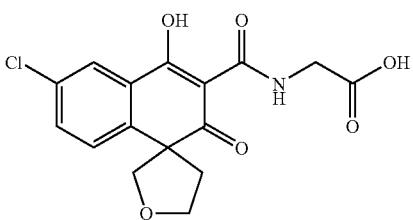

Step A: Preparation of 3-(4-Chlorophenyl)-tetrahydrofuran-3-carbonitrile

To a solution of the NaH (60% by weight, 4 g, 98 mmol) and 1-methylpyrrolidin-2-one (82.5 mL) at −20° C., was added dropwise a mixture of 2-(4-chlorophenyl)acetonitrile (5 g, 33 mmol) and 2-chloroethyl chloromethyl ether (4 mL, 33 mmol) in diethyl ether (16.5 mL, 33 mmol). The mixture was allowed to warm to room temperature over 24 hours. The reaction was then slowly quenched with ice water and extracted with ether (3×). The organic layers were combined, washed with H$_2$O (3×) and brine, dried over Na$_2$SO$_4$, concentrated in vacuo, and purified by silica flash chromatography (13% EtOAc/hexane) to give the desired compound as a yellow oil. MS m/e=208.0 (M+H)$^+$.

Step B: Preparation of 3-(4-Chlorophenyl)-tetrahydrofuran-3-carboxylic acid

To a solution of 3-(4-chlorophenyl)-tetrahydrofuran-3-carbonitrile (9.18 g, 44.21 mmol) in dioxane (26 mL, 44 mmol) was added 9M (aq) H$_2$SO$_4$ (44.21 mL, 44 mmol). The resulting mixture was heated at 110° C. for 12 hours. The mixture was then cooled and extracted with EtOAc. The organic layer was then washed with 2N NaOH. The aqueous wash was acidified with concentrated HCl and extracted with EtOAc. The organic layer was then dried over Na$_2$SO$_4$, filtered, and concentrated in vacuo to give the desired carboxylic acid as a light yellow solid. MS m/e=227.2 (M+H)$^+$.

Step C: Preparation of Diethyl 2-(3-(4-chlorophenyl)-tetrahydrofuran-3-carbonyl)malonate 3-(4-Chlorophenyl)-tetrahydrofuran-3-carboxylic acid (375.2 mg, 1655 μmol) was mixed with thionyl chloride (1.21 mL, 16554 μmol) and heated at 70° C. for 3 hours. The solution was cooled, concentrated in vacuo, and pumped on under high vacuum for 3 hours. To a flame-dried round bottom flask containing diethyl malonate (0.25 mL, 1655 μmol) in ACN (3 mL), was added MgCl$_2$ (158 mg, 1655 μmol). The resulting solution was cooled to 0° C. The reaction was then stirred for 15 minutes at 0° C. To the resulting mixture was slowly added TEA (0.48 mL, 3476 μmol), and the reaction was stirred at room temperature for 3 hours. The acid chloride intermediate in ACN (1.9 mL), was added to the malonate solution, and the resulting mixture was stirred at 50° C. for 13 hours. The reaction was then cooled and concentrated in vacuo to give a light yellow solid which was mixed with 1N HCl and EtOAc. The aqueous layer was extracted with EtOAc (2×), and the combined organic layers were dried over Na$_2$SO$_4$, filtered, and concentrated in vacuo. Purification by silica flash chromatography (10-30% EtOAc/hexane) gave the title compound as a light yellow oil. MS m/e=369.2 (M+H)$^+$.

Step D: Preparation of Ethyl (6'-chloro-4'-hydroxy-2'-oxo-4,5-dihydro-spiro[furan-3,1'-naphthalen]-3'-yl)carboxylate Concentrated H$_2$SO$_4$ (66483 mg, 677858 μmol) was cooled to 0° C. and treated with P$_2$O$_5$ (11546 mg, 81343 μmol). The reaction was stirred for 60 minutes and treated with diethyl 2-(3-(4-chlorophenyl)-tetrahydrofuran-3-carbonyl)malonate (5 g, 13557 μmol). After 60 minutes, the reaction was diluted with EtOAc and poured onto ice. The aqueous layer was extracted with EtOAc (3×), and the combined organic layers were washed with brine and dried over MgSO$_4$. Purification by silica flash chromatography (2-5% MeOH/DCM) gave the title compound as a white solid. MS m/e=323.2 (M+H)$^+$.

Step E: Preparation of 1,1-Dimethylethyl N-((6'-chloro-4'-hydroxy-2'-oxo-4,5-dihydro-spiro[furan-3,1'-naphthalen]-3'-yl)carbonyl)glycinate To a solution of ethyl (6'-chloro-4'-hydroxy-2'-oxo-4,5-dihydro-spiro[furan-3,1'-naphthalen]-3'-yl)carboxylate (284.4 mg, 881 μmol) in 1,4-dioxane (8812 μL, 881 μmol) was added DIPEA (460 μL, 2644 μmol), and the resulting solution was warmed to 80° C. for 2 hours. The reaction was then cooled, diluted with EtOAc, washed with water (2×) and brine, dried over Na$_2$SO$_4$, and purified by silica flash chromatography (10-30% EtOAc/hexanes) to give the title compound as a light yellow solid. MS m/e=430.0 (M+Na)⁺.

Step F: Preparation of N-((6'-Chloro-4'-hydroxy-2'-oxo-4,5-dihydro-spiro[furan-3,1'-naphthalen]-3'-yl) carbonyl)glycine 1,1-Dimethylethyl N-(6'-chloro-4'-hydroxy-2'-oxo-4,5-dihydro-2'H-spiro[furan-3,1'-naphthalen]-3'-yl)carbonyl)glycinate (430.5 mg, 1056 µmol) was dissolved in TFA (10555 µL, 1056 µmol) and stirred for 30 minutes. The reaction was then concentrated in vacuo to give the title compound as a white solid. MS m/e=352.0 (M+H)⁺. Calculated for $C_{16}H_{14}ClNO_6$ 351.05.

Example 13

N-((6-Fluoro-4-hydroxy-1,1-dimethyl-2-oxo-naphthalene-3-yl)carbonyl)glycine

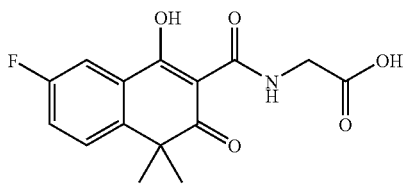

Step A: Preparation of Ethyl 2-(4-fluorophenyl)acetate

A mixture of 2-(4-fluorophenyl)acetic acid (23.5 g, 152 mmol) in thionyl chloride 56 mL, 762 mmol) was refluxed for 2 hours and then concentrated in vacuo. The residue was diluted with 200 mL DCM, and stirred at 0° C. The mixture was treated with EtOH (9.8 mL, 168 mmol) and TEA (26 mL) dropwise. The mixture was then stirred for 2 hours. The mixture was quenched with 20 mL H₂O and extracted with DCM (3×50 mL). The combined organics were washed with H₂O (3×50 mL) and brine 20 mL, dried over anhydrous Na₂SO₄, and concentrated in vacuo to give 24.7 g of a pale yellow oil.

Step B: Preparation of Ethyl 2-(4-fluorophenyl)-2-methylpropanoate

A mixture of NaH (5 g, 115 mmol) in 100 mL NMP and stirred at 0° C., was treated dropwise with a mixture of ethyl 2-(4-fluorophenyl)acetate (7 g, 38 mmol) and MeI (5 mL, 85 mmol) in 20 mL ether. The mixture was allowed to warm to room temperature and was stirred for 15 hours. The resulting mixture was quenched with 100 mL H₂O carefully and the pH was adjusted to 5. The mixture was extracted with ether (3×100 mL). The combined organics were washed with H₂O (3×50 mL) and brine 20 mL. The organic layer was dried over anhydrous Na₂SO₄, concentrated in vacuo, and purified by column chromatography eluting with 10% EtOAc/hexane to give 6.0 g of the product as a pale yellow oil. MS m/e=211 (M+H)⁺.

Step C: Preparation of 2-(4-Fluorophenyl)-2-methylpropanoic acid

A mixture of ethyl 2-(4-fluorophenyl)-2-methylpropanoate (6 g, 29 mmol), KOH (3 g, 57 mmol) and 100 mL EtOH/H₂O (4:1) was refluxed for 4 hours. The mixture was cooled to room temperature. The mixture was extracted with EtOAc and the organic layer discarded. The water layer was acidified with concentrated HCl, extracted with EtOAc, washed with H₂O and brine, dried over anhydrous Na₂SO₄, and concentrated in vacuo to give 3.1 g of the product as a white solid. MS m/e=211 (M−1)⁻.

Step D: Preparation of Diethyl 2-(2-(4-fluorophenyl)-2-methylpropanoyl)malonate

A mixture of diethyl malonate (3 g, 16 mmol) in 50 mL ACN was stirred at 0° C., was treated with MgCl₂ (2 g, 18 mmol) in one portion, and was treated dropwise with TEA (3 g, 33 mmol). The mixture was stirred at room temperature for 2.5 hours. A mixture of 2-(4-fluorophenyl)-2-methylpropanoic acid (3 g, 16 mmol) in thionyl chloride (20 mL) was refluxed for 2 hours and then concentrated in vacuo. The residue was diluted with 10 mL ACN, and was added dropwise to the above mixture. The mixture was stirred at 50° C. for 15 hours. The resulting mixture was then cooled to room temperature, diluted with 100 mL ether, washed with H₂O (2×50 mL) and brine 20 mL, dried over anhydrous Na₂SO₄, and concentrated in vacuo. The crude product was purified by column chromatography eluting with 10-20% EtOAc/hexane to give 5 g of the product as pale yellow oil. MS m/e=325 (M+H)⁺.

Step E: Preparation of Ethyl 6-fluoro-4-hydroxy-1,1-dimethyl-2-oxo-naphthalene-3-carboxylate To 5 mL concentrated H₂SO₄ stirred at 0° C., was slowly added diethyl 2-(2-(4-fluorophenyl)-2-methylpropanoyl)malonate (1.6 g, 4.9 mmol). The reaction was stirred at 0° C. to room temperature for 1 hour, M+1=279. The resulting mixture was poured into 100 g crushed ice and extracted with EtOAc (3×50 mL). The combined organic layers were washed with H₂O (20 mL), brine (20 mL), dried over anhydrous Na₂SO₄, and concentrated in vacuo. The crude product was purified by column chromatography eluting with 20% EtOAc/hexane to give 1.2 g of the product as pale yellow solid. MS m/e=279 (M+H)⁺.

Step F: Preparation of 1,1-Dimethylethyl N-((6-fluoro-4-hydroxy-1,1-dimethyl-2-oxo-naphthalen-3-yl)carbonyl)glycinate A mixture of ethyl 6-fluoro-4-hydroxy-1,1-dimethyl-2-oxo-naphthalene-3-carboxylate (1.1 g, 4.0 mmol), tert-butyl 2-aminoacetate hydrochloride (0.99 g, 5.9 mmol) in 10 mL dioxane, was treated with N-ethyl-N-isopropylpropan-2-amine (1.5 g, 12 mmol). The mixture was warmed to 95° C. and stirred for 15 hours. The mixture was then cooled to room temperature and concentrated in vacuo. The crude product was purified by column chromatography eluting with 10-30% EtOAc/hexane to give 1.13 g of the title compound as a white solid. MS m/e=364 (M+Na)⁺.

Step G: N-((6-Fluoro-4-hydroxy-1,1-dimethyl-2-oxo-naphthalen-3-yl)carbonyl)glycine A mixture of 1,1-dimethylethyl N-((6-fluoro-4-hydroxy-1,1-dimethyl-2-oxo-naphthalen-3-yl)carbonyl)glycinate (0.6 g, 2 mmol) in 3 mL TFA was stirred at room temperature for 30 minutes. The mixture was concentrated and triturated in ether 20 mL. The solid was filtered, washed with 10 mL ether, and dried under high vacuum to give 0.46 g of the product as an off-white solid. MS m/e=308 (M+H)⁺. Calculated for C₁₅H₁₄FNO₅ 307.09.

Example 14

N-((7-Bromo-4-hydroxy-6-(methyloxy)-2-oxo-2',3',5',6'-tetrahydro-spiro[naphthalene-1,4'-pyran]-3-yl)carbonyl)glycine

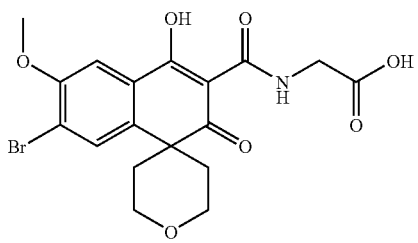

Step A: Preparation of 4-(3-Bromo-4-methoxyphenyl)-tetrahydro-2H-pyran-4-carbonitrile A mixture of sodium tert-butoxide (6.7 g, 70 mmol) in 100 mL NMP stirred at 0° C. was treated dropwise with a mixture of 2-(3-bromo-4-methoxyphenyl)acetonitrile (6.3 g, 28 mmol) and 1-bromo-2-(2-bromoethoxy)ethane (6.5 g, 28 mmol) in 30 mL ether. The mixture was allowed to warm to room temperature and was stirred for 3 hours, M+Na=318/320. The mixture was quenched with 100 mL H₂O carefully and the pH was adjusted to 5. The mixture was extracted with ether (3×100 mL). The combined organic layers were washed with H₂O (3×50 mL) and brine (20 mL). The organic layer was then dried over anhydrous Na₂SO₄, concentrated in vacuo, and purified by column chromatography eluting with 10-20% EtOAc/hexane to give 5.18 g of crude product as a yellow solid. MS m/e=318/320 (M+Na)⁺.

Step B: Preparation of 4-(3-Bromo-4-methoxyphenyl)-tetrahydro-2H-pyran-4-carboxylic acid A mixture of 4-(3-bromo-4-methoxyphenyl)-tetrahydro-2H-pyran-4-carbonitrile (5.7 g, 19 mmol) in 20 mL dioxane was treated with 6M aqueous H₂SO₄ (64 mL, 385 mmol). The resulting mixture was then stirred at 180° C. for 30 minutes, M−1=313/315. The reaction mixture was cooled to room temperature. The mixture was extracted with EtOAc and the organic layer discarded. The water layer was acidified with concentrated HCl, extracted with EtOAc, washed with H₂O and brine, dried over anhydrous Na₂SO₄, and concentrated in vacuo to give 5.5 g of the product as an off white solid. MS m/e=315/317 (M+H)⁺.

Step C: Preparation of Diethyl 2-(4-(3-bromo-4-methoxyphenyl)-tetrahydro-2H-pyran-4-carbonyl)malonate A mixture of diethyl malonate (2.8 g, 17 mmol) in 50 mL ACN was stirred at 0° C. This mixture was treated with MgCl₂ (1.7 g, 17 mmol) in one portion and dropwise with TEA (3.9 g, 38 mmol). The resulting mixture was then stirred at room temperature for 2.5 hours. A mixture of 4-(3-bromo-4-methoxyphenyl)-tetrahydro-2H-pyran-4-carboxylic acid (5.5 g, 17 mmol) in thionyl chloride (21 g, 175 mmol) was refluxed for 2 hours and then concentrated in vacuo. The residue was diluted with 10 mL ACN and added dropwise to the above mixture. The mixture was stirred at 50° C. for 15 hours, M−1=455/457. The mixture was cooled to room temperature, diluted with 100 mL ether, washed with H₂O (2×50 mL) and brine (20 mL), dried over anhydrous Na₂SO₄, and concentrated in vacuo. The crude product was purified by column chromatography eluting with 10-20% EtOAc/hexane to give 1.25 g of the intermediate as a pale yellow oil. MS m/e=455/457 (M+H)⁺.

Step D: Preparation of Ethyl 7-bromo-4-hydroxy-6-methoxy-2-oxo-2',3',5',6'-tetrahydro-spiro[naphthalene-1,4'-pyran]-3-carboxylate In a 100 mL round bottom flask, 5 mL concentrated H₂SO₄ stirred at 0° C. was carefully treated with 2.5 g P₂O₅. The resulting mixture was stirred for 10 minutes. A mixture of diethyl 2-(4-(3-bromo-4-methoxyphenyl)-tetrahydro-2H-pyran-4-carbonyl)malonate (1.25 g, 2.7 mmol) in 2 mL EtOAc was added to the above H₂SO₄ mixture, and the mixture was stirred at room temperature for 2 hours, M+1=411/413. The reaction mixture was then poured into 200 g crushed ice. The mixture was extracted with EtOAc (3×50 mL). The combined organic layers were washed with brine (20 mL), dried over anhydrous Na₂SO₄, concentrated in vacuo, and purified by column chromatography eluting with 10-50% EtOAc/hexane to give 0.28 g of the product as a pale yellow solid. MS m/e=411/413 (M+H)⁺.

Step E: Preparation of 1,1-Dimethylethyl N-((7-bromo-4-hydroxy-6-(methyloxy)-2-oxo-2',3',5',6'-tetrahydro-spiro[naphthalene-1,4'-pyran]-3-yl)carbonyl)glycinate A mixture of ethyl 7-bromo-4-hydroxy-6-methoxy-2-oxo-2',3',5',6'-tetrahydro-spiro[naphthalene-1,4'-pyran]-3-carboxylate (0.28 g, 0.68 mmol) and tert-butyl 2-aminoacetate hydrochloride (0.17 g, 1.0 mmol) in 5 mL dioxane was treated with DIPEA (0.26 g, 2.0 mmol). The mixture was warmed to 95° C. and stirred for 3 hours, M+1=496/498. The mixture was then cooled to room temperature and concentrated in vacuo. The crude product was purified by column chromatography eluting with 10-30% EtOAc/hexane to give 0.28 g of the title compound as a white yellow solid. MS m/e=496/498 (M+H)⁺.

Step F: Preparation of N-((7-Bromo-4-hydroxy-6-(methyloxy)-2-oxo-2',3',5',6'-tetrahydro-spiro[naphthalene-1,4'-pyran]-3-yl)carbonyl)glycine A mixture of 1,1-dimethylethyl N-((7-bromo-4-hydroxy-6-(methyloxy)-2-oxo-2',3',5',6'-tetrahydro-spiro[naphthalene-1,4'-pyran]-3-yl)carbonyl)glycinate (0.27 g, 0.54 mmol) in 3 mL TFA was stirred at room temperature for 30 minutes, M+1=440/442. The mixture was concentrated and triturated in ether (20 mL). The solid was filtered, washed with 10 mL ether and dried under high vacuum to give 0.22 g of the product as a white solid. MS m/e=440/442 (M+H)⁺. Calculated for C₁₈H₁₈BrNO₇ 439.03/441.02.

Example 15

N-((6-Chloro-1-ethyl-4-hydroxy-1-methyl-2-oxo-naphthalen-3-yl)carbonyl)glycine

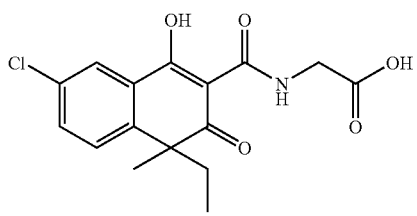

Step A: Preparation of 2-(4-Chlorophenyl)butanenitrile

A mixture of NaH (4.0 g, 99 mmol) in 50 mL NMP stirred at 0° C., was treated dropwise with a mixture of bromoethane (11 g, 99 mmol) and 2-(4-chlorophenyl)acetonitrile (15 g, 99 mmol) in 20 mL ether. The mixture was stirred at room temperature for 2 hours, cooled to 0° C., and quenched carefully with $H_2O$. The resulting mixture was neutralized with 10% HCl to a pH of 5. The mixture was extracted with ether (3×50 mL). The combined organic layers were washed with brine (30 mL), dried over anhydrous $Na_2SO_4$, concentrated in vacuo, and purified by column chromatography eluting with 5% EtOAc/hexane to give 9.1 g of the product as a pale yellow oil.

Step B: Preparation of 2-(4-Chlorophenyl)-2-methylbutanenitrile

A mixture of 2-(4-chlorophenyl)butanenitrile (6.2 g, 35 mmol) in 50 mL DMF stirred at 0° C., was treated with NaH (0.99 g, 41 mmol). The mixture was stirred at 0° C. for 30 minutes, and was treated with MeI (7.3 g, 52 mmol). The mixture was stirred at 0° C. to room temperature for 2 hours, and was carefully quenched with $H_2O$, and neutralized with 10% HCl to pH=5. The mixture was extracted with ether (3×50 mL). The combined organic layers were washed with brine (30 mL), dried over anhydrous $Na_2SO_4$, concentrated in vacuo, and purified by column chromatography eluting with 10% EtOAc/hexane to give 6.5 g of the product as a pale yellow oil.

Step C: Preparation of 2-(4-Chlorophenyl)-2-methylbutanoic acid

A mixture of 2-(4-chlorophenyl)-2-methylbutanenitrile (6.5 g, 34 mmol) in 50 mL EtOH/$H_2O$ (5:1) was treated with KOH (3.8 g, 67 mmol). The mixture was stirred at 120° C. for 4 hours and then at 180° C. for 30 minutes. The mixture was cooled to room temperature. The mixture was extracted with EtOAc and the organic layer discarded. The water layer was acidified with concentrated HCl, extracted with EtOAc, washed with $H_2O$ and brine, dried over anhydrous $Na_2SO_4$, and concentrated in vacuo to give 1.16 g of the product as a pale yellow oil. MS m/e=213 $(M+H)^+$.

Step D: Preparation of 2-(4-Chlorophenyl)-2-methylbutanoic acid

A mixture of diethyl malonate (0.874 g, 5.45 mmol) in 30 mL ACN stirred at 0° C. was treated with $MgCl_2$ (0.224 mL, 5.45 mmol) in one portion and then was treated dropwise with TEA (1.59 mL, 11.5 mmol). The mixture was then stirred at room temperature for 2.5 hours. A mixture of 2-(4-chlorophenyl)-2-methylbutanoic acid (1.16 g, 5.45 mmol) in thionyl chloride (3.98 mL, 54.5 mmol) was refluxed for 2 hours and then concentrated in vacuo. The residue was diluted with 10 mL ACN and added dropwise to the above mixture. The resulting mixture was stirred at 50° C. for 15 hours, M+Na=377. The mixture was cooled to room temperature, diluted with 100 mL ether, washed with $H_2O$ (2×50 mL) and brine 20 mL, dried over anhydrous $Na_2SO_4$, and concentrated in vacuo. The crude product was purified by column chromatography eluting with 10-20% EtOAc/hexane to give 1.71 g of the title intermediate compound as a pale yellow oil. MS m/e=355 $(M+H)^+$.

Step E: Preparation of Ethyl 6-chloro-1-ethyl-4-hydroxy-1-methyl-2-oxo-naphthalene-3-carboxylate A mixture of diethyl 2-(2-(4-chlorophenyl)butan-2-yl)malonate (1.71 g, 5.23 mmol) in concentrated $H_2SO_4$ (5.58 mL, 105 mmol) was stirred at room temperature for 2 hours, M+1=309, M−1=307. The mixture was poured into 200 g ice. The mixture was extracted with EtOAc (3×50 mL). The combined organic layers were washed with brine (20 mL), dried over anhydrous $Na_2SO_4$, concentrated in vacuo, and purified by column chromatography eluting with 10-50% EtOAc/hexane to provide 1.18 g of the title product as a pale yellow oil. MS m/e=309 $(M+H)^+$.

Step F: Preparation of 1,1-Dimethylethyl N-((6-chloro-1-ethyl-4-hydroxy-1-methyl-2-oxo-naphthalen-3-yl)carbonyl)glycinate A mixture of ethyl 6-chloro-4-ethyl-1-hydroxy-4-methyl-3-oxo-naphthalene-2-carboxylate (0.5 g, 2 mmol), and tert-butyl 2-aminoacetate hydrochloride (0.4 g, 2 mmol) in 5 mL dioxane, was treated with N-ethyl-N-isopropylpropan-2-amine (0.6 g, 5 mmol). The resulting mixture was warmed to 95° C. and stirred for 4 hours, M+Na=416, M−1=392. The mixture was then cooled to room temperature and concentrated in vacuo. The crude product was purified by column chromatography eluting with 10-20% EtOAc/hexane to give 0.44 g of the title compound as a white yellow solid. MS m/e=416 $(M+Na)^+$.

Step G: Preparation of N-((6-Chloro-1-ethyl-4-hydroxy-1-methyl-2-oxo-naphthalen-3-yl)carbonyl)glycine A mixture of 1,1-dimethylethyl N-((6-chloro-1-ethyl-4-hydroxy-1-methyl-2-oxo-naphthalen-3-yl)carbonyl)glycinate (0.4 g, 1 mmol) in 3 mL TFA was stirred at room temperature for 30 minutes, M+1=338, M−1=336. The mixture was concentrated in vacuo and the residue was sonicated in 10 mL heptane. The solid was filtered, washed with 10 mL heptane, and dried under high vacuum to give 0.27 g of the title compound as an off-white solid. MS (m/z)=338 $(M+H)^+$. Calculated for $C_{16}H_{16}ClNO_5$ 337.07.

Example 16

N-((4-Hydroxy-6-(methyloxy)-2-oxo-2',3',5',6'-tetrahydro-spiro[naphthalene-1,4'-pyran]-3-yl)carbonyl)glycine

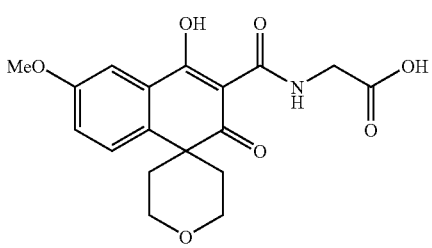

Step A: Preparation of 4-(4-Methoxyphenyl)-tetrahydro-2H-pyran-4-carbonitrile A mixture of NaH (3.1 g, 76 mmol) in 100 mL NMP stirred at 0° C., was treated dropwise with the mixture of 2-(4-methoxyphenyl)acetonitrile (4.5 g, 31 mmol) and 1-bromo-2-(2-bromoethoxy)ethane (7.1 g, 31 mmol) in 30 mL ether. The mixture was allowed to warm to room temperature and stirred for 5 hours, M+Na=240. The mixture was carefully quenched with 100 mL H$_2$O, and the pH was adjusted to 5. The mixture was extracted with ether (3×100 mL). The combined organic layers were washed with H$_2$O (3×50 mL) and brine (20 mL). The organic layer was dried over anhydrous Na$_2$SO$_4$, concentrated in vacuo, and purified by column chromatography eluting with 10-20% EtOAc/hexane to give 5.2 g of the product as a pale yellow oil. MS (m/z)=240 (M+H)$^+$.

Step B: Preparation of 4-(4-Methoxyphenyl)-tetrahydro-2H-pyran-4-carboxylic acid A mixture of 4-(4-methoxyphenyl)-tetrahydro-2H-pyran-4-carbonitrile (5.2 g, 24 mmol) in 10 mL dioxane was treated with 6M aqueous H$_2$SO$_4$ (40 mL, 239 mmol), and the mixture was stirred at 180° C. for 1 hour, M+Na=259, M-1=235. The resulting mixture was cooled to room temperature. The mixture was extracted with EtOAc and the organic layer discarded. The water layer was acidified with concentrated HCl, extracted with EtOAc, washed with H$_2$O and brine, dried over anhydrous Na$_2$SO$_4$, and concentrated in vacuo to give 4.88 g of the product as an off white solid. MS (m/z)=237 (M+H)$^+$.

Step C: Preparation of Diethyl 2-(4-(4-methoxyphenyl)-tetrahydro-2H-pyran-4-carbonyl)malonate A mixture of magnesium (0.28 g, 12 mmol) and diethyl malonate (1.9 g, 12 mmol) was treated with 2 mL anhydrous EtOH and 0.1 mL CCl$_4$. The mixture was stirred at room temperature for 20 minutes, was diluted with 50 mL anhydrous ether, and was then refluxed for 1 hour under nitrogen. All the magnesium was consumed.

A mixture of 4-(4-methoxyphenyl)-tetrahydro-2H-pyran-4-carboxylic acid (2.5 g, 11 mmol) in thionyl chloride (13 g, 106 mmol) was refluxed for 2 hours, and the resulting mixture was then concentrated in vacuo. The residue was diluted with 20 mL ether, and was added dropwise to the above refluxed mixture. The resulting mixture was refluxed for 20 minutes, M+Na=401. The mixture was then cooled to room temperature, diluted with 100 mL ether, washed with H$_2$O (2×50 mL) and brine (20 mL), dried over anhydrous Na$_2$SO$_4$, and concentrated in vacuo. The crude product was purified by column chromatography eluting with 10-20% EtOAc/hexane to give 2.2 g of the intermediate as a pale yellow oil. MS (m/z)=377 (M-1)$^-$.

Step D: Preparation of Ethyl 4-hydroxy-6-methoxy-2-oxo-2',3',5',6'-tetrahydro-spiro[naphthalene-1,4'-pyran]-3-carboxylate Diethyl 2-(4-(4-methoxyphenyl)-tetrahydro-2H-pyran-4-carbonyl)malonate (2.2 g) in 1 mL IPAc was added to 20 mL of concentrated H$_2$SO$_4$, and the resulting mixture was stirred at room temperature for 2 hours, M+1=333, M-1=331. The mixture was then poured into 200 g of ice. The mixture was extracted with EtOAc (3×50 mL). The combined organic layers were washed with brine (20 mL), dried over anhydrous Na$_2$SO$_4$, concentrated in vacuo, and purified by column chromatography eluting with 10-50% EtOAc/hexane to give 0.66 g of the title product as a yellow oil. MS (m/z)=333 (M+H)$^+$.

Step E: Preparation of 1,1-Dimethylethyl N-((4-hydroxy-6-(methyloxy)-2-oxo-2',3',5',6'-tetrahydro-spiro[naphthalene-1,4'-pyran]-3-yl)carbonyl)glycinate A mixture of ethyl 4-hydroxy-6-methoxy-2-oxo-2',3',5',6'-tetrahydro-spiro[naphthalene-1,4'-pyran]-3-carboxylate (0.6 g, 2 mmol), tert-butyl 2-aminoacetate hydrochloride (0.5 g, 3 mmol) in 5 mL dioxane was treated with N-ethyl-N-isopropylpropan-2-amine (0.7 g, 5 mmol). The mixture was warmed to 95° C. and stirred for 4 hours, M+1=418. The mixture was then cooled to room temperature and concentrated in vacuo. The crude product was purified by column chromatography eluting with 10-30% EtOAc/hexane to give 0.74 g of the title compound as a white yellow solid. MS (m/z)=418 (M+H)$^+$.

Step F: Preparation of N-((4-Hydroxy-6-(methyloxy)-2-oxo-2',3',5',6'-tetrahydro-spiro[naphthalene-1,4'-pyran]-3-yl)carbonyl)glycine A mixture of 1,1-dimethylethyl N-((4-hydroxy-6-(methyloxy)-2-oxo-2',3',5',6'-tetrahydro-spiro[naphthalene-1,4'-pyran]-3-yl)carbonyl)glycinate (0.66 g, 1.6 mmol) in 3 mL TFA was stirred at room temperature for 30 minutes, M+1=362, M-1=360. The mixture was concentrated and triturated in DCM/heptane (5:10). The solid was filtered, washed with 10 mL DCM/heptane (5:10), and dried under high vacuum to give 0.52 g of the product as a white solid. MS (m/z)=362 (M+H)$^+$. Calculated for C$_{18}$H$_{19}$NO$_7$ 361.12.

Example 17

N-((6-Fluoro-4-hydroxy-2-oxo-2',3',5',6'-tetrahydro-spiro[naphthalene-1,4'-pyran]-3-yl)carbonyl)glycine

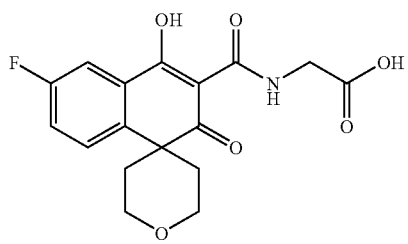

Step A: Preparation of Ethyl 4-(4-fluorophenyl)-tetrahydro-2H-pyran-4-carboxylate A mixture of NaH (1.7 g, 71 mmol) in 100 mL NMP stirred at 0° C., was treated dropwise with a mixture of ethyl 2-(4-fluorophenyl)acetate (5.2 g, 29 mmol) and 1-bromo-2-(2-bromoethoxy)ethane (6.6 g, 29 mmol) in 20 mL ether. The mixture was allowed to warm to room temperature and stirred for 5 hours, M+1=253. The mixture was then carefully quenched with 100 mL H$_2$O, and the pH was adjusted to 5. The mixture was extracted with ether (3×100 mL). The combined organic layers were washed with H$_2$O (3×50 mL) and brine (20 mL). The combined organic layers were then dried over anhydrous Na$_2$SO$_4$ and concentrated in vacuo to give 7.1 g of the crude product as a pale yellow oil. MS (m/z)=253 (M+H)$^+$.

Step B: Preparation of 4-(4-Fluorophenyl)-tetrahydro-2H-pyran-4-carboxylic acid A mixture of ethyl 4-(4-fluorophenyl)-tetrahydro-2H-pyran-4-carboxylate (7.1 g, 28 mmol) and KOH (3.2 g, 56 mmol) in 100 mL EtOH/H$_2$O (4:1) was refluxed for 4 hours, M−1=223. The mixture was cooled to room temperature. The mixture was extracted with EtOAc and the organic layer discarded. The water layer was acidified with concentrated HCl, extracted with EtOAc washed with H$_2$O and brine, dried over anhydrous Na$_2$SO$_4$, and concentrated in vacuo to give 4.9 g of the product as a white solid. MS (m/z)=223 (M−1)$^-$.

Step C: Preparation of Diethyl 2-(4-(4-fluorophenyl)-tetrahydro-2H-pyran-4-carbonyl)malonate A mixture of diethyl malonate (2.1 g, 13 mmol) in 50 mL ACN stirred at 0° C., was treated with MgCl$_2$ (1.4 g, 15 mmol) in one portion and dropwise with TEA (2.7 g, 27 mmol). The mixture was stirred at room temperature for 2.5 hours.

A mixture of 4-(4-fluorophenyl)-tetrahydro-2H-pyran-4-carboxylic acid (3.0 g, 13 mmol) in thionyl chloride 50 mL was refluxed for 2 hours, then concentrated in vacuo. The residue was diluted with 10 mL ACN, and was then added dropwise to the above mixture. The resulting mixture was stirred at 50° C. for 15 hours, M+Na=389. The mixture was cooled to room temperature, diluted with 100 mL ether, washed with H$_2$O (2×50 mL) and brine (20 mL), dried over anhydrous Na$_2$SO$_4$, and concentrated in vacuo. The crude product was purified by column chromatography eluting with 10-20% EtOAc/hexane to give the intermediate 2.1 g as pale yellow oil. MS (m/z)=367 (M+H)$^+$.

Step D: Preparation of Ethyl 6-fluoro-4-hydroxy-2-oxo-2',3',5',6'-tetrahydro-spiro[naphthalene-1,4'-pyran]-3-carboxylate The diethyl 2-(4-(4-fluorophenyl)-tetrahydro-2H-pyran-4-carbonyl) malonate (2.1 g, 6 mmol) was added to 5 mL H$_2$SO$_4$ stirred at 0° C. The mixture was stirred at room temperature for 1 hour, M−1=319. The mixture was then poured into 100 g crushed ice and extracted with EtOAc (3×50 mL). The combined organic layers were washed with H$_2$O (20 mL) and brine (20 mL), dried over anhydrous Na$_2$SO$_4$, and concentrated in vacuo. The crude product was purified by column chromatography eluting with 20% EtOAc/hexane to give 0.5 g product. MS (m/z)=321 (M+H)$^+$.

Step E: Preparation of 1,1-Dimethylethyl N-(6-fluoro-4-hydroxy-2-oxo-2',3',5',6'-tetrahydro-spiro[naphthalene-1,4'-pyran]-3-yl)carbonyl)glycinate A mixture of ethyl 6-fluoro-4-hydroxy-2-oxo-2',3',5',6'-tetrahydro-spiro[naphthalene-1,4'-pyran]-3-carboxylate (0.5 g, 2 mmol), tert-butyl 2-aminoacetate hydrochloride (0.4 g, 2 mmol) in 5 mL dioxane was treated with N-ethyl-N-isopropylpropan-2-amine (0.6 g, 5 mmol). The mixture was warmed to 95° C. and stirred for 13 hours, M−1=404. The mixture was then cooled to room temperature and concentrated in vacuo. The crude product was purified by column chromatography eluting with 10-30% EtOAc/hexane and further purified by HPLC to give 0.12 g of the title compound as a pale yellow solid. MS (m/z)=406 (M+H)$^+$.

Step F: Preparation of N-(6-Fluoro-4-hydroxy-2-oxo-2',3',5',6'-tetrahydro-spiro[naphthalene-1,4'-pyran]-3-yl)carbonyl)glycine A mixture of 1,1-dimethylethyl N-(6-fluoro-4-hydroxy-2-oxo-2',3',5',6'-tetrahydro-spiro[naphthalene-1,4'-pyran]-3-yl)carbonyl)glycinate (0.12 g, 0.30 mmol) in 3 mL TFA was stirred at room temperature for 30 minutes, M+1=350, M−1=348. The mixture was concentrated and then triturated in ether 5 mL. The solid was filtered, washed with 1 mL ether and dried under high vacuum to give 0.1 g of the product as a white solid. MS (m/z)=350 (M+H)$^+$. Calculated for C$_{17}$H$_{16}$FNO$_6$ 349.1.

Example 18

N-((5-Methoxy-4-hydroxy-2-oxo-2',3',5',6'-tetrahydro-spiro[naphthalene-1,4'-pyran]-3-yl)carbonyl) glycine

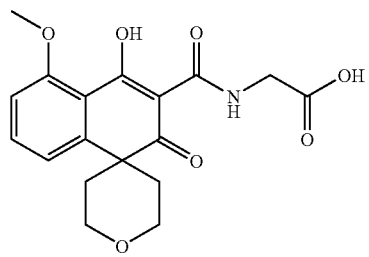

Step A: Preparation of 4-(3-Methoxyphenyl)-tetrahydro-2H-pyran-4-carbonitrile A mixture of NaH (3.2 g, 79 mmol) in 50 mL NMP stirred at 0° C., was treated dropwise with a mixture of 2-(3-methoxyphenyl)acetonitrile (3.9 g, 26 mmol) and 1-bromo-2-(2-bromoethoxy)ethane (6.1 g, 26 mmol) in 20 mL. The mixture was allowed to warm to room temperature and stirred for 15 hours, M+1=218. The mixture was then carefully quenched with 100 mL H$_2$O and the pH was adjusted to 5. The mixture was extracted with ether (3×100 mL). The combined organic layers were washed with H$_2$O (3×50 mL) and brine (20 mL). The organic layer was dried over anhydrous Na$_2$SO$_4$, concentrated in vacuo, and purified by column chromatography eluting with 10-20% EtOAc/hexane to give 5.28 g of the crude product 5.28 g as a pale yellow oil. MS (m/z)=218 (M+H)$^+$.

Step B: Preparation of 4-(3-Methoxyphenyl)-tetrahydro-2H-pyran-4-carboxylic acid A mixture of 4-(3-methoxyphenyl)-tetrahydro-2H-pyran-4-carbonitrile (5.2 g, 24 mmol) in 10 mL dioxane was treated with 6N $H_2SO_4$ (40 mL, 239 mmol), and the mixture was refluxed at 120° C. for 15 hours, M−1=235 and starting material. The mixture was then stirred at 180° C. in a sealed tube for another 0.5 hours, M−1=235 (all starting material was consumed). The mixture was cooled to room temperature. The mixture was extracted with EtOAc and the organic layer discarded. The water layer was acidified with concentrated HCl, extracted with EtOAc, washed with $H_2O$ and brine, dried over anhydrous $Na_2SO_4$, and concentrated in vacuo to give 5.14 g of the product as a pale yellow solid. MS (m/z)= 237 $(M+H)^+$.

Step C: Preparation of Diethyl 2-(4-(3-methoxyphenyl)-tetrahydro-2H-pyran-4-carbonyl)malonate A mixture of magnesium (149 mg, 6146 μmol), and diethyl malonate (984 mg, 6146 μmol) was treated with anhydrous EtOH 2 mL and 0.1 mL $CCl_4$. The mixture was stirred at room temperature for 20 minutes and was then diluted with 50 mL anhydrous ether and refluxed for 1 hour under nitrogen. All magnesium was consumed.

4-(3-Methoxyphenyl)-tetrahydro-2H-pyran-4-carboxylic acid (1.32 g, 5587 μmol) in thionyl chloride (4.078 mL, 55 mmol) was refluxed for 2 hours and then concentrated in vacuo. The residue was diluted with 20 mL ether and added dropwise to the above refluxed mixture, and the resulting mixture was refluxed for 20 minutes, M+1=379, M−1=377. The mixture was cooled to room temperature, diluted with 100 mL ether, washed with $H_2O$ (2×50 mL) and brine (20 mL), dried over anhydrous $Na_2SO_4$, and concentrated in vacuo to give 2.1 g of the intermediate, diethyl 2-(4-(3-methoxyphenyl)-tetrahydro-2H-pyran-4-carbonyl)malonate, as a pale yellow oil. MS (m/z)=379 $(M+H)^+$.

Step D: Preparation of Ethyl 5-methoxy-4-hydroxy-2-oxo-2',3',5',6'-tetrahydro-spiro[naphthalene-1,4'-pyran]-3-carboxylate Diethyl 2-(4-(3-methoxyphenyl)-tetrahydro-2H-pyran-4-carbonyl)malonate (2.1 g) was added to 5 mL $H_2SO_4$ stirred at 0° C. The mixture was stirred at room temperature for 1 hour, M+1=379. The mixture was then poured into 100 g crushed ice and extracted with EtOAc (3×50 mL). The combined organic layers were washed with $H_2O$ (20 mL) and brine (20 mL), dried over anhydrous $Na_2SO_4$, and concentrated in vacuo. The crude product was purified by column chromatography eluting with 20% EtOAc/hexane to give 0.05 g of the title compound. MS (m/z)=379 $(M+H)^+$.

Step E: Preparation of 1,1-Dimethylethyl N-((4-hydroxy-5-(methyloxy)-2-oxo-2',3',5',6'-tetrahydro-spiro[naphthalene-1,4'-pyran]-3-yl)carbonyl)glycinate A mixture of ethyl 5-methoxy-4-hydroxy-2-oxo-2',3',5',6'-tetrahydro-spiro[naphthalene-1,4'-pyran]-3-carboxylate (44 mg, 132 μmol), tert-butyl 2-aminoacetate hydrochloride (33 mg, 199 μmol) in 2 mL dioxane was treated with N-ethyl-N-isopropylpropan-2-amine (51 mg, 397 μmol). The mixture was warmed to 86° C. and stirred for 14 hours, M+1=418. The mixture was then cooled to room temperature and concentrated in vacuo. The crude product was purified by column chromatography eluting with 10-30% EtOAc/hexane to give 35 mg of the title compound as a yellow oil. MS (m/z) 418 $(M+H)^+$.

Step F: Preparation of N-((4-Hydroxy-5-(methyloxy)-2-oxo-2',3',5',6'-tetrahydro-spiro[naphthalene-1,4'-pyran]-3-yl)carbonyl)glycine A mixture of 1,1-dimethylethyl N-((4-hydroxy-5-(methyloxy)-2-oxo-2',3',5',6'-tetrahydro-spiro[naphthalene-1,4'-pyran]-3-yl)carbonyl)glycinate (32 mg, 77 μmol) in 2 mL TFA was stirred at room temperature for 30 minutes, M+1=362, M−1=360. The mixture was concentrated in vacuo, and purified by column chromatography eluting with 0.1:10:100 TFA/MeOH/DCM to give 9 mg of the product as a pale yellow solid. MS (m/z)=362 $(M+H)^+$. Calculated for $C_{18}H_{19}NO_7$ 361.12.

Example 19

N-((4-Hydroxy-7-(methyloxy)-2-oxo-2',3',5',6'-tetrahydro-spiro[naphthalene-1,4'-pyran]-3-yl)carbonyl)glycine

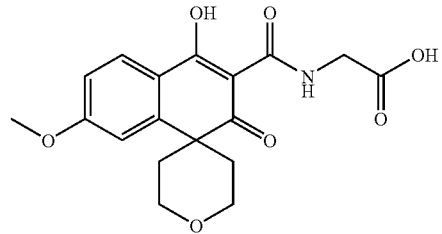

Step A: Preparation of Ethyl 4-hydroxy-7-methoxy-2-oxo-2',3',5',6'-tetrahydro-spiro[naphthalene-1,4'-pyran]-3-carboxylate Diethyl 2-(4-(3-methoxyphenyl)-tetrahydro-2H-pyran-4-carbonyl)malonate (2.1 g, see Example 18) was added to 5 mL $H_2SO_4$ stirred at 0° C. The mixture was stirred at room temperature for 1 hour, M+1=379. The mixture was then poured into 100 g crushed ice and extracted with EtOAc (3×50 mL). The combined organic layers were washed with $H_2O$ (20 mL) and brine (20 mL), dried over anhydrous $Na_2SO_4$, and concentrated in vacuo. The crude product was purified by column chromatography eluting with 20% EtOAc/hexane to give 0.55 g of the title compound. MS (m/z)=379 $(M+H)^+$.

Step B: Preparation of 1,1-Dimethylethyl N-((4-hydroxy-7-methoxy-2-oxo-2',3',5',6'-tetrahydro-spiro[naphthalene-1,4'-pyran]-3-yl)carbonyl)glycinate A mixture of ethyl 4-hydroxy-7-methoxy-2-oxo-2',3',5',6'-tetrahydro-spiro[naphthalene-1,4'-pyran]-3-carboxylate (0.52 g, 1.6 mmol), tert-butyl 2-aminoacetate hydrochloride (0.39 g, 2.3 mmol) in 5 mL dioxane was treated with N-ethyl-N-isopropylpropan-2-amine (0.61 g, 4.7 mmol). The mixture was warmed to 86° C. and stirred for 4 hours, M+1=418. The mixture was cooled to room temperature and concentrated in vacuo. The crude product was purified by column chromatography eluting with 10-30% EtOAc/hexane to give 0.35 g of the title compound as a pale yellow solid. MS (m/z)=418 (M+H)$^+$.

Step C: Preparation of N-((4-Hydroxy-7-(methyloxy)-2-oxo-2',3',5',6'-tetrahydro-spiro[naphthalene-1,4'-pyran]-3-yl)carbonyl)glycine A mixture of 1,1-dimethylethyl N-((4-hydroxy-7-methoxy-2-oxo-2',3',5',6'-tetrahydro-spiro[naphthalene-1,4'-pyran]-3-yl)carbonyl)glycinate (0.36 g, 0.9 mmol) in 2 mL TFA was stirred at room temperature for 30 minutes, M+1=362, M−1=360. The mixture was concentrated and then triturated in DCM/hexane (5:10). The solid was filtered, washed with 10 mL DCM/hexane (5:10), and dried under high vacuum to give 0.3 g of the product as an off-white solid. MS (m/z)=362 (M+H)$^+$. Calculated for $C_{18}H_{19}NO_7$ 361.12.

Example 20

N-((8-Fluoro-4-hydroxy-1,1-dimethyl-2-oxo-7-((phenylmethyl)oxy)-naphthalen-3-yl)carbonyl)glycine

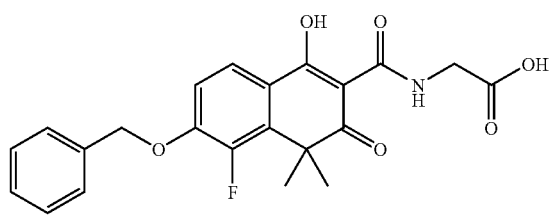

Step A: Preparation of 1,1-Dimethylethyl N-((8-fluoro-4-hydroxy-1,1-dimethyl-2-oxo-7-((phenylmethyl)oxyl)-naphthalen-3-yl)carbonyl)glycinate A mixture of 1,1-dimethylethyl N-((8-fluoro-4,7-dihydroxy-1,1-dimethyl-2-oxo-naphthalene-3-yl)carbonyl)glycinate (0.29 g, 0.76 mmol, prepared in Example 23A-D) and $K_2CO_3$ (0.21 g, 1.5 mmol) in 5 mL ACN stirred at room temperature, was treated with 1-(bromomethyl)benzene (0.26 g, 1.5 mmol), and the resulting mixture was stirred for 12 hours, M+Na=492. The mixture was concentrated in vacuo and purified by column chromatography eluting with 10-30% EtOAc/hexane to give 0.27 g of the title compound as a white solid. MS (m/z)=492 (M+H)$^+$.

Step B: Preparation of N-((8-Fluoro-4-hydroxy-1,1-dimethyl-2-oxo-7-((phenylmethyl)oxy)-naphthalen-3-yl)carbonyl)glycine A mixture of 1,1-dimethylethyl N-((8-fluoro-2-hydroxy-1,1-dimethyl-4-oxo-7-((phenylmethyl)oxyl)-naphthalene-3-yl)carbonyl)glycinate (0.21 g, 447 μmol) in 2 mL TFA was stirred at room temperature for 30 minutes, M+1=414. The mixture was concentrated and then triturated in DCM/hexane (5:10). The solid was filtered, washed with 10 mL DCM/hexane (5:10), and dried under high vacuum to give 0.16 g of a pale yellow solid. LCMS showed about 10% of debenzylated product. The product was further purified by column chromatography eluting with 1:10:100 TFA/MeOH/DCM to give 108 mg of the pure compound. MS (m/z)=414 (M+H)$^+$. Calculated for $C_{22}H_{20}FNO_6$ 413.13.

Example 21

N-((8-Fluoro-4-hydroxy-1,1-dimethyl-7-((2-methylpropyl)oxy)-2-oxo-naphthalen-3-yl)carbonyl)glycine

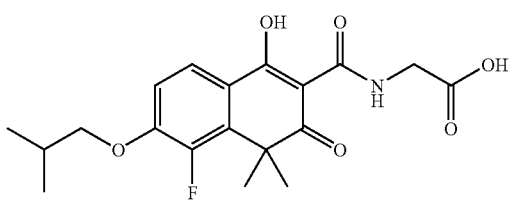

Step A: Preparation of 1,1-Dimethylethyl N-((8-fluoro-4-hydroxy-1,1-dimethyl-7-((2-methylpropyl)oxy)-2-oxo-naphthalen-3-yl)carbonyl)glycinate A mixture of 1,1-dimethylethyl N-((8-fluoro-4,7-dihydroxy-1,1-dimethyl-2-oxo-naphthalen-3-yl)carbonyl)glycinate (0.29 g, 0.76 mmol, see Example 23) and $K_2CO_3$ (0.21 g, 1.5 mmol) in 5 mL ACN stirred at room temperature, was treated with 1-bromo-2-methylpropane (0.52 g, 3.8 mmol). The mixture was stirred at room temperature for 12 hours. The mixture was then warmed to 80° C. and stirred for 24 hours. The mixture was concentrated in vacuo and purified by column chromatography eluting with 10-30% EtOAc/hexane to give 0.25 g of the title compound as a white solid. MS (m/z)=458 (M+Na)$^+$.

Step B: Preparation of N-((8-Fluoro-4-hydroxy-1,1-dimethyl-7-((2-methylpropyl)oxy)-2-oxo-naphthalen-3-yl)carbonyl)glycine A mixture of 1,1-dimethylethyl N-((8-fluoro-4-hydroxy-1,1-dimethyl-7-((2-methylpropyl)oxy)-2-oxo-naphthalen-3-yl)carbonyl)glycinate (0.22 g, 0.51 mmol) in 2 mL TFA was stirred at room temperature for 30 minutes, M+1=380. The mixture was concentrated and triturated in DCM/hexane (5:10). The solid was filtered, washed with 10 mL DCM/hexane (5:10), and dried under high vacuum to give 0.18 g of the product as a pale yellow solid. MS (m/z)=380 (M+H)$^+$. Calculated for $C_{19}H_{22}FNO_6$ 379.14.

Example 22

N-((8-Fluoro-4-hydroxy-1,1-dimethyl-7-(methyloxy)-2-oxo-naphthalen-3-yl)carbonyl)glycine

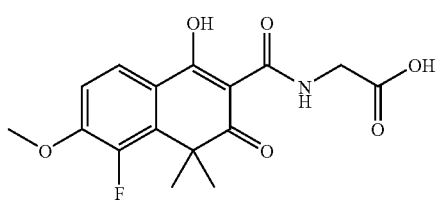

Step A: Preparation of 1,1-Dimethylethyl N-((8-fluoro-4-hydroxy-1,1-dimethyl-7-methoxyl-2-oxo-naphthalen-3-yl)carbonyl)glycinate A mixture of 1,1-dimethylethyl N-((8-fluoro-4,7-dihydroxy-1,1-dimethyl-2-oxo-naphthalen-3-yl)carbonyl)glycinate (0.1 g, 0.3 mmol, see Example 23), and $K_2CO_3$ (0.04 g, 0.3 mmol) in 4 mL ACN stirred at room temperature, was treated with MeI (0.06 g, 0.4 mmol), and the resulting mixture was stirred for 12 hours, M+Na=416. The mixture was concentrated in vacuo and purified by column chromatography eluting with 10-30% EtOAc/hexane to give 98 mg of the title compound as a white solid. MS (m/z)=416 (M+H)$^+$.

Step B: Preparation of N-((8-Fluoro-4-hydroxy-1,1-dimethyl-7-methoxyl-2-oxo-naphthalene-3-yl)carbonyl)glycine A mixture of 1,1-dimethylethyl N-((8-fluoro-4-hydroxy-1,1-dimethyl-7-methoxyl-2-oxo-naphthalene-3-yl)carbonyl)glycinate (92 mg, 234 μmol) in 2 mL TFA was stirred at room temperature for 30 minutes, M+1=338. The mixture was concentrated and then triturated in DCM/hexane (5:10). The solid was filtered, washed with 10 mL DCM/hexane (5:10), and dried under high vacuum to give 72 mg of the product as a pale yellow solid. MS (m/z)=338 (M+H)$^+$. Calculated for $C_{16}H_{16}FNO_6$ 337.10.

Example 23

N-((8-Fluoro-4,7-dihydroxy-1,1-dimethyl-2-oxo-naphthalen-3-yl)carbonyl)glycine

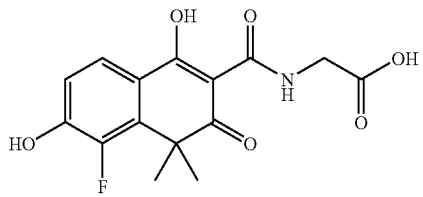

Step A: Preparation of 2-(2,3-Difluorophenyl)-2-methylpropanenitrile

A mixture of NaH (5.7 g, 144 mmol) in 100 mL NMP stirred at 0° C., was treated dropwise with a mixture of MeI (9.0 mL, 144 mmol) and 2-(2,3-difluorophenyl)acetonitrile (10 g, 65 mmol) in 50 mL ether. The mixture was stirred at room temperature for 15 hours. The mixture was then carefully quenched with 20 mL $H_2O$ and extracted with ether (3×100 mL). The combined organic layers were washed with $H_2O$ (2×50 mL) and brine (20 mL), dried over anhydrous $Na_2SO_4$, concentrated in vacuo, and purified by column chromatography eluting with 10-20% EtOAc/hexane to give 11.4 g of the title compound as a pale yellow oil.

Step B: Preparation of 2-(2-Fluoro-3-hydroxyphenyl)-2-methylpropanoic acid

A mixture of 2-(2,3-difluorophenyl)-2-methylpropanenitrile (11.4 g, 63 mmol) in 100 mL ethylene glycol was treated with KOH (11 g, 189 mmol) and stirred at 200° C. for 3 hours, M-1=197. The mixture was then cooled to room temperature. The mixture was extracted with EtOAc and the organic layer discarded. The water layer was acidified with concentrated HCl, extracted with EtOAc, washed with $H_2O$ and brine, dried over anhydrous $Na_2SO_4$, and concentrated in vacuo to give the title compound in 10 g. MS (m/z)=197 (M−1)$^−$.

Step C: Preparation of Diethyl 2-(2-(2-fluoro-3-hydroxyphenyl)-2-methylpropanoyl)malonate A mixture of magnesium (1.2 g, 50 mmol) and diethyl malonate (8.1 g, 50 mmol) was treated with anhydrous EtOH 10 mL and 0.1 mL $CCl_4$. The mixture was stirred at room temperature for 20 minutes and was then diluted with 50 mL anhydrous THF and refluxed for 1 hour under nitrogen.

A mixture of 2-(2-fluoro-3-hydroxyphenyl)-2-methylpropanoic acid (10 g, 50 mmol) in thionyl chloride (37 mL, 505 mmol) was refluxed for 2 hours and then concentrated in vacuo. The residue was diluted with 20 mL THF and added dropwise to the above refluxed mixture, and the resulting mixture was refluxed for 20 minutes M+1=341, M−1=339. The mixture was then cooled to room temperature, diluted with 100 mL ether, washed with $H_2O$ (2×50 mL) and brine (20 mL), dried over anhydrous $Na_2SO_4$, concentrated in vacuo, and purified by column chromatography eluting with 10-30% EtOAc/hexane to give 3.7 g of the title compound. MS (m/z)=341 (M+H)$^+$.

Step D: Preparation of Ethyl 8-fluoro-4,7-dihydroxy-1,1-dimethyl-2-oxo-naphthalene-3-carboxylate To 20 mL concentrated $H_2SO_4$ stirred at room temperature, was added diethyl 2-(2-(2-fluoro-3-hydroxyphenyl)-2-methylpropanoyl)malonate (3.6 g, 11 mmol). The mixture was stirred at room temperature for 2 hours, M+1=295. The mixture was then poured into 100 g crushed ice and extracted with EtOAc (3×50 mL). The combined organic layers were washed with brine (20 mL), dried over anhydrous $Na_2SO_4$, concentrated in vacuo, and purified by column chromatography eluting with 10-30% EtOAc/hexane to give 2.9 g of the title compound as a pale yellow solid. MS (m/z)=295 (M+H)$^+$.

Step E: Preparation of 1,1-Dimethylethyl N-((8-fluoro-4,7-dihydroxy-1,1-dimethyl-2-oxo-naphthalen-3-yl)carbonyl)glycinate A mixture of ethyl 8-fluoro-4,7-dihydroxy-1,1-dimethyl-2-oxo-naphthalene-3-carboxylate (0.4 g, 1 mmol) and tert-butyl 2-aminoacetate hydrochloride (0.3 g, 2 mmol) in 2 mL dioxane, was treated with N-ethyl-N-isopropylpropan-2-amine (0.5 g, 4 mmol). The resulting mixture was warmed to 85° C. and stirred for 4 hours, M+Na=402, M+1=380. The mixture was then cooled to room temperature and concentrated in vacuo. The crude product was purified by column chromatography eluting with 10-30% EtOAc/hexane to give 0.4 g of the title compound as a pale white solid. MS (m/z)= 378 (M−1)$^−$.

Step F: Preparation of N-((8-Fluoro-4,7-dihydroxy-1,1-dimethyl-2-oxo-naphthalen-3-yl)carbonyl)glycine A mixture of 1,1-dimethylethyl N-((8-fluoro-4,7-dihydroxy-1,1-dimethyl-2-oxo-naphthalen-3-yl)carbonyl)glycinate (0.21 g, 0.55 mmol) in 2 mL TFA was stirred at room temperature for 30 minutes, M+1=324, M−1=322. The mixture was concentrated and triturated in ether/hexane (1:10). The solid was filtered, washed with 10 mL ether/hexane (1:10), and dried under high vacuum to give 0.17 g of the product as a yellow solid. MS (m/z)=324 (M+H)$^+$. Calculated for $C_{15}H_{14}FNO_6$ 323.08.

Example 24

N-((7,8-Difluoro-4-hydroxy-1,1-dimethyl-2-oxo-naphthalen-3-yl)carbonyl)glycine

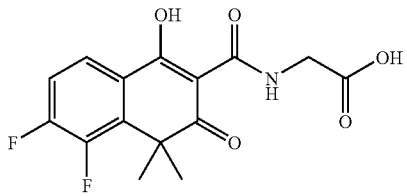

Step A: Preparation of 2-(2,3-Difluorophenyl)-2-methylpropanoic acid

A mixture of 2-(2,3-difluorophenyl)-2-methylpropanenitrile (9.5 g, 52 mmol) in 50 mL dioxane was treated with 10 mL $H_2O$ and concentrated $H_2SO_4$ (3 mL, 105 mmol). The resulting mixture was stirred at 110° C. for 16 hours, M+1=201. The reaction was then cooled to room temperature. The mixture was extracted with EtOAc and the organic layer discarded. The water layer was acidified with concentrated HCl, extracted with EtOAc, washed with $H_2O$ and brine, dried over anhydrous $Na_2SO_4$, and concentrated in vacuo to give 4.74 g of the title compound as a pale yellow solid. MS (m/z)=201 (M+H)$^+$.

Step B: Preparation of Diethyl 2-(2-(2,3-difluorophenyl)-2-methylpropanoyl)malonate A mixture of magnesium (0.57 g, 23 mmol), and diethyl malonate (3.8 g, 23 mmol) was treated with anhydrous EtOH 10 mL and 0.1 mL $CCl_4$. The mixture was stirred at room temperature for 20 minutes and was then diluted with 50 mL anhydrous THF and refluxed for 1 hour under nitrogen.
A mixture of 2-(2,3-difluorophenyl)-2-methylpropanoic acid (4.7 g, 23 mmol) in thionyl chloride (28 g, 235 mmol) was refluxed for 2 hours and then concentrated in vacuo. The residue was diluted with 20 mL THF, and added dropwise to the above refluxed mixture, and the resulting mixture was refluxed for 20 minutes, M+1=343 M−1=341. The mixture was then cooled to room temperature, diluted with 100 mL ether, washed with $H_2O$ (2×50 mL) and brine (20 mL), dried over anhydrous $Na_2SO_4$, concentrated in vacuo, and purified by column chromatography eluting with 10-30% EtOAc/hexane to give 1.53 g of the title compound as a colorless oil. MS (m/z)=343 (M+H)$^+$.

Step C: Preparation of Ethyl 7,8-difluoro-4-hydroxy-1,1-dimethyl-2-oxo-naphthalene-3-carboxylate To 10 mL concentrated $H_2SO_4$ stirred at room temperature, was added diethyl 2-(2-(2,3-difluorophenyl)-2-methylpropanoyl)malonate (1.53 g, 4.5 mmol). The mixture was stirred at room temperature for 2 hours, M+1=297. The mixture was then poured into 100 g crushed ice and extracted with EtOAc (3×50 mL). The combined organic layers were washed with brine (20 mL), dried over anhydrous $Na_2SO_4$, and concentrated in vacuo to give 1.2 g of the title compound as a pale yellow solid. MS (m/z)=297 (M+H)$^+$.

Step D: Preparation of 1,1-Dimethylethyl N-((7,8-difluoro-4-hydroxy-1,1-dimethyl-2-oxo-naphthalen-3-yl)carbonyl)glycinate A mixture of ethyl 7,8-difluoro-4-hydroxy-1,1-dimethyl-2-oxo-naphthalene-3-carboxylate (0.46 g, 1.6 mmol) and tert-butyl 2-aminoacetate hydrochloride (0.39 g, 2.3 mmol) in 2 mL dioxane was treated with N-ethyl-N-isopropylpropan-2-amine (0.60 g, 4.7 mmol). The mixture was warmed to 85° C. and stirred for 15 hours, M+Na=404, M−1=380. The mixture was then cooled to room temperature and concentrated in vacuo. The crude product was purified by column chromatography eluting with 10-30% EtOAc/hexane to give the title compound (0.53 g) as a pale yellow solid. MS (m/z)=404 (M+Na)$^+$.

Step E: Preparation of N-((7,8-Difluoro-4-hydroxy-1,1-dimethyl-2-oxo-naphthalen-3-yl)carbonyl)glycine A mixture of 1,1-dimethylethyl N-((7,8-difluoro-4-hydroxy-1,1-dimethyl-2-oxo-naphthalen-3-yl)carbonyl)glycinate (0.4 g, 1 mmol) in 3 mL TFA was stirred at room temperature for 30 minutes, M+1=325, M−1=324. The mixture was concentrated and then triturated in DCM/hexane (5:10). The solid was filtered, washed with 10 mL DCM/hexane (5:10), and dried under high vacuum to give 0.24 g of the product as a pale yellow solid. MS (m/z)=326 (M+H)$^+$. Calculated for $C_{15}H_{13}F_2NO_5$ 325.07.

Example 25

N-((6'-Chloro-4'-hydroxy-2'-oxo-spiro[cyclopentane-1,1'-naphthalen]-3'-yl)carbonyl)glycine

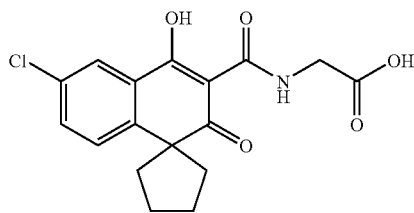

Step A: Preparation of Ethyl 6'-chloro-4'-hydroxy-2'-oxo-spiro[cyclopentane-1,1'-naphthalen]-3'-carboxylate A mixture of diethyl malonate (5.3 g, 33 mmol) and magnesium (0.80 g, 33 mmol) was treated with anhydrous EtOH 10 mL and 0.1 mL $CCl_4$. The mixture was stirred at room temperature for 20 minutes and was then diluted with 50 mL anhydrous ether and refluxed for 1 hour under nitrogen. 1-(4-Chlorophenyl)cyclopentanecarbonyl chloride (7.3 g, 30 mmol) in 20 mL ether was then added dropwise to the above refluxed mixture, and the resulting mixture was refluxed for 20 minutes, M+1=341. The mixture was cooled to room temperature, diluted with 100 mL ether, washed with $H_2O$ (2×50 mL) and brine (20 mL), dried over anhydrous $Na_2SO_4$, and concentrated in vacuo to give 11 g of the crude product as a pale yellow solid. The crude product was treated with concentrated $H_2SO_4$ (48 mL, 900 mmol) and stirred for 4 hours, M+1=321. The mixture was poured into 500 g ice and extracted with ether (3×100 mL). The organic layers were combined and washed with $H_2O$ (20 mL) and brine (20 mL), dried over anhydrous $Na_2SO_4$, concentrated in vacuo, and purified by column chromatography eluting with 10-20% ether/hexane to give the title compound (6.5 g) as a pale yellow solid. MS (m/z)=321 (M+H)+.

Step B: Preparation of 1,1-Dimethylethyl N-((6'-chloro-4'-hydroxy-2'-oxo-spiro[cyclopentane-1,1'-naphthalen]-3'-yl)carbonyl)glycinate A mixture of ethyl 6'-chloro-4'-hydroxy-2'-oxo-spiro[cyclopentane-1,1'-naphthalen]-3'-carboxylate (0.66 g, 2 mmol) and glycine tert-butyl ester hydrochloride (0.5 g, 3 mmol) in 10 mL dioxane was treated with DIPEA (1 mL, 6 mmol). The mixture was warmed to 85° C. and stirred for 4 hours, M+1=406. The mixture was then cooled to room temperature and concentrated in vacuo. The crude product was purified by column chromatography eluting with 10-30% EtOAc hexane to give the title compound (0.8 g) as a pale yellow solid. MS (m/z)=406 (M+Na)+.

Step C: Preparation of N-((6'-Chloro-4'-hydroxy-2'-oxo-2'H-spiro[cyclopentane-1,1'-naphthalen]-3'-yl)carbonyl)glycine A mixture of 1,1-dimethylethyl N-((6'-chloro-4'-hydroxy-2'-oxo-2'H-spiro[cyclopentane-1,1'-naphthalen]-3'-yl)carbonyl)glycinate (0.2 g, 0.5 mmol) in 2 mL TFA was stirred at room temperature for 30 minutes, M+1=350. The mixture was concentrated and triturated in ether/hexane (10:1). The solid was filtered, washed with 10 mL ether/hexane (10:1), and dried under high vacuum to give 135 mg of the salt as an off-white solid. MS (m/z)=350 (M+H)+. Calculated for $C_{17}H_{16}ClNO_5$ 349.07.

Example 26

N-((4-Hydroxy-1,1-dimethyl-2-oxo-5-(trifluoromethyl)-naphthalen-3-yl)carbonyl)glycine

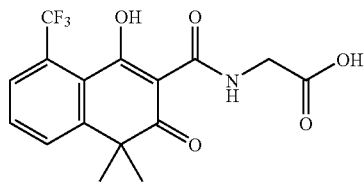

Step A: Preparation of 2-Iodo-3-(trifluoromethyl)benzoic acid

30% $H_2SO_4$ (30 mL) was added to a solution of 3-(trifluoromethyl)anthranilic acid (10.0 g, 48.8 mmol) in DMSO (10 mL) at room temperature. The mixture was cooled to 0° C., and a solution of sodium nitrite (5.05 g, 73.2 mmol) in water (10 mL) was added dropwise over 5 minutes. The mixture was stirred for 1 hour at 0° C., and a solution of KI in water (10 mL) was added dropwise over 5 minutes. The ice bath was removed, and the mixture was stirred for 1 hour. EtOAc was added, and the solution was washed with 2N sodium nitrite twice, brine once, and dried over $MgSO_4$. The solvent was then removed under vacuum to give the product as an off-white solid (12.6 g). [M−H]−=315.2.

Step B: Preparation of 2-Iodo-3-(trifluoromethyl)benzoyl chloride

2-Iodo-3-(trifluoromethyl)benzoic acid (10.0 g, 31.6 mmol) was stirred in thionyl chloride (100 mL, 31.6 mmol) at reflux for 2 hours. The mixture was then cooled to room temperature. The thionyl chloride was removed under vacuum, and the residue was azeotroped with dry toluene to give the product as a yellow-orange semi-solid (10.51 g).

Step C: Preparation of Ethyl 2-(2-iodo-3-(trifluoromethyl)phenyl)acetate (Trimethylsilyl)diazomethane (2.0M in diethyl ether, 55 mL, 110 mmol) was added to 2-iodo-3-(trifluoromethyl)benzoyl chloride (9.24 g, 27.6 mmol) in 25 mL $Et_2O$ in a heavy-walled reaction vessel. The reaction was stirred for 5 hours at room temperature. The mixture was then cooled to 0° C., and AcOH was added until gas evolution ceased. The mixture was partitioned between EtOAc and saturated $NaHCO_3$, the layers were separated, and the organic layer was washed twice with saturated $NaHCO_3$, once with brine, and then dried over $MgSO_4$. The solvent was removed under vacuum to give the product as a yellow oil (9.10 g).

Silver(I) oxide (0.97 g, 4.2 mmol) was added to a solution of the material obtained from the above reaction (7.10 g, 21 mmol) in anhydrous, 200 proof EtOH (180 mL), and the mixture was heated to 75° C. for 30 minutes. The mixture was cooled to room temperature, filtered through celite, and concentrated under vacuum. The resulting yellow oil was purified by column chromatography (0-60% DCM/hexane gradient) to give the product as a light yellow solid (5.4 g).

Step D: Preparation of Ethyl 2-(3,3,3-triethoxyprop-1-ynyl)-3-(trifluoromethyl)phenyl)acetate Copper(I) iodide (160 mg, 0.840 mmol), dichlorobis(triphenylphosphine)palladium(II) (197 mg, 0.280 mmol), and ethyl 2-(2-iodo-3-(trifluoromethyl)phenyl)acetate (1.00 g, 2.80 mmol) were mixed in a heavy-walled microwave tube, and ACN (6 mL) and TEA (3 mL) were added. The tube was sealed and placed under an argon atmosphere before 3,3,3-triethoxyprop-1-yne (723 mg, 4.20 mmol) was added via syringe. The mixture was stirred overnight at 65° C. An additional 0.5 equiv alkyne was added, and the resulting mixture was stirred at 75° C. for 4 hours. The mixture was cooled to room temperature, concentrated under vacuum, and purified by column chromatography to give the product as a light yellow oil (500 mg).

Step E: Preparation of Ethyl 3-(2-(1-ethoxy-2-methyl-1-oxopropan-2-yl)-6-(trifluoromethyl)phenyl)propiolate A solution of ethyl 2-(2-(3,3,3-triethoxyprop-1-ynyl)-3-(trifluoromethyl)phenyl)acetate (500 mg, 1.24 mmol) in DMF (3 mL) was added to a suspension of NaH (89 mg, 3.72 mmol) in DMF (2 mL) at 0° C. After 10 minutes, MeI (0.31 mL, 4.96 mmol) was added, and the mixture was stirred at room temperature overnight. One more equivalent of NaH and MeI were then added, and the mixture was stirred for 3 hours, at which time distilled HMPA (2 mL) was added. After 2 hours at room temperature, the mixture was cooled to 0° C. and partitioned between Et$_2$O and saturated NH$_4$Cl. The layers were separated, and the organic layer was washed twice with water, once with brine, and then dried over MgSO$_4$. The solvent was removed under vacuum to give a colorless oil (530 mg). The oil was dissolved in 4 mL EtOH and 1 mL H$_2$O. p-TSA monohydrate (5 mg) was added, and the mixture was stirred at room temperature for 1 hour. Saturated NaHCO$_3$ and EtOAc were added, and the layers were separated. The organic layer was dried (MgSO$_4$) and then concentrated under vacuum. The residue was purified by column chromatography to give the product as a colorless oil (276 mg).

Step F: Preparation of Ethyl 4-hydroxy-1,1-dimethyl-2-oxo-5-(trifluoromethyl)-naphthalene-3-carboxylate Benzaldehyde oxime (112 mg, 0.92 mmol) in 6 mL dry DMF under argon, was added via syringe to a suspension of NaH (22 mg, 0.92 mmol) in dry dioxane (6 mL) under argon at room temperature. The mixture was stirred for 30 minutes, and ethyl 3-(2-(1-ethoxy-2-methyl-1-oxopropan-2-yl)-6-(trifluoromethyl)phenyl)propiolate (275 mg, 0.77 mmol) was added as a solution in dry DMF (6 mL) via syringe. The reaction was stirred at room temperature for 11 hours. The dioxane was removed under vacuum, and the remaining DMF was partitioned between EtOAc and water. The layers were separated, and the organic layer was washed with twice with water and once with brine. The combined aqueous extracts were back extracted twice with EtOAc, and these organic layers were added to the organic layer already obtained. The combined extracts were dried over MgSO$_4$, concentrated under vacuum, and the resulting residue was purified by column chromatography to give the product as a light yellow oil (50 mg). MS (m/z)=329 (M+H)$^+$ Step G: Preparation of 1,1-Dimethylethyl N-((4-hydroxy-1,1-dimethyl-2-oxo-5-(trifluoromethyl)-naphthalen-3-yl)carbonyl)glycinate DIPEA (40 µL, 0.23 mmol), tert-butylglycine hydrochloride (38 mg), and ethyl 4-hydroxy-1,1-dimethyl-2-oxo-5-(trifluoromethyl)-naphthalene-3-carboxylate (50 mg, 0.15 mmol) were heated in dioxane (2 mL) for 5 hours, cooled to room temperature, and then concentrated under vacuum. The residue was purified by column chromatography to give the product as a yellow oil (30 mg). MS (m/z)=358.4 [M-tBu]$^+$ Step H: Preparation of N-((4-Hydroxy-1,1-dimethyl-2-oxo-5-(trifluoromethyl)-naphthalen-3-yl)carbonyl) glycine 1,1-Dimethylethyl N-((4-hydroxy-1,1-dimethyl-2-oxo-5-(trifluoromethyl)-naphthalen-3-yl)carbonyl)glycinate (30 mg, 73 µmol) was stirred in TFA (5 mL) for 15 minutes. The TFA was then removed under vacuum. The residue was purified by preparatory scale TLC (5% MeOH/DCM eluent) to give the desired product as a light yellow oil (1.6 mg). MS (m/z)=358.4 (M+H)$^+$. Calculated for C$_{16}$H$_{14}$F$_3$NO$_5$ 357.08.

Example 27

N-((8-Fluoro-4-hydroxy-1,1-dimethyl-2-oxo-naphthalen-3-yl)carbonyl)glycine

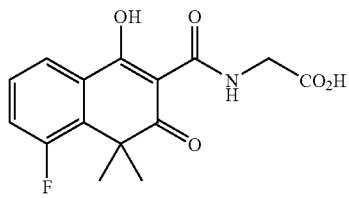

Step A: Preparation of Methyl 2-(2-fluorophenyl)acetate

To a stirred solution of 2-fluorophenylacetic acid (9.6 g, 62 mmol) in MeOH (100 mL) was added concentrated HCl (0.7 mL, 19 mmol). The mixture was heated at 68° C. for 4 hours, and then the reaction was concentrated in vacuo to remove MeOH. The residue was dissolved in ether and then washed with saturated NaHCO$_3$ solution (1×50 mL). The organic extracts were separated, dried with Na$_2$SO$_4$, filtered, and concentrated in vacuo to give a yellow oil (10 g). MS (m/z)= 169.0 (M+H)$^+$.

Step B: Preparation of Methyl 2-(2-fluorophenyl)-2-methylpropanoate

A stirred solution of methyl 2-(2-fluorophenyl)acetate (10.0 g, 59 mmol), MeI (11 mL, 178 mmol), and 18-crown-6 (4 g, 15 mmol) in THF (150 mL) was carefully treated with potassium tert-butoxide (20 mL, 178 mmol). After stirring the reaction mixture at room temperature for 24 hours, NaH (2 g, 62 mmol) was added, and the resulting white mixture was stirred for an additional 12 hours. Water (100 mL) was added cautiously, and then the solution was extracted with EtOAc (2×150 mL). Organic extracts were separated, dried over Na$_2$SO$_4$, filtered, and concentrated in vacuo to provide a yellow oil. Purification via flash chromatography (5% EtOAc/hexanes) provided a pale yellow oil (5.2 g). MS (m/z)=197 (M+H)$^+$.

Step C: Preparation of 2-(2-Fluorophenyl)-2-methylpropanoic acid

A flask containing a solution of methyl 2-(2-fluorophenyl)-2-methylpropanoate (5.2 g, 27 mmol), KOH (2.9 mL, 106 mmol), water (20.0 mL), and EtOH (100 mL) was sealed and heated at 130° C. for 2 hours. Removal of solvent in vacuo provided a yellow oil that was diluted with water. The aqueous mixture was extracted with DCM (1×100 mL), and the organic layer was separated. The aqueous layer was acidified to a pH of 1 with 5N HCl and then extracted with EtOAc (2×100 mL). The organic layers were dried (Na$_2$SO$_4$), filtered, and concentrated in vacuo to afford 4 g of the product as a solid. MS (m/z)=181 (M−1)$^-$.

Step D: Preparation of Diethyl 2-(2-(2-fluorophenyl)-2-methylpropanoyl)malonate

To a solution of 2-(2-fluorophenyl)-2-methylpropanoic acid (3.98 g, 22 mmol), IPAc (31 mL) and DMF (0.017 mL), was slowly added oxalyl chloride (2.0 mL, 23 mmol) over 10 minutes. The resulting solution was stirred for 16 hours and then concentrated in vacuo to afford an oil. In a separate flask, IPAc (30.0 mL) and diethyl malonate (4.2 mL, 27 mmol) were combined. To this mixture was added anhydrous MgCl$_2$ (2.6 g, 27 mmol). The resulting white slurry was stirred at room temperature for 30 minutes, and then TEA (10 mL, 73 mmol) was added. After stirring for an additional 2.5 hours, the reaction was chilled in an ice water bath for 10 minutes, and then the crude acid chloride (previously prepared above) was added to the white mixture via syringe over 10 minutes. The ice bath was removed, and the reaction was stirred for 1.5 hours at room temperature. The mixture was acidified with 5N HCl and added IPAc (50 mL) was added. The aqueous layer was separated and set aside. The organic layer was sequentially washed with saturated NaHCO$_3$ solution and then water. The separated organic layer was dried over Na$_2$SO$_4$, filtered, and concentrated in vacuo to give the crude product. MS (m/z)=325 (M+H)$^+$.

Step E: Preparation of Ethyl 8-fluoro-4-hydroxy-1,1-dimethyl-2-oxo-naphthalene-3-carboxylate A flask containing H$_2$SO$_4$ (12 mL, 219 mmol) and P$_2$O$_5$ (12 g, 88 mmol) was cooled in an ice-water bath for 20 minutes. To this viscous mixture was slowly added diethyl 2-(2-(2-fluorophenyl)-2-methylpropanoyl)malonate (7.1 g, 22 mmol). The ice bath was removed, and the mixture was stirred at room temperature for 1 hour before being poured over crushed ice and diluted with IPAc (100 mL). Water (50 mL) was added, and the resulting mixture was extracted with EtOAc (2×100 mL). The organic layers were combined, dried over Na$_2$SO$_4$, filtered, and concentrated in vacuo to afford a yellow oil that was further purified using flash chromatography (10% EtOAc/hexane, 2.5 g). MS (m/z)=279 (M+H)$^+$.

Step F: Preparation of 1,1-Dimethylethyl N-((8-fluoro-4-hydroxy-1,1-dimethyl-2-oxo-naphthalen-3-yl)carbonyl)glycinate To a solution of ethyl 5-fluoro-1-hydroxy-4,4-dimethyl-3-oxo-3,4-dihydronaphthalene-2-carboxylate (2.0 g, 7.2 mmol) in 1,4-dioxane (15 mL), was added N-ethyl-N-isopropylpropan-2-amine (2.3 mL, 13 mmol) and tert-butyl 2-aminoacetate hydrochloride (1.6 g, 9.3 mmol). After heating at 80° C. for 12 hours, the solvent was removed in vacuo, and the residue was purified using flash chromatography (15% EtOAc/hexane) to afford the product as a white solid (1.6 g). MS (m/z)=362 (M+H)$^+$.

Step G: Preparation of N-((8-Fluoro-4-hydroxy-1,1-dimethyl-2-oxo-naphthalen-3-yl)carbonyl)glycine To a flask containing 1,1-dimethylethyl N-((8-fluoro-4-hydroxy-1,1-dimethyl-2-oxo-naphthalen-3-yl)carbonyl)glycinate (1.5 g, 4.1 mmol) was added TFA (20 mL). The reaction was stirred under nitrogen for 1 hours and then concentrated in vacuo to afford an oil. Addition of water caused a white precipitate to form. The solid was collected by filtration, washed with water, washed with ether, and then dried in vacuo (0.68 g). MS (m/z)=308 (M+H)$^+$. Calculated for C$_{15}$H$_{14}$FNO$_5$ 307.08.

Example 28

N-((1-Cyano-4-hydroxy-1-methyl-2-oxo-naphthalen-3-yl)carbonyl)glycine

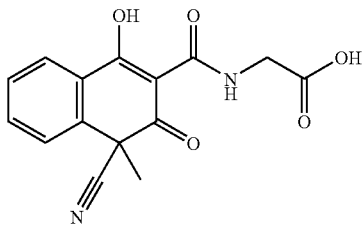

Step A: Preparation of 2-(2-Iodophenyl)propanenitrile 2-(2-Iodophenyl)acetonitrile (3.0 g, 12 mmol) and sodium tert-butoxide (3.6 g, 37 mmol) were stirred in 20 mL of DMF, and MeI (0.77 mL, 12 mmol) was added dropwise. The reaction was then stirred for 3 hours. The solvent was removed under vacuum. The crude residue was purified by silica flash chromatography 0-15% EtOAc/hexanes.

Step B: Preparation of 2-(2-(2-(Trimethylsilyl)ethynyl)phenyl)-proanenitrile Dichlorobis(triphenylphosphine)palladium (II) (0.67 g, 0.95 mmol), copper(I) iodide (0.065 mL, 1.9 mmol), 1-(trimethylsilyl)acetylene (4.0 mL, 29 mmol), and 2-(2-iodophenyl)propanenitrile (2.45 g, 9.5 mmol) were stirred in a 250 mL round bottom flask with 100 mL of TEA at 70° C. The solution was then filtered through a plug of Celite, washed with EtOAc, and the filtrate was concentrated in vacuo. The crude material was purified using silica flash chromatography with a gradient of 0-20% EtOAc/hexanes. MS (m/z)=228 (M+H)$^+$.

Step C: Preparation of 2-(2-Ethynylphenyl)propanenitrile 2-(2-(2-(Trimethylsilyl)ethynyl)phenyl)propanenitrile (2.16 g, 9 mmol) was stirred with 5N NaOH (10 mL, 50 mmol) and THF (20 mL) at room temperature for 1 hour. The reaction mixture was acidified with 5N HCl (13 mL) until the pH was about 2. The aqueous mixture was then extracted with EtOAc (3×50 mL). The combined organic layers were extracted with water (3×50 mL) and once with brine (50 mL), dried with MgSO$_4$, and concentrated in vacuo to afford a brown oil. MS (m/z)=156 (M+H)+.

Step D: Preparation of Ethyl 3-(2-(2-cyano-1-ethoxy-1-oxopropan-2-yl)phenyl)propiolate Butyllithium (5.8 mL, 14 mmol) was added to a stirred solution of diisopropylamine (2.1 mL, 15 mmol) in THF at −78° C. The reaction mixture was then allowed to warm to ambient temperature for 5 minutes before being cooled back down to −78° C. 2-(2-Ethynylphenyl)propanenitrile (0.750 g, 4.8 mmol) was added dropwise as a solution in 5 mL of THF, and the reaction was stirred for 30 minutes. Ethyl carbonochloridate (1.5 mL, 15 mmol) in 5 mL of THF was added to the reaction. The resulting solution was allowed to warm to room temperature and was stirred for an additional 30 minutes. 2 mL of MeOH and 20 mL of water were added to the mixture. The aqueous mixture was extracted with EtOAc. The combined organic layers were washed with NH₄Cl (3×20 mL) and brine (1×20 mL), dried with MgSO₄, and concentrated in vacuo. The resulting oil was purified using silica flash chromatography with a gradient of 0-15% EtOAc/hexanes. MS (m/z)=300 (M+H)+.

Step E: Preparation of Ethyl 1-cyano-4-hydroxy-1-methyl-2-oxo-naphthalene-3-carboxylate A solution of benzaldehyde oxime (0.37 mL, 3.7 mmol) in dry DMF (4 mL) was added to a stirred suspension of NaH (0.16 mL, 3.7 mmol) in dry dioxane (50 mL) in a nitrogen atmosphere at room temperature. After 30 minutes, a solution of ethyl 3-(2-(2-cyano-1-ethoxy-1-oxopropan-2-yl)phenyl) propiolate (1.12 g, 3.7 mmol) was added in dry DMF (5 mL), and the solution was stirred overnight. The solvent was removed under vacuum, and water was added to the residue. The product was extracted with EtOAc. The organic layer was washed with water, dried with MgSO₄, concentrated in vacuo, and purified by silica flash chromatography eluting with 0-30% EtOAc/hexane. MS (m/z)=272 (M+H)+.

Step F: Preparation of 1,1-Dimethylethyl N-((1-cyano-4-hydroxy-1-methyl-2-oxo-naphthalen-3-yl) carbonyl)glycinate Ethyl 1-cyano-4-hydroxy-1-methyl-2-oxo-naphthalene-3-carboxylate (0.225 g, 0.829 mmol), glycine tert-butyl ester hydrochloride (0.167 g, 0.995 mmol), and glycine tert-butyl ester hydrochloride (0.167 g, 0.995 mmol) were refluxed in dioxane (50 mL) for 14 hours. The solvent was then removed in vacuo. The resulting residue was concentrated in vacuo and purified using silica flash chromatography (10-40% EtOAc/hexanes). MS (m/z)=301 (M+H)+(hydrolyzed product) 379.1 (product+Na).

Step G: Preparation of N-((1-Cyano-4-hydroxy-1-methyl-2-oxo-naphthalen-3-yl)carbonyl)glycine 1,1-Dimethylethyl N-((1-cyano-4-hydroxy-1-methyl-2-oxo-naphthalen-3-yl)carbonyl)glycinate (0.100 g, 0.28 mmol) was placed in a 25 mL round bottom flask and TFA (10 mL) was added. The resulting mixture was then stirred for 45 minutes. TFA was then removed under vacuum, and DCM was used to azeotrope off TFA (3×) resulting in a yellow solid. MS (m/z)=301 (M+H)+. Calculated for C₁₅H₁₂N₂O₅ 300.07.

Examples 29 and 30

N-(((1S)-6-Chloro-1-(4-chlorophenyl)-4-hydroxy-1-methyl-2-oxo-naphthalen-3-yl)carbonyl)glycine and N-(((1R)-6-Chloro-1-(4-chlorophenyl)-4-hydroxy-1-methyl-2-oxo-naphthalen-3-yl)carbonyl)glycine

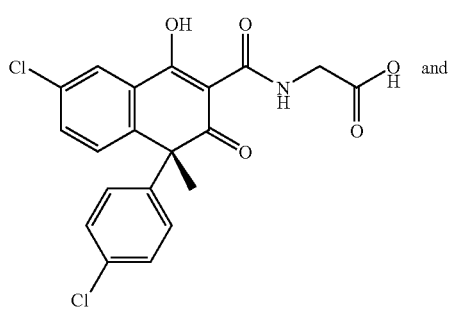

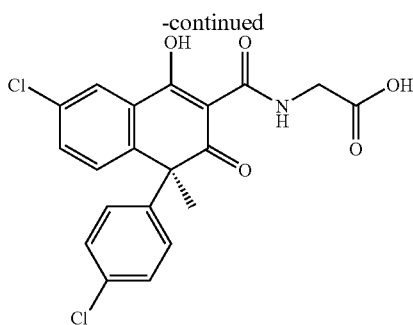

N-((6-Chloro-1-(4-chlorophenyl)-4-hydroxy-1-methyl-2-oxo-naphthalen-3-yl)carbonyl)glycine (0.309 g, see Example 34) was dissolved in dimethoxy ethylenegycol (10 mL) and separated into the two enantiomers on a chiralpack ADH (21×250 mm, 5 μm) column in ten 1 mL injections (flow: 60 mL/min, eluent: 50% MeOH in supercritical fluid and carbon dioxide). The second peak (t=5.3 minutes) was concentrated and dried in vacuo to give Example 29 (0.141 g). The first peak (t=3.38 minutes) was concentrated and dried in vacuo to give Example 30 (0.146 g). MS m/e=420 (M+H)⁺. Calculated for C₂₀H₁₅Cl₂NO₅ 419.03.

Example 31

N-((7,8-Dichloro-4-hydroxy-1,1-dimethyl-2-oxo-naphthalen-3-yl)carbonyl)glycine

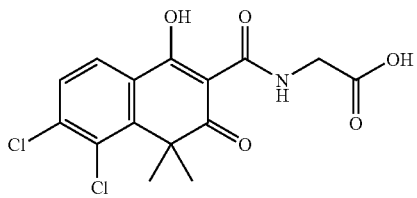

Step A: Preparation of Methyl 2-(2,3-dichlorophenyl)-2-methylpropanoate

A solution of NaH (2.87 g, 71.8 mmol) in DMF (100 mL) was cooled to 0° C. A solution of methyl 2-(2,3-dichlorophenyl)acetate (5.24 g, 23.9 mmol) in DMF (50 mL) was added dropwise, and the resulting mixture was stirred for 5 minutes. A solution of MeI (4.36 mL, 69.8 mmol) in DMF (50 mL) was then added to the reaction. After 10 minutes, the mixture was allowed to warm to 25° C. and the reaction was stirred for 16 hours. The mixture was diluted with 10% HCl(aq) (150 mL), and the resulting mixture was extracted with EtOAc (2×200 mL) and washed with 10% HCl(aq) (100 mL), deionized water (2×150 mL), and brine (100 mL). The organic layer was dried over MgSO₄ and concentrated and dried in vacuo to give 7.06 g crude product. The crude product was purified by flash column chromatography (silica, 0-50% DCM in hexane) to give the title compound (5.53 g). MS m/e=247 (M+H)⁺.

Step B: Preparation of 2-(2,3-Dichlorophenyl)-2-methylpropanoic acid

A mixture of methyl 2-(2,3-dichlorophenyl)-2-methylpropanoate (5.50 g, 22.3 mmol) and KOH (6.24 g, 111 mmol) in EtOH/water (5:1, 150 mL) in a 500 mL round bottom flask, was heated at 95° C. for 18 hours. The solution was diluted with diethyl ether (200 mL), and washed with 1N NaOH(aq) (3×75 mL). The aqueous solution was made acidic (pH=2) with concentrated HCl. The mixture was then extracted with EtOAc (3×100 mL), and the combined organic layers were washed with deionized water (100 mL) and with brine (75 mL). The organic layer was then dried over MgSO$_4$, concentrated, and dried in vacuo. The crude product was purified by flash column chromatography (silica, 0-100% DCM in hexane) to give the title compound (4.1338 g). MS m/e=233 (M+H)$^+$.

Step C: Preparation of Ethyl 7,8-dichloro-4-hydroxy-1,1-dimethyl-2-oxo-naphthalene-3-carboxylate A solution of 2-(2,3-dichlorophenyl)-2-methylpropanoic acid (2.00 g, 8.58 mmol) in thionyl chloride (80.0 mL, 1097 mmol) was stirred at 95° C. for 2.5 hours. The mixture was then concentrated, azeotroped in toluene (2×100 mL), and dried in vacuo for 2 hours to give the crude acid chloride.

A solution of diethyl malonate (1.30 mL, 8.58 mmol) in ACN (50 mL) in a 500 mL round bottom flask, was cooled to 0° C. MgCl$_2$ (0.353 mL, 8.58 mmol) followed by TEA (2.51 mL, 18.0 mmol) were added, and the mixture was stirred at 25° C. for 2 hours. A solution of the above acid chloride in ACN (50 mL) was added, and the mixture was heated at 50° C. for 14 hours. The solution was diluted with 10% HCl(aq) (100 mL) and then extracted with EtOAc (3×100 mL). The organic solution was washed with 10% HCl(aq) (100 mL), with 1N NaOH(aq) (2×100 mL), and then with brine (75 mL). The organic layer was dried over MgSO$_4$, concentrated, and dried in vacuo to give 3.34 g of crude product. The crude product was purified by flash column chromatography (silica, 0-100% DCM in hexane) to give the intermediate, diethyl 2-(2-(2,3-dichlorophenyl)-2-methylpropanoyl)malonate (1.603 g) MS m/e=375 (M+H)$^+$.

P$_2$O$_5$ (5.00 g, 35 mmol) was treated with H$_2$SO$_4$ (4.5 mL, 81 mmol) at 0° C. in a 100 mL round bottom flask. Diethyl 2-(2-(2,3-dichlorophenyl)-2-methylpropanoyl)malonate (0.500 g, 1.0 mmol) was added, and the mixture was stirred at 25° C. for 1.5 hours. The reaction was quenched with ice, extracted with EtOAc (2×50 mL), and the combined organic layers were washed with brine (50 mL). The organic layers were then dried over MgSO$_4$, concentrated, and dried in vacuo to give the title compound (0.235 g). MS m/e=329 (M+H)$^+$.

Step D: Preparation of 1,1-Dimethylethyl N-((7,8-dichloro-4-hydroxy-1,1-dimethyl-2-oxo-naphthalen-3-yl)carbonyl)glycinate A solution of ethyl 7,8-dichloro-4-hydroxy-1,1-dimethyl-2-oxo-naphthalene-3-carboxylate (0.200 g, 0.456 mmol), glycine tert-butyl ester hydrochloride (0.0993 g, 0.592 mmol), and DIPEA (0.159 mL, 0.911 mmol) in 1,4-dioxane (5 mL) was heated to 120° C. in a 15 mL sealed vessel for 3 hours. The reaction was then diluted with deionized water (50 mL) and extracted with DCM (2×50 mL). The combined organic layers were washed with deionized water (50 mL) and then with brine (50 mL). The organic layer was then dried over MgSO$_4$, concentrated, and dried in vacuo to give 0.338 g of the crude product. The crude product was purified by flash column chromatography (silica, 0-50% DCM in hexane) to give the title compound (0.185 g). MS m/e 412 (M−H)$^−$.

Step E: Preparation of N-((7,8-Dichloro-4-hydroxy-1,1-dimethyl-2-oxo-naphthalen-3-yl)carbonyl)glycine A solution of 1,1-dimethylethyl N-((7,8-dichloro-4-hydroxy-1,1-dimethyl-2-oxo-naphthalen-3-yl)carbonyl)glycinate (0.130 g, 0.314 mmol) in TFA (5.00 mL, 68.3 mmol) was stirred at 25° C. for 10 minutes. The resulting mixture was concentrated, azeotroped using DCM (2×100 mL), and dried in vacuo to give the title compound (0.0925 g). MS m/e=358 (M+H)$^+$. Calculated for C$_{15}$H$_{13}$Cl$_2$NO$_5$ 357.02.

Example 32

N-((6-(4-Fluorophenyl)-4-hydroxy-1,1-dimethyl-2-oxo-naphthalen-3-yl)carbonyl)glycine

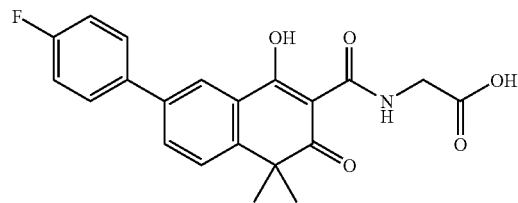

The title compound was prepared using a procedure similar to that outlined in Example 5. MS m/e=384 (M+H)$^+$. Calculated for C$_{21}$H$_{18}$FNO$_5$ 383.12.

Example 33

N-((4-Hydroxy-1,1-dimethyl-6-(methylthio)-2-oxo-naphthalen-3-yl)carbonyl)glycine

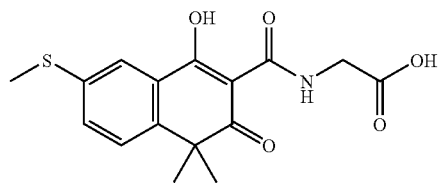

Step A: Preparation of Ethyl 2-(4-(methylthio)phenyl)acetate

A mixture of 4-(methylthio)phenylacetic acid (5.10 g, 28.0 mmol) and H$_2$SO$_4$ (0.155 mL, 2.80 mmol) in EtOH (150 mL) in a 500 mL round bottom flask, were stirred at 100° C. for 26 hours. The reaction was concentrated in vacuo, diluted with EtOAc (200 mL), washed with deionized water (2×150 mL), and then with brine (100 mL). The organic layer was dried over MgSO$_4$, concentrated, and dried in vacuo. The crude product was purified by flash column chromatography (silica, 0-20% EtOAc in hexane) to give the title compound (5.95 g). MS m/e=211 (M+H)$^+$.

Step B: Preparation of 2-Methyl-2-(4-(methylthio)phenyl)propanoic acid

A mixture of NaH (2.83 g, 70.7 mmol) in DMF (150 mL) in an oven dried 500 mL round bottom flask, was cooled to 0°

C. A solution of ethyl 2-(4-(methylthio)phenyl)acetate (5.95 g, 28.3 mmol) and MeI (5.29 mL, 84.9 mmol) in DMF (50 mL) was cooled to 0° C. and added dropwise to the mixture over 15 minutes. The mixture was allowed to warm room temperature and stirred for 20 hours. The solution was diluted with EtOAc (300 mL), and the organic layer was washed with 10% HCl(aq) (200 mL), with deionized water (200 mL), and then with brine (100 mL). The organic layer was then dried over MgSO$_4$, concentrated, and dried in vacuo to give 11.35 g of the crude product. The crude product was purified by flash column chromatography (silica, 0-100% DCM in hexane) to give a 7:3 mixture of ethyl 2-methyl-2-(4-(methylthio)phenyl)propanoate and methyl 2-methyl-2-(4-(methylthio)phenyl)propanoate (6.23 g).

A solution of the above esters (6.23 g, 26.1 mmol) and KOH (7.33 g, 131 mmol) in EtOH (160 mL) and deionized water (40 mL) in a 250 mL round bottom flask, was refluxed at 95° C. for 1.5 hours. The reaction mixture was concentrated in vacuo, diluted with deionized water (100 mL), and then extracted with diethyl ether (3×100 mL). The combined ether solutions were extracted with 1N NaOH(aq) (2×100 mL). All the aqueous solutions were combined, and brought to a pH=2 with 10% HCl(aq). The resulting mixture was extracted with EtOAc (3×100 mL), dried over MgSO$_4$, concentrated, and dried in vacuo to give title compound (4.998 g). MS m/e=211 (M+H)$^+$.

Step C: Preparation of Ethyl 4-hydroxy-1,1-dimethyl-6-(methylthio)-2-oxo-naphthalen-3-carboxylate A mixture of 2-methyl-2-(4-(methylthio)phenyl)propanoic acid (4.00 g, 19.0 mmol) in thionyl chloride (40.0 mL, 548 mmol) in a 500 mL round bottom flask, was refluxed at 75° C. for 2 hours. The mixture was concentrated, azeotroped in toluene (2×100 mL), and dried in vacuo to give the crude acid chloride.

A solution of diethyl malonate (2.87 mL, 19.0 mmol) in ACN (100 mL) in a 500 mL round bottom flask was cooled to 0° C. MgCl$_2$ (1.81 g, 19.0 mmol) and TEA (5.57 mL, 39.9 mmol) were added slowly, and the mixture was stirred at room temperature for 3 hours. A solution of the above acid chloride in ACN (40 mL) was added, and the mixture was stirred at 50° C. for 16 hours. The solution was concentrated in vacuo and partitioned between EtOAc (75 mL), and 10% HCl(aq) (75 mL). The aqueous layer was extracted with EtOAc (2×75 mL). The combined organic layers were dried over MgSO$_4$, concentrated, and dried in vacuo to give 7.05 g of the crude product which was purified by flash column chromatography (silica, 0-75% DCM in hexane) to give the intermediate, diethyl 2-(2-methyl-2-(4-(methylthio)phenyl)propanoyloxy)malonate (4.604 g). MS m/e=370 (M+H)$^+$.

A solution of diethyl 2-(2-methyl-2-(4-(methylthio)phenyl)propanoyloxy)-malonate (2.55 g, 6.92 mmol) in H$_2$SO$_4$, 36N (0.585 mL, 6.92 mmol) was stirred at 25° C. for 30 minutes. The reaction was quenched by adding ice (400 mL) and EtOAc (100 mL) and stirring for 15 minutes. The layers were separated, and the aqueous solution was extracted with EtOAc (2×100 mL). The combined organic layers were washed with brine (100 mL), dried over MgSO$_4$, concentrated, and dried in vacuo to give 1.41 g crude product which was purified by flash column chromatography (silica, 0-100% DCM in hexane) to give the title compound (1.098 g). MS m/e=307 (M+H)$^+$.

Step D: Preparation of 1,1-Dimethylethyl N-((4-hydroxy-1,1-dimethyl-6-(methylthio)-2-oxo-naphthalen-3-yl)carbonyl)glycinate A solution of ethyl 4-hydroxy-1,1-dimethyl-6-(methylthio)-2-oxo-naphthalen-3-carboxylate (0.800 g, 2.61 mmol), glycine tert-butyl ester hydrochloride (0.525 g, 3.13 mmol) and DIPEA (0.910 mL, 5.22 mmol in 1,4-dioxane (25 mL) in a 75 mL sealed vessel, was stirred at 120° C. for 3 hours. Deionized water (75 mL) was added, and the resulting mixture was extracted with EtOAc (2×50 mL). The combined organic layers were then washed with brine (50 mL). The organic layer was dried over MgSO$_4$, concentrated, and dried in vacuo to give 1.44 g crude product which was purified by flash column chromatography (silica, 0-50% DCM in hexane) to give the title compound (0.886 g). MS m/e=336 (M+H-tBu)$^+$.

Step E: Preparation of N-((4-Hydroxy-1,1-dimethyl-6-(methylthio)-2-oxo-naphthalen-3-yl)carbonyl)glycine A solution of 1,1-dimethylethyl N-((4-hydroxy-1,1-dimethyl-6-(methylthio)-2-oxo-naphthalen-3-yl)carbonyl)glycinate (0.180 g, 0.460 mmol) in TFA (0.0342 mL, 0.460 mmol) was stirred at 25° C. for 10 minutes. The solution was concentrated, azeotroped in DCM (2×300 mL), and dried in vacuo to give the title compound (0.150 g). MS m/e=336 (M+H)$^+$. Calculated for C$_{16}$H$_{17}$NO$_5$S 335.08.

Example 34

N-((6-Chloro-1-(4-chlorophenyl)-4-hydroxy-1-methyl-2-oxo-naphthalen-3-yl)carbonyl)glycine

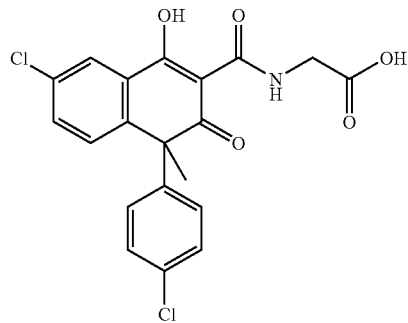

Step A: Preparation of Ethyl 2,2-bis(4-chlorophenyl)acetate

To a solution of bis(4-chlorophenyl)acetic acid (5.00 g, 17.8 mmol) in EtOH (100 mL) in a 500 mL round bottom flask, was added H$_2$SO$_4$, 36N (0.0988 mL, 1.78 mmol). The mixture was stirred at 100° C. for 18 hours. The mixture was then concentrated in vacuo, diluted with EtOAc (200 mL), and washed with deionized water (3×100 mL) and then with brine (100 mL). The organic layer was dried over MgSO$_4$, concentrated, and dried in vacuo to give the crude product ethyl 2,2-bis(4-chlorophenyl)acetate (5.473 g). MS m/e=309 (M+H)$^+$.

Step B: Preparation of 2,2-Bis(4-chlorophenyl)propanoic acid

A solution of NaH (60% dispersion in mineral oil) (2.1 g, 53 mmol) in DMF (100 mL) in a 500 mL round bottom flask was cooled 0° C. A solution of ethyl 2,2-bis(4-chlorophenyl) acetate (5.47 g, 18 mmol) and MeI (3.3 mL, 53 mmol) in DMF (50 mL) was added dropwise over 15 minutes. The mixture was stirred at 0° C. for 15 minutes and then allowed to warm to room temperature and stirred for 20 hours. A mixture of products was observed by LC/MS. The solution was diluted with EtOAc (200 mL), and then washed with 10% HCl(aq) (200 mL), with deionized water (200 mL), and then with brine (100 mL). The organic layer was dried over $MgSO_4$, concentrated, and dried in vacuo to give 10.11 g crude product which was purified by flash column chromatography (silica, 0-100%, hexane/EtOAc) to give 2,2-bis(4-chlorophenyl)propanoic acid (3.05 g).

Step C: Preparation of Diethyl 2-(2,2-bis(4-chlorophenyl)propanoyl)-malonate A solution of 2,2-bis(4-chlorophenyl)propanoic acid (3.05 g, 10.3 mmol) in thionyl chloride (20.0 mL, 274 mmol) in a 500 mL round bottom flask was refluxed at 75° C. for 1.5 hours. The solution was concentrated, azeotroped in toluene (2×200 mL), and dried in vacuo to give the crude acid chloride.

A solution of diethyl malonate (1.56 mL, 10.3 mmol) in ACN (60 mL) in a 500 mL round bottom flask was cooled to 0° C. $MgCl_2$ (0.984 g, 10.3 mmol) and TEA (3.02 mL, 21.7 mmol) were slowly added, and the mixture was then stirred at 25° C. for 2 hours. A solution of the acid chloride in ACN (40 mL) was added to the reaction, and the mixture was stirred at 50° C. for 16 hours. The solution was concentrated in vacuo and then partitioned between EtOAc (75 mL) and 10% HCl (aq) (75 mL). The aqueous layer was extracted with EtOAc (2×75 mL). The combined organic layers were dried over $MgSO_4$ and concentrated in vacuo to give 5.68 g of crude product which was purified by flash column chromatography (silica, 0-50% DCM in hexane) to give diethyl 2-(2,2-bis(4-chlorophenyl)propanoyl)malonate (3.61 g) MS m/e=437 $(M+H)^+$.

Step D: Preparation of Ethyl 6-chloro-1-(4-chlorophenyl)-4-hydroxy-1-methyl-2-oxo-naphthalene-3-carboxylate A solution of diethyl 2-(2,2-bis(4-chlorophenyl)propanoyl)malonate (2.00 g, 4.57 mmol) in $H_2SO_4$, 36N (10.0 mL, 180 mmol) in a 500 mL round bottom flask was stirred at 25° C. for 30 minutes. The reaction was quenched by adding 400 mL of ice and 100 mL of EtOAc and then stirring for 15 minutes. The layers were separated, and the aqueous solution was extracted with EtOAc (2×100 mL). The combined organic layers were washed with brine (100 mL). The organic layer was then dried over $MgSO_4$ and concentrated in vacuo to give 2.24 g of crude product which was purified by flash column chromatography (silica, 0-100% DCM in hexane) to give the title compound (1.448 g). MS m/e=391 $(M+H)^+$.

Step E: Preparation of 1,1-Dimethylethyl N-((6-chloro-1-(4-chlorophenyl)-4-hydroxy-1-methyl-2-oxo-naphthalen-3-yl)carbonyl)glycinate A solution of ethyl 6-chloro-1-(4-chlorophenyl)-4-hydroxy-1-methyl-2-oxo-naphthalene-3-carboxylate (0.998 g, 2.55 mmol), glycine tert-butyl ester hydrochloride (0.513 g, 3.06 mmol), and DIPEA (0.889 mL, 5.10 mmol) in 1,4-dioxane (15 mL) in a 75 mL sealed vessel was stirred at 120° C. for 3 hours. The solution was diluted with deionized water (75 mL) and extracted with DCM (2×50 mL). The combined organic layers were then washed with brine (50 mL), dried over $MgSO_4$, and concentrated in vacuo to give 1.42 g crude product. The crude product was purified by flash column chromatography (silica, 0-25% DCM in hexane) to give the title compound (0.888 g). MS m/e=420 $(M+H-tBu)^+$.

Step F: Preparation of N-((6-Chloro-1-(4-chlorophenyl)-4-hydroxy-1-methyl-2-oxo-naphthalen-3-yl) carbonyl)glycine A solution of 1,1-dimethylethyl N-((6-chloro-1-(4-chlorophenyl)-4-hydroxy-1-methyl-2-oxo-naphthalen-3-yl)carbonyl)glycinate (0.675 g, 1.42 mmol) in TFA (10.0 mL, 127 mmol) was stirred at 25° C. for 10 minutes. The solution was concentrated, azeotroped in DCM (2×300 mL), and dried in a vacuum oven at 60° C. to give the title compound (0.580 g). MS m/e=420 $(M+H)^+$. Calculated for $C_{20}H_{15}Cl_2NO_5$ 419.03.

Example 35

N-((6-(2-(Dimethylamino)phenyl)-4-hydroxy-1,1-dimethyl-2-oxo-naphthalen-3-yl)carbonyl)glycine

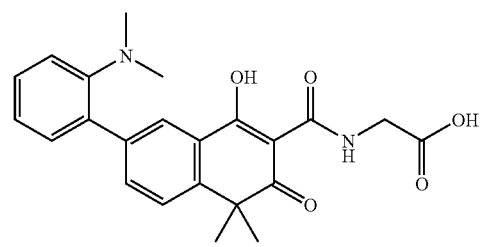

The title compound was prepared using a procedure similar to that outlined in Example 5. MS m/e=409 $(M+H)^+$. Calculated for $C_{23}H_{24}N_2O_5$ 408.17.

Example 36

N-((6-(4-(Dimethylamino)phenyl)-4-hydroxy-1,1-dimethyl-2-oxo-naphthalen-3-yl)carbonyl)glycine

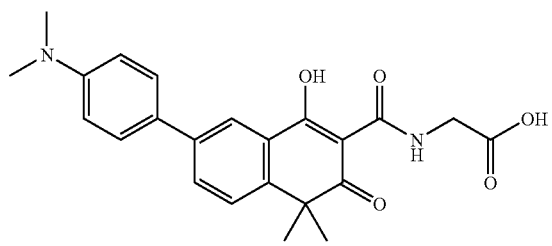

The title compound was prepared using a procedure similar to that outlined in Example 5. MS m/e=409 $(M+H)^+$. Calculated for $C_{23}H_{24}N_2O_5$ 408.17.

Example 37

N-((6-Chloro-1-(4-chlorophenyl)-4-hydroxy-1-methyl-2-oxo-naphthalen-3-yl)carbonyl)glycine

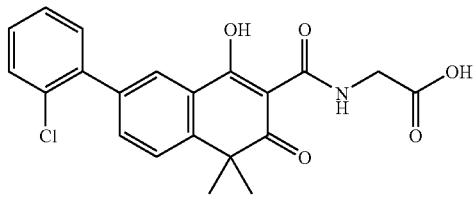

The title compound was prepared using a procedure similar to that outlined in Example 5. MS m/e=400 (M+H)+. Calculated for $C_{21}H_{18}ClNO_5$ 399.09.

Example 38

N-((6-(4-Chlorophenyl)-4-hydroxy-1,1-dimethyl-2-oxo-naphthalen-3-yl)carbonyl)glycine

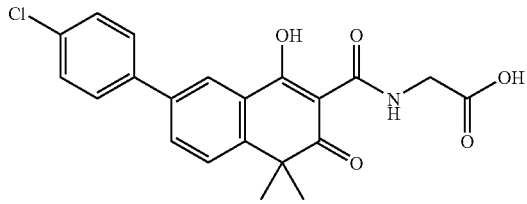

The title compound was prepared using a procedure similar to that outlined in Example 5. MS m/e=400 (M+H)+. Calculated for $C_{21}H_{18}ClNO_5$ 399.09.

Example 39

N-((6-(3-(Dimethylamino)phenyl)-4-hydroxy-1,1-dimethyl-2-oxo-naphthalen-3-yl)carbonyl)glycine

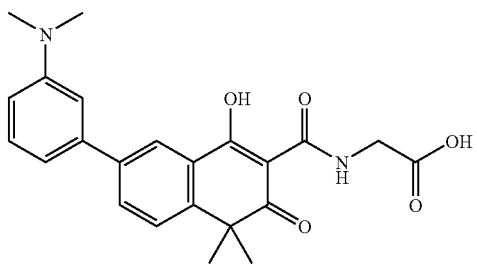

The title compound was prepared using a procedure similar to that outlined in Example 5. MS m/e=409 (M+H)+. Calculated for $C_{23}H_{24}N_2O_5$ 408.17.

Example 40

N-((6-Bromo-4-hydroxy-1,1-dimethyl-2-oxo-naphthalen-3-yl)carbonyl)glycine

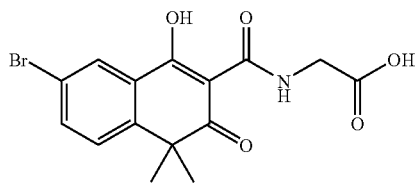

Step A: Preparation of 2-(4-Bromophenyl)-2-methylpropanoic acid

A solution of methyl 2-(4-bromophenyl)-2,2-dimethylacetate (3880 μL, 15090 μmol) in EtOH (80 mL) and water (20 mL) was treated with KOH (4233 mg, 75450 μmol). The reaction was heated to 90° C. After 15 hours, the reaction was cooled to 23° C. and concentrated in vacuo. The crude mixture was partitioned between water/diethyl ether (150 mL each). The aqueous layer was separated and extracted with diethyl ether (100 mL). The combined ether layers were then extracted with a 1N NaOH solution (25 mL). The combined aqueous washes were acidified with concentrated HCl to pH=2.0 and extracted with EtOAc (3×100 mL). The combined EtOAc layers were dried over MgSO₄, and concentrated in vacuo to afford 3144 mg of 2-(4-bromophenyl)-2-methylpropanoic acid.

Steps B-D: Preparation of 1,1-Dimethylethyl N-((6-bromo-4-hydroxy-1,1-dimethyl-2-oxo-naphthalen-3-yl)carbonyl)glycinate A solution of 2-(4-bromophenyl)-2-methylpropanoic acid (3144 mg, 12933 μmol) in thionyl chloride (9434 μL, 129331 μmol) was heated at reflux under nitrogen. After 2 hours, the reaction was cooled to 23° C. and concentrated in vacuo to afford the crude acid chloride.

In an oven-dried round-bottomed flask, magnesium turnings (472 mg, 19400 μmol) and diethyl malonate (2931 μL, 19400 μmol) were added to EtOH (20 mL) and CCl₄ (0.2 mL). The reaction was stirred at 23° C. for 30 minutes followed by the addition of THF (30 mL). The reaction was then heated at reflux under nitrogen. After 1 hour, a solution of the crude acid chloride in THF (15 mL) was added in a dropwise fashion. After 30 minutes, the reaction was cooled to 23° C., diluted with diethyl ether (150 mL) and washed with water (150 mL). The layers were separated, and the aqueous layer was extracted with diethyl ether (150 mL). The combined ether layers were washed with brine (100 mL), dried over MgSO₄, and concentrated in vacuo affording diethyl 2-(2-(4-bromophenyl)-2-methylpropanoyl)malonate as the crude product.

A solution of the crude diethyl 2-(2-(4-bromophenyl)-2-methylpropanoyl)malonate (4982 mg, 12932 μmol) in concentrated H₂SO₄ (30 mL) was stirred at 23° C. After 2 hours, the reaction was poured into an ice-water mixture (200 mL) and extracted with EtOAc (3×200 mL). The combined organic layers were washed with brine (100 mL), dried over MgSO₄, and concentrated in vacuo affording ethyl 6-bromo-4-hydroxy-1,1-dimethyl-2-oxo-naphthalen-3-carboxylate as the product.

A solution of crude ethyl 6-bromo-4-hydroxy-1,1-dimethyl-2-oxo-naphthalen-3-carboxylate (4100 mg, 12088 µmol) and glycine tert-butyl ester hydrochloride (2229 mg, 13297 µmol) in 1,4-dioxane (100 mL) was treated with DIPEA (4211 µL, 24176 µmol). The reaction was heated at 120° C. in a sealed vessel. After 17 hours, the reaction was cooled to 23° C., diluted with EtOAc (200 mL) and washed with 10% HCl solution (2×150 mL) and brine (100 mL). The organic layer was dried over $MgSO_4$, concentrated in vacuo, and purified by silica gel chromatography (eluant: 5-10% EtOAc/hexane) affording 2523 mg of 1,1-dimethylethyl N-((6-bromo-4-hydroxy-1,1-dimethyl-2-oxo-naphthalen-3-yl)carbonyl)glycinate. MS m/e=422.0 (M−H)⁻.

Step E: Preparation of N-((6-Bromo-4-hydroxy-1,1-dimethyl-2-oxo-naphthalen-3-yl)carbonyl)glycine A solution of 1,1-dimethylethyl N-((6-bromo-4-hydroxy-1,1-dimethyl-2-oxo-naphthalen-3-yl)carbonyl)glycinate (145 mg, 342 µmol) in TFA (2 mL) was stirred at 23° C. After 30 minutes, the reaction was concentrated in vacuo, and diluted with water (25 mL). A white solid precipitated which was collected by filtration, washed with diethyl ether (5 mL), and dried under vacuum, affording 63 mg of N-((6-bromo-4-hydroxy-1,1-dimethyl-2-oxo-naphthalen-3-yl)carbonyl)glycine. MS m/e=366.0 (M−H)⁻. Calculated for $C_{15}H_{14}BrNO_5$ 367.01.

Example 41

N-((7-Cyano-4-hydroxy-1,1-dimethyl-2-oxo-naphthalen-3-yl)carbonyl)glycine

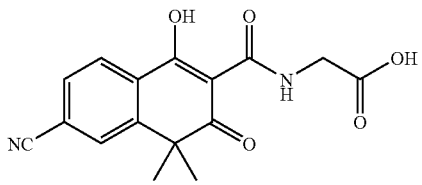

Step A: Preparation of 1,1-Dimethylethyl N-((7-cyano-4-hydroxy-1,1-dimethyl-2-oxo-naphthalen-3-yl)carbonyl)glycinate 1,1-Dimethylethyl N-((7-bromo-4-hydroxy-1,1-dimethyl-2-oxo-naphthalen-3-yl)carbonyl)glycinate (310 mg, 731 µmol, see Example 53), dppf (162 mg, 292 µmol), tris(dibenzylideneacetone)dipalladium (66.9 mg, 73.1 µmol), copper cyanide (262 mg, 2923 µmol), and tetraethylammonium cyanide (126 mg, 804 µmol) were mixed in dioxane (6 mL) in a microwave tube under a nitrogen atmosphere. The reaction mixture was then stirred at 75° C. for 16 hours. The reaction mixture was returned to room temperature, fused to silica gel, and purified by silica flash chromatography (0-100% DCM/hexane) to give the desired ester as a white solid (163 mg). MS (m/e)=315.1 (M+H-tBu)⁺.

Step B: Preparation of N-((7-Cyano-4-hydroxy-1,1-dimethyl-2-oxo-naphthalen-3-yl)carbonyl)glycine 1,1-Dimethylethyl N-((7-cyano-4-hydroxy-1,1-dimethyl-2-oxo-naphthalene-3-yl)carbonyl)glycinate (163 mg, 440 µmol) was stirred in TFA (1 mL, 13462 µmol) at room temperature for 20 minutes. Water was added. The resulting precipitate was filtered and washed with water to give the desired product as an off-white solid (126 mg). MS (m/e)= 315.1 (M+H)⁺. Calculated for $C_{16}H_{14}N_2O_5$ 314.09.

Example 42

N-((6-Cyano-4-hydroxy-1,1-dimethyl-2-oxo-naphthalen-3-yl)carbonyl)glycine

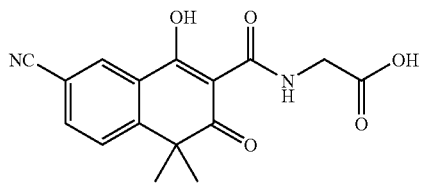

Step A: Preparation of 1,1-Dimethylethyl N-((6-cyano-4-hydroxy-1,1-dimethyl-2-oxo-naphthalen-3-yl)carbonyl)glycinate 1,1-Dimethylethyl N-((6-bromo-4-hydroxy-1,1-dimethyl-2-oxo-naphthalene-3-yl)carbonyl)glycinate (297 mg, 700 µmol, prepared in Example 40A-D), dppf (155 mg, 280 µmol), tris(dibenzylideneacetone)dipalladium (64.1 mg, 70.0 µmol), copper cyanide (251 mg, 2800 µmol), and tetraethylammonium cyanide (120 mg, 770 µmol) were mixed in dioxane (6 mL) in a microwave tube under a nitrogen atmosphere. The reaction mixture was then stirred at 75° C. for 5.5 hours. The reaction mixture was returned to room temperature, fused to silica gel, and purified by silica flash chromatography (0-100% DCM/hexane) to give the desired ester as an off-white solid (127 mg). MS (m/e)=315.1 (M+H-tBu)⁺.

Step B: Preparation of N-((6-Cyano-4-hydroxy-1,1-dimethyl-2-oxo-naphthalen-3-yl)carbonyl)glycine 1,1-Dimethylethyl N-((6-cyano-4-hydroxy-1,1-dimethyl-2-oxo-naphthalene-3-yl)carbonyl)glycinate (124 mg, 335 µmol) was stirred in TFA (1 mL, 13462 µmol) at room temperature for 15 minutes. Water was added. The resulting precipitate was filtered. The green solid was dissolved in saturated $NaHCO_3$ and washed with DCM. The aqueous layer was separated and acidified with 10% HCl. The resulting precipitate was filtered and washed with water to give the desired product as a white solid (41 mg). MS (m/e)=315.1 (M+H)⁺. Calculated for $C_{16}H_{14}N_2O_5$ 314.09.

Example 43

N-((7-Chloro-1-ethyl-4-hydroxy-1-methyl-2-oxo-naphthalen-3-yl)carbonyl)glycine

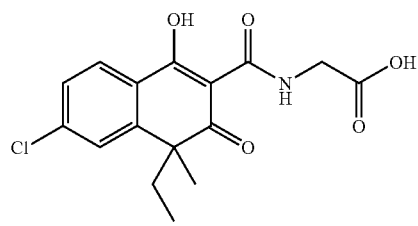

Step A: Preparation of 2-(3-Chlorophenyl)butanenitrile

A solution of 2-(3-chlorophenyl)acetonitrile (10.00 g, 66 mmol) and ethyl bromide (4.9 mL, 66 mmol) in DMSO (25 mL) was added dropwise to a stirred solution of NaH (60% dispersion in mineral oil (2.6 g, 66 mmol)) in DMSO (75 mL) at 0° C. under a nitrogen atmosphere. The reaction mixture was stirred for 30 minutes at 0° C. and then brought to room temperature and stirred for 23 hours. The reaction mixture was carefully quenched with water, and was then diluted with EtOAc. The organic layer was separated, washed with water (2×) and brine, dried ($MgSO_4$), and concentrated in vacuo to give the crude product as an orange oil. The crude oil was purified by silica flash chromatography (0-5% EtOAc/hexane) to give the desired compound as a colorless oil (4.69 g).

Step B: Preparation of 2-(3-Chlorophenyl)-2-methylbutanenitrile

A solution of 2-(3-chlorophenyl)butanenitrile (4.69 g, 26 mmol) and MeI (2.0 mL, 31 mmol) in DMSO (15 mL) was added dropwise to a stirred solution of NaH (60% dispersion in mineral oil (1.3 g, 31 mmol)) in DMSO (35 mL) at 0° C. under a nitrogen atmosphere. The reaction mixture was stirred for 30 minutes at 0° C. and then brought to room temperature and stirred for 15 hours. The reaction mixture was quenched with water carefully and then diluted with EtOAc. The organic layer was separated, washed with water (2×) and brine, dried ($MgSO_4$), and concentrated in vacuo to give the desired compound as a light yellow oil (5.54 g).

Step C: Preparation of 2-(3-Chlorophenyl)-2-methylbutanoic acid 2-(3-Chlorophenyl)-2-methylbutanenitrile (5.49 g, 28 mmol) was dissolved in AcOH (15 mL, 260 mmol), and the mixture was heated to 100° C. 60% $H_2SO_4$ (10 mL, 118 mmol) was added dropwise, and the reaction mixture was stirred at 110° C. for 45 hours. The reaction mixture was cooled to room temperature and partitioned between DCM and water. The organic layer was separated, and the aqueous layer was extracted with DCM (2×). The combined organic layers were extracted with 2M NaOH (2×). The combined aqueous layers were washed with EtOAc and acidified to pH=1 with 10% HCl. The aqueous mixture was then extracted with DCM (2×), and the combined organic layers were concentrated in vacuo to give the desired product as a yellow oil (4.63 g). MS (m/e)=213.1 $(M+H)^+$.

Step D: Preparation of Diethyl 2-(2-(3-chlorophenyl)-2-methylbutanoyl)malonate Thionyl chloride (30 mL) was added to 2-(3-chlorophenyl)-2-methylbutanoic acid (4.63 g, 21.8 mmol). The reaction mixture was stirred at 75° C. for 1.5 hours. The mixture was then concentrated in vacuo to give the acid chloride.

Diethyl malonate (3.62 mL, 23.9 mmol) in ACN (50 mL) was cooled to 0° C. $MgCl_2$ (2.28 g, 23.9 mmol) was added, followed by addition of TEA (6.66 mL, 47.9 mmol) slowly via syringe. The mixture was stirred at 0° C. for 15 minutes before being brought to room temperature and stirred for 2.5 hours. The above prepared acid chloride was dissolved in ACN (20 mL) and added to the malonate solution. The reaction mixture was then stirred at 50° C. for 15 hours. The reaction mixture was then cooled to room temperature, concentrated in vacuo, and partitioned between 1M HCl and EtOAc. The aqueous layer was separated and extracted with EtOAc (2×). The combined organic layers were dried ($MgSO_4$) and concentrated in vacuo to give the desired compound as an orange oil (7.67 g). MS (m/e)=355.2 $(M+H)^+$.

Step E: Preparation of Ethyl 7-chloro-1-ethyl-4-hydroxy-1-methyl-2-oxo-naphthalene-3-carboxylate $H_2SO_4$ (40 mL, 473 mmol) was cooled to 0° C. and treated with $P_2O_5$ (15 g, 106 mmol). The mixture was brought to room temperature and added to diethyl 2-(2-(3-chlorophenyl)-2-methylbutanoyl)malonate (7.67 g, 22 mmol). The reaction mixture was then stirred for 1.5 hours. Ice ($H_2O$) was added, and the aqueous mixture was extracted with EtOAc (3×). The combined organic layers were washed with water (2×) and brine, dried ($MgSO_4$), and concentrated in vacuo to give the crude compound as an orange oil. The crude oil was purified by silica flash chromatography (0-100% DCM/hexane) to give the desired compound as a yellow solid (3.16 g). MS (m/e)=309.1 $(M+H)^+$.

Step F: Preparation of 1,1-Dimethylethyl N-((7-chloro-1-ethyl-4-hydroxy-1-methyl-2-oxo-naphthalen-3-yl)carbonyl)glycinate DIPEA (0.253 mL, 1.45 mmol, 1.2 eq) was added to a mixture of ethyl 7-chloro-1-ethyl-4-hydroxy-1-methyl-2-oxo-naphthalene-3-carboxylate (373 mg, 1.21 mmol) and glycine tert-butyl ester hydrochloride (0.243 g, 1.45 mmol) in dioxane (8 mL). The reaction mixture was stirred at 80° C. for 3.5 hours. The reaction mixture was cooled to room temperature and concentrated in vacuo to give a yellow oil. The crude oil was purified by silica flash chromatography (0-75% DCM/hexane) to give the desired compound as a white solid (407 mg). MS (m/e)=338.1 $(M+H-tBu)^+$.

Step G: Preparation of N-((7-Chloro-1-ethyl-4-hydroxy-1-methyl-2-oxo-naphthalen-3-yl)carbonyl)glycine 1,1-Dimethylethyl N-((7-chloro-1-ethyl-4-hydroxy-1-methyl-2-oxo-naphthalen-3-yl)carbonyl)glycinate (393 mg, 998 μmol) was stirred in TFA (3 mL, 40.4 mmol) at room temperature for 20 minutes. The TFA was removed in vacuo, and water was added. The resulting precipitate was filtered and washed with water to give the desired product as a white solid (274 mg). MS (m/e)=338 $(M+H)^+$. Calculated for $C_{16}H_{16}ClNO_5$ 337.07.

Example 44

N-((7-Fluoro-4-hydroxy-2-oxo-2',3',5',6'-tetrahydrospiro[naphthalene-1,4'-pyran]-3-yl)carbonyl)glycine

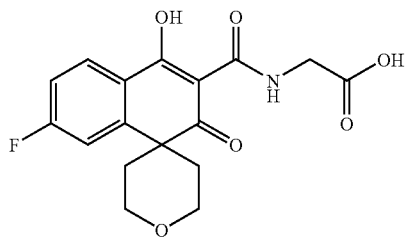

Step A: Preparation of 4-(3-Fluorophenyl)-tetrahydro-2H-pyran-4-carbonitrile Potassium tert-butoxide (5.48 g, 48.8 mmol) was added to a stirred solution of 2-(3-fluorophenyl)acetonitrile (2.58 mL, 22.2 mmol) in DMF (30 mL) at 0° C. under a nitrogen atmosphere. The mixture was stirred for 10 minutes at 0° C. before 1-chloro-2-(2-chloroethoxy)ethane (2.86 mL, 24.4 mmol) was added dropwise via syringe. The reaction mixture was allowed to warm to room temperature and stirred for 6 hours. The reaction mixture was then cooled to 0° C. and quenched with 10% HCl. The aqueous mixture was extracted with EtOAc (2×). The combined organic layers were washed with brine, dried (MgSO$_4$), and concentrated in vacuo to give the product as an orange oil (7.53 g).

Step B: Preparation of 4-(3-Fluorophenyl)-tetrahydro-2H-pyran-4-carboxylic acid 60% H$_2$SO$_4$ (30 mL) was added to a stirred mixture of 4-(3-fluorophenyl)-tetrahydro-2H-pyran-4-carbonitrile (7.53 g, 37 mmol) in dioxane (30 mL), and the reaction mixture was refluxed at 110° C. for 16 hours. The reaction mixture was cooled to room temperature and partitioned between DCM and water. The organic layer was separated, and the aqueous layer was extracted with DCM (2×). The combined organic layers were extracted with 2M NaOH (2×). The combined aqueous layers were washed with EtOAc and acidified to pH 1 with 10% HCl. The resulting precipitate was filtered and washed with water to give the desired product as a white solid (2.37 g).

Step C: Preparation of Diethyl 2-(4-(3-fluorophenyl)-tetrahydro-2H-pyran-4-carbonyl)malonate Thionyl chloride (15 mL) was added to 4-(3-fluorophenyl)-tetrahydro-2H-pyran-4-carboxylic acid (2.37 g, 10.6 mmol). The reaction mixture was stirred at 75° C. for 3 hours. The mixture was then concentrated in vacuo to give the acid chloride.

Diethyl malonate (1.76 mL, 11.6 mmol) in ACN (25 mL) was cooled to 0° C. MgCl$_2$ (1.11 g, 11.6 mmol) was added, followed by addition of TEA (3.23 mL, 23.3 mmol) slowly via syringe. The mixture was stirred at 0° C. for 15 minutes before being brought to room temperature and stirred for 3 hours. The above prepared acid chloride was dissolved in ACN (10 mL) and added to the malonate solution. The reaction mixture was then stirred at 50° C. for 16 hours. The reaction mixture was cooled to room temperature, concentrated in vacuo, and partitioned between 1M HCl and EtOAc. The aqueous layer was separated and extracted with EtOAc (2×). The combined organic layers were dried (MgSO$_4$) and concentrated in vacuo to give the desired compound as an orange oil (4.23 g). MS (m/e)=367.2 (M+H)$^+$.

Step D: Preparation of Ethyl 7-fluoro-4-hydroxy-2-oxo-2',3',5',6'-tetrahydro-spiro[naphthalene-1,4'-pyran]-3-carboxylate H$_2$SO$_4$ (25 mL, 296 mmol) was cooled to 0° C. and treated with P$_2$O$_5$ (10 g, 70 mmol). The mixture was brought to room temperature and was then added to diethyl 2-(4-(3-fluorophenyl)-tetrahydro-2H-pyran-4-carbonyl)malonate (4.23 g, 12 mmol). The resulting reaction mixture was then stirred for 1 hour. Ice (H$_2$O) was added, and the aqueous mixture was extracted with EtOAc (2×). The combined organic layers were washed with water (2×) and brine, dried (MgSO$_4$), and concentrated in vacuo to give the crude compound as an orange oil. The crude oil was purified by silica flash chromatography (50-100% DCM/hexane) to give the desired compound as a white solid (850 mg). MS (m/e)=321.1 (M+H)$^+$.

Step E: Preparation of 1,1-Dimethylethyl N-((7-fluoro-4-hydroxy-2-oxo-2',3',5',6'-tetrahydro-spiro[naphthalene-1,4'-pyran]-3-yl)carbonyl)glycinate DIPEA (0.693 mL, 3.98 mmol, 1.5 eq) was added to a mixture of ethyl 7-fluoro-4-hydroxy-2-oxo-2',3',5',6'-tetrahydro-spiro[naphthalene-1,4'-pyran]-3-carboxylate (850 mg, 2.65 mmol, 1.0 eq) and glycine tert-butyl ester hydrochloride (0.534 g, 3.18 mmol, 1.2 eq) in dioxane (20 mL). The reaction mixture was stirred at 75° C. for 17 hours. The reaction mixture was then cooled to room temperature and concentrated in vacuo to give a yellow solid. The crude solid was suspended in ether and filtered to give the title compound as an off-white solid (703 mg). MS (m/e)=406.2 (M+H)$^+$.

Step F: Preparation of N-((7-Fluoro-4-hydroxy-2-oxo-2',3',5',6'-tetrahydro-spiro[naphthalene-1,4'-pyran]-3-yl)carbonyl)glycine 1,1-Dimethylethyl N-((7-fluoro-4-hydroxy-2-oxo-2',3',5',6'-tetrahydro-spiro[naphthalene-1,4'-pyran]-3-yl)carbonyl)glycinate (703 mg, 1.73 mmol) was stirred in TFA (2 mL, 26.9 mmol) at room temperature for 25 minutes. Water was added. The resulting precipitate was filtered and washed with water to give the desired product as an off-white solid (237 mg). MS (m/e)=350.1 (M+H)$^+$. Calculated for C$_{18}$H$_{16}$F$_3$NO$_6$ 349.10.

Example 45

N-((7-Trifluoromethyl-4-hydroxy-2-oxo-2',3',5',6'-tetrahydro-spiro[naphthalene-1,4'-pyran]-3-yl)carbonyl)glycine

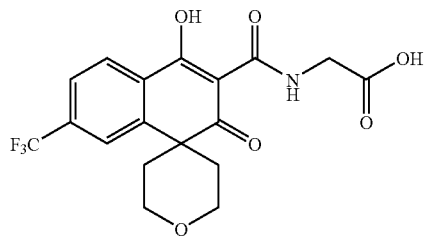

Step A: Preparation of 4-(3-(Trifluoromethyl)phenyl)-tetrahydro-2H-pyran-4-carbonitrile Potassium tert-butoxide (4.00 g, 35.6 mmol, 2.20 eq) was added to a stirred solution of 2-(3-(trifluoromethyl)phenyl)acetonitrile (2.53 mL, 16.2 mmol, 1.0 eq) in DMF (30 mL) at 0° C. under a nitrogen atmosphere. The mixture was stirred for 10 minutes at 0° C. before 1-chloro-2-(2-chloroethoxy)ethane (2.09 mL, 17.8 mmol, 1.1 eq) was added dropwise via syringe. The reaction mixture was allowed to warm to room temperature and stirred for 6 hours. The reaction mixture was then cooled to 0° C. and quenched with 10% HCl. The aqueous mixture was extracted with EtOAc (2×). The combined organic layers were washed with brine, dried (MgSO$_4$), and concentrated in vacuo to give the product as an orange oil (6.73 g).

Step B: Preparation of 4-(3-(Trifluoromethyl)phenyl)-tetrahydro-2H-pyran-4-carboxylic acid 60% $H_2SO_4$ (30 mL) was added to a stirred mixture of 4-(3-(trifluoromethyl)phenyl)-tetrahydro-2H-pyran-4-carbonitrile (6.73 g, 26 mmol) in dioxane (30 mL), and the reaction mixture was refluxed at 110° C. for 21 hours. The reaction mixture was cooled to room temperature and partitioned between DCM and water. The organic layer was separated, and the aqueous layer was extracted with DCM (2×). The combined organic layers were extracted with 2M NaOH (2×). The combined aqueous layers were washed with EtOAc and acidified to pH=1 with 10% HCl. The resulting precipitate was filtered and washed with water to give the desired product as a white solid (2.39 g).

Step C: Preparation of Diethyl 2-(4-(3-(trifluoromethyl)phenyl)-tetrahydro-2H-pyran-4-carbonyl)malonate Thionyl chloride (15 mL) was added to 4-(3-(trifluoromethyl)phenyl)-tetrahydro-2H-pyran-4-carboxylic acid (2.39 g, 8.72 mmol). The reaction mixture was stirred at 75° C. for 1.5 hours. The mixture was then concentrated in vacuo to give the acid chloride.

Diethyl malonate (1.45 mL, 9.59 mmol) in ACN (25 mL) was cooled to 0° C. $MgCl_2$ (0.913 g, 9.59 mmol) was added, followed by addition of TEA (2.67 mL, 19.2 mmol) slowly via syringe. The mixture was stirred at 0° C. for 15 minutes and then brought to room temperature and stirred for 4 hours. The above prepared acid chloride was dissolved in ACN (10 mL) and added to the malonate solution. The reaction mixture was then stirred at 50° C. for 17 hours. The reaction mixture was cooled to room temperature, concentrated in vacuo, and partitioned between 1M HCl and EtOAc. The aqueous layer was separated and extracted with EtOAc (2×). The combined organic layers were dried ($MgSO_4$) and concentrated in vacuo to give the desired compound as an orange oil (4.27 g). MS (m/e)=417.2 $(M+H)^+$.

Step D: Preparation of Ethyl 7-trifluoromethyl-4-hydroxy-2-oxo-2',3',5',6'-tetrahydro-spiro[naphthalene-1,4'-pyran]-3-carboxylate $H_2SO_4$ (25 mL, 296 mmol) was cooled to 0° C. and treated with $P_2O_5$ (10 g, 70 mmol). The mixture was brought to room temperature and added to diethyl 2-(4-(3-(trifluoromethyl)phenyl)-tetrahydro-2H-pyran-4-carbonyl)malonate (4.27 g, 10 mmol). The reaction mixture was then stirred for 1.5 hours. Ice ($H_2O$) was added, and the aqueous mixture was extracted with EtOAc (2×). The combined organic layers were washed with water (2×) and brine, dried ($MgSO_4$), and concentrated in vacuo to give the crude compound as a brown oil. The crude oil was purified by silica flash chromatography (0-100% DCM/hexane) to give the desired compound as a white solid (1.32 g). MS (m/e)=371.2 $(M+H)^+$.

Step E: Preparation of 1,1-Dimethylethyl N-((7-trifluoromethyl-4-hydroxy-2-oxo-2',3',5',6'-tetrahydro-spiro[naphthalene-1,4'-pyran]-3-yl)carbonyl)glycinate DIPEA (0.931 mL, 5.35 mmol) was added to a mixture of ethyl 7-trifluoromethyl-4-hydroxy-2-oxo-2',3',5',6'-tetrahydro-spiro[naphthalene-1,4'-pyran]-3-carboxylate (1.32 g, 3.56 mmol) and glycine tert-butyl ester hydrochloride (0.717 g, 4.28 mmol) in dioxane (30 mL). The reaction mixture was stirred at 75° C. for 17 hours. The reaction mixture was cooled to room temperature and concentrated in vacuo to give a yellow solid. The crude solid was suspended in ether and filtered to give the desired compound as a light yellow solid (1.29 g). MS (m/e)=456.2 $(M+H)^+$.

Step F: Preparation of N-((7-Trifluoromethyl-4-hydroxy-2-oxo-2',3',5',6'-tetrahydro-spiro[naphthalene-1,4'-pyran]-3-yl)carbonyl)glycine 1,1-Dimethylethyl N-((7-trifluoromethyl-4-hydroxy-2-oxo-2',3',5',6'-tetrahydro-spiro[naphthalene-1,4'-pyran]-3-yl)carbonyl)glycinate (1.29 g, 2.82 mmol) was stirred in TFA (3 mL, 40.4 mmol) at room temperature for 25 minutes. Water was added. The resulting precipitate was filtered and washed with water to give the desired product as a white solid (550 mg). MS (m/e)=400.1 $(M+H)^+$. Calculated for $C_{18}H_{16}F_3NO_6$ 399.09.

Example 46

N-((7-Chloro-4-hydroxy-2-oxo-2',3',5',6'-tetrahydro-spiro[naphthalene-1,4'-pyran]-3-yl)carbonyl)glycine

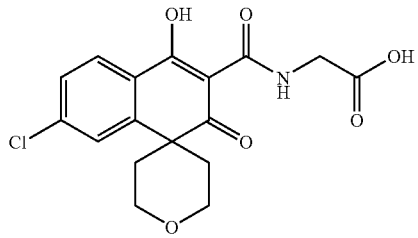

Step A: Preparation of 4-(3-Chlorophenyl)-tetrahydro-2H-pyran-4-carbonitrile Potassium tert-butoxide (8.90 g, 79.3 mmol, 2.20 eq) was added to a stirred solution of 2-(3-chlorophenyl)acetonitrile (4.26 mL, 36.1 mmol) in DMF (50 mL) at 0° C. under a nitrogen atmosphere. The mixture was stirred for 10 minutes at 0° C. before 1-chloro-2-(2-chloroethoxy)ethane (4.65 mL, 39.7 mmol) was added dropwise via syringe. The reaction mixture was allowed to warm to room temperature and stirred for 20 hours. The reaction mixture was then cooled to 0° C. and quenched with 10% HCl. The aqueous mixture was extracted with EtOAc (2×). The combined organic layers were washed with brine, dried ($MgSO_4$), and concentrated in vacuo to give the product as an orange oil (12.51 g).

Step B: Preparation of 4-(3-Chlorophenyl)-tetrahydro-2H-pyran-4-carboxylic acid 60% $H_2SO_4$ (50 mL) was added to a stirred mixture of 4-(3-chlorophenyl)-tetrahydro-2H-pyran-4-carbonitrile (12.51 g, 56 mmol) in dioxane (50 mL), and the reaction mixture was refluxed at 110° C. for 16 hours. The reaction mixture was cooled to room temperature and partitioned between DCM and water. The organic layer was separated, and the aqueous layer was extracted with DCM (2×). The combined organic layers were extracted with 2M NaOH (2×). The combined aqueous layers were washed with EtOAc and acidified to pH=1 with 10% HCl. The resulting precipitate was filtered and washed with water to give the desired product as a white solid (6.13 g).

Step C: Preparation of Diethyl 2-(4-(3-chlorophenyl)-tetrahydro-2H-pyran-4-carbonyl)malonate Thionyl chloride (25 mL) was added to 4-(3-chlorophenyl)-tetrahydro-2H-pyran-4-carboxylic acid (6.13 g, 25.5 mmol). The reaction mixture was stirred at 70° C. for 2.5 hours. The mixture was then concentrated in vacuo to give the acid chloride.

Diethyl malonate (4.23 mL, 28.0 mmol) in ACN (50 mL) was cooled to 0° C. MgCl$_2$ (2.67 g, 28.0 mmol) was added, followed by addition of TEA (7.79 mL, 56.0 mmol) slowly via syringe. The mixture was stirred at 0° C. for 15 minutes and was then brought to room temperature and stirred for 3.5 hours. The above prepared acid chloride was dissolved in ACN (20 mL) and added to the malonate solution. The reaction mixture was then stirred at 50° C. for 17 hours. The reaction mixture was cooled to room temperature, concentrated in vacuo, and partitioned between 1M HCl and EtOAc. The aqueous layer was separated and extracted with EtOAc (2×). The combined organic layers were dried (MgSO$_4$) and concentrated in vacuo to give the desired compound as an orange oil (10.66 g). MS (m/e)=383.2 (M+H)$^+$.

Step D: Preparation of Ethyl 7-chloro-4-hydroxy-2-oxo-2',3',5',6'-tetrahydro-spiro[naphthalene-1,4'-pyran]-3-carboxylate Diethyl 2-(4-(3-chlorophenyl)-tetrahydro-2H-pyran-4-carbonyl)malonate (10.66 g, 27.8 mmol) was added to H$_2$SO$_4$ (50 mL, 591 mmol), and the mixture was stirred at room temperature for 1 hour. Ice (H$_2$O) was added, and the aqueous mixture was extracted with EtOAc (2×). The combined organic layers were washed with water (2×) and brine, dried (MgSO$_4$), and concentrated in vacuo to give the crude compound as an orange oil. The crude oil was purified by silica flash chromatography (0-100% DCM/hexane) to give the desired compound as a yellow solid (4.93 g). MS (m/e)=337.1 (M+H)$^+$.

Step E: Preparation of 1,1-Dimethylethyl N-((7-chloro-4-hydroxy-2-oxo-2',3',5',6'-tetrahydro-spiro[naphthalene-1,4'-pyran]-3-yl)carbonyl)glycinate DIPEA (1.47 mL, 8.42 mmol, 1.5 eq) was added to a mixture of ethyl 7-chloro-4-hydroxy-2-oxo-2',3',5',6'-tetrahydro-spiro[naphthalene-1,4'-pyran]-3-carboxylate (1.89 g, 5.61 mmol, 1.0 eq) and glycine tert-butyl ester hydrochloride (1.13 g, 6.73 mmol, 1.2 eq) in dioxane (50 mL). The reaction mixture was stirred at 80° C. for 3 hours. The reaction mixture was cooled to room temperature and concentrated in vacuo to give a yellow solid. The crude solid was suspended in ether and filtered to give the desired ester as a white solid (2.23 g). MS (m/e)=422.2 (M+H)$^+$.

Step F: Preparation of N-((7-Chloro-4-hydroxy-2-oxo-2',3',5',6'-tetrahydro-spiro[naphthalene-1,4'-pyran]-3-yl)carbonyl)glycine The mixture of 1,1-dimethylethyl N-((7-chloro-4-hydroxy-2-oxo-2',3',5',6'-tetrahydro-spiro[naphthalene-1,4'-pyran]-3-yl)carbonyl)glycinate (2.23 g, 5 mmol) in TFA (8 mL, 108 mmol) was stirred at room temperature for 20 minutes. The majority of the TFA was removed in vacuo and then water was added. The resulting precipitate was filtered and washed with water to give the desired product as a white solid (1.13 g). MS (m/e)=366.1 (M+H)$^+$. Calculated for C$_{17}$H$_{16}$ClNO$_6$ 365.07.

Example 47

N-((7-Fluoro-4-hydroxy-1,1-dimethyl-2-oxo-naphthalen-3-yl)carbonyl)glycine

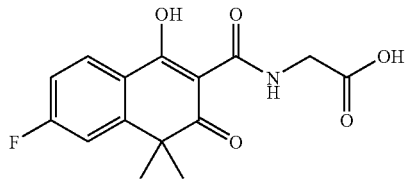

Step A: Preparation of 2-(3-Fluorophenyl)-2-methylpropanenitrile

A solution of 2-(3-fluorophenyl)acetonitrile (4.30 mL, 37.0 mmol) and MeI (6.91 mL, 111 mmol) in DMSO (20 mL) was added dropwise to a stirred solution of NaH (60% dispersion in mineral oil (4.43 g, 111 mmol)) in DMSO (40 mL) at 0° C. under a nitrogen atmosphere. The reaction mixture was stirred for 30 minutes at 0° C. and was then brought to room temperature and stirred for 17 hours. The reaction mixture was quenched with water carefully and then diluted with EtOAc. The organic layer was separated, washed with water (2×) and brine, dried (MgSO$_4$), and concentrated in vacuo to give the desired compound as an orange oil (8.58 g).

Step B: Preparation of 2-(3-Fluorophenyl)-2-methylpropanoic acid

60% H$_2$SO$_4$ (50 mL) was added to a stirred mixture of 2-(3-fluorophenyl)-2-methylpropanenitrile (8.58 g, 53 mmol) in dioxane (50 mL), and the reaction mixture was refluxed at 110° C. for 16 hours. The reaction mixture was cooled to room temperature and partitioned between DCM and water. The organic layer was separated, and the aqueous layer was extracted with DCM (2×). The combined organic layers were washed with brine, dried (MgSO$_4$), and concentrated in vacuo to give the desired acid as a dark brown oil (9.14 g).

Step C: Preparation of Diethyl 2-(2-(3-fluorophenyl)-2-methylpropanoyl)malonate Thionyl chloride (25 mL) was added to 2-(3-fluorophenyl)-2-methylpropanoic acid (6.74 g, 37.0 mmol). The reaction mixture was stirred at 70° C. for 1.5 hours. The mixture was then concentrated in vacuo to give the acid chloride.

Diethyl malonate (5.59 mL, 37.0 mmol) in ACN (50 mL) was cooled to 0° C. MgCl$_2$ (3.52 g, 37.0 mmol) was added, followed by addition of TEA (10.8 mL, 77.7 mmol) slowly via syringe. The mixture was stirred at 0° C. for 15 minutes and was then brought to room temperature and stirred for 3.5 hours. The above prepared acid chloride was dissolved in ACN (20 mL) and added to the malonate solution. The reaction mixture was then stirred at 50° C. for 18 hours. The reaction mixture was cooled to room temperature, concentrated in vacuo, and partitioned between 1M HCl and EtOAc.

The aqueous layer was separated and extracted with EtOAc (2×). The combined organic layers were dried (MgSO$_4$) and concentrated in vacuo to give the desired compound as a brown oil (13.03 g). MS (m/e)=325.2 (M+H)$^+$.

Step D: Preparation of Ethyl 7-fluoro-4-hydroxy-1,1-dimethyl-2-oxo-naphthalene-3-carboxylate Diethyl 2-(2-(3-fluorophenyl)-2-methylpropanoyl)malonate (13.03 g, 40 mmol) was added to concentrated H$_2$SO$_4$ (65 mL, 769 mmol), and the mixture was stirred at room temperature for 45 minutes. Ice (H$_2$O) was added, and the aqueous mixture was extracted with EtOAc (2×). The combined organic layers were washed with water (2×) and brine, dried (MgSO$_4$), and concentrated in vacuo to give the crude compound as an orange oil. The crude oil was purified by silica flash chromatography (0-100% DCM/hexane) to give the desired compound as a white solid (4.26 g). MS (m/e)=279.1 (M+H)$^+$.

Step E: Preparation of 1,1-Dimethylethyl N-((7-fluoro-4-hydroxy-1,1-dimethyl-2-oxo-naphthalen-3-yl)carbonyl)glycinate DIPEA (939 µL, 5390 µmol) was added to a mixture of ethyl 7-fluoro-4-hydroxy-1,1-dimethyl-2-oxo-naphthalene-3-carboxylate (1.00 g, 3594 µmol) and glycine tert-butyl ester hydrochloride (723 mg, 4312 µmol) in dioxane (25 mL). The reaction mixture was stirred at 75° C. for 16 hours. The reaction mixture was cooled to room temperature and concentrated in vacuo to give a yellow solid. The crude solid was suspended in ether and filtered to give the desired ester as a white solid (590 mg). MS (m/e)=308.1 (M+H-tBu)$^+$.

Step F: Preparation of N-((7-Fluoro-4-hydroxy-1,1-dimethyl-2-oxo-naphthalen-3-yl)carbonyl)glycine 1,1-Dimethylethyl N-((7-fluoro-4-hydroxy-1,1-dimethyl-2-oxo-naphthalen-3-yl)carbonyl)glycinate (590 mg, 1624 µmol) was stirred in TFA (3 mL, 40386 µmol) at room temperature for 15 minutes. Water was added. The resulting precipitate was filtered and washed with water to give the desired product as a white solid (481 mg). MS (m/e)=308.1 (M+H)$^+$. Calculated for C$_{15}$H$_{14}$FNO$_5$ 307.09.

Example 48

N-((7-Chloro-4-hydroxy-1,1-dimethyl-2-oxo-naphthalen-3-yl)carbonyl)glycine

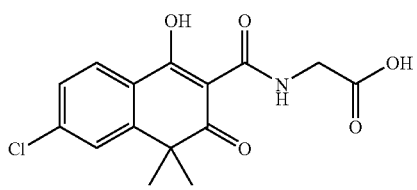

Step A: Preparation of 2-(3-Chlorophenyl)-2-methylpropanenitrile

MeI (14 g, 99 mmol) and 2-(3-chlorophenyl)acetonitrile (5.0 g, 33.0 mmol) were added as a solution in DMSO (75 mL) to a suspension of NaH (2.4 g, 99 mmol) in DMSO (50 mL) that was cooled to 0° C. The mixture was stirred at room temperature overnight, partitioned between EtOAc and water, and the layers were separated. The organic layer was washed with water (2×), dried (MgSO$_4$), and concentrated in vacuo to give the product as a yellow oil (5.7 g).

Step B: Preparation of 2-(3-Chlorophenyl)-2-methylpropanoic acid 2-(3-Chlorophenyl)-2-methylpropanenitrile (5.5 g, 30.6 mmol) was dissolved in 1,4-dioxane (50 mL) and 60% aqueous H$_2$SO$_4$ (50 mL). The mixture was heated at 120° C. for 16 hours, cooled to room temperature, partitioned between EtOAc and water, and the layers were separated. The organic layer was washed with water several times, dried (MgSO$_4$), and concentrated in vacuo to give the product as a brown oil (5.74 g).

Step C: Preparation of 2-(3-Chlorophenyl)-2-methylpropanoyl chloride 2-(3-Chlorophenyl)-2-methylpropanoic acid (5.7 g, 28.7 mmol) was stirred in thionyl chloride (100 mL) for 2 hours at reflux. The thionyl chloride was removed under vacuum to give the product (5.69 g).

Step D: Preparation of Diethyl 2-(2-(3-chlorophenyl)-2-methylpropanoyl)malonate

Diethyl malonate (3.72 mL, 24.6 mmol) in ACN (50 mL) was cooled to 0° C. MgCl$_2$ (2.34 g, 24.6 mmol) was added, followed by addition of TEA (7.18 mL, 51.7 mmol) slowly via syringe. The mixture was stirred at 0° C. for 15 minutes before being brought to room temperature and stirred for 2.5 hours. 2-(3-Chlorophenyl)-2-methylpropanoyl chloride (5.69 g, 24.6 mmol) was dissolved in ACN (20 mL) and added to the malonate solution. The reaction mixture was then stirred at 50° C. for 16 hours. The reaction mixture was cooled to room temperature, concentrated in vacuo, and partitioned between 1M HCl and EtOAc. The aqueous layer was separated and extracted with EtOAc (2×). The combined organic layers were dried (MgSO$_4$) and concentrated in vacuo to give the desired compound as a brown oil (8.76 g). MS (m/e)=341.2 (M+H)$^+$.

Step E: Preparation of Ethyl 7-chloro-4-hydroxy-1,1-dimethyl-2-oxo-naphthalene-3-carboxylate Diethyl 2-(2-(3-chlorophenyl)-2-methylpropanoyl)malonate (8.76 g, 26 mmol) was added to H$_2$SO$_4$ (60 mL, 710 mmol), and the mixture was stirred at room temperature for 45 minutes. Ice (H$_2$O) was added, and the aqueous mixture was extracted with EtOAc (2×). The combined organic layers were washed with water (2×) and brine, dried (MgSO$_4$), and concentrated in vacuo to give the crude compound as an orange oil. The crude oil was purified by silica flash chromatography (0-50% DCM/hexane) to give the desired compound as a white solid (3.90 g). MS (m/e)=295.1 (M+H)$^+$.

Step F: Preparation of 1,1-Dimethylethyl N-((7-chloro-4-hydroxy-1,1-dimethyl-2-oxo-naphthalen-3-yl)carbonyl)glycinate DIPEA (0.718 mL, 4.12 mmol) was added to a mixture of ethyl 7-chloro-4-hydroxy-1,1-dimethyl-2-oxo-naphthalene-3-carboxylate (810 mg, 2.75 mmol) and glycine tert-butyl ester hydrochloride (553 mg, 3.30 mmol) in dioxane (25 mL).

The reaction mixture was stirred at 85° C. for 2 hours. The reaction mixture was cooled to room temperature and concentrated in vacuo to give a yellow solid. The crude solid was suspended in ether and filtered to give the desired ester as a white solid (1.21 g). MS (m/e)=324.1 (M+H-tBu)$^+$.

Step G: Preparation of N-((7-Chloro-4-hydroxy-1,1-dimethyl-2-oxo-naphthalen-3-yl)carbonyl)glycine 1,1-Dimethylethyl N-((7-chloro-4-hydroxy-1,1-dimethyl-2-oxo-naphthalen-3-yl)carbonyl)glycinate (1.21 g, 3 mmol) was stirred in TFA (5 mL, 67 mmol) at room temperature for 20 minutes. Water was added. The resulting precipitate was filtered and washed with water to give the desired product as a white solid (650 mg). MS (m/e)=324.1 (M+H)$^+$. Calculated for $C_{15}H_{14}ClNO_5$ 323.06.

Example 49

N-((7-Trifluoromethyl-4-hydroxy-1,1-dimethyl-2-oxo-naphthalen-3-yl)carbonyl)glycine

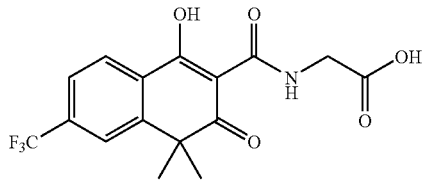

Step A: Preparation of 2-Methyl-2-(3-(trifluoromethyl)phenyl)-propanenitrile

A solution of 2-(3-(trifluoromethyl)phenyl)acetonitrile (4.21 mL, 27.0 mmol) and MeI (5.05 mL, 81.0 mmol) in DMSO (20 mL) was added dropwise to a stirred solution of NaH (60% dispersion in mineral oil (3.23 g, 81.0 mmol)) in DMSO (40 mL) at 0° C. under a nitrogen atmosphere. The reaction mixture was stirred for 30 minutes at 0° C. and then brought to room temperature and stirred for 17 hours. The reaction mixture was quenched with water carefully and then diluted with EtOAc. The organic layer was separated, washed with water (2x) and brine, dried (MgSO$_4$), and concentrated in vacuo to give the desired compound as a dark orange oil (7.79 g).

Step B: Preparation of 2-Methyl-2-(3-(trifluoromethyl)phenyl)propanoic acid

60% H$_2$SO$_4$ (50 mL) was added to a stirred mixture of 2-methyl-2-(3-(trifluoromethyl)phenyl)propanenitrile (7.79 g, 37 mmol) in dioxane (50 mL), and the reaction mixture was refluxed at 110° C. for 15 hours. The reaction mixture was cooled to room temperature and partitioned between DCM and water. The organic layer was separated, and the aqueous layer was extracted with DCM (2x). The combined organic layers were washed with brine, dried (MgSO$_4$), and concentrated in vacuo to give the desired acid as a brown oil (7.85 g).

Step C: Preparation of Diethyl 2-(2-methyl-2-(3-(trifluoromethyl)-phenyl)propanoyl)malonate Thionyl chloride (20 mL) was added to 2-methyl-2-(3-(trifluoromethyl)phenyl)propanoic acid (2.45 g, 10.6 mmol). The reaction mixture was stirred at 70° C. for 1.5 hours. The mixture was then concentrated in vacuo to give the acid chloride.

Diethyl malonate (1.59 mL, 10.6 mmol) in ACN (25 mL) was cooled to 0° C. MgCl$_2$ (1.00 g, 10.6 mmol) was added, followed by addition of TEA (3.08 mL, 22.2 mmol) slowly via syringe. The mixture was stirred at 0° C. for 15 minutes and then brought to room temperature and stirred for 3.5 hours. The above prepared acid chloride was dissolved in ACN (10 mL) and added to the malonate solution. The reaction mixture was then stirred at 50° C. for 18 hours. The reaction mixture was cooled to room temperature, concentrated in vacuo, and partitioned between 1M HCl and EtOAc. The aqueous layer was separated and extracted with EtOAc (2x). The combined organic layers were dried (MgSO$_4$) and concentrated in vacuo to give the desired compound as a brown oil (3.73 g). MS (m/e)=375.2 (M+H)$^+$.

Step D: Preparation of Ethyl 4-hydroxy-1,1-dimethyl-2-oxo-7-(trifluoromethyl)-naphthalene-3-carboxylate Diethyl 2-(2-methyl-2-(3-(trifluoromethyl)phenyl)propanoyl)malonate (2.80 g, 7.5 mmol) was added to H$_2$SO$_4$ (40 mL, 237 mmol), and the mixture was stirred at room temperature for 1 hour. Ice (H$_2$O) was added, and the aqueous mixture was extracted with EtOAc (2x). The combined organic layers were washed with water (2x) and brine, dried (MgSO$_4$), and concentrated in vacuo to give the crude compound as a yellow oil. The crude oil was purified by silica flash chromatography (0-50% DCM/hexane) to give the desired compound as a yellow semi-solid (1.07 g). MS (m/e)=329.1 (M+H)$^+$.

Step E: Preparation of 1,1-Dimethylethyl N-((7-trifluoromethyl-4-hydroxy-1,1-dimethyl-2-oxo-naphthalen-3-yl)carbonyl)glycinate DIPEA (1870 µL, 10738 µmol, 2.5 eq) was added to a mixture of ethyl 4-hydroxy-1,1-dimethyl-2-oxo-7-(trifluoromethyl)-naphthalene-3-carboxylate (1.41 g, 4295 µmol) and glycine tert-butyl ester hydrochloride (864 mg, 5154 µmol) in dioxane (50 mL). The reaction mixture was stirred at 75° C. for 15 hours. The reaction mixture was cooled to room temperature and concentrated in vacuo to give a yellow solid. The crude solid was purified by silica flash chromatography (0-40% DCM/hexane) to give the desired ester as a white solid (380 mg). MS (m/e)=358.1 (M+H-tBu)$^+$.

Step F: Preparation of N-((7-Trifluoromethyl-4-hydroxy-1,1-dimethyl-2-oxo-naphthalen-3-yl)carbonyl) glycine 1,1-Dimethylethyl N-((7-trifluoromethyl-4-hydroxy-1,1-dimethyl-2-oxo-naphthalen-3-yl)carbonyl)glycinate (380 mg, 919 µmol) was stirred in TFA (2 mL, 26924 µmol) at room temperature for 30 minutes. The reaction mixture was partitioned between water and EtOAc. The organic layer was separated, dried (MgSO$_4$), and concentrated in vacuo to give a yellow solid. The solid was then washed with water, ether, and EtOAc to give the desired product as an off-white solid (100 mg). MS (m/e)=358.1 (M+H)$^+$. Calculated for $C_{16}H_{14}F_3NO_5$ 357.08.

Example 50

N-((7-Bromo-4-hydroxy-1,1-dimethyl-2-oxo-naphthalen-3-yl)carbonyl)-L-alanine

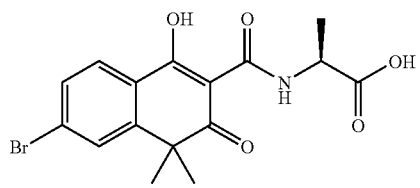

Step A: Preparation of 1,1-Dimethylethyl N-((7-bromo-4-hydroxy-1,1-dimethyl-2-oxo-naphthalen-3-yl)carbonyl)-L-alaninate DIPEA (120 µL, 690 µmol, 1.5 eq) was added to a mixture of ethyl 7-bromo-4-hydroxy-1,1-dimethyl-2-oxo-naphthalen-3-carboxylate (156 mg, 460 µmol, prepared in Example 53A-D) and (S)-tert-butyl 2-aminopropanoate hydrochloride (100 mg, 552 µmol) in dioxane (5 mL). The reaction mixture was stirred at 75° C. for 16 hours. The reaction mixture was cooled to room temperature and partitioned between EtOAc and water. The organic layer was separated, washed with brine, dried (MgSO$_4$), and concentrated in vacuo to give a yellow oil. The crude oil was purified by silica flash chromatography (0-50% DCM/hexane) to give the desired ester as a transparent oil (137 mg). MS (m/e)=382.1 (M+H-tBu)$^+$.

Step B: Preparation of N-((7-Bromo-4-hydroxy-1,1-dimethyl-2-oxo-naphthalen-3-yl)carbonyl)-L-alanine 1,1-Dimethylethyl N-((7-bromo-4-hydroxy-1,1-dimethyl-2-oxo-naphthalen-3-yl)carbonyl)-L-alaninate (184 mg, 436 µmol) was stirred in TFA (2 mL, 26924 µmol) at room temperature for 30 minutes. Water was added. The resulting precipitate was filtered and washed with water to give the desired product as a white solid (93 mg). MS (m/e)=382.1 (M+H)$^+$. Calculated for C$_{21}$H$_{19}$NO$_5$ 381.02.

Example 51

N-((7-(3-Pyridyl)-4-hydroxy-1,1-dimethyl-2-oxo-naphthalene-3-yl)carbonyl)glycine

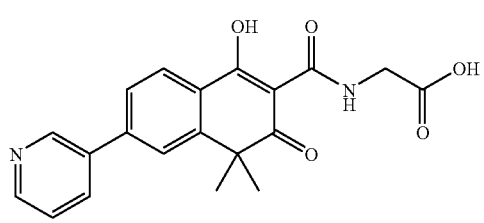

Step A: Preparation of 1,1-Dimethylethyl N-((7-(3-pyridyl)-4-hydroxy-1,1-dimethyl-2-oxo-naphthalen-3-yl)carbonyl)glycinate 1,1-Dimethylethyl N-((7-bromo-4-hydroxy-1,1-dimethyl-2-oxo-naphthalen-3-yl)carbonyl)glycinate (265 mg, 625 µmol, see Example 53), 3-pyridylboronic acid (115 mg, 937 µmol), and tetrakis(triphenylphosphine)palladium (72 mg, 62 µmol) were mixed in dioxane (4 mL) in a microwave tube under a nitrogen atmosphere. 2M Na$_2$CO$_3$ (937 µL, 1874 µmol) was added via syringe, and the reaction mixture was stirred at 75° C. for 15 hours. The reaction mixture was cooled to room temperature and partitioned between EtOAc and water. The organic layer was separated, washed with brine, dried (MgSO$_4$), and concentrated in vacuo to give the crude product as a yellow solid. The crude product was purified by silica flash chromatography (0-10% EtOAc/DCM) to give the desired compound as an off-white solid (190 mg). MS (m/e)=423.2 (M+H)$^+$.

Step B: Preparation of N-((7-(3-Pyridyl)-4-hydroxy-1,1-dimethyl-2-oxo-naphthalen-3-yl)carbonyl)glycine 1,1-Dimethylethyl N-((7-(3-pyridyl)-4-hydroxy-1,1-dimethyl-2-oxo-naphthalen-3-yl)carbonyl)glycinate (184 mg, 436 µmol) was stirred in TFA (2 mL, 26924 µmol) at room temperature for 30 minutes. The reaction mixture was partitioned between water and EtOAc. The organic layer was separated, and the aqueous layer was extracted with EtOAc (2×). The combined organic layers were dried (MgSO$_4$) and concentrated in vacuo to give the desired product as a yellow solid (95 mg). MS (m/e)=367.2 (M+H)$^+$. Calculated for C$_{21}$H$_{19}$NO$_5$ 366.12.

Example 52

N-((7-Phenyl-4-hydroxy-1,1-dimethyl-2-oxo-naphthalen-3-yl)carbonyl)glycine

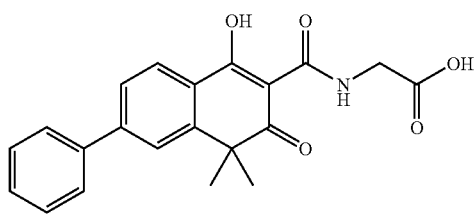

Step A: Preparation of 1,1-Dimethylethyl N-((7-phenyl-4-hydroxy-1,1-dimethyl-2-oxo-naphthalen-3-yl)carbonyl)glycinate 1,1-Dimethylethyl N-((7-bromo-4-hydroxy-1,1-dimethyl-2-oxo-naphthalene-3-yl)carbonyl)glycinate (250 mg, 0.59 mmol, prepared in Example 53A-E), phenylboronic acid (108 mg, 0.9 mmol), tetrakis(triphenylphosphine)palladium (68 mg, 0.06 mmol), and 2M Na$_2$CO$_3$ (885 µL, 2 mmol) were mixed in dioxane (4 mL). The reaction vessel was placed under an argon atmosphere and stirred at 75° C. for 16 hours. The reaction mixture was cooled to room temperature and partitioned between EtOAc and water. The organic layer was separated, washed with brine, dried (MgSO$_4$), and concentrated in vacuo to give the crude product. The crude product was purified by silica flash chromatography (0-100% DCM/hexane) to give the desired compound as a yellow solid (172 mg). MS (m/e)=366.2 (M+H-tBu)$^+$.

Step B: Preparation of N-((7-Phenyl-4-hydroxy-1,1-dimethyl-2-oxo-naphthalen-3-yl)carbonyl)glycine 1,1-Dimethylethyl N-((7-phenyl-4-hydroxy-1,1-dimethyl-2-oxo-naphthalen-3-yl)carbonyl)glycinate (169 mg, 401 µmol) was stirred in TFA (1 mL, 13462 µmol) at room temperature for 20 minutes. The reaction mixture was partitioned between water and EtOAc. The organic layer was separated, dried (MgSO$_4$), and concentrated in vacuo to give the desired product as a yellow solid (140 mg). MS (m/z)= 366.2 (M+H)$^+$. Calculated for C$_{21}$H$_{19}$NO$_5$ 365.13.

Example 53

N-((7-Bromo-4-hydroxy-1,1-dimethyl-2-oxo-naphthalen-3-yl)carbonyl)glycine

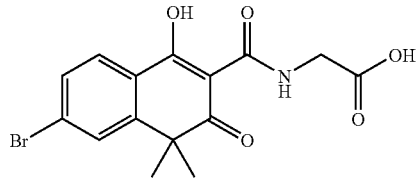

Step A: Preparation of 2-(3-Bromophenyl)-2-methylpropanenitrile

A solution of 3-bromophenylacetonitrile (12 g, 61 mmol) and MeI (11 mL, 184 mmol) in DMSO (30 mL) was added dropwise to a stirred solution of NaH (60% dispersion in mineral oil (7.3 g, 184 mmol)) in DMSO (70 mL) at 0° C. under a nitrogen atmosphere. The reaction mixture was stirred for 30 minutes at 0° C. and then brought to room temperature and stirred for 23 hours. The reaction mixture was quenched with water carefully and then diluted with EtOAc. The aqueous layer was separated and extracted again with EtOAc. The combined organic layers were separated, washed with water (2×) and brine, dried (MgSO$_4$), and concentrated in vacuo to give the desired compound as an orange oil (16.75 g).

Step B: Preparation of 2-(3-Bromophenyl)-2-methylpropanoic acid 2-(3-Bromophenyl)-2-methylpropanenitrile (14.0 g, 62.47 mmol) was heated in dioxane (150 mL) and 60% H$_2$SO$_4$ (150 mL) for 16 hours, cooled to room temperature, and partitioned between DCM and water. The layers were separated, and the aqueous layer was extracted with DCM (2×). The combined organic layers were washed with water (2×) and brine, dried (MgSO$_4$), and concentrated in vacuo to give the product as an oil that solidified upon standing (14.75 g).

Step C: Preparation of Diethyl 2-(2-(3-bromophenyl)-2-methylpropanoyl)malonate

Thionyl chloride (50 mL) was added to 2-(3-bromophenyl)-2-methylpropanoic acid (10.63 g, 43.7 mmol). The reaction mixture was stirred at 75° C. for 2.5 hours. The mixture was then concentrated in vacuo to give the acid chloride.
Diethyl malonate (7.27 mL, 48.1 mmol) in ACN (100 mL) was cooled to 0° C. MgCl$_2$ (4.58 g, 48.1 mmol) was added, followed by addition of TEA (13.4 mL, 96.2 mmol) slowly via syringe. The mixture was stirred at 0° C. for 15 minutes and was then brought to room temperature and stirred for 2.5 hours. The above prepared acid chloride was dissolved in ACN (20 mL) and added to the malonate solution. The reaction mixture was then stirred at 50° C. for 15 hours. The resulting reaction mixture was cooled to room temperature, concentrated in vacuo, and partitioned between 1M HCl and EtOAc. The aqueous layer was separated and extracted with EtOAc (2×). The combined organic layers were dried (MgSO$_4$) and concentrated in vacuo to give the desired compound as a brown oil (17.44 g). MS (m/z)=385.1 (M+H)$^+$.

Step D: Preparation of Ethyl 7-bromo-4-hydroxy-1,1-dimethyl-2-oxo-naphthalene-3-carboxylate H$_2$SO$_4$ (60 mL, 710 mmol) was cooled to 0° C. and treated with P$_2$O$_5$ (20 g, 141 mmol). The mixture was brought to room temperature and added to diethyl 2-(2-(3-bromophenyl)-2-methylpropanoyl)malonate (17.44 g, 45 mmol). The reaction mixture was then stirred for 2 hours. Ice (H$_2$O) was added, and the aqueous mixture was extracted with EtOAc (3×). The combined organic layers were washed with water (2×) and brine, dried (MgSO$_4$), and concentrated in vacuo to give the crude compound as an orange oil. The crude oil was purified by silica flash chromatography (0-100% DCM/hexane) to give the desired compound as a white solid (6.27 g). MS (m/e)=339.1 (M+H)$^+$.

Step E: Preparation of 1,1-Dimethylethyl N-((7-bromo-4-hydroxy-1,1-dimethyl-2-oxo-naphthalen-3-yl)carbonyl)glycinate DIPEA (3.86 mL, 22.2 mmol, 1.2 eq) was added to a mixture of ethyl 7-bromo-4-hydroxy-1,1-dimethyl-2-oxo-naphthalene-3-carboxylate (6.27 g, 18.5 mmol) and glycine tert-butyl ester hydrochloride (3.72 g, 22.2 mmol) in dioxane (30 mL). The reaction mixture was stirred at 85° C. for 3 hours. The reaction mixture was cooled to room temperature and concentrated in vacuo to give a light yellow solid. The crude solid was suspended in ether, filtered, and washed with water to give the desired ester as a white solid (6.53 g). MS (m/e)=368.1 (M+H-tBu)$^+$.

Step F: Preparation of N-((7-Bromo-4-hydroxy-1,1-dimethyl-2-oxo-naphthalen-3-yl)carbonyl)glycine 1,1-Dimethylethyl N-((7-bromo-4-hydroxy-1,1-dimethyl-2-oxo-naphthalen-3-yl)carbonyl)glycinate (328 mg, 773 µmol) was stirred in TFA (2 mL, 26.9 mmol) at room temperature for 25 minutes. Water was added. The resulting precipitate was filtered and washed with water to give the desired product as an off-white solid (263 mg). MS (m/e)= 368.1 (M+H)$^+$. Calculated for C$_{15}$H$_{14}$BrNO$_5$ 367.01.

Example 54

N-((6-Chloro-4-hydroxy-2-oxo-2',3',5',6'-tetrahydrospiro[naphthalene-1,4'-pyran]-3-yl)carbonyl)-2-methylalanine

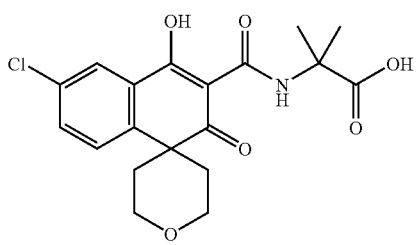

Step A: Preparation of 1,1-Dimethylethyl N-((6-chloro-4-hydroxy-2-oxo-2',3',5',6'-tetrahydro-spiro[naphthalene-1,4'-pyran]-3-yl)carbonyl)-2-methylalaninate Ethyl 6-chloro-4-hydroxy-2-oxo-2',3',5',6'-tetrahydro-spiro[naphthalene-1,4'-pyran]-3-carboxylate (320 mg, 950 μmol, prepared according to Example 1 A-C) was dissolved in 1,4-dioxane (950 μL) and N-ethyl-N-isopropylpropan-2-amine (507 μL, 2851 μmol) before tert-butyl 2-amino-2-methylpropanoate hydrochloride (279 mg, 1425 μmol) was added. The resulting mixture was heated at 80° C. for 24 hours and then diluted with 150 mL of EtOAc. The resulting mixture was added to a separatory funnel, partitioned with NaHCO$_3$ (saturated, aqueous), washed with saturated aqueous NaHCO$_3$ (2×75 mL), separated, dried over Na$_2$SO$_4$, and concentrated in vacuo to give the title compound (260 mg) after chromatography as an amorphous solid. MS (m/z)=394 (M+H-tert-butyl)$^+$.

Step B: Preparation of N-((6-Chloro-4-hydroxy-2-oxo-2',3',5',6'-tetrahydro-spiro[naphthalene-1,4'-pyran]-3-yl)carbonyl)-2-methylalanine 1,1-Dimethylethyl N-((6-chloro-4-hydroxy-2-oxo-2',3',5', 6'-tetrahydro-spiro[naphthalene-1,4'-pyran]-3-yl)carbonyl)-2-methylalaninate (245 mg, 545 μmol) was dissolved in TFA at ambient temperature for 1 hour before it was concentrated, precipitated with hexanes, filtered, washed with hexanes, and dried in a vacuum oven to give the title compound (179 mg) as a white solid. MS (m/z)=394 (M+H)$^+$. Calculated for C$_{19}$H$_{20}$ClNO$_6$ 393.10.

Example 55

N-((6-Chloro-4-hydroxy-2-oxo-2',3',5',6'-tetrahydro-spiro[naphthalene-1,4'-pyran]-3-yl)carbonyl)-L-alanine

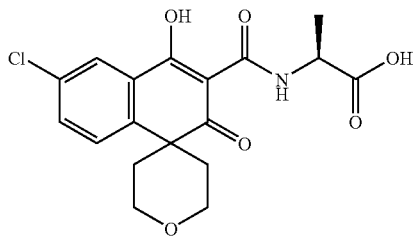

Step A: Preparation of 1,1-Dimethylethyl N-((6-chloro-4-hydroxy-2-oxo-2',3',5',6'-tetrahydro-spiro[naphthalene-1,4'-pyran]-3-yl)carbonyl)-L-alaninate Ethyl 6-chloro-4-hydroxy-2-oxo-2',3',5',6'-tetrahydro-spiro[naphthalene-1,4'-pyran]-3-carboxylate (610 mg, 1811 μmol, prepared in Example 1 A-C) was dissolved in 1,4-dioxane (1811 μL) and N-ethyl-N-isopropylpropan-2-amine (947 μL, 5434 μmol). L-Alanine t-butyl ester hydrochloride (494 mg, 2717 μmol) was added, and the reaction mixture was heated to 80° C. for 24 hours. The reaction mixture was then cooled to ambient temperature, diluted with 150 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (525 mg) as an oil after flash chromatography. MS (m/z)=436 (M+H)$^+$.

Step B: Preparation of N-((6-Chloro-4-hydroxy-2-oxo-2',3',5',6'-tetrahydro-spiro[naphthalene-1,4'-pyran]-3-yl)carbonyl)-L-alanine 1,1-Dimethylethyl N-((6-chloro-4-hydroxy-2-oxo-2',3',5', 6'-tetrahydro-spiro[naphthalene-1,4'-pyran]-3-yl)carbonyl)-L-alaninate (525 mg, 1204 μmol) was dissolved in TFA for 30 minutes before it was concentrated, precipitated with hexanes, washed with hexanes, and dried in a vacuum oven to give the title compound (384 mg) as a white solid. MS (m/z)= 380 (M+H)$^+$. Calculated for C$_{18}$H$_{18}$ClNO$_6$ 379.08.

Example 56

N-((6-Chloro-4-hydroxy-2-oxo-2',3',5',6'-tetrahydro-spiro[naphthalene-1,4'-pyran]-3-yl)carbonyl)-D-alanine

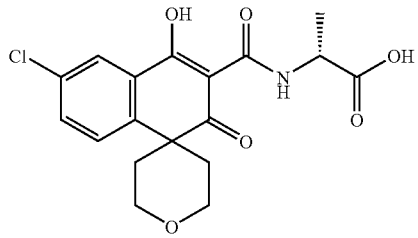

Step A: Preparation of 1,1-Dimethylethyl N-((6-chloro-4-hydroxy-2-oxo-2',3',5',6'-tetrahydro-2H-spiro[naphthalene-1,4'-pyran]-3-yl)carbonyl)-D-alaninate Ethyl 6-chloro-4-hydroxy-2-oxo-2',3',5',6'-tetrahydro-spiro[naphthalene-1,4'-pyran]-3-carboxylate (705 mg, 2093 μmol, prepared in Example 1 A-C) was dissolved in 1,4-dioxane (2093 μL) and N-ethyl-N-isopropylpropan-2-amine (1094 μL, 6280 μmol). D-Alanine tert-butyl ester hydrochloride (570 mg, 3140 μmol) was added, and the reaction mixture was heated to 80° C. for 24 hours. The resulting mixture was then diluted with 150 mL of EtOAc, added to a separatory funnel, partitioned with NaHCO$_3$ (saturated, aqueous), washed 2 times with 75 mL of NaHCO$_3$ (saturated, aqueous), separated, dried over Na$_2$SO$_4$, and concentrated in vacuo to give the title compound (501 mg) after flash chromatography. MS (m/z)=436 (M+H)$^+$.

Step B: Preparation of N-((6-Chloro-4-hydroxy-2-oxo-2',3',5',6'-tetrahydro-spiro[naphthalene-1,4'-pyran]-3-yl)carbonyl)-D-alanine 1,1-Dimethylethyl N-((6-chloro-4-hydroxy-2-oxo-2',3',5', 6'-tetrahydro-spiro[naphthalene-1,4'-pyran]-3-yl)carbonyl)-D-alaninate (501 mg, 1149 μmol) was dissolved in TFA at ambient temperature for 30 minutes before it was concentrated, precipitated with hexanes, filtered, washed with hex-

Example 57

N-((6-Chloro-8-fluoro-4-hydroxy-1,1-dimethyl-2-oxo-naphthalen-3-yl)carbonyl)glycine

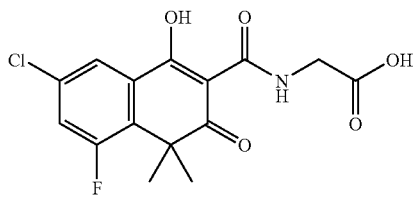

Step A: Preparation of Methyl 2-(4-chloro-2-fluorophenyl)acetate 2-(4-Chloro-2-fluorophenyl)acetic acid (25.0 g, 133 mmol) was dissolved in MeOH (133 mL). Sulfuryl dichloride (9.67 mL, 133 mmol) was then added, and the reaction was stirred at ambient temperature for 3 hours. The reaction mixture was concentrated in vacuo to give the title compound which was used without further purification. MS (m/z)=203 $(M+H)^+$.

Step B: Preparation of Methyl 2-(4-chloro-2-fluorophenyl)-2-methylpropanoate A 60% NaH dispersion in mineral oil (11.7 g, 292 mmol) was added to THF (266 mL). The mixture was then cooled to 0° C. and methyl 2-(4-chloro-2-fluorophenyl)acetate (26.9 g, 133 mmol) and MeI (18.2 mL, 292 mmol) dissolved in ether were added dropwise via addition funnel. The reaction mixture was stirred at ambient temperature for 16 hours and then quenched dropwise with water. The resulting mixture was acidified with 3N HCl, diluted with 200 mL of EtOAc, added to a separatory funnel, partitioned with water, washed 2 times with 100 mL of water, separated, dried over $Na_2SO_4$, and concentrated in vacuo to give the title compound (19.23 g) after flash chromatography. MS (m/z)=231 $(M+H)^+$.

Step C: Preparation of 2-(4-Chloro-2-fluorophenyl)-2-methylpropanoic acid

Methyl 2-(4-chloro-2-fluorophenyl)-2-methylpropanoate (8.11 g, 35.2 mmol) was dissolved in EtOH (70.3 mL) in a vial. KOH (3.95 g, 70.3 mmol) was added, and the sealed vial was heated at 120° C. for 2 hours. The reaction mixture was then diluted with 75 mL of diethyl ether, added to a separatory funnel, partitioned with water, washed with 75 mL of water, and separated. The aqueous layer was acidified to pH=3 with 3N HCl and extracted 2 times with 100 mL of diethyl ether. The combined organic layers were dried over $Na_2SO_4$, filtered, and concentrated in vacuo to give the title compound (6.46 g) as a light yellow solid. MS (m/z)=217 $(M+H)^+$.

Step D: Preparation of Diethyl 2-(2-(4-chloro-2-fluorophenyl)-2-methylpropanoyl)malonate To a mixture of diethyl malonate (5.01 mL, 33.1 mmol) and magnesium (0.805 g, 33.1 mmol), were added EtOH (11.6 mL) and $CCl_4$ (0.160 mL). THF (66.3 mL) was slowly added to the reaction, and the reaction was stirred at 70° C. for 1 hour. The reaction was then allowed to cool and the acid chloride formed from 2-(4-chloro-2-fluorophenyl)-2-methylpropanoic acid (6.46 g, 29.8 mmol converted to the acid chloride by reaction with thionyl chloride at 65° C. for 1 hour and then concentrated) was added dropwise as an ether solution via addition funnel. The resulting reaction mixture was stirred at ambient temperature for 1 hour. The reaction mixture was then quenched with 2N HCl, diluted with 200 mL of diethyl ether, added to a separatory funnel, partitioned with water, washed 2 times with 75 mL of water, separated, dried over $Na_2SO_4$, and concentrated in vacuo to give the title compound (10.46 g) as a yellow oil. MS (m/z)=359 $(M+H)^+$.

Step E: Preparation of Ethyl 6-chloro-8-fluoro-4-hydroxy-1,1-dimethyl-2-oxo-naphthalene-3-carboxylate To diethyl 2-(2-(4-chloro-2-fluorophenyl)-2-methylpropanoyl)malonate (2.20 g, 6.1 mmol), was added $P_2O_5$ (3.5 g, 25 mmol) in $H_2SO_4$ (3.3 mL) at 0° C. The reaction was then allowed to warm to ambient temperature and stirred for 1 hour. The reaction mixture was poured into ice, diluted with 100 mL of EtOAc, added to a separatory funnel, partitioned with water, washed 2 times with 75 mL of water, separated, dried over $Na_2SO_4$, and concentrated in vacuo to give the title compound (0.75 g) which was used without further purification. MS (m/z)=313 $(M+H)^+$.

Step F: Preparation of 1,1-Dimethylethyl N-((6-chloro-8-fluoro-4-hydroxy-1,1-dimethyl-2-oxo-naphthalene-3-yl)carbonyl)glycinate Ethyl 6-chloro-8-fluoro-4-hydroxy-1,1-dimethyl-2-oxo-naphthalene-3-carboxylate (0.75 g, 2398 µmol) was dissolved in 1,4-dioxane (4797 µL) and N-ethyl-N-isopropyl-propan-2-amine (1253 µL, 7195 µmol). tert-Butyl 2-aminoacetate hydrochloride (603 mg, 3597 µmol) was added, and the reaction was stirred at 80° C. for 3 hours. The reaction was then diluted with 150 mL of EtOAc, added to a separatory funnel, partitioned with $NaHCO_3$ (saturated, aqueous), washed 2 times with 75 mL of $NaHCO_3$ (saturated, aqueous), separated, dried over $Na_2SO_4$, and concentrated in vacuo to give the title compound (227 mg) as a white solid. MS (m/z)=420 $(M+Na)^+$.

Step G: Preparation of N-((6-Chloro-8-fluoro-4-hydroxy-1,1-dimethyl-2-oxo-naphthalen-3-yl)carbonyl)glycine 1,1-Dimethylethyl N-((6-chloro-8-fluoro-4-hydroxy-1,1-dimethyl-2-oxo-naphthalene-3-yl)carbonyl)glycinate (227 mg, 571 µmol) was dissolved in TFA (2 mL) and stirred at ambient temperature for 30 minutes. The resulting mixture was concentrated, precipitated with hexanes, filtered, washed with hexanes, and dried in a vacuum oven to give the title compound (219 mg, 112% yield) as a white solid. MS (m/z)=342 $(M+H)^+$. Calculated for $C_{15}H_{13}ClFNO_5$ 341.05.

Example 58

N-((6,7-Difluoro-4-hydroxy-2-oxo-2',3',5',6'-tetrahydro-spiro[naphthalene-1,4'-pyran]-3-yl)carbonyl)glycine

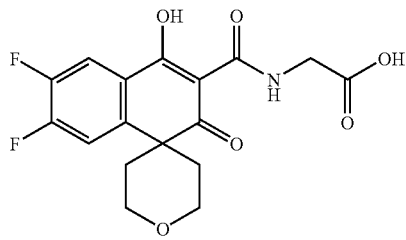

Step A: Preparation of 4-(3,4-Difluorophenyl)-tetrahydro-2H-pyran-4-carbonitrile A mixture 2-(3,4-difluorophenyl)acetonitrile (25.00 g, 163 mmol) and 2-bromoethyl ether (22.8 mL, 163 mmol) in ether was added dropwise through an addition funnel to a mixture of sodium 2-methylpropan-2-olate (39.2 g, 408 mmol) in DMF (163 mL) at 0° C. The reaction was then allowed to warm to ambient temperature and stirred for 3 hours. The reaction mixture was quenched with 12N HCl, diluted with 400 mL of EtOAc, added to a separatory funnel, partitioned with NaHCO$_3$ (saturated, aqueous), washed 2 times with 100 mL of NaHCO$_3$ (saturated, aqueous), separated, dried over Na$_2$SO$_4$, and concentrated in vacuo to give the title compound which was used without further purification. MS (m/z)=224 (M+H)$^+$.

Step B: Preparation of 4-(3,4-Difluorophenyl)-tetrahydro-2H-pyran-4-carboxylic acid 4-(3,4-Difluorophenyl)-tetrahydro-2H-pyran-4-carbonitrile (21.96 g, 98.4 mmol) was suspended in H$_2$SO$_4$ (109 mL, 984 mmol) in a sealed vial and then heated to 160° C. for 4 hours. The resulting reaction mixture was then cooled, diluted with 100 mL of EtOAc, added to a separation funnel, partitioned with 5N NaOH (aqueous), washed 2 times with 50 mL of 5N NaOH (aqueous), and separated. The aqueous layer was acidified to pH=3 with concentrated HCl and extracted 3 times with 75 mL of EtOAc. The combined organic layers were dried over Na$_2$SO$_4$, filtered, and concentrated in vacuo to give the title compound (9.52 g) as a yellow oil which was used without further purification. MS (m/z)=243 (M+H)$^+$.

Step C: Preparation of Diethyl 2-(4-(3,4-difluorophenyl)-tetrahydro-2H-pyran-4-carbonyl)malonate To diethyl malonate (11.6 mL, 76.5 mmol) and magnesium (1.86 g, 76.5 mmol), were added EtOH (26.7 mL, 459 mmol) and CCl$_4$ (0.369 mL). THF (76.5 mL) was slowly added to control the reaction, which was later heated to 70° C. to consume all the magnesium. The reaction mixture was then cooled, and the acid chloride formed from 4-(3,4-difluorophenyl)-tetrahydro-2H-pyran-4-carboxylic acid (12.36 g, 51.0 mmol; converted to the acid chloride by reaction with thionyl chloride at 65° C. for 1 hour and then concentrated) was added dropwise as an ether solution via addition funnel. After stirring for 30 minutes at ambient temperature, the reaction mixture was quenched with 5N HCl, diluted with 400 mL of EtOAc, added to a separatory funnel, partitioned with water, washed 3 times with 100 mL of water, separated, dried over Na$_2$SO$_4$, and concentrated in vacuo to give the title compound (20.52 g) as a brown oil. MS (m/z)=385 (M+H)$^+$.

Step D: Preparation of Ethyl 6,7-difluoro-4-hydroxy-2-oxo-2',3',5',6'-tetrahydro-spiro[naphthalene-1,4'-pyran]-3-carboxylate P$_2$O$_5$ (4.45 g, 31.3 mmol) was added to H$_2$SO$_4$ (4.17 mL, 78.3 mmol), the mixture was cooled to 0° C., and diethyl 2-(4-(3,4-difluorophenyl)-tetrahydro-2H-pyran-4-carbonyl)malonate (3.01 g, 7.83 mmol) was added at 0° C. The reaction mixture was stirred for 4 hours and then poured into ice, diluted with 200 mL of EtOAc, added to a separatory funnel, partitioned with water, washed 2 times with 75 mL of water, separated, dried over Na$_2$SO$_4$, and concentrated in vacuo to give the title compound which was used without further purification. MS (m/z)=339 (M+H)$^+$.

Step E: Preparation of 1,1-Dimethylethyl N-((6,7-difluoro-4-hydroxy-2-oxo-2',3',5',6'-tetrahydro-spiro[naphthalene-1,4'-pyran]-3-yl)carbonyl)glycinate Ethyl 6,7-difluoro-4-hydroxy-2-oxo-2',3',5',6'-tetrahydro-spiro[naphthalene-1,4'-pyran]-3-carboxylate (1.06 g, 3133 μmol) was dissolved in 1,4-dioxane (3133 μL) and N-ethyl-N-isopropylpropan-2-amine (1637 μL, 9400 μmol). tert-Butyl 2-aminoacetate hydrochloride (788 mg, 4700 μmol) was added, and the reaction was placed in a microwave at 140° C. for 10 minutes. The reaction mixture was then diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound as a white solid after purification via preparatory LC. MS (m/z)=424 (M+H)$^+$.

Step F: Preparation of N-((6,7-Difluoro-4-hydroxy-2-oxo-2',3',5',6'-tetrahydro-spiro[naphthalene-1,4'-pyran]-3-yl)carbonyl)glycine 1,1-Dimethylethyl N-((6,7-difluoro-4-hydroxy-2-oxo-2',3',5',6'-tetrahydro-spiro[naphthalene-1,4'-pyran]-3-yl)carbonyl)glycinate (152 mg, 359 μmol) was dissolved in TFA at ambient temperature for 30 minutes and then concentrated, precipitated with hexanes, filtered, washed with hexanes, and dried in a vacuum oven to give the title compound (115 mg) as a white solid. MS (m/z)=368 (M+H)$^+$. Calculated for C$_{17}$H$_{15}$F$_2$NO$_6$ 367.09.

Example 59

N-((6,7-Difluoro-4-hydroxy-1,1-dimethyl-2-oxo-naphthalen-3-yl)carbonyl)glycine

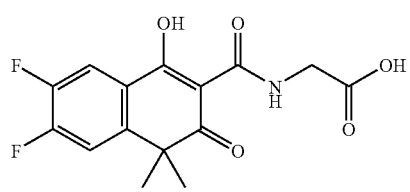

Step A: Preparation of 2-(3,4-Difluorophenyl)-2-methylpropanenitrile 2-(3,4-Difluorophenyl)acetonitrile (25.0 g, 163 mmol) and MeI (25.4 mL, 408 mmol) were dissolved in DMF (163 mL) and added dropwise to a suspension of sodium tert-butoxide (39.2 g, 408 mmol) in DMF at 0° C. The resulting reaction mixture was stirred at 0° C. for 1 hour and then allowed to warm to ambient temperature for 1 hour. The reaction mixture was diluted with 400 mL of EtOAc, added to a separatory funnel, partitioned with water, washed 3 times with 200 mL of water, separated, dried over $Na_2SO_4$, and concentrated in vacuo to give the title compound (26.45 g) as a yellow oil.

Step B: Preparation of 2-(3,4-Difluorophenyl)-2-methylpropanoic acid

9M $H_2SO_4$ (176 mL) was added to 2-(3,4-difluorophenyl)-2-methylpropanenitrile (19.15 g, 106 mmol). The resulting mixture was heated at 180° C. for 2 hours and then was diluted with 100 mL of diethyl ether. The resulting mixture was added to a separatory funnel, and the organic phase was separated from the aqueous layer. The organic layer was partitioned with 5N NaOH (aqueous), and extracted 1 time with 50 mL of 5N NaOH (aqueous). The aqueous layers were acidified to pH=2 with 3N HCl and extracted 2 times with 200 mL of diethyl ether, dried over $Na_2SO_4$, and concentrated in vacuo to give the title compound.

Step C: Preparation of Diethyl 2-(2-(3,4-difluorophenyl)-2-methylpropanoyl)malonate EtOH (44.5 mL) and $CCl_4$ (0.614 mL) were added to a mixture of diethyl malonate (19.2 mL, 127 mmol) and magnesium (3.09 g, 127 mmol) at ambient temperature. THF (255 mL) was slowly added to control the temperature. The reaction mixture was then heated at 70° C. for 1 hour. The acid chloride formed from 2-(3,4-difluorophenyl)-2-methylpropanoic acid (17.0 g, 84.9 mmol; converted to the acid chloride by reaction with thionyl chloride at 65° C. for 1 hour and then concentrated) was added dropwise as an ether solution via addition funnel to the cooling reaction mixture above, and the reaction was then stirred for 1 hour. The reaction mixture was diluted with 400 mL of EtOAc, added to a separatory funnel, partitioned with $NaHCO_3$ (saturated, aqueous), washed 2 times 150 mL of $NaHCO_3$ (saturated, aqueous), separated, dried over $Na_2SO_4$, and concentrated in vacuo to give the title compound (32.42 g) which was used without further purification. MS (m/z)=343 (M+H)$^+$.

Step D: Preparation of Ethyl-6,7-difluoro-4-hydroxy-1,1-dimethyl-2-oxo-naphthalene-3-carboxylate $P_2O_5$ (26.9 g, 189 mmol) was added to concentrated $H_2SO_4$ (50.5 mL) at 0° C. Diethyl 2-(2-(3,4-difluorophenyl)-2-methylpropanoyl)malonate (32.42 g, 94.7 mmol) was added at 0° C., and the reaction mixture was allowed to warm to ambient temperature and stirred for 16 hours. The resulting reaction mixture was then poured into ice, diluted with 400 mL of EtOAc, added to a separatory funnel, partitioned with water, washed 3 times with 75 mL of water, separated, dried over $Na_2SO_4$, and concentrated in vacuo to give the title compound as a beige yellow amorphous solid which was used without further purification. MS (m/z)=297 (M+H)$^+$.

Step E: Preparation of 1,1-Dimethylethyl N-((6,7-difluoro-4-hydroxy-1,1-dimethyl-2-oxo-naphthalen-3-yl)carbonyl)glycinate To a mixture of ethyl 6,7-difluoro-4-hydroxy-1,1-dimethyl-2-oxo-naphthalene-3-carboxylate (570 mg, 1924 µmol) in 1,4-dioxane (3848 µL) and N-ethyl-N-isopropylpropan-2-amine (1005 µL, 5772 µmol), was added tert-butyl 2-aminoacetate hydrochloride (484 mg, 2886 µmol). The reaction was then heated at 80° C. for 3 hours. The reaction mixture was then diluted with 100 mL of EtOAc, added to a separatory funnel, partitioned with $NaHCO_3$ (saturated, aqueous), washed 2 times with 50 mL of $NaHCO_3$ (saturated, aqueous), separated, dried over $Na_2SO_4$, and concentrated in vacuo to give the title compound (312 mg) as a white solid after flash chromatography. MS (m/z)=404 (M+Na)$^+$.

Step F: Preparation of N-((6,7-Difluoro-4-hydroxy-1,1-dimethyl-2-oxo-naphthalen-3-yl)carbonyl)glycine 1,1-Dimethylethyl N-((6,7-difluoro-4-hydroxy-1,1-dimethyl-2-oxo-naphthalen-3-yl)carbonyl)glycinate (312 mg, 818 µmol) was dissolved in TFA (2 mL) at ambient temperature and reacted for 30 minutes. The mixture was then concentrated, precipitated with hexanes, filtered, and dried in a vacuum oven to give the title compound (228 mg, 85.7% yield) as a white solid. MS (m/z)=326 (M+H)$^+$. Calculated for $C_{15}H_{13}F_2NO_5$ 325.08.

Example 60

N-((6'-Chloro-4'-hydroxy-2'-oxo-spiro[cyclohexane-1,1'-naphthalen]-3'-yl)carbonyl)glycine

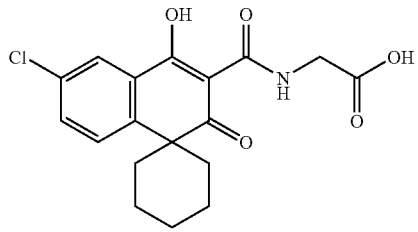

Step A: Preparation of Diethyl 2-(1-(4-chlorophenyl)-cyclohexanecarbonyl)malonate To diethyl malonate (23.7 mL, 157 mmol) and magnesium (3.82 g, 157 mmol) were added EtOH (54.9 mL, 942 mmol) and $CCl_4$ (0.758 mL, 7.85 mmol). THF (157 mL) was added to control the reaction temperature. The reaction mixture was then heated at 70° C. for 1.5 hours and then cooled to ambient temperature. The acid chloride formed from 1-(4-chlorophenyl)cyclohexanecarboxylic acid (25.0 g, 105 mmol; converted to the acid chloride by reaction with thionyl chloride at 65° C. for 1 hour and then concentrated) was then added dropwise as an ether solution via addition funnel. The reaction mixture was stirred for 1 hour at ambient temperature and then quenched with 5N HCl, diluted with 200 mL of EtOAc, added to a separatory funnel, partitioned with water, washed 2 times with 50 mL of water, separated, dried over $Na_2SO_4$, and concentrated in vacuo to give the title compound (43.8 g).

Step B: Preparation of Ethyl 6'-chloro-4'-hydroxy-2'-oxo-spiro[cyclohexane-1,1'-naphthalene]-3'-carboxylate Triflic acid (40.4 mL) was added dropwise via addition funnel to diethyl 2-(1-(4-chlorophenyl)cyclohexanecarbonyl)malonate (17.65 g, 46.3 mmol) at 0° C. The resulting mixture was stirred for 1 hour and then poured into a beaker of ice. The resulting mixture was diluted with 150 mL of EtOAc, added to a separatory funnel, partitioned with water, washed 2 times with 75 mL of NaHCO$_3$ (saturated, aqueous), separated, dried over Na$_2$SO$_4$, and concentrated in vacuo to give the title compound (7.24 g) which was used without further purification. MS (m/z)=335 (M+H)$^+$.

Step C: Preparation of 1,1-Dimethylethyl N-((6'-chloro-4'-hydroxy-2'-oxo-spiro[cyclohexane-1,1'-naphthalen]-3'-yl)carbonyl)glycinate tert-Butyl 2-aminoacetate hydrochloride (901 mg, 5376 µmol) was added to a mixture of ethyl 6'-chloro-4'-hydroxy-2'-oxo-spiro[cyclohexane-1,1'-naphthalene]-3'-carboxylate (1.20 g, 3584 µmol) in 1,4-dioxane (3584 µL) and N-ethyl-N-isopropylpropan-2-amine (1873 µL, 10753 µmol). The resulting mixture was heated at 80° C. for 2 hours. The resulting mixture was then diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (185 mg) as a light yellow solid after purification via preparatory HPLC. MS (m/z)=364 (M+H-tBu)$^+$.

Step D: Preparation of N-((6'-Chloro-4'-hydroxy-2'-oxo-spiro[cyclohexane-1,1'-naphthalen]-3'-yl)carbonyl)glycine 1,1-Dimethylethyl N-((6'-chloro-4'-hydroxy-2'-oxo-spiro[cyclohexane-1,1'-naphthalen]-3'-yl)carbonyl)glycinate (185 mg, 441 µmol) was dissolved in TFA (2 mL) at ambient temperature for 30 minutes. The reaction mixture was then concentrated, and the product was precipitated with hexanes, filtered, washed with ether, and dried in a vacuum oven to give the title compound (119 mg) as a white solid. MS (m/z)=364 (M+H)$^+$. Calculated for $C_{18}H_{18}ClNO_5$ 363.09.

Example 61

N-((6-Methyl-4-hydroxy-1,1-dimethyl-2-oxo-naphthalen-3-yl)carbonyl)glycine

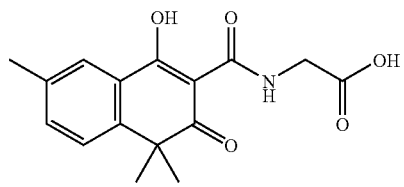

Step A: Preparation of 2-Methyl-2-p-tolylpropanenitrile

NaH (60% dispersion in oil, 14.2 g, 354 mmol) was added to THF (322 mL). The mixture was then cooled to 0° C., and an ether solution of p-tolylacetonitrile (21.12 g, 161 mmol) and MeI (22.1 mL, 354 mmol) was added dropwise via addition funnel. The reaction mixture was allowed to warm to ambient temperature and stirred for 16 hours. The reaction mixture was then quenched with water, acidified with 5N HCl, diluted with 200 mL of diethyl ether, added to a separatory funnel, partitioned with water, washed 2 times with 50 mL of water, separated, dried over Na$_2$SO$_4$, and concentrated in vacuo to give the title compound (17.0 g) as an amber oil. MS (m/z)=319 (M+H)$^+$ (dimer).

Step B: Preparation of 2-Methyl-2-p-tolylpropanoic acid

9M H$_2$SO$_4$ (65.0 mL) was added to 2-methyl-2-p-tolylpropanenitrile (6.21 g, 39.0 mmol). The reaction mixture was then heated at 180° C. in a sealed tube for 2 hours. The reaction mixture was cooled to ambient temperature, diluted with 100 mL of diethyl ether, added to a separation funnel, washed with 5N HCl, partitioned with 5N NaOH (aqueous), washed 2 times with 20 mL of 5N NaOH (aqueous), and separated before the aqueous layer was acidified to pH=3 with 3N HCl and extracted 3 times with 75 mL of diethyl ether, dried over Na$_2$SO$_4$, and concentrated in vacuo to give the title compound (5.27 g) as brownish yellow amorphous solid. MS (m/z)=180 (M+H)$^+$.

Step C: Preparation of Diethyl 2-(2-methyl-2-p-tolylpropanoyl)malonate

To a mixture of magnesium (1.08 g, 44.3 mmol) and diethyl malonate (6.70 mL, 44.3 mmol) were added EtOH (15.5 mL, 266 mmol) and CCl$_4$ (0.21 mL) at ambient temperature. The reaction was controlled by slowly adding THF (44 mL). The reaction mixture was stirred at 70° C. for 1 hour and then allowed to cool. The acid chloride formed from 2-methyl-2-p-tolylpropanoic acid (5.27 g, 29.6 mmol; converted to the acid chloride by reaction with thionyl chloride at 65° C. for 1 hour, and then concentrating) was added dropwise as an ether solution via addition funnel. The resulting mixture was stirred for 30 minutes at ambient temperature and then quenched with 5N HCl. The mixture was diluted with 200 mL of diethyl ether, added to a separatory funnel, partitioned with water, washed 2 times with 75 mL of water, separated, dried over Na$_2$SO$_4$, and concentrated in vacuo to give the title compound (9.24 g) as a brown oil which was used without further purification. MS (m/z)=321 (M+H)$^+$.

Step D: Preparation of Ethyl 4-hydroxy-1,1,6-trimethyl-2-oxo-naphthalene-3-carboxylate Concentrated H$_2$SO$_4$ (11.5 mL, 216 mmol) was added dropwise via addition funnel to stirred diethyl 2-(2-methyl-2-p-tolylpropanoyl)malonate (6.92 g, 21.6 mmol) at 0° C. The reaction mixture was stirred for 1.5 hours and then poured into a flask of ice, diluted with 200 mL of EtOAc, added to a separatory funnel, partitioned with water, washed 2 times with 75 mL of water, separated, dried over Na$_2$SO$_4$, and concentrated in vacuo to give the title compound (3.05 g) as a brown oil which was used without further purification. MS (m/z)=275 (M+H)$^+$.

Step E: Preparation of 1,1-Dimethylethyl N-((6-methyl-4-hydroxy-1,1-dimethyl-2-oxo-naphthalen-3-yl)carbonyl)glycinate Ethyl 4-hydroxy-1,1,6-trimethyl-2-oxo-naphthalene-3-carboxylate (750 mg, 2734 µmol) was dissolved in 1,4-dioxane (2734 μL) and N-ethyl-N-isopropylpropan-2-amine (1429 μL, 8202 μmol). tert-Butyl 2-aminoacetate hydrochloride (687 mg, 4101 μmol) was added, and the reaction was stirred at 80° C. for 1 hour. The reaction mixture was cooled to ambient temperature, diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (266 mg) as a white solid after flash chromatography. MS (m/z)=304 (M+H-tBu)$^+$.

Step F: Preparation of N-((6-Methyl-4-hydroxy-1,1-dimethyl-2-oxo-naphthalen-3-yl)carbonyl)glycine 1,1-Dimethylethyl N-((6-methyl-4-hydroxy-1,1-dimethyl-2-oxo-naphthalen-3-yl)carbonyl)glycinate (255 mg, 709 μmol) was dissolved in TFA (3 mL) at ambient temperature for 30 minutes. The reaction mixture was then concentrated, precipitated with hexanes, filtered, and dried in a vacuum oven to give the title compound (192 mg) as a white solid. MS (m/z)=304 (M+H)$^+$. Calculated for C$_{16}$H$_{17}$NO$_5$ 303.11.

Example 62

N-((6,7-Dichloro-4-hydroxy-2-oxo-2',3',5',6'-tetrahydro-spiro[naphthalene-1,4'-pyran]-3-yl)carbonyl)glycine

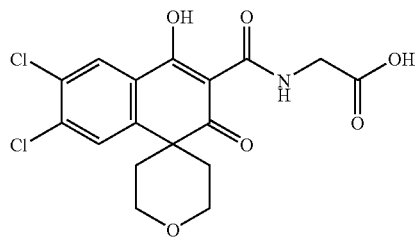

Step A: Preparation of 4-(3,4-Dichlorophenyl)-tetrahydro-2H-pyran-4-carbonitrile 3,4-Dichlorophenylacetonitrile (10.00 g, 53.8 mmol) and bis(2-bromoethyl)ether (12.5 g, 53.8 mmol) were dissolved in ether and added dropwise via addition funnel to a suspension of NaH (60% dispersion in mineral oil; 6.45 g, 161 mmol) in 1-methylpyrrolidone (108 mL) at 0° C. The reaction mixture was stirred at 0° C. for 1 hour and was then allowed to warm to ambient temperature. The reaction was then quenched with water. 5N HCl was added, and the reaction mixture was diluted with 200 mL of diethyl ether, added to a separatory funnel, washed 2 times with 100 mL of ether, separated, dried over Na$_2$SO$_4$, and concentrated in vacuo to give the purified title compound (7.97 g) after flash chromatography.

Step B: Preparation of 4-(3,4-Dichlorophenyl)-tetrahydro-2H-pyran-4-carboxylic acid 9M H$_2$SO$_4$ (43.7 mL) was added to 4-(3,4-dichlorophenyl)-tetrahydro-2H-pyran-4-carbonitrile (6.72 g, 26.2 mmol) in a vial. The sealed vial was heated to 180° C. for 1 hour, and the reaction mixture was cooled to ambient temperature, diluted with 200 mL of diethyl ether, added to a separation funnel, partitioned with 5N NaOH (aqueous), washed 1 time with 75 mL of 5N NaOH (aqueous), and separated before the aqueous layer was acidified to pH=4 with 3N HCl and extracted 3 times with 75 mL of diethyl ether, dried over Na$_2$SO$_4$, and concentrated in vacuo to give the title compound which was used without further purification.

Step C: Preparation of Diethyl 2-(4-(3,4-dichlorophenyl)-tetrahydro-2H-pyran-4-carbonyl)malonate To magnesium (0.868 g, 35.7 mmol) and diethyl malonate (5.39 mL, 35.7 mmol) were added EtOH (12.5 mL, 214 mmol) and CCl$_4$ (0.172 mL). THF (35.7 mL) was slowly added to keep the temperature down and control the reaction. The reaction mixture was then heated at 70° C. for 1 hour and then cooled to room temperature. Meanwhile, the acid chloride of 4-(3,4-dichlorophenyl)-tetrahydro-2H-pyran-4-carboxylic acid (6.55 g, 23.8 mmol) was formed by addition of thionyl chloride (20 mL) followed by heating to 65° C. for 1 hour. The mixture was cooled, concentrated and redissolved in ether (20 mL). The resulting acid chloride solution was added dropwise via addition funnel to the magnesium enolate as prepared above. The reaction mixture was stirred for 1 hour and quenched with 5N HCl and then diluted with 200 mL of EtOAc, added to a separatory funnel, partitioned with water, washed 3 times with 75 mL of water, separated, dried over Na$_2$SO$_4$, and concentrated in vacuo to give the title compound (3.94 g) as an off-white after flash chromatography. MS (m/z)=417 (M+H)$^+$.

Step D: Preparation of Ethyl 6,7-dichloro-4-hydroxy-2-oxo-2',3',5',6'-tetrahydro-spiro[naphthalene-1,4'-pyran]-3-carboxylate Concentrated H$_2$SO$_4$ (4203 μL) was added to solid diethyl 2-(4-(3,4-dichlorophenyl)-tetrahydro-2H-pyran-4-carbonyl)malonate (3.29 g, 7884 μmol) at ambient temperature. The reaction was heated at 50° C. for 6 hours and then poured into a flask of ice, diluted with 150 mL of EtOAc, added to a separatory funnel, partitioned with water, washed 2 times with 50 mL of water, separated, dried over Na$_2$SO$_4$, and concentrated in vacuo to give the purified title compound (375 mg) after flash chromatography as a pale yellow solid. MS (m/z)=371 (M+H)$^+$.

Step E: Preparation of 1,1-Dimethylethyl N-((6,7-dichloro-4-hydroxy-2-oxo-2',3',5',6'-tetrahydro-spiro [naphthalene-1,4'-pyran]-3-yl)carbonyl)glycinate Ethyl 6,7-dichloro-4-hydroxy-2-oxo-2',3',5',6'-tetrahydro-spiro[naphthalene-1,4'-pyran]-3-carboxylate (550 mg, 1482 μmol) was dissolved in 1,4-dioxane (1482 μL), and N-ethyl-N-isopropylpropan-2-amine (774 μL, 4445 μmol). tert-Butyl 2-aminoacetate hydrochloride (373 mg, 2222 μmol) was added to the reaction, and the reaction was stirred at 80° C. for 3 hours. The reaction mixture was diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (350 mg) as a white solid after flash chromatography. MS (m/z)= 456 (M+H)$^+$.

Step F: Preparation of N-((6,7-Dichloro-4-hydroxy-2-oxo-2',3',5',6'-tetrahydro-spiro[naphthalene-1,4'-pyran]-3-yl)carbonyl)glycine 1,1-Dimethylethyl N-((6,7-dichloro-4-hydroxy-2-oxo-2', 3',5',6'-tetrahydro-spiro[naphthalene-1,4'-pyran]-3-yl)carbonyl)glycinate (350 mg, 767 μmol) was dissolved in TFA (3 mL). The resulting mixture was stirred for 1 hour and then concentrated, precipitated with hexanes, sonicated, filtered, washed with hexanes, and dried in a vacuum oven to give the title compound (268 mg, 87.3% yield) as a white solid. MS (m/z)=400 (M+H)$^+$. Calculated for $C_{17}H_{15}Cl_2NO_6$ 399.03.

Example 63

N-((4-Hydroxy-1,1-dimethyl-2-oxo-naphthalen-3-yl)carbonyl)glycine

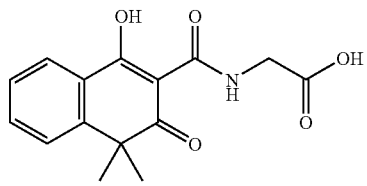

Step A: Preparation of Diethyl 2-(2-methyl-2-phenylpropanoyl)malonate

EtOH (31.9 mL) and CCl$_4$ (0.441 mL) were added to magnesium (2.22 g, 91.3 mmol) and diethyl malonate (13.8 mL, 91.3 mmol) at ambient temperature. THF (91.3 mL) was added slowly to control the reaction and maintain the temperature under reflux. The reaction mixture was then heated to 70° C. for 2 hours and cooled to room temperature. Meanwhile, the acid chloride of alpha,alpha-dimethylphenylacetic acid (10.0 g, 60.9 mmol) was formed by addition of thionyl chloride (30 mL) followed by heating to 65° C. for 1 hour. The mixture was cooled, concentrated and redissolved in ether (20 mL). The resulting acid chloride solution was added dropwise via addition funnel to the magnesium enolate as prepared above. The reaction mixture was stirred for 1 hour and then quenched with 1N HCl, diluted with 200 mL of diethyl ether, added to a separatory funnel, partitioned with water, washed 2 times with 50 mL of water, separated, dried over Na$_2$SO$_4$, and concentrated in vacuo to give the title compound (22.11 g). MS (m/z)=307 (M+H)$^+$.

Step B: Preparation of Ethyl 4-hydroxy-1,1-dimethyl-2-oxo-naphthalene-3-carboxylate Concentrated H$_2$SO$_4$ (38.5 mL) was added dropwise via addition funnel to diethyl 2-(2-methyl-2-phenylpropanoyl)malonate (22.1 g, 72.1 mmol) cooled to 0° C. The reaction mixture was stirred for 2 hours at 0° C. and then poured into a flask containing ice, diluted with 400 mL of EtOAc, added to a separatory funnel, partitioned with water, washed 2 times with 100 mL of water, separated, dried over Na$_2$SO$_4$, and concentrated in vacuo to give the title compound (10.82 g) as a white amorphous solid after flash chromatography. MS (m/z)=261 (M+H)$^+$.

Step C: Preparation of 1,1-Dimethylethyl N-((4-hydroxy-1,1-dimethyl-2-oxo-naphthalen-3-yl)carbonyl)glycinate Ethyl 4-hydroxy-1,1-dimethyl-2-oxo-naphthalene-3-carboxylate (425 mg, 1633 μmol) was dissolved in 1,4-dioxane (1633 μL) and N-ethyl-N-isopropylpropan-2-amine (853 μL, 4898 μmol). tert-Butyl 2-aminoacetate hydrochloride (411 mg, 2449 μmol) was added, and the mixture was heated at 80° C. for 4 hours. The reaction mixture was then cooled, diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (279 mg) as a white solid after purification via preparatory LC. MS (m/z)=290 (M+H-tBu)$^+$.

Step D: Preparation of N-((4-Hydroxy-1,1-dimethyl-2-oxo-naphthalen-3-yl)carbonyl)glycine 1,1-Dimethylethyl N-((4-hydroxy-1,1-dimethyl-2-oxo-naphthalen-3-yl)carbonyl)glycinate (270 mg, 782 μmol) was dissolved in TFA (2 mL) at ambient temperature. The mixture was then stirred for 30 minutes. The reaction mixture was concentrated, suspended in hexanes, filtered, washed with hexanes, and dried in a vacuum oven to give the title compound (215 mg) as a white solid. MS (m/z)=290 (M+H)$^+$. Calculated for $C_{15}H_{15}NO_5$ 289.1.

Example 64

N-((6,7-Dichloro-4-hydroxy-1,1-dimethyl-2-oxo-naphthalen-3-yl)carbonyl)glycine

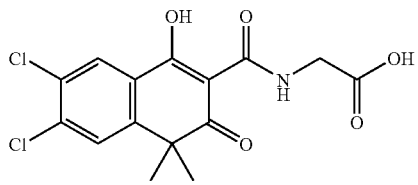

Step A: Preparation of Methyl 2-(3,4-dichlorophenyl)acetate 2-(3,4-Dichlorophenyl)acetic acid (25.0 g, 122 mmol) was dissolved in MeOH (122 mL) at ambient temperature. Sulfuryl dichloride (8.89 mL, 122 mmol) was then added, and the mixture was stirred for 2 hours. The reaction mixture was concentrated in vacuo to give the title compound as a light yellow oil which was used without further purification. MS (m/z)=219 (M+H)$^+$.

Step B: Preparation of Methyl 2-(3,4-dichlorophenyl)-2-methylpropanoate

To NaH (60% in mineral oil) (10.7 g, 268 mmol) in THF (244 mL), was added dropwise through an addition funnel a mixture of methyl 2-(3,4-dichlorophenyl)acetate (26.7 g, 122 mmol) and MeI (16.7 mL, 268 mmol) in ether at 0° C. The reaction mixture was warmed to ambient temperature and stirred for 4 hours and then quenched with water and acidified with 3N HCl. The reaction mixture was diluted with 200 mL of diethyl ether, added to a separatory funnel, partitioned with water, washed 3 times with 50 mL of water, separated, dried over Na$_2$SO$_4$, and concentrated in vacuo to give the title compound (22.03 g) as a brown oil after flash chromatography. MS (m/z)=247 (M+H)$^+$.

Step C: Preparation of 2-(3,4-Dichlorophenyl)-2-methylpropanoic acid

To methyl 2-(3,4-dichlorophenyl)-2-methylpropanoate (22.03 g, 89.1 mmol) was added THF/water (4:1) (178 mL)

and lithium hydroxide hydrate (22.4 g, 535 mmol). The reaction was then stirred at 50° C. for 3 days. The reaction mixture was acidified with 3N HCl, diluted with 200 mL of diethyl ether, added to a separatory funnel, partitioned with water, washed 2 times with 100 mL of water, separated, dried over $Na_2SO_4$, and concentrated in vacuo to give the title compound which was used without further purification. MS (m/z)=233 $(M+H)^+$.

Step D: Preparation of Diethyl 2-(2-(3,4-dichlorophenyl)-2-methylpropanoyl)malonate To magnesium (3.23 g, 133 mmol) and diethyl malonate (20.1 mL, 133 mmol) were added EtOH (46.4 mL) and $CCl_4$ (0.641 mL) at ambient temperature. THF (133 mL) was slowly added to control the reaction and keep the temperature below reflux. After the Mg was visibly consumed, the reaction mixture was stirred at 70° C. for 2 hours and cooled to room temperature. Meanwhile, 2-(3,4-dichlorophenyl)-2-methylpropanoyl chloride (22.4 g, 89.1 mmol) was prepared by heating to 65° C. for 2 hours with thionyl chloride (50 mL). The acid chloride solution was concentrated, dissolved in THF (20 mL) and added dropwise to the magnesium enolate as prepared above. The resulting reaction mixture was stirred at 70° C. for 1 hour and then cooled, quenched with 3N HCl, diluted with 400 mL of diethyl ether, added to a separatory funnel, partitioned with water, washed 2 times with 100 mL of water, separated, dried over $Na_2SO_4$, and concentrated in vacuo to give the title compound (27.85 g) as a yellow oil after flash chromatography. MS (m/z)=375 $(M+H)^+$.

Step E: Preparation of Ethyl 6,7-dichloro-4-hydroxy-1,1-dimethyl-2-oxo-naphthalene-3-carboxylate Concentrated $H_2SO_4$ (52.5 mL, 621 mmol) was added dropwise via an addition funnel to diethyl 2-(2-(3,4-dichlorophenyl)-2-methylpropanoyl)malonate (11.66 g, 31.1 mmol) cooled to 0° C. The reaction mixture was allowed to slowly warm to ambient temperature and then poured into a beaker of ice, diluted with 200 mL of EtOAc, added to a separatory funnel, partitioned with water, washed 2 times with 50 mL of water, separated, dried over $Na_2SO_4$, and concentrated in vacuo to give the title compound (9.61 g) as a white amorphous solid. MS (m/z)=329 $(M+H)^+$.

Step F: Preparation of 1,1-Dimethylethyl N-((6,7-dichloro-4-hydroxy-1,1-dimethyl-2-oxo-naphthalen-3-yl)carbonyl)glycinate Ethyl 6,7-dichloro-4-hydroxy-1,1-dimethyl-2-oxo-naphthalene-3-carboxylate (325 mg, 987 μmol) was dissolved in 1,4-dioxane (987 μL) and N-ethyl-N-isopropylpropan-2-amine (516 μL, 2962 μmol). tert-Butyl 2-aminoacetate hydrochloride (248 mg, 1481 μmol) was added, and the reaction was stirred at 80° C. for 4 hours. The reaction mixture was then diluted with 100 mL of EtOAc, added to a separatory funnel, partitioned with $NaHCO_3$ (saturated, aqueous), washed 2 times with 20 mL of $NaHCO_3$ (saturated, aqueous), separated, dried over $Na_2SO_4$, and concentrated in vacuo to give the title compound (235 mg) as an off-white solid after purification via preparatory LC. MS (m/z)=358 $(M+H-tBu)^+$.

Step G: Preparation of N-((6,7-Dichloro-4-hydroxy-1,1-dimethyl-2-oxo-naphthalen-3-yl)carbonyl)glycine To 1,1-dimethylethyl N-((6,7-dichloro-4-hydroxy-1,1-dimethyl-2-oxo-naphthalen-3-yl)carbonyl)glycinate (235 mg, 567 μmol) was added TFA (2 mL) at ambient temperature. The mixture was stirred for 30 minutes and then concentrated, precipitated with ether, filtered, washed with ether, and dried in a vacuum oven to give the title compound (95 mg) as a white solid. MS (m/z)=358 $(M+H)^+$. Calculated for $C_{15}H_{13}Cl_2NO_5$ 357.02.

Example 65

N-((6-(2-Methylphenyl)-4-hydroxy-1,1-dimethyl-2-oxo-naphthalen-3-yl)carbonyl)glycine

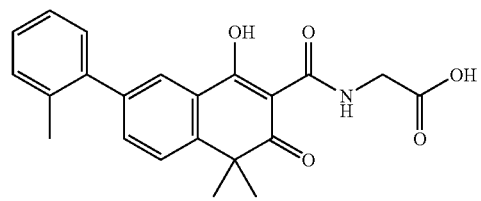

Step A: Preparation of 1,1-Dimethylethyl N-((6-(2-methylphenyl)-4-hydroxy-1,1-dimethyl-2-oxo-naphthalen-3-yl)carbonyl)glycinate To 1,1-dimethylethyl N-((6-chloro-4-hydroxy-1,1-dimethyl-2-oxo-naphthalen-3-yl)carbonyl)glycinate (250 mg, 658 μmol, Example 40A-D) and o-tolylboronic acid (134 mg, 987 μmol), were added 1,4-dioxane (3291 μL), and $K_2CO_3$ in water (987 μL, 1975 mmol). The reaction was flushed with nitrogen for 10 minutes. Next, $Pd_2(dba)_3$ (60.3 mg, 65.8 μmol) and X-Phos (62.8 mg, 132 μmol) were added, and the reaction was heated at 110° C. for 4 hours. The reaction mixture was then diluted with 100 mL of EtOAc, added to a separatory funnel, partitioned with $NaHCO_3$ (saturated, aqueous), washed 2 times with 50 mL of $NaHCO_3$ (saturated, aqueous), separated, dried over $Na_2SO_4$, and concentrated in vacuo to give the title compound (160 mg) as a yellow oil. MS (m/z)=380 $(M+H-tBu)^+$.

Step B: Preparation of N-((6-(2-Methylphenyl)-4-hydroxy-1,1-dimethyl-2-oxo-naphthalen-3-yl)carbonyl)glycine 1,1-Dimethylethyl N-((6-(2-methylphenyl)-4-hydroxy-1,1-dimethyl-2-oxo-naphthalen-3-yl)carbonyl)glycinate (160 mg, 367 μmol) was dissolved in TFA (2 mL) at ambient temperature. The reaction was stirred for 30 minutes and then concentrated, precipitated with hexanes, filtered, washed with hexanes, and dried in a vacuum oven to give the title compound (57 mg) as a light yellow solid. MS (m/z)=380 $(M+H)^+$. Calculated for $C_{22}H_{21}NO_5$ 379.14.

Example 66

N-((6-Chloro-4-hydroxy-1,1-dimethyl-2-oxo-naphthalen-3-yl)carbonyl)-L-alanine

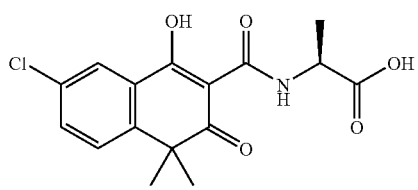

Step A: Preparation of 1,1-Dimethylethyl N-((6-chloro-4-hydroxy-1,1-dimethyl-2-oxo-naphthalen-3-yl)carbonyl)-L-alaninate To ethyl 6-chloro-4-hydroxy-1,1-dimethyl-2-oxo-naphthalene-3-carboxylate (2.44 g, 8.28 mmol, see Example 2) and L-alanine t-butyl ester hydrochloride (2.26 g, 12.4 mmol), were added 1,4-dioxane (5.52 mL) and N-ethyl-N-isopropylpropan-2-amine (4.33 mL, 24.8 mmol). The reaction mixture was then heated in a microwave at 140° C. for 10 minutes. The reaction mixture was diluted with 150 mL of EtOAc, added to a separatory funnel, partitioned with NaHCO$_3$ (saturated, aqueous), washed 3 times with 50 mL of NaHCO$_3$ (saturated, aqueous), separated, dried over Na$_2$SO$_4$, and concentrated in vacuo to give the title compound (0.815 g) as a light yellow amorphous solid after flash chromatography. MS (m/z)=338 (M+H-tBu)$^+$.

Step B: Preparation of N-((6-Chloro-4-hydroxy-1,1-dimethyl-2-oxo-naphthalen-3-yl)carbonyl)-L-alanine To 1,1-dimethylethyl N-((6-chloro-4-hydroxy-1,1-dimethyl-2-oxo-naphthalen-3-yl)carbonyl)-L-alaninate (320 mg, 812 µmol) was added TFA (2 mL) at ambient temperature. The mixture was stirred for 30 minutes and was then concentrated, precipitated with hexanes, filtered, washed, and dried in a vacuum oven to give the title compound (220 mg) as a white solid. MS (m/z)=338 (M+H)$^+$. Calculated for C$_{16}$H$_{16}$ClNO$_5$ 337.07.

Example 67

N-((4'-Hydroxy-2'-oxo-6'-phenyl-spiro[cyclopentane-1,1'-naphthalen]-3'-yl)carbonyl)glycine

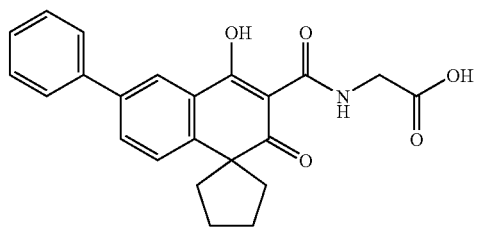

Step A: Preparation of 1,1-Dimethylethyl N-((4'-hydroxy-2'-oxo-6'-phenyl-spiro[cyclopentane-1,1'-naphthalen]-3'-yl)carbonyl)glycinate To 1,1-dimethylethyl N-((4'-hydroxy-2'-oxo-6'-chloro-spiro[cyclopentane-1,1'-naphthalen]-3'-yl)carbonyl)glycinate (250 mg, 616 µmol, Example 25A-B) and phenylboronic acid (113 mg, 924 µmol) were added 1,4-dioxane (3080 µL) and K$_2$CO$_3$ in water (924 µL, 1848 µmol). The reaction was then flushed with nitrogen for 10 minutes. Pd$_2$(dba)$_3$ (56.4 mg, 61.6 µmol) and X-Phos (58.7 mg, 123 µmol) were then added, and the reaction mixture was stirred at 110° C. for 6 hours. The reaction mixture was diluted with 75 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (115 mg) as an oil after preparatory LC. MS (m/z)=392 (M+H-tBu)$^+$.

Step B: Preparation of N-((4'-Hydroxy-2'-oxo-6'-phenyl-spiro[cyclopentane-1,1'-naphthalen]-3'-yl)carbonyl)glycine 1,1-Dimethylethyl N-((4'-hydroxy-2'-oxo-6'-phenyl-spiro[cyclopentane-1,1'-naphthalen]-3'-yl)carbonyl)glycinate (115 mg, 257 µmol) was dissolved in TFA (2 mL) at ambient temperature. The reaction was stirred for 30 minutes and was then concentrated to give an oil, dissolved in ether, concentrated again to give an amorphous solid, precipitated with ether, filtered, washed with ether, and dried in a vacuum oven to give the title compound (21 mg) as a white solid. MS (m/z)=392 (M+H)$^+$. Calculated for the C$_{23}$H$_{21}$NO$_5$ 391.14.

Example 68

N-((6-Phenyl-4-hydroxy-1,1-dimethyl-2-oxo-naphthalen-3-yl)carbonyl)glycine

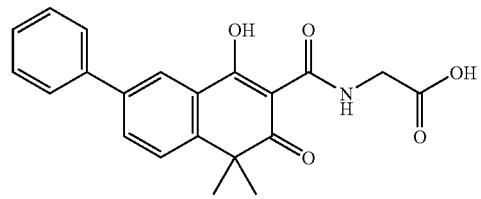

Step A: Preparation of 1,1-Dimethylethyl N-((6-phenyl-4-hydroxy-1,1-dimethyl-2-oxo-naphthalen-3-yl)carbonyl)glycinate To 1,1-dimethylethyl N-((6-bromo-4-hydroxy-1,1-dimethyl-2-oxo-naphthalen-3-yl)carbonyl)glycinate (250 mg, 658 µmol, Example 40A-D), phenylboronic acid (120 mg, 987 µmol), Pd$_2$(dba)$_3$ (60.3 mg, 65.8 µmol), and X-Phos (62.8 mg, 132 µmol), were added dioxane (3291 µL) and K$_2$CO$_3$ in water (987 µL, 1975 µmol). The reaction was then heated at 110° C. for 6 hours. The resulting reaction mixture was cooled to ambient temperature, diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (190 mg) as an amber amorphous solid after purification via prep-LC. MS (m/z)=444 (M+Na)$^+$.

Step B: Preparation of N-((6-Phenyl-4-hydroxy-1,1-dimethyl-2-oxo-naphthalen-3-yl)carbonyl)glycine 1,1-Dimethylethyl N-((6-phenyl-4-hydroxy-1,1-dimethyl-2-oxo-naphthalen-3-yl)carbonyl)glycinate (190 mg, 451 µmol) was dissolved in TFA (2 mL) at ambient temperature. The resulting mixture was then stirred for 30 minutes. The reaction mixture was concentrated, precipitated with ether, filtered, washed with ether, and dried in a vacuum oven to give the title compound (57 mg) as a white solid. MS (m/z)=366 (M+H)$^+$. Calculated for C$_{21}$H$_{19}$NO$_5$ 365.13.

Example 69

N-((4-Hydroxy-2-oxo-2',3',5',6'-tetrahydro-N-benzyl-spiro[naphthalene-1,4'-piperidine]-3-yl)carbonyl)glycine

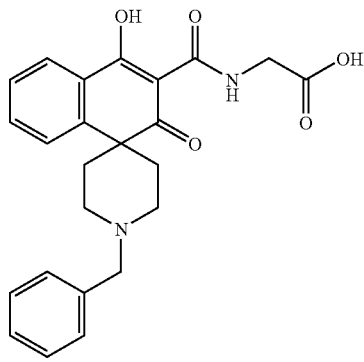

Step A: Preparation of Ethyl 1-benzyl-4-(2-(2-(triethylsilyl)ethynyl)-phenyl)piperidine-4-carboxylate At 0° C., n-BuLi (1.6N, 2 mL, 3.2 mmol, 1.6 eq.) was syringed into a solution of HNCy2 (615 mg, 3.4 mmol, 1.7 eq.) in toluene (6 mL) in a $N_2$-filled 40 mL vial equipped with a stirbar, an open-top cap and an I-Chem septum. The solution was warmed to room temperature, and ethyl 1-benzylpiperidine carboxylate (840 mg, 3.4 mmol, 1.7 eq.) was then syringed into the mixture.

$[PdBrP(t-Bu)_3]_2$ (15 mg, 0.02 mmol, 1%) was weighed into a separate 20 mL vial containing a stir bar. The vial was then capped with an 1-Chem septum cap, and evacuated/refilled with $N_2$ (repeated twice). With $N_2$ needled into the vial, toluene (4 mL) was syringed in, followed by (2-(2-bromo-phenyl)ethynyl)triethylsilane (590 mg, 2.0 mmol). The needle was then removed from the vial, and the vial was heated at 100° C. for 2 minutes with stirring. The vial was allowed to cool for about 1 minute. The whole solution was then pulled into a 10 mL syringe before it completely cooled. The solution was then syringed into the above vial containing the lithium/anion with $N_2$ needled in. The needle was removed. The whole solution was heated at 100° C. and monitored using GC. No (2-(2-bromo-phenyl)ethynyl)triethylsilane remained after 20 minutes. The reaction was cooled to room temperature and filtered through a silica gel plug, eluted with EtOAc (30 mL). The resulting solution was concentrated, absorbed on silica gel and purified by silica flash chromatography (10-30% EtOAc/hexanes) to afford the title compound as a pale-yellow oil (533 mg). MS m/e=462 (M+H)$^+$.

Step B: Preparation of Ethyl 1-benzyl-4-(2-ethynylphenyl)piperidine-4-carboxylate To a solution of ethyl-1-benzyl-4-(2-(2-(triethylsilyl)ethynyl)phenyl)-piperidine-4-carboxylate (0.50 g, 1.1 mmol) and MeOH (10 mL), was added potassium t-butoxide (0.15 g, 1.3 mmol). The reaction mixture was heated at 40° C. for 15 hours. The reaction mixture was then concentrated in vacuo and loaded on a silica gel column and purified by Isco HPLC (0-50% EtOAc/hexane) to give the title compound as a viscous light yellow oil (0.22 g). MS m/e=348 (M+H)$^+$.

Step C: Preparation of Ethyl 1-benzyl-4-(2-(3-ethoxy-3-oxoprop-1-ynyl)phenyl)piperidine-4-carboxylate n-Butyllithium (0.76 mL, 1.9 mmol) was added to a stirred solution of diisopropylamine (0.28 mL, 2.0 mmol) in THF (20 mL, 244 mmol) at −78° C. The reaction mixture was then allowed to warm to ambient temperature for 5 minutes before it was cooled down to −78° C. Ethyl 1-benzyl-4-(2-ethynylphenyl)piperidine-4-carboxylate (0.22 g, 0.63 mmol) was then added dropwise as a solution in THF (20 mL, 244 mmol). After 15 minutes, ethyl chloroformate (0.19 mL, 2.0 mmol) in 5 mL of THF was added to the reaction. The resulting solution was allowed to warm to ambient temperature and then stirred for 30 minutes. MeOH (3 mL) was added, and the resulting mixture was concentrated in vacuo to give a bright-yellow oil. The residue was dissolved in DCM and purified by Isco HPLC (0-80% EtOAc/hexane) to give the title compound as a yellow oil (0.15 g). MS m/e=420 (M+H)$^+$.

Step D: Preparation of Ethyl 4-hydroxy-2-oxo-2',3',5',6'-tetrahydro-N-benzyl-spiro[naphthalene-1,4'-piperidine]-3-carboxylate A solution of benzaldehyde oxime (0.05 g, 0.4 mmol) in dry DMF (5 mL, 65 mmol) was added to a stirred suspension of NaH (0.032 g, 0.4 mmol) in dry 1,4-dioxane (5 mL, 58 mmol) under a $N_2$ atmosphere at room temperature. After 0.5 hours, a solution of the ethyl 1-benzyl-4-(2-(3-ethoxy-3-oxoprop-1-ynyl)phenyl)piperidine-4-carboxylate (0.15 g, 0.4 mmol) in dry DMF (5 mL, 65 mmol) was added, and the solution was stirred for 1 hour. The reaction mixture was concentrated in vacuo. The resulting residue was treated with water (0.5 mL). The crude product was purified by Isco HPLC (0-75% EtOAc/hexane then 10% MeOH/DCM) to afford the title compound as a white solid (0.035 g, 25%). MS m/e=392 (M+H)$^+$.

Step E: Preparation of 1,1-Dimethylethyl N-((4-hydroxy-2-oxo-2',3',5',6'-tetrahydro-N-benzyl-spiro[naphthalene-1,4'-piperidine]-3-yl)carbonyl)glycinate DIPEA (0.1 mL, 766 μmol) was added to a stirred mixture of ethyl 4-hydroxy-2-oxo-2',3',5',6'-tetrahydro-N-benzyl-spiro[naphthalene-1,4'-piperidine]-3-carboxylate (30 mg, 77 mmol) and glycine tert-butyl ester hydrochloride (64 mg, 383 μmol) in 1,4-dioxane (3 mL). The reaction mixture was then stirred at 100° C. for 0.5 hours. The reaction mixture was concentrated in vacuo, and the residue was purified by Isco HPLC (0-50% EtOAc/hexane) to give the title compound as a light-yellow oil (30 mg, 82%). MS m/e=477 (M+H)$^+$.

Step F: Preparation of N-((4-Hydroxy-2-oxo-2',3',5',6'-tetrahydro-N-benzyl-spiro[naphthalene-1,4'-piperidine]-3-yl)carbonyl)glycine A solution of 1,1-dimethylethyl N-((4-hydroxy-2-oxo-2',3',5',6'-tetrahydro-N-benzyl-spiro[naphthalene-1,4'-piperidine]-3-yl)carbonyl)glycinate (30 mg, 63 μmol) and TFA (3 mL) was stirred at room temperature. After 0.5 hours, the reaction was concentrated in vacuo. DCM was added, and the solution was concentrated in vacuo to give the title compound as an off-white solid (33 mg, 100%). MS m/e=421 (M+H)+. Calculated for $C_{24}H_{24}N_2O_5$ 420.46.

Example 70

N-((4-Hydroxy-2-oxo-2',3',5',6'-tetrahydro-spiro [naphthalene-1,4'-piperidine]-3-yl)carbonyl)glycine

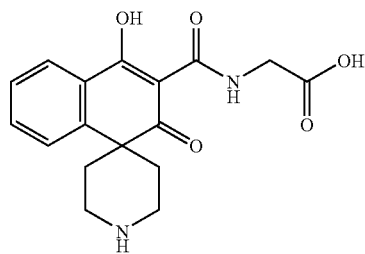

A solution of N-((4-hydroxy-2-oxo-2',3',5',6'-tetrahydro-N-benzyl-spiro[naphthalene-1,4'-piperidine]-3-yl)carbonyl) glycine (8.0 mg, 15 µmol, See Example 69) and MeOH (2 mL) was hydrogenated over 10% Pd/C (0.02 mg, 0.2 µmol) at room temperature and 1 atm. After 3 hours, the reaction mixture was filtered and concentrated in vacuo to give the title compound as a white solid (4.3 mg). MS m/e=331 (M+H)+. Calculated for $C_{17}H_{18}N_2O_5$ 330.34.

Example 71

N-((6-Chloro-4-hydroxy-2-oxo-2',3',5',6'-tetrahydro-N-benzyl-spiro[naphthalene-1,4'-piperidine]-3-yl) carbonyl)glycine

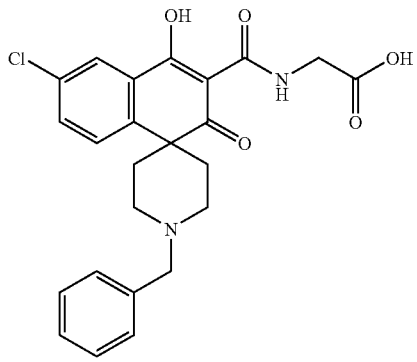

Step A: Preparation of 2-Bromo-5-chlorobenzenamine

A solution of 1-bromo-4-chloro-2-nitrobenzene (13.92 g, 58.87 mmol) in MeOH (300 mL) was treated with water (50 mL), ammonium chloride (22.99 g, 429.8 mmol), and iron powder (325 mesh, 16.44 g, 294.4 mmol). The suspension was stirred at 23° C. After 18 hours, the suspension was filtered through celite. The filter cake was washed with MeOH (500 mL). The combined filtrate/washings were concentrated, partitioned in EtOAc/water (500 mL/200 mL), and the organic layer was separated. The aqueous layer was washed with EtOAc (2×200 mL). The organic layers were combined, washed with brine (200 mL), dried (MgSO4), and concentrated in vacuo affording 11.51 g of 2-bromo-5-chlorobenzenamine.

Step B: Preparation of 1-Bromo-4-chloro-2-iodobenzene

A suspension of 2-bromo-5-chlorobenzenamine (11.348 g, 54.963 mmol) in concentrated HCl (100 mL) was cooled to 0° C. and treated dropwise over 20 minutes (using an addition funnel) with a solution of sodium nitrite (4.5506 g, 65.955 mmol) in water (20 mL). The reaction was stirred at 0° C. for 75 minutes. A solution of potassium iodide (27.372 g, 164.89 mmol) in water (50 mL) was added, and the reaction was stirred at 23° C. After 1 hour, the reaction was heated to 70° C. After 18 hours, the reaction was diluted with EtOAc (500 mL) and washed with water (300 mL), 2N NaOH solution (300 mL), saturated sodium thiosulfate solution (300 mL) and brine (250 mL), dried over MgSO4, concentrated in vacuo, and purified by silica gel chromatography (eluant: hexane) affording 11.11 g of 1-bromo-4-chloro-2-iodobenzene.

Step C: Preparation of 3,3,3-Triethoxyprop-1-yne

A solution of trimethylsilylacetylene (29.4 mL, 20.8 mmol) in diethyl ether (100 mL, anhydrous) was cooled to 0° C. in an oven-dried round bottomed flask under nitrogen. The solution was treated dropwise with butyllithium (2.5M solution in hexanes (83.2 mL, 208.0 mmol)). After 1 hour, the reaction mixture was cooled to −78° C.

A solution of tetraethyl orthocarbonate (21.8 mL, 104.0 mmol) in diethyl ether (50 mL) was added to a separate oven-dried round bottomed flask and cooled to 0° C. under nitrogen. A solution of boron trifluoride diethyletherate (17.6 mL, 140.4 mmol) in diethyl ether (25 mL) was added to the tetraethyl orthocarbonate mixture in a dropwise fashion over 20 minutes (via an addition funnel). The white mixture was stirred at 0° C. for 5 minutes, and then cooled to −78° C., followed by the addition of the TMS-acetylide solution via cannula.

After 1 hour, the reaction was removed from the dry ice-acetone bath and stirred at 23° C. for 15 minutes. The reaction was then quenched with saturated aqueous $K_2CO_3$ solution (300 mL) and extracted with diethyl ether (2×300 mL). The combined organic layers were dried over MgSO4, and concentrated in vacuo affording trimethyl(3,3,3-triethoxyprop-1-ynyl)silane.

A solution of trimethyl(3,3,3-triethoxyprop-1-ynyl)silane (25 g, 102 mmol) in MeOH (400 mL) was treated with $K_2CO_3$ (14 g, 102 mmol). The reaction was stirred at 23° C. After 15 hours, the reaction was diluted with pentane (500 mL). The pentane layer was separated, and the MeOH layer was extracted with pentane (2×250 mL). The combined pentane layers were washed with water (200 mL), dried over MgSO4, and concentrated (at 220 torr on rotary evaporator). The crude product was filtered through a silica gel plug using 10% diethyl ether/pentane as the eluant. The filtrate was then concentrated (at 220 torr on rotary evaporator) affording 13.25 g of 3,3,3-triethoxyprop-1-yne.

Step D: Preparation of 1-Bromo-4-chloro-2-(3,3,3-triethoxyprop-1-ynyl)benzene

A suspension of 1-bromo-4-chloro-2-iodobenzene (2.5 g, 7.9 mmol), 3,3,3-triethoxyprop-1-yne (2.4 g, 13.9 mmol), copper(I) iodide, (455 mg, 2.3 mmol), and trans-dichlorobis (triphenylphosphine)palladium(II) (559 mg, 0.79 mmol) was treated with ACN (30 mL). The reaction was capped, evacuated under vacuum, backfilled with argon, and treated with TEA (9.9 mL, 71.6 mmol). The reaction was stirred at 23° C. After 2 hours, the reaction mixture was concentrated in vacuo to remove all solvents, diluted with EtOAc (250 mL) and washed with brine (150 mL), dried over MgSO$_4$, concentrated in vacuo and purified by silica gel chromatography (eluant: 4% EtOAc/hexane+1% TEA), affording 2.6 g of 1-bromo-4-chloro-2-(3,3,3-triethoxyprop-1-ynyl)benzene.

Step E: Preparation of Ethyl 1-benzyl-4-(4-chloro-2-(3,3,3-triethoxyprop-1-ynyl)phenyl)piperidine-4-carboxylate In a glovebox, ethyl 1-benzylpiperidine-4-carboxylate (2.0 g, 8.1 mmol), LiNCy2 (1.55 g, 8.3 mmol), and toluene (10 mL) were loaded sequentially into a 40 mL vial. In a separate vial, Pd(OAc)$_2$ (22 mg, 0.1 mmol), P(t-Bu)$_3$ (44 mg, 0.22 mmol), 1-bromo-4-chloro-2-(3,3,3-triethoxyprop-1-ynyl) benzene (1.5 g, 4.1 mmol), and toluene (10 mL) were loaded sequentially and were then heated at 100° C. for 1 minute. The enolate solution in vial 1 was then added to the reaction mixture in vial 2 via a syringe. The combined mixture was heated at 100° C. for 40 minutes. The reaction mixture was cooled to 23° C. and passed through a short plug of silica gel eluting with EtOAc (20 mL). The filtrate was concentrated in vacuo and purified by silica gel chromatography (eluant: 5-20% EtOAc/hexane+2% TEA), affording 833 mg of ethyl 1-benzyl-4-(4-chloro-2-(3,3,3-triethoxyprop-1-ynyl)phenyl) piperidine-4-carboxylate.

Step F: Preparation of Ethyl 1-benzyl-4-(4-chloro-2-(3-ethoxy-3-oxoprop-1-ynyl)phenyl)piperidine-4-carboxylate A solution of ethyl 1-benzyl-4-(4-chloro-2-(3,3,3-triethoxyprop-1-ynyl)phenyl)piperidine-4-carboxylate (820 mg, 1.5 mmol) and p-toluenesulfonic acid monohydrate (443 mg, 2.3 mmol) in EtOH (25 mL) and water (5 mL) was stirred at 23° C. After 30 minutes, the solvents were removed in vacuo, and the residue was diluted with EtOAc (200 mL) and washed with 10% HCl solution (100 mL), saturated NaHCO$_3$ solution (100 mL) and brine (100 mL), dried over MgSO$_4$, and concentrated in vacuo affording 620 mg of ethyl 1-benzyl-4-(4-chloro-2-(3-ethoxy-3-oxoprop-1-ynyl)phenyl)piperidine-4-carboxylate. MS m/e=454.1 (M+H)$^+$.

Step G: Preparation of 1,1-Dimethylethyl N-((6-chloro-4-hydroxy-2-oxo-1'-(phenylmethyl)-spiro [naphthalene-1,4'-piperidin]-3-yl)carbonyl)glycinate A suspension of NaH (60% dispersion in mineral oil (36 mg, 895 µmol)) in dioxane (5 mL) in an oven-dried round-bottomed flask was treated with a solution of (E)-benzaldehyde oxime (108 mg, 895 µmol) in DMF (4 mL) in a dropwise fashion. The reaction was stirred at 23° C. under nitrogen. After 30 minutes, the reaction was cooled to 0° C., and was then treated with a solution of ethyl 1-benzyl-4-(4-chloro-2-(3-ethoxy-3-oxoprop-1-ynyl)phenyl)piperidine-4-carboxylate (325 mg, 716 mmol) in DMF (4 mL) which was added in a dropwise fashion over 10 minutes. After 1 hour, the solution was diluted with EtOAc (150 mL) and washed with a saturated NaHCO$_3$ solution (100 mL), water (100 mL) and brine (100 mL), dried over MgSO$_4$, concentrated in vacuo, and purified by silica gel chromatography (eluant: 2-10% MeOH/ DCM), affording the cyclized product, a solution of which (160 mg, 376 mmol) in 1,4-dioxane (7 mL) was treated with glycine tert-butyl ester hydrochloride (94.5 mg, 564 µmol) and DIPEA (131 µL, 751 µmol). The reaction was heated to 120° C. After 19 hours, the reaction was cooled to 23° C., diluted with EtOAc (50 mL) and washed with a saturated NaHCO$_3$ solution (50 mL) and brine (50 mL), dried over MgSO$_4$, concentrated in vacuo and purified by silica gel chromatography (eluant: 0-5% MeOH/EtOAc+1% TEA), affording 120 mg (62%, 2 steps) of 1,1-dimethylethyl N-((6-chloro-4-hydroxy-2-oxo-1'-(phenylmethyl)-4H-spiro[naphthalene-1,4'-piperidin]-3-yl)carbonyl)glycinate. MS m/e=512.2 (M+H)$^+$.

Step H: Preparation of N-((6-Chloro-4-hydroxy-2-oxo-1'-(phenylmethyl)-spiro[naphthalene-1,4'-piperidin]-3-yl)carbonyl)glycine A solution of 1,1-dimethylethyl N-((6-chloro-4-hydroxy-2-oxo-1'-(phenylmethyl)-4H-spiro[naphthalene-1,4'-piperidin]-3-yl)carbonyl)glycinate (117 mg, 229 µmol) in TFA (1701 µL, 22896 µmol) was stirred at 23° C. After 25 minutes, the reaction was concentrated and the product was precipitated by addition of water (20 mL). The solid was collected by filtration, and the residue was washed with water (10 mL) and diethyl ether (5 mL), and dried under vacuum, affording 100 mg (77%) of N-((6-chloro-4-hydroxy-2-oxo-1'-(phenylmethyl)-spiro[naphthalene-1,4'-piperidin]-3-yl)carbonyl)glycine as the trifluoroacetate salt. MS m/e=455.2 (M+H)$^+$. Calculated for $C_{26}H_{24}ClF_3N_2O_7$ 454.13.

Example 72

N-((6'-Chloro-4'-hydroxy-2'-oxo-4,5-dihydro-spiro [furan-2,1'-naphthalen]-3'-yl)carbonyl)glycine

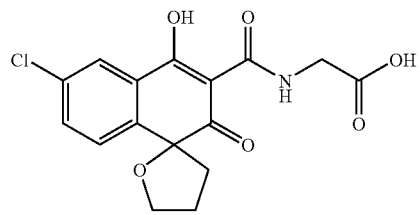

Step A: Preparation of Methyl tetrahydrofuran-2-carboxylate

To a mixture of methyl tetrahydrofuran-2-carboxylic acid (11.6 g, 100 mmol), MeOH (20 mL), and toluene (30 mL) was slowly added concentrated H$_2$SO$_4$ (6 g). The resulting biphasic mixture was heated in a sealed pressure vessel for 1 hour at 95° C. The reaction was then cooled to 0° C. and 7N NH$_3$ in MeOH was added until the pH reached between 7 and 9. Na$_2$SO$_4$ was then added, and the reaction was passed through short plug of silica gel, eluting with DCM. The resulting mixture was distilled at 64° C. under vacuum to afford the product as a clear liquid.

Step B: Preparation of ((Dihydrofuran-2(3H)-ylidene)(methoxy)-methoxy)trimethylsilane To a suspension of LDA (2.6 g, 24.3 mmol) in THF (30 mL) at −78° C. was slowly added methyl tetrahydrofuran-2-carboxylate (3.0 g, 23.0 mmol). The resulting mixture was stirred at −78° C. for 20 minutes, and TMS chloride (2.6 g, 24.3 mmol) was slowly added. The reaction was stirred for 1 hour at −78° C. and then warmed to room temperature for 2 hours. The reaction mixture was concentrated under reduced pressure, avoiding contact with water. Hexanes (20 mL) was then added, and the mixture was passed through a short plug of celite, eluting with hexanes (10 mL). The solution was then concentrated, affording the crude product in good purity.

Step C: Preparation of 2-Bromo-5-chlorobenzenamine

A solution of 1-bromo-4-chloro-2-nitrobenzene (13.92 g, 58.87 mmol) in MeOH (300 mL) was treated with water (50 mL), ammonium chloride (22.99 g, 429.8 mmol) and iron powder (325 mesh, 16.44 g, 294.4 mmol). The suspension was stirred at 23° C. After 18 hours, the suspension was filtered through celite. The filter cake was washed with MeOH (500 mL). The combined filtrate/washings were concentrated, partitioned in EtOAc/water (500 mL/200 mL), and the organic layer was separated. The aqueous layer was extracted with EtOAc (2×200 mL). The organic layers were combined, washed with brine (200 mL), dried ($MgSO_4$), and concentrated in vacuo affording 11.51 g of 2-bromo-5-chlorobenzenamine.

Step D: Preparation of 1-Bromo-4-chloro-2-iodobenzene

A suspension of 2-bromo-5-chlorobenzenamine (11.348 g, 54.963 mmol) in concentrated HCl (100 mL) was cooled to 0° C. and treated dropwise (using an addition funnel) over 20 minutes with a solution of sodium nitrite (4.5506 g, 65.955 mmol) in water (20 mL). The reaction was stirred at 0° C. for 75 minutes. A solution of potassium iodide (27.372 g, 164.89 mmol) in water (50 mL) was added, and the reaction was stirred at 23° C. After 1 hour, the reaction was heated to 70° C. After 18 hours, the reaction was diluted with EtOAc (500 mL) and washed with water (300 mL), a 2N NaOH solution (300 mL), saturated sodium thiosulfate solution (300 mL) and brine (250 mL), dried over $MgSO_4$, concentrated in vacuo, and purified by silica gel chromatography (eluant: hexane), affording 11.11 g of 1-bromo-4-chloro-2-iodobenzene.

Step E: Preparation of 3,3,3-Triethoxyprop-1-yne

A solution of trimethylsilylacetylene (29.4 mL, 20.8 mmol) in diethyl ether (100 mL, anhydrous) was cooled to 0° C. in an oven-dried round bottomed flask under nitrogen. The solution was treated dropwise with butyllithium (2.5M solution in hexanes (83.2 mL, 208.0 mmol)). After 1 hour, the reaction mixture was cooled to −78° C.

A solution of tetraethyl orthocarbonate (21.8 mL, 104.0 mmol) in diethyl ether (50 mL) in a separate oven-dried round bottomed flask was cooled to 0° C. under nitrogen. The solution was then treated dropwise over 20 minutes with a solution of boron trifluoride diethyletherate (17.6 mL, 140.4 mmol) in diethyl ether (25 mL). The white mixture was stirred at 0° C. for 5 minutes, and then cooled to −78° C., followed by the addition of the TMS-acetylide solution via cannula.

After 1 hour, the reaction was removed from the dry ice-acetone bath and stirred at 23° C. for 15 minutes. The reaction was then quenched with saturated aqueous $K_2CO_3$ solution (300 mL) and extracted with diethyl ether (2×300 mL). The combined organic layers were dried over $MgSO_4$ and concentrated in vacuo affording trimethyl(3,3,3-triethoxyprop-1-ynyl)silane.

A solution of trimethyl(3,3,3-triethoxyprop-1-ynyl)silane (25 g, 102 mmol) in MeOH (400 mL), was treated with $K_2CO_3$ (14 g, 102 mmol). The reaction was stirred at 23° C. After 15 hours, the reaction was diluted with pentane (500 mL). The pentane layer was separated, and the MeOH layer was extracted with pentane (2×250 mL). The combined pentane layers were washed with water (200 mL), dried over $MgSO_4$, and concentrated (at 220 torr on rotary evaporator). The crude product was filtered through a silica gel plug using 10% diethyl ether/pentane as the eluant and concentrated (at 220 torr on rotary evaporator) affording 13.25 g of 3,3,3-triethoxyprop-1-yne.

Step F: Preparation of Ethyl 3-(2-bromo-5-chlorophenyl)propiolate

A suspension of 1-bromo-4-chloro-2-iodobenzene (5.4 g, 17.0 mmol), 3,3,3-triethoxyprop-1-yne (4.4 g, 25.6 mmol), copper(I) iodide (976 mg, 5.1 mmol), and trans-dichlorobis (triphenylphosphine)palladium(II) (1.19 g, 1.7 mmol) in ACN (60 mL) was degassed and backfilled with argon. The resulting mixture was treated with TEA (22.0 mL, 157.9 mmol). The reaction flask was capped with a septum and stirred at 23° C. After 90 minutes, the reaction was diluted with EtOAc (300 mL) and washed with water (150 mL). The aqueous layer was extracted with EtOAc (300 mL). The combined organic layers were washed with brine (100 mL), dried over $MgSO_4$, concentrated in vacuo, dissolved in EtOH (50 mL) and water (5 mL) and then treated with p-toluenesulfonic acid monohydrate (5 mg). After stirring at 23° C. for 60 minutes, the solution was concentrated, dissolved in diethyl ether (300 mL) and washed with saturated $NaHCO_3$ solution (100 mL), water (100 mL) and brine (100 mL), dried over $MgSO_4$, and concentrated in vacuo affording 2.7 g of ethyl 3-(2-bromo-5-chlorophenyl)propiolate.

Step G: Preparation of Methyl 2-(4-chloro-2-(3-ethoxy-3-oxoprop-1-ynyl)phenyl)-tetrahydrofuran-2-carboxylate Ethyl 3-(2-bromo-5-chlorophenyl)propiolate (1.2 g, 4.16 mmol), PdBr(Pt-Bu$_3$) dimer (32 mg, 0.04 mmol), and DMF (5 mL) were loaded into a vial in a glove box, and the resulting mixture was stirred at 80° C. for 4-5 minutes. This mixture was then transferred via syringe into a separate vial containing $ZnCl_2$ hydrate (0.84 g), ((dihydrofuran-2(3H)-ylidene) (methoxy)methoxy)trimethylsilane (1.26 g, 6.2 mmol), and DMF (5 mL). The combined mixture was then heated at 80° C. for 40 minutes, at which time more of the Pd catalyst and ((dihydrofuran-2(3H)-ylidene)(methoxy)methoxy) trimethylsilane were added as necessary. Upon completion, the reaction mixture was cooled to room temperature and filtered through a silica gel plug, eluting with EtOAc (~30 mL). The combined solution was concentrated in vacuo. Purification by silica flash chromatography (5-10% EtOAc/hexanes) gave the desired phenyl carboxylate as a brown liquid.

Step H: Preparation of Ethyl 6'-chloro-4'-hydroxy-2'-oxo-4,5-dihydro-spiro[furan-2,1'-naphthalen]-3'-carboxylate To a suspension of NaH (74 mg, 1856 µmol) in 1,4-dioxane (11 mL, 1485 µmol) in a flame-dried flask was added dropwise (E)-benzaldehyde oxime (0.14 mL, 1856 µmol) in DMF (9.1 mL, 1485 µmol). The reaction was stirred for 30 minutes under argon and then cooled to −20° C. The reaction mixture was next treated dropwise with methyl 2-(4-chloro-2-(3- ethoxy-3-oxoprop-1-ynyl)phenyl)-tetrahydrofuran-2-carboxylate (500 mg, 1485 μmol) in DMF (9.109 mL, 1485 μmol). The reaction was maintained at −20° C. Upon completion of the reaction, EtOAc was added and the reaction was washed with 1M aqueous HCl, H₂O, and brine.

Purification by silica flash chromatography (0.5-3% MeOH/DCM) gave the desired ester. 1N aqueous NaOH was added to the pooled fractions, and the aqueous layer was acidified with concentrated HCl and extracted with EtOAc. The organic layer was then dried over Na₂SO₄, filtered, and concentrated in vacuo to provide the pure ester as a white solid. MS m/e 323.2 (M+H)⁺.

Step I: Preparation of 1,1-Dimethylethyl N-((6'-chloro-4'-hydroxy-2'-oxo-4,5-dihydro-spiro[furan-2, 1'-naphthalen]-3'-yl)carbonyl) glycinate A mixture of tert-butyl 2-aminoacetate hydrochloride (399 mg, 2380 μmol) and ethyl 6'-chloro-4'-hydroxy-2'-oxo-4,5-dihydro-spiro[furan-2,1'-naphthalen]-3'-carboxylate (256 mg, 793 μmol) in 1,4-dioxane (7932 μL, 793 μmol), was treated with DIPEA (829 μL, 4759 μmol) and warmed to 80° C. After 2 hours, the reaction was cooled to room temperature, diluted with EtOAc, washed with H₂O (2×) and brine, dried over Na₂SO₄, filtered, and concentrated in vacuo to provide the glycine ester as a white solid. MS m/e=430.8 (M+Na)⁺.

Step J: Preparation of N-((6'-Chloro-4'-hydroxy-2'-oxo-4,5-dihydro-spiro[furan-2,1'-naphthalen]-3'-yl) carbonyl)glycine 1,1-Dimethylethyl N-((6'-chloro-4'-hydroxy-2'-oxo-4,5-dihydro-spiro[furan-2,1'-naphthalen]-3'-yl)carbonyl) glycinate (323 mg, 793 μmol) was mixed with TFA (7930 μL, 793 μmol) and stirred for 30 minutes. The product was co-evaporated with DCM (5×) to give the title compound. MS m/e=352.0 (M+H)⁺. Calculated for C₁₆H₁₄ClNO₆ 351.05.

Examples 73 and 74

N-(((2S)-6'-Chloro-4'-hydroxy-2'-oxo-4,5-dihydro-spiro[furan-2,1'-naphthalen]-3'-yl)carbonyl)glycine and N-(((2R)-6'-Chloro-4'-hydroxy-2'-oxo-4,5-dihydro-spiro[furan-2,1'-naphthalen]-3'-yl)carbonyl)glycine

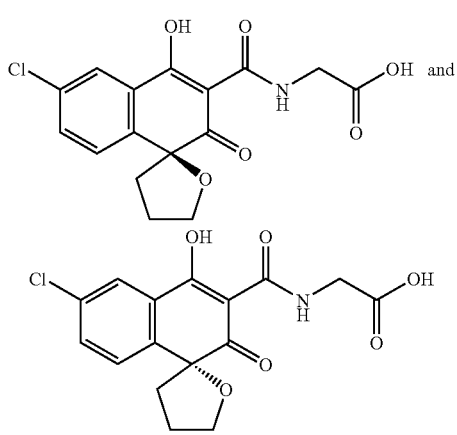

The title compounds were obtained by chiral separation of N-((6'-chloro-4'-hydroxy-2'-oxo-4,5-dihydro-spiro[furan-2, 1'-naphthalen]-3'-yl)carbonyl)glycine (Example 72) into its two enantiomers using chiral HPLC. MS m/e=352.0 (M+H)⁺. Calculated for C₁₆H₁₄ClNO₆ 351.05.

Example 75

N-((6-Chloro-4-hydroxy-2-oxo-5',6'-dihydro-spiro [naphthalene-1,3'-pyran]-3-yl)carbonyl)glycine

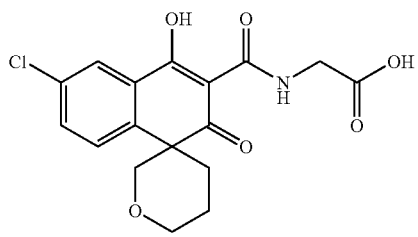

Step A: Preparation of 1-Chloro-3-(chloromethoxy)propane

Paraformaldehyde (18 g, 598 mmol) in DCM (239 mL, 598 mmol) was cooled to −10° C., and HCl gas (22 g, 598 mmol) was bubbled through the reaction until the solution became clear. 3-Chloropropan-1-ol (50 mL, 598 mmol) was then added dropwise, the HCl gas was discontinued, and the reaction was stirred for 10 minutes. The reaction was poured into a suspension of anhydrous K₂CO₃ in DCM (893 mL, 598 mmol) and stirred until bubbling ceased. The reaction was filtered and concentrated in vacuo to give the desired product as a clear liquid.

Step B: Preparation of 3-(4-Chlorophenyl)-tetrahydro-2H-pyran-3-carbonitrile

A mixture of 2-(4-chlorophenyl)acetonitrile (73 g, 483 mmol) and 1-chloro-3-(chloromethoxy)propane (69.1 g, 483 mmol) in ethoxyethane (242 mL, 483 mmol) was added dropwise to a mixture of NaH (57 g, 1437 mmol) in 1-methylpyrrolidin-2-one (1208 mL, 483 mmol) at −20° C. The reaction was stirred for 12 hours and then slowly quenched with H₂O. The reaction mixture was extracted with ether (5×), and the combined organic layers were washed with H₂O (3×) and brine (1×), dried over Na₂SO₄, filtered, and concentrated in vacuo to give the desired nitrile as a yellow oil. MS m/e=223.2 (M+H)⁺.

Step C: Preparation of 3-(4-Chlorophenyl)-tetrahydrofuran-3-carboxylic acid

A solution of 3-(4-chlorophenyl)-tetrahydro-2H-pyran-3-carbonitrile (8.62 g, 39 mmol), 9M H₂SO₄ (39 mL, 39 mmol), and 1,4-dioxane (8 mL, 39 mmol) was stirred at 100° C. Upon completion of the reaction, the reaction was cooled and extracted with EtOAc. The organic layer was washed with 2N aqueous NaOH. The aqueous layer was acidified with concentrated HCl and extracted with EtOAc. This was repeated and the combined organic layers were then dried over Na₂SO₄, filtered, and concentrated in vacuo to give the desired acid as a light yellow solid. MS m/e=263.2 (M+Na)⁺.

Step D: Preparation of Diethyl 2-(3-(4-chlorophenyl)-tetrahydro-2H-pyran-3-carbonyl)malonate 3-(4-Chlorophenyl)-tetrahydrofuran-3-carboxylic acid (2.73 g, 11 mmol) was dissolved in thionyl chloride (8 mL, 113 mmol) and heated at 70° C. for 3 hours. The solution was cooled, concentrated under reduced pressure, and pumped down under high vacuum for 3 hours. In a flame-dried round-bottom flask, MgCl₂ (1 g, 11 mmol) was added to diethyl malonate (2 mL, 11 mmol) in ACN (23 mL, 11 mmol) and cooled to 0° C. The reaction was stirred for 15 minutes and then TEA (3 mL, 24 mmol) was slowly added. The resulting solution was allowed to warm to room temperature while stirring for 3 hours. The furan acid chloride was dissolved in ACN (10 mL, 11 mmol) and added to the malonate solution. The resulting mixture was stirred at 50° C. for 12 hours. Upon completion, the reaction was concentrated and mixed with 1N aqueous HCl and EtOAc. The aqueous layer was washed with EtOAc (2×), and the combined organic layers were dried over Na₂SO₄, filtered, and concentrated in vacuo. Purification by silica flash chromatography (10-60% EtOAc/hexane) gave the desired malonate as a light yellow oil. MS m/e=383.2 (M+H)⁺.

Step E: Preparation of Ethyl 6-chloro-4-hydroxy-2-oxo-5',6'-dihydro-spiro[naphthalene-1,3'-pyran]-3-carboxylate A mixture of diethyl 2-(3-(4-chlorophenyl)-tetrahydro-2H-pyran-3-carbonyl)malonate (1.7771 g, 4642 μmol) in IPAc (3868 μL, 4642 μmol) was added to concentrated H₂SO₄ (11605 μL, 4642 μmol) at 0° C. The reaction was stirred at 0° C. and then slowly warmed to room temperature. The reaction was poured over ice and extracted with EtOAc. The aqueous layer was washed with EtOAc, and the combined organic layers were washed with brine, dried over Na₂SO₄, filtered, and concentrated in vacuo. Purification by silica flash chromatography (1-5% MeOH/DCM) gave the desired naphthalenone as a white solid. MS m/e=337.2 (M+H)⁺.

Step F: Preparation of 1,1-Dimethylethyl N-((6-chloro-4-hydroxy-2-oxo-5',6'-dihydro-spiro[naphthalene-1,3'-pyran]-3-yl)carbonyl)glycinate To a solution of 1,1-dimethylethyl N-((6-chloro-4-hydroxy-2-oxo-5',6'-dihydro-spiro[naphthalene-1,3'-pyran]-3-yl)carbonyl)glycinate (85 mg, 252 μmol) in 1,4-dioxane (2524 μL, 252 μmol) was added DIPEA (132 μL, 757 μmol). The resulting reaction mixture was heated at 80° C. for 3 hours. The reaction was then cooled, diluted with EtOAc, washed with water (2×) and brine, dried over Na₂SO₄, and concentrated in vacuo to give the desired glycine ester as a light yellow oil. MS m/e=422.0 (M+H)⁺.

Step G: Preparation of N-((6-Chloro-4-hydroxy-2-oxo-5',6'-dihydro-spiro[naphthalene-1,3'-pyran]-3-yl)carbonyl)glycine 1,1-Dimethylethyl N-((6-chloro-4-hydroxy-2-oxo-5',6'-dihydro-spiro[naphthalene-1,3'-pyran]-3-yl)carbonyl)glycinate (106 mg, 252 μmol) was mixed with TFA (6300 μL, 252 μmol) and stirred for 30 minutes. The product was co-evaporated with DCM (5×) to give the title compound. MS m/e=366.0 (M+H)⁺. Calculated for C₁₇H₁₆ClNO₆ 365.07.

Examples 76 and 77

N-(((1S)-6-Chloro-4-hydroxy-2-oxo-5',6'-dihydro-spiro[naphthalene-1,3'-pyran]-3-yl)carbonyl)glycine and N-(((1R)-6-Chloro-4-hydroxy-2-oxo-5',6'-dihydro-spiro[naphthalene-1,3'-pyran]-3-yl)carbonyl)glycine

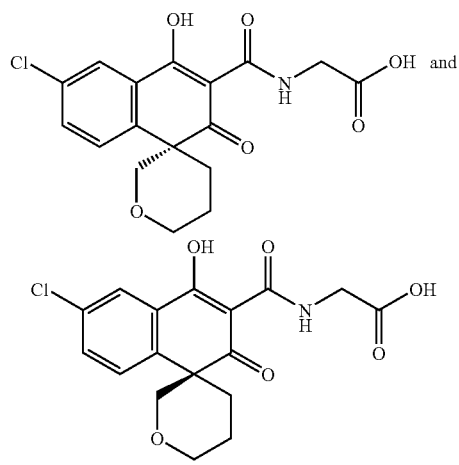

The title compounds were obtained by chiral separation of N-((6-chloro-4-hydroxy-2-oxo-5',6'-dihydro-spiro[naphthalene-1,3'-pyran]-3-yl)carbonyl)glycine (Example 75) into its separate enantiomers using chiral HPLC. MS m/e=366.0 (M+H)⁺. Calculated for C₁₇H₁₆ClNO₆ 365.07.

Examples 78 and 79

N-(((1R)-6-Chloro-4-hydroxy-1-ethyl-1-methyl-2-oxo-naphthalen-3-yl)carbonyl)glycine and N-(((1S)-6-Chloro-4-hydroxy-1-ethyl-1-methyl-2-oxo-naphthalen-3-yl)carbonyl)glycine

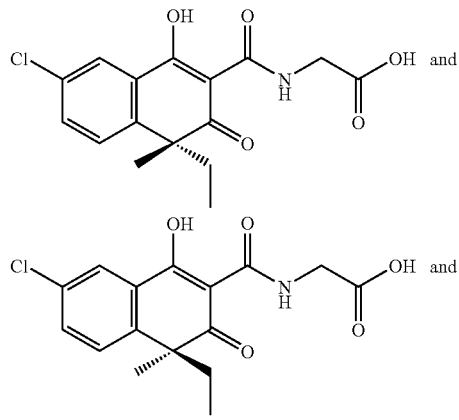

The title compounds were obtained by chiral separation of N-((6-chloro-1-ethyl-4-hydroxy-1-methyl-2-oxo-naphthalen-3-yl)carbonyl)glycine (Example 15) into its separate enantiomers using chiral HPLC. MS (m/z)=338 (M+H)+. Calculated for $C_{16}H_{16}ClNO_5$ 337.07.

Example 80

N-((6'-Chloro-4'-hydroxy-2',4-dioxo-spiro[cyclohexane-1,1'-naphthalen]-3'-yl)carbonyl)glycine

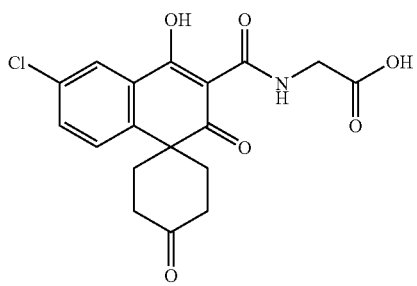

Step A: Preparation of 1-Bromo-4-chloro-2-iodobenzene

A stirred mixture of copper(II) bromide (11 mL, 237 mmol) in 250 mL ACN at 0° C. was slowly treated with tert-butyl nitrite (33 mL, 276 mmol). The mixture was then warmed to 65° C., and stirred for 30 minutes. The mixture was next treated dropwise with a mixture of 4-chloro-2-iodoaniline (50 g, 197 mmol) in 100 mL ACN. The resulting mixture was stirred for 1 hour. The mixture was cooled to room temperature and poured over 200 mL ice/10% HCl. The mixture was extracted with ether (3×100 mL). The combined organic layers were washed with $H_2O$ (2×100 mL), 1% ammonia water (2×100 mL), brine (100 mL), dried over anhydrous $Na_2SO_4$, and concentrated in vacuo to give 63 g brown oil as crude product. The crude product was purified by running it through a short silica plug eluting with 5% ether/hexane to give 54.2 g of the title compound as a yellow solid.

Step B: Preparation of 1-Bromo-4-chloro-2-(3,3,3-triethoxyprop-1-ynyl)benzene A mixture of 1-bromo-4-chloro-2-iodobenzene (10 g, 32 mmol) in 100 mL degassed ACN and TEA (29 g, 284 mmol), was treated with 3,3,3-triethoxyprop-1-yne (6.0 g, 35 mmol), copper(I) iodide (0.60 g, 3.2 mmol), and dichlorobis(triphenylphosphine)palladium(II) (1.1 g, 1.6 mmol). The mixture was stirred at room temperature for 2 hours at room temperature (the mixture turned dark green after 5 minutes). TLC showed that all starting material was converted, and a new spot was produced. The mixture was concentrated in vacuo. The residue was diluted with 100 mL ether, washed with $H_2O$ (2×20 mL), 5% ammonia water (2×20 mL), brine (20 mL), dried over anhydrous $Na_2SO_4$, and concentrated in vacuo. The crude product was purified by column chromatography pretreated with TEA and eluted with 0-15% EtOAc/hexane to give 7.6 g of the product as a pale yellow oil. The oil solidified after it was stored in the refrigerator.

Step C: Preparation of Ethyl 4'-(4-chloro-2-(3-ethoxy-3-oxoprop-1-ynyl)phenyl)-5,5-dimethyl-spiro[1,3-dioxane-2,1'-cyclohexane]-4'-carboxylate A stirred mixture of dicyclohexylamine (5.5 g, 31 mmol) in 30 mL toluene at 0° C. was treated with butyllithium (12 mL, 31 mmol) and stirred for 15 minutes at 0° C. The resulting mixture was treated with ethyl 5,5-dimethyl-spiro[1,3-dioxane-2,1'-cyclohexane]-4'-carboxylate (7.8 g, 31 mmol) and stirred at room temperature for 10 minutes.

To a different round-bottom flask was added 50 mL toluene and 1-bromo-4-chloro-2-(3,3,3-triethoxyprop-1-ynyl)benzene (9.2 g, 25 mmol). The flask was degassed by applying a vacuum and then filling it with nitrogen. The mixture was treated with $[PdBrP(t-Bu)_3]_2$ (0.84 g, 2.2 mmol) at room temperature. The reaction was then warmed to 85° C. and quickly treated with above anion mixture (within 3 minutes). The mixture was stirred under nitrogen, warmed to 100° C., and stirred for 20 minutes. TLC showed a new spot. The resulting mixture was cooled to room temperature, filtered through a short silica plug, and washed with 500 mL 4:1=hexane/EtOAc. The organic solution was concentrated in vacuo, diluted with 100 mL EtOAc, washed with 5% HCl (20 mL), $H_2O$ (3×20 mL), and brine 20 mL. The organic layer was dried over anhydrous $Na_2SO_4$, concentrated in vacuo, and purified by column chromatography eluting with 0-15% EtOAc/hexane to give 3.68 g of the product as a yellow oil. MS (m/z)=463 (M+H)+.

Step D: Preparation of Ethyl 6"-chloro-4"-hydroxy-5,5-dimethyl-2"-oxo-dispiro[1,3-dioxane-2,1'-cyclohexane-4',1"-naphthalene]-3"-carboxylate A stirred mixture of NaH (60% dispersion in mineral oil (0.39 mL, 9.3 mmol)) in 40 mL dioxane at room temperature, was treated with a mixture of (E)-benzaldehyde oxime (1.0 g, 8.6 mmol) in 40 mL DMF. The resulting mixture was stirred for 30 minutes. The mixture was then cooled to 0° C. and treated with a mixture of ethyl 4'-(4-chloro-2-(3-ethoxy-3-oxoprop-1-ynyl)phenyl)-5,5-dimethyl-spiro[1,3-dioxane-2,1'-cyclohexane]-4'-carboxylate (3.6 g, 7.8 mmol) in 30 mL DMF. The resulting mixture was stirred for 1 hour. The mixture was then carefully quenched with 10 mL $H_2O$ and brought to a pH of 5 by addition of 10% HCl. The mixture was extracted with ethyl ether (3×50 mL). The combined organic layers were washed with brine (20 mL), dried over anhydrous $Na_2SO_4$, concentrated in vacuo, and purified by column chromatography eluting with 20-30% EtOAc to give 2.2 g of the product as a pale yellow solid. MS (m/z)=435 (M+H)+.

Step E: Preparation of 1,1-Dimethylethyl N-((6"-chloro-4"-hydroxy-5,5-dimethyl-2"-oxo-dispiro[1,3-dioxane-2,1'-cyclohexane-4',1"-naphthalen]-3"-yl)carbonyl)glycinate A mixture of ethyl 6"-chloro-4"-hydroxy-5,5-dimethyl-2"-oxo-dispiro[1,3-dioxane-2,1'-cyclohexane-4',1"-naphthalene]-3"-carboxylate (69 mg, 159 μmol) and tert-butyl 2-aminoacetate hydrochloride (53 mg, 317 μmol) in 1.5 mL dioxane was treated with N-ethyl-N-isopropylpropan-2-amine (62 mg, 476 μmol). The mixture was warmed to 95° C. and stirred for 2 hours, M+1=420. The mixture was cooled to room temperature and concentrated in vacuo. The crude product was purified by column chromatography eluting with 10-20% EtOAc/hexane to give 66 mg of the title compound as a white yellow solid. MS (m/z)=520 (M+H)+.

Step F: Preparation of N-((6'-Chloro-4'-hydroxy-2',4-dioxo-spiro[cyclohexane-1,1'-naphthalen]-3'-yl)carbonyl)glycine A mixture of 1,1-dimethylethyl N-((6"-chloro-4"-hydroxy-5,5-dimethyl-2"-oxo-dispiro[1,3-dioxane-2,1'-cyclohexane-4',1''-naphthalen]-3''-yl)carbonyl)glycinate (18 mg, 35 μmol) in 1 mL TFA was stirred at room temperature for 30 minutes, M+1=378. The mixture was concentrated in vacuo, and dried under high vacuum to give 11 mg of the product as an off-white solid. MS (m/z)=378 (M+H)$^+$. Calculated for $C_{18}H_{16}ClNO_6$ 377.07.

Example 81

N-((5-Fluoro-4-hydroxy-1,1-dimethyl-2-oxo-naphthalen-3-yl)carbonyl)glycine

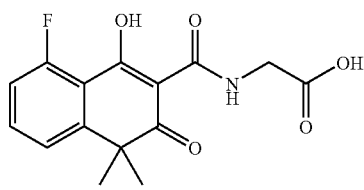

Step A: Preparation of 3-Fluoro-2-iodobenzoic acid

Sodium nitrite (6.7 g, 97 mmol) in water (25 mL) was added to a solution of 2-amino-3-fluorobenzoic acid (10.0 g, 64 mmol) in DMSO (25 mL) and 30% $H_2SO_4$ (75 mL) at 0° C. The mixture was stirred for 1 hour at 0° C. and then potassium iodide (27 g, 161 mmol) was added dropwise as a solution in water (25 mL). The ice bath was removed and the mixture was stirred at room temperature for 4 hours, and then partitioned between EtOAc and 2M sodium sulfite. The layers were mixed, separated, and the organic layer was washed with 2M sodium sulfite once and brine once, dried over anhydrous $MgSO_4$, and concentrated in vacuo to give 14.90 g of a yellow solid. MS m/e=265 (M−H)$^+$.

Step B: Preparation of Ethyl 2-(3-fluoro-2-iodophenyl)acetate

A solution of 3-fluoro-2-iodobenzoic acid (14.90 g, 56.0 mmol) was stirred in thionyl chloride (150 mL) for 1 hour at reflux. The mixture was cooled to room temperature, and the excess thionyl chloride was removed in vacuo to give the corresponding acid chloride. $Et_2O$ (20 mL) was added, and a solution of TMSCHN$_2$ (2.0M in $Et_2O$, 110 mL, 220 mmol) was added. The mixture was stirred for 4 hours, and the excess reagent was quenched by the addition of AcOH. The mixture was then partitioned between EtOAc (200 mL) and saturated NaHCO$_3$ solution. The layers were separated, and the organic layer was washed twice with saturated NaHCO$_3$, once with water, and once with brine once. The organic layer was then dried over anhydrous $MgSO_4$ and concentrated in vacuo. This material was dissolved in EtOH (200 proof) and silver(I) oxide (2.60 g, 11.2 mmol) was added. The suspension was heated to 80° C. for 30 minutes, cooled to room temperature, and filtered through celite. The filtrate was concentrated in vacuo, and the resulting oil was purified by flash chromatography to give 9.90 g of product as a yellow oil.

Step C: Preparation of Ethyl 2-(3-fluoro-2-(3,3,3-triethoxyprop-1-ynyl)phenyl)acetate Bis(triphenylphosphine)palladium(II) chloride (456 mg, 0.649 mmol), cuprous iodide (371 mg, 1.95 mmol), and ethyl 2-(3-fluoro-2-iodophenyl)acetate (2.0 g, 6.49 mmol), were mixed in a 20 mL microwave tube. The tube was sealed, and ACN (12 mL) and TEA (6 mL) were added. The mixture was placed under argon atmosphere and 3,3,3-triethoxyprop-1-yne (1.68 g, 9.74 mmol) was added via syringe. The reaction was heated at 60° C. for 16 hours, cooled to room temperature, and concentrated under vacuum. The residue was purified by flash chromatography to give 820 mg of ethyl 2-(3-fluoro-2-(3,3,3-triethoxyprop-1-ynyl)phenyl)acetate as a yellow oil.

Step D: Preparation of Ethyl 3-(2-chloro-6-(1-ethoxy-2-methyl-1-oxopropan-2-yl)phenyl)propiolate Ethyl 2-(3-fluoro-2-(3,3,3-triethoxyprop-1-ynyl)phenyl)acetate (820 mg, 2.32 mmol) was added as a solution in DMF (6 mL) to a suspension of NaH (139 mg, 5.80 mmol) in DMF (4 mL) at 0° C. The mixture was stirred for 10 minutes, and MeI (0.58 mL, 9.28 mmol) was added via syringe. The ice bath was removed, and the mixture was stirred at room temperature for 1 hour, quenched with saturated NaHCO$_3$, and extracted with EtOAc (3×). This material was dissolved in EtOH (5 mL) and water (1 mL) and p-TSA (cat.) was added. The mixture was stirred for 30 minutes, quenched with saturated NaHCO$_3$, and extracted with EtOAc (3×). The combined extracts were dried over anhydrous $MgSO_4$ and concentrated in vacuo. The resulting residue was purified to give 452 mg ethyl 3-(2-chloro-6-(1-ethoxy-2-methyl-1-oxopropan-2-yl)phenyl)propiolate as a light yellow oil. MS m/e=307 (M+H)$^+$.

Step E: Preparation of Ethyl 5-fluoro-4-hydroxy-1,1-dimethyl-2-oxo-naphthalene-3-carboxylate A solution of (E)-Benzaldehyde oxime (214 mg, 1.76 mmol) in dry DMF (9 mL) was added to a suspension of NaH (42 mg, 1.76 mmol) in dry dioxane (9 mL). The mixture was stirred for 30 minutes at room temperature, cooled to 0° C., and a solution of ethyl 3-(2-chloro-6-(1-ethoxy-2-methyl-1-oxopropan-2-yl)phenyl)propiolate (450 mg, 1.4 mmol) in DMF (9 mL) was added. The mixture was stirred at 0° C. for 3 hours and then warmed to room temperature and stirred for 1 hour. Water was added, and the mixture was extracted with EtOAc (2×). The aqueous layer was then made acidic with 2 mL 10% HCl. This was extracted with EtOAc (3×), and the combined organic layers were dried over MgSO$_4$ and concentrated under vacuum. The resulting residue was purified by flash chromatography to give 226 mg ethyl 5-fluoro-4-hydroxy-1,1-dimethyl-2-oxo-naphthalene-3-carboxylate as a colorless oil. MS m/e=279 (M+H)$^+$.

Step F: Preparation of 1,1-Dimethylethyl N-((5-fluoro-4-hydroxy-1,1-dimethyl-2-oxo-naphthalen-3-yl)carbonyl)glycinate DIPEA (0.14 mL, 809 mmol, tert-butylglycine hydrochloride (136 mg, 809 μmol), and ethyl 5-fluoro-4-hydroxy-1,1-dimethyl-2-oxo-naphthalene-3-carboxylate (150 mg, 539 μmol) were heated to 75° C. in dioxane (4 mL) for 3 hours. The resulting mixture was cooled to room temperature and concentrated in vacuo. The residue was purified by flash chromatography to give 116 mg of 1,1-dimethylethyl N-((5-fluoro-4-hydroxy-1,1-dimethyl-2-oxo-naphthalen-3-yl)carbonyl)glycinate as a white solid. MS m/e=386 (M+Na)$^+$.

Step G: Preparation of N-((5-Fluoro-4-hydroxy-1,1-dimethyl-2-oxo-naphthalen-3-yl)carbonyl)glycine 1,1-Dimethylethyl N-((5-fluoro-4-hydroxy-1,1-dimethyl-2-oxo-naphthalen-3-yl)carbonyl)glycinate (116 mg, 319

μmol) was stirred in TFA (5 mL) for 15 minutes. The solvent was then removed in vacuo, and the residue was partitioned between DCM and water. The DCM layer was removed, and the solvent was removed in vacuo to give the product as a light yellow solid. MS m/e=308 (M+H)$^+$. Calculated for $C_{15}H_{14}FNO_5$ 307.09.

Example 82

N-((5-Chloro-4-hydroxy-1,1-dimethyl-2-oxo-naphthalen-3-yl)carbonyl)glycine

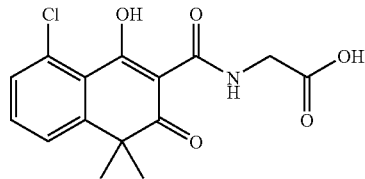

Step A: Preparation of 3-Chloro-2-iodobenzoic acid

A solution of sodium nitrite (4.82 g, 69.9 mmol) in water (25 mL) was added dropwise via addition funnel to a solution of 2-amino-3-chlorobenzoic acid (8.0 g, 46.6 mmol) in DMSO (25 mL) and 30% $H_2SO_4$ (75 mL) that had previously been cooled to 0° C. The mixture was stirred at 0° C. for 1 hour, at which time a solution of potassium iodide (19.3 g, 117 mmol) in water (25 mL) was added via addition funnel. The ice bath was removed, and the mixture was stirred for 2 hours. EtOAc (200 mL) was added, and the mixture was washed with 2N sodium sulfite (3×). The organic layer was then washed once with water and once with brine, dried over anhydrous $MgSO_4$, and concentrated in vacuo to give 8.83 g of 3-chloro-2-iodobenzoic acid as a yellow solid.

Step B: Preparation of Ethyl 2-(3-chloro-2-iodophenyl)acetate

3-Chloro-2-iodobenzoic acid (8.83 g, 31.3 mmol) was stirred in thionyl chloride (125 mL) at reflux for 2 hours. The mixture was cooled to room temperature, the thionyl chloride was removed under vacuum, and the residue was azeotroped once with toluene to give the acid chloride as a dark red solid. Trimethylsilyldiazomethane (2.0M in $Et_2O$, 124 mmol) was added to the acid chloride, and the mixture was stirred for 5 hours at room temperature. Excess reagent was destroyed by the addition of AcOH (until bubbling stopped), and the mixture was partitioned between EtOAc and saturated $NaHCO_3$. The layers were separated, and the organic layer was washed with water once, brine once, dried over anhydrous $MgSO_4$ and concentrated in vacuo. This material was dissolved in absolute EtOH (250 mL) and silver (I) oxide (catalytic amount) was added. The mixture was heated at 80° C. for 30 minutes, cooled to room temperature, and filtered through celite. The filtrate was concentrated and purified by flash chromatography to give 7.89 g of ethyl 2-(3-chloro-2-iodophenyl)acetate as an orange oil.

Step C: Preparation of Ethyl 3-(2-chloro-6-(1-ethoxy-2-methyl-1-oxopropan-2-yl)phenyl)propiolate Cuprous iodide (CuI) (352 mg, 1.85 mmol), dichlorobis(triphenylphosphine)palladium(II) (432.5 mg, 0.62 mmol), and ethyl 2-(3-chloro-2-iodophenyl)acetate (2.0 g, 6.16 mmol) were mixed in a 20 mL microwave tube. ACN (14 mL) and TEA (4 mL) were added, the mixture was degassed and backfilled with argon, and 3,3,3-triethoxyprop-1-yne (1.27 g, 7.40 mmol) was added via syringe. The mixture was stirred for 18 hours at 45° C., cooled to room temperature, concentrated in vacuo, and the residue was flushed through a plug of silica gel with a 1:1 mixture of EtOAc and hexane. The eluent was concentrated in vacuo, dissolved in 20 mL dry DMF, and added to a suspension of NaH (370 mg, 15.4 mmol) in DMF (20 mL) that had previously been cooled to 0° C. The mixture was stirred for 10 minutes and MeI (1.15 mL, 18.5 mmol) was added via syringe. The mixture was stirred overnight at room temperature, quenched with aqueous $NH_4Cl$, and extracted with EtOAc (3×). The combined extracts were dried over anhydrous $MgSO_4$ and concentrated in vacuo. This material was dissolved in EtOH (15 mL) and water (2 mL). p-TSA (10 mg), was added and the mixture was stirred for 30 minutes. The reaction was quenched with saturated $NaHCO_3$, and the mixture was extracted with EtOAc three times. The extracts were dried over anhydrous $MgSO_4$ and concentrated to give a red oil, which was purified by flash chromatography to give 520 mg of ethyl 3-(2-chloro-6-(1-ethoxy-2-methyl-1-oxopropan-2-yl)phenyl)propiolate as a light yellow oil. MS m/e=323 (M+H)$^+$.

Step D: Preparation of Ethyl 5-chloro-4-hydroxy-1,1-dimethyl-2-oxo-naphthalene-3-carboxylate A solution of (E)-benzaldehyde oxime (234 mg, 1.93 mmol) in dry DMF (9 mL) was added to a suspension of NaH (46 mg, 1.93 mmol) in dioxane (9 mL) at room temperature. The mixture was stirred for 30 minutes and then cooled to 0° C. A solution of ethyl 3-(2-chloro-6-(1-ethoxy-2-methyl-1-oxopropan-2-yl)phenyl)propiolate (520 mg, 1.61 mmol) in dry DMF (9 mL) was added, and the mixture was stirred at 0° C. for 3 hours and then at room temperature for 1 hour. The mixture was quenched with water and then washed with EtOAc (2×). The aqueous layer was made acidic with 10% HCl and then extracted with EtOAc (2×). The extracts were dried over anhydrous $MgSO_4$ and concentrated under vacuum. The residue was purified by flash chromatography to give 210 mg of ethyl 5-chloro-4-hydroxy-1,1-dimethyl-2-oxo-naphthalene-3-carboxylate as a colorless oil. MS m/e=295 (M+H)$^+$.

Step E: Preparation of tert-Butyl N-((5-chloro-4-hydroxy-1,1-dimethyl-2-oxo-naphthalen-3-yl)carbonyl)glycinate Ethyl 5-chloro-4-hydroxy-1,1-dimethyl-2-oxo-naphthalene-3-carboxylate (210 mg, 713 μmol, 1.0 eq) and glycine tert-butyl ester hydrochloride (143 mg, 855 μmol, 1.20 eq) were mixed in dioxane (5 mL) in a round bottom flask. DIPEA (186 μL, 1069 μmol, 1.5 eq) was added via syringe, and the reaction was stirred at 75° C. for 4 hours. The reaction mixture was cooled to room temperature and concentrated in vacuo to give a yellow solid. The crude product was purified by silica flash chromatography (0-50% DCM/hexane) to give the desired compound as a white solid (204 mg). MS m/e=380 (M+H)$^+$.

Step F: Preparation of N-((5-Chloro-4-hydroxy-1,1-dimethyl-2-oxo-naphthalen-3-yl)carbonyl)glycine tert-Butyl N-((5-chloro-4-hydroxy-1,1-dimethyl-2-oxo-naphthalen-3-yl)carbonyl)glycinate (204 mg, 537 μmol) was stirred in TFA (2 mL, 26924 µmol) for 25 minutes. Water was added. The resulting precipitate was filtered and washed with water to give a white solid (169 mg). MS m/e=324 (M+H)⁺. Calculated for $C_{15}H_{14}ClNO_5$ 323.06.

Example 83

N-((8-Fluoro-4-hydroxy-2-oxo-2',3',5',6'-tetrahydro-spiro[naphthalene-1,4'-pyran]-3-yl)carbonyl)glycine

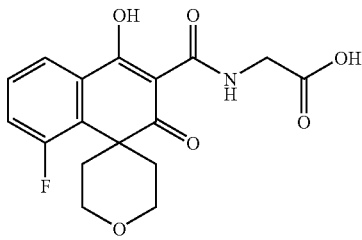

Step A: Preparation of Methyl 2-(2-fluorophenyl)acetate

To a stirred solution of 2-fluorophenylacetic acid (9.6 g, 62 mmol) in MeOH (100 mL) was added concentrated HCl (0.7 mL, 19 mmol). The solution was heated at 68° C. for 4 hours, and then the reaction was concentrated in vacuo to remove MeOH. The residue was dissolved in ether and then washed with saturated NaHCO₃ solution (1×50 mL). The organic extracts were separated, dried with Na₂SO₄, filtered and concentrated to give a yellow oil (10 g). MS m/e=169.0 (M+H)⁺.

Step B: Preparation of Methyl 4-(2-fluorophenyl)-tetrahydro-2H-pyran-4-carboxylate To an ice-bath cooled, stirred solution of methyl 2-(2-fluorophenyl)acetate (3.4 g, 20 mmol) in THF (100 mL) was added NaH (1.8 g, 44 mmol). The reaction was stirred at 0° C. for 10 minutes and then dichloroethyl ether (2.7 mL, 22 mmol) and tetrabutylammonium bromide (0.33 g, 1.0 mmol) were added sequentially. The yellow reaction mixture was stirred for 16 hours at room temperature and then quenched with a saturated ammonium chloride solution. The aqueous layer was extracted with EtOAc (3×60 mL), and the organic layers were combined, dried (Na₂SO₄), filtered and concentrated to afford a yellow oil. Purification by flash chromatography (100% DCM) provided a pale yellow oil (2.5 g). MS m/e=239.0 (M+H)⁺.

Step C: Preparation of 4-(2-Fluorophenyl)-tetrahydro-2H-pyran-4-carboxylic acid

A solution of methyl 4-(2-fluorophenyl)-tetrahydro-2H-pyran-4-carboxylate (2.45 g, 10 mmol), water (10 mL, 555 mmol), EtOH (50 mL, 10 mmol) and KOH (2.3 g, 41 mmol) was placed in a sealed flask and then heated at 130° C. for 10 hours. After cooling to room temperature, the reaction was concentrated to afford a yellow oil. The residue was diluted with water (100 mL) and extracted with DCM (120 mL). The separated aqueous phase was then acidified to pH=1 and then extracted with EtOAc (3×10 mL). The organic later was dried (Na₂SO₄), filtered, and concentrated to afford a tan solid (1.9 g). MS m/e=223.1 (M−1)−.

Step D: Preparation of Diethyl 2-(4-(2-fluorophenyl)-tetrahydro-2H-pyran-4-carbonyl)malonate To a stirred solution of 4-(2-fluorophenyl)-tetrahydro-2H-pyran-4-carboxylic acid (1.9 g, 8.5 mmol) in DCM (50 mL) and DMF (5 mL) was carefully added oxalyl chloride (0.79 mL, 8.9 mmol). Gas evolution was observed. The reaction was stirred at room temperature for 3 hours. In a separate flask was combined IPAc (1.0 mL, 8.7 mmol), diethyl malonate (1.6 mL, 11 mmol). and anhydrous MgCl₂ (1.0 g, 11 mmol). The resulting white slurry was stirred for 30 minutes, and then TEA (4.0 mL, 29 mmol) was added and the reaction was stirred for 2.5 hours. The reaction was chilled in an ice water bath for 10 minutes, and then the concentrated acid chloride oil was added via syringe over 10 minutes. The ice bath was removed, and the reaction was stirred for 16 hours at 50° C. After cooling to room temperature, the reaction was acidified with 5N HCl solution (100 mL). The aqueous layer was removed, and the organic layer was washed with saturated NaHCO₃ solution (150 mL). The aqueous layer was removed, and the organic extract was washed with water. The organic layer was dried (Na₂SO₄), filtered and concentrated to afford a dark colored oil. The crude reaction mixture was used in the next step.

Step E: Preparation of Ethyl 8-fluoro-4-hydroxy-2-oxo-2',3',5',6'-tetrahydro-spiro[naphthalene-1,4'-pyran]-3-carboxylate A flask containing H₂SO₄ (12 mL, 218 mmol) and P₂O₅ (12 g, 87 mmol) was cooled in an ice bath for 20 minutes under nitrogen, and then diethyl 2-(4-(2-fluorophenyl)-tetrahydro-2H-pyran-4-carbonyl)malonate (8.0 g, 22 mmol) was added dropwise over 10 minutes. The reaction was stirred an additional 10 minutes at 0° C., and then was stirred at room temperature for 1 hour. The reaction was poured over ice and allowed to melt. The aqueous mixture was extracted with EtOAc (3×100 mL) and then the separated organic extracts were dried (Na₂SO₄), filtered and concentrated to provide an oil. Flash chromatography (20% EtOAc/hexane) afforded an oil (3.6 g). MS m/e=321.0 (M+H)⁺.

Step F: Preparation of 1,1-Dimethylethyl N-((8-fluoro-4-hydroxy-2-oxo-2',3',5',6'-tetrahydro-spiro[naphthalene-1,4'-pyran]-3-yl)carbonyl)glycinate In a sealed flask was combined ethyl 8-fluoro-4-hydroxy-2-oxo-2',3',5',6'-tetrahydro-spiro[naphthalene-1,4'-pyran]-3-carboxylate (1.8 g, 5.6 mmol), dioxane (75 mL), tert-butyl 2-aminoacetate hydrochloride (3.8 g, 22 mmol), and N-ethyl-N-isopropylpropan-2-amine (3.9 mL, 22 mmol). The flask was sealed and heated at 90° C. for 10 hours. After cooling to room temperature, the reaction was concentrated to give a solid that was purified by flash chromatography (20% EtOAc/hexane) to afford a white solid (1.9 g). MS m/e=406.1 (M+H)⁺.

Step G: Preparation of N-((8-Fluoro-4-hydroxy-2-oxo-2',3',5',6'-tetrahydro-spiro[naphthalene-1,4'-pyran]-3-yl)carbonyl)glycine In a flask was combined 1,1-dimethylethyl N-((8-fluoro-4-hydroxy-2-oxo-2',3',5',6'-tetrahydro-spiro[naphthalene-1,4'-pyran]-3-yl)carbonyl)glycinate (1.7 g, 4.2 mmol) and TFA (50 mL). The reaction was stirred for 15 minutes and then concentrated to afford an oil. Water was added, affording a white precipitate that was filtered off and washed with water and ether. The solid was dried under vacuum at 50° C. (1.4 g, 98%). MS m/e=348 (M−1)⁻. Calculated for $C_{17}H_{16}FNO_6$ 349.1.

Example 84

N-((6-Chloro-1-cyano-4-hydroxy-1-methyl-2-oxo-naphthalen-3-yl)carbonyl)glycine

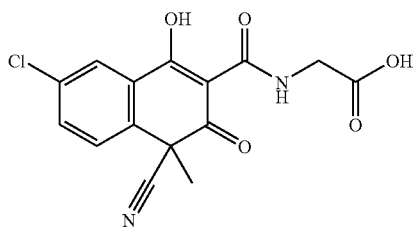

Step A: Preparation of (4-Chloro-2-iodophenyl)methanol

4-Chloro-2-iodobenzoic acid (5.0 g, 18 mmol) was dissolved in THF (40 mL) and cooled to 0° C. Borane-THF complex (1M in THF) (35 mL, 35 mmol) was added by syringe. The solution was allowed to warm to room temperature and stirred overnight. The reaction was monitored by LCMS and TLC. When the reaction was complete, water was added until gas evolution ceased and then the THF was removed under vacuum. EtOAc (100 mL) was added, and the organic layer was washed with water (3×50 mL), brine (3×50 mL), dried with $MgSO_4$, and concentrated in vacuo resulting in a white solid.

Step B: Preparation of 2-(4-Chloro-2-iodophenyl)acetonitrile (4-Chloro-2-iodophenyl)methanol (4.67 g, 17 mmol) and $PPh_3$ (6 mL, 26 mmol) were stirred in $Et_2O$ at 0° C. Diisopropyl azodicarboxylate (5 mL, 26 mmol) was added dropwise, and the reaction was stirred for 20 minutes (a white precipitate formed). A solution of acetone cyanohydrin (2 mL, 26 mmol) in diethyl ether (5 mL) was added dropwise to the reaction. The resulting solution was stirred for 5 minutes at 0° C. and then allowed to warm to room temperature over two hours. The reaction was monitored by TLC and LCMS. The mixture was filtered, and the filtrate was concentrated in vacuo. Purification was done using silica flash chromatography with a gradient of 0-15% EtOAc/hexanes. MS m/e=278 (M+H)⁺.

Step C: Preparation of 2-(4-Chloro-2-iodophenyl)propanenitrile 2-(4-Chloro-2-iodophenyl)acetonitrile (1.070 g, 3.9 mmol) was dissolved in THF (50 mL) and cooled to 0° C. Sodium tert-butoxide (0.74 g, 7.7 mmol) was added, and the solution was stirred for 10 minutes (the reaction color changed from colorless to orange.) MeI (0.24 mL, 3.9 mmol) was then added dropwise as a solution in THF (10 mL). The reaction was complete in ten minutes as determined by TLC. The crude residue was purified by silica flash chromatography using 0-15% EtOAc/hexanes. MS m/e=292 (M+H)⁺.

Step D: Preparation of 2-(4-Chloro-2-(2-(trimethylsilyl)ethynyl)phenyl)propanenitrile 2-(4-Chloro-2-iodophenyl)propanenitrile (0.620 g, 2.13 mmol), (trimethylsilyl)acetylene (0.451 mL, 3.19 mmol), copper(I) iodide (0.0144 mL, 0.425 mmol), dichlorobis(triphenylphosphine)palladium (II) (0.149 g, 0.213 mmol), and TEA (20 mL) were stirred at 70° C. for 3 hours. The reaction was monitored by LC-MS. The solution was filtered through a plug of Celite, and the filtrate was concentrated under vacuum. The residue was purified by silica flash chromatography, 0-15% EtOAc/hexanes. MS m/e=262 (M+H)⁺.

Step E: Preparation of 2-(4-Chloro-2-ethynylphenyl)propanenitrile

To a solution of 2-(4-chloro-2-(2-(trimethylsilyl)ethynyl)phenyl)-propanenitrile (0.550 g, 2.1 mmol) in THF (25 mL) was added 5N NaOH (15 mL). After one hour, the reaction was complete as determined by LC-MS and TLC. The solution was acidified with 5N HCl until the pH was about 2. The solution was extracted with EtOAc (3×40 mL). The combined organic layers were washed with water (2×30 mL) and brine (2×30 mL), dried with $MgSO_4$, and concentrated in vacuo. The resulting orange oil was purified using silica flash chromatography on the ISCO with 0-20% EtOAc/hexanes. MS m/e=190 (M+H)⁺.

Step F: Preparation of Ethyl 3-(5-chloro-2-(2-cyano-1-ethoxy-1-oxopropan-2-yl)phenyl)propiolate n-Butyllithium (0.11 g, 1.7 mmol) was added to a stirred solution of diisopropylamine (0.24 mL, 1.7 mmol) in THF (20 mL) at −78° C. The reaction was allowed to warm to room temperature for 15 minutes and was then cooled back down to −78° C. A solution of 2-(4-chloro-2-ethynylphenyl)propanenitrile (0.322 g, 1.7 mmol) in THF (5 mL) was then added dropwise to the reaction. After 20 minutes, a solution of ethyl chloroformate (0.16 mL, 1.7 mmol) in THF (5 mL) was added dropwise to the reaction mixture. The mixture was then allowed to warm to room temperature. After 15 minutes, the reaction was complete as determined by TLC and LC-MS. MeOH (2 mL) and water (35 mL) were added to the reaction mixture, and the mixture was extracted with EtOAc (3×40 mL). The combined organic layers were washed with saturated $NH_4Cl$ (3×35 mL), once with brine (35 mL), dried with $MgSO_4$, and concentrated in vacuo to afford a dark brown oil. The crude residue was purified by silica flash chromatography using a gradient of 0-20% EtOAc/hexanes. MS m/e=334 (M+H)⁺.

Step G: Preparation of Ethyl 6-chloro-1-cyano-4-hydroxy-1-methyl-2-oxo-naphthalene-3-carboxylate A solution of benzaldehyde oxime (0.16 g, 1.3 mmol) in DMF (3 mL) was added dropwise to a stirred suspension of 60% NaH (0.033 mL, 1.3 mmol) in dry 1,4-dioxane (5 mL) under a nitrogen atmosphere at room temperature. After 30 minutes, a solution of ethyl 3-(5-chloro-2-(2-cyano-1-ethoxy-1-oxopropan-2-yl)phenyl)propiolate (0.445 g, 1.3 mmol) in DMF (3 mL) was added dropwise. The reaction was monitored by LC-MS and, when complete, the solvent was removed. The residual brown oil was dissolved in DCM (50 mL), water (30 mL), and AcOH (2 mL). The layers were separated, and the aqueous layer was extracted with DCM (3×30 mL). The combined organic layers were dried with $MgSO_4$ and concentrated in vacuo. The crude residue was purified using silica flash chromatography with a gradient of 10-50% EtOAc/hexanes. MS m/e=306 (M+H)+.

Step H: Preparation of 1,1-Dimethylethyl N((6-chloro-1-cyano-4-hydroxy-1-methyl-2-oxo-naphtha-len-3-yl)carbonyl)glycinate Ethyl 6-chloro-1-cyano-4-hydroxy-1-methyl-2-oxo-naphthalene-3-carboxylate (0.165 g, 0.54 mmol) was dissolved in 1,4-dioxane (30 mL), and glycine tert-butyl ester hydrochloride (0.090 g, 0.54 mmol) and TEA (TEA) (0.11 mL, 0.81 mmol) were added. The reaction was stirred overnight at 70° C. The reaction was stirred for 18 hours. Another 0.5 equivalents of glycine and one equivalent of TEA were added, and the reaction was stirred at 105° C. for 1 hour. The solvent was then removed, and the crude residue was dissolved in EtOAc and washed with water (3×25 mL), dried with MgSO4, and concentrated. The crude product was purified by silica flash chromatography using the 10-50% EtOAc/hexanes. MS m/e=392 (M+H)+.

Step I: Preparation of N((6-Chloro-1-cyano-4-hydroxy-1-methyl-2-oxo-naphthalen-3-yl)carbonyl)glycine 1,1-Dimethylethyl N((6-chloro-1-cyano-4-hydroxy-1-methyl-2-oxo-naphthalen-3-yl)carbonyl)glycinate (0.160 g, 0.41 mmol) was placed in a 25 mL round bottom flask and TFA (20 mL) was added. The mixture was stirred for 45 minutes. TFA was then removed under vacuum, and DCM was used to azeotrope off the remaining TFA (3×) until the oil turned into a solid. MS m/e=335 (M+H)+. Calculated for $C_{15}H_{11}ClN_2O_5$ 334.04.

Examples 85 and 86

N-(((1R)-6-Chloro-1-cyano-4-hydroxy-1-methyl-2-oxo-naphthalen-3-yl)carbonyl)glycine and N-(((1S)-6-Chloro-1-cyano-4-hydroxy-1-methyl-2-oxo-naphthalen-3-yl)carbonyl)glycine

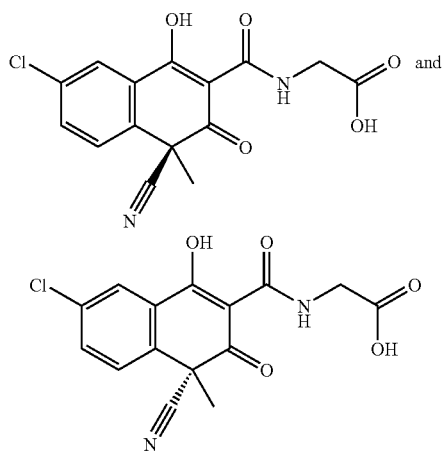

The title compounds were obtained by chiral separation N-((6-chloro-1-cyano-4-hydroxy-1-methyl-2-oxo-naphthalen-3-yl)carbonyl)glycine (Example 84) into its separate enantiomers using chiral HPLC. MS m/e=335 (M+H)+. Calculated for $C_{15}H_{11}ClN_2O_5$ 334.04.

Examples 87 and 88

N-(((1R)-1-Cyano-4-hydroxy-1-methyl-2-oxo-naphthalen-3-yl)carbonyl)glycine and N-(((1S)-1-Cyano-4-hydroxy-1-methyl-2-oxo-naphthalen-3-yl)carbonyl)glycine

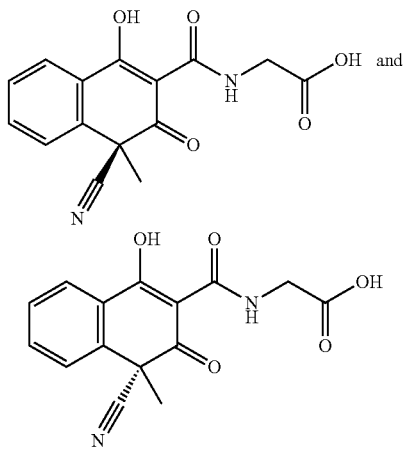

The title compounds were obtained by chiral separation of N-((1-cyano-4-hydroxy-1-methyl-2-oxo-naphthalen-3-yl)carbonyl)glycine (Example 28) into its separate enantiomers using chiral HPLC. MS (m/z)=301 (M+H)+. Calculated for $C_{15}H_{12}N_2O_5$ 300.07.

Example 89

N-((8-Chloro-4-hydroxy-1,1-dimethyl-2-oxo-naphthalen-3-yl)carbonyl)glycine

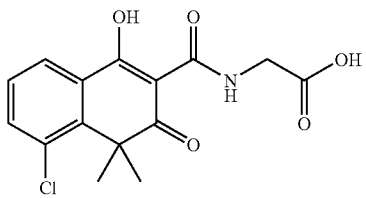

Step A: Preparation of Ethyl 2-(2-chlorophenyl)acetate

A solution of 2-chlorophenylacetic acid (10.12 g, 59.3 mmol) in EtOH (150 mL, 2576 mmol) in a 500 mL round bottom flask was treated with concentrated $H_2SO_4$ (0.700 mL, 8.28 mmol) and heated at 90° C. for 16 hours. The solution was concentrated in vacuo, diluted with 1N NaOH (aq) (200 mL), and extracted with EtOAc (2×200 mL). The combined organic layers were washed with 1N NaOH(aq) (200 mL), water (100 mL), and brine (100 mL). The organic layer was dried over MgSO4, concentrated, and dried in vacuo to give ethyl 2-(2-chlorophenyl)acetate (11.344 g). MS m/e=217 (M+H)+.

Step B: Preparation of Ethyl 2-(2-chlorophenyl)-2-methylpropanoate

A suspension of NaH (60% dispersion in mineral oil (4.03 g, 101 mmol)) and ethyl 2-(2-chlorophenyl)acetate (5.00 g, 25.2 mmol) in DMF (100 mL) in a 500 mL round bottom flask was cooled to 0° C. A solution of MeI (4.70 mL, 75.5 mmol) in DMF (50 mL) was added, dropwise, and the mixture was stirred at 25° C. for 18 hours. The reaction was quenched with 10% HCl(aq) (200 mL) and extracted with EtOAc (3×100 mL). The combined organic layers were washed with 10% HCl(aq) (100 mL), water (100 mL), and brine (100 mL). The organic layer was then dried over $MgSO_4$, concentrated, and purified by flash column chromatography (silica, 0-50% DCM in hexane) to give ethyl 2-(2-chlorophenyl)-2-methylpropanoate (3.96 g). MS m/e=227 $(M+H)^+$.

Step C: Preparation of 2-(2-Chlorophenyl)-2-methylpropanoic acid

A solution of ethyl 2-(2-chlorophenyl)-2-methylpropanoate (3.48 g, 15.4 mmol) and KOH (8.61 g, 154 mmol) in EtOH/water (1:1, 200 mL) was heated at 150° C. in a sealed vessel for 2 hours. The solution was concentrated in vacuo, suspended in diethyl ether (200 mL), and extracted with 1N NaOH(aq) (3×100 mL). The aqueous solution was made acidic with concentrated HCl and extracted with EtOAc (3×100 mL). The combined organic layers were washed with brine (100 mL), dried over $MgSO_4$, concentrated, and dried in vacuo to give to give 2-(2-chlorophenyl)-2-methylpropanoic acid (2.578 g). MS m/e=199 $(M+H)^+$.

Step D: Preparation of Diethyl 2-(2-(2-chlorophenyl)-2-methylpropanoyl)malonate A solution of 2-(2-chlorophenyl)-2-methylpropanoic acid (2.55 g, 12.8 mmol) in thionyl chloride (50.0 mL, 685 mmol) was heated at 95° C. for 2 hours. The solution was concentrated in vacuo, azeotroped using toluene (2×100 mL), and dried in vacuo to give the crude acid chloride. A mixture of diethyl malonate (1.94 mL, 12.8 mmol) and $MgCl_2$ (1.22 g, 12.8 mmol) in ACN (50 mL) was cooled to 0° C. TEA (3.75 mL, 27.0 mmol) was added slowly, and the mixture was stirred at 25° C. for 2 hours. A solution of the acid chloride in ACN (50 mL) was added, and the mixture was heated at 50° C. for 2 days. The solution was diluted with 10% HCl (aq) (200 mL) and extracted with EtOAc (3×100 mL). The combined organic layers were washed with 2N NaOH (aq) (3×200 mL) and then with brine (75 mL). The organic layer was dried over $MgSO_4$, concentrated, and purified by flash column chromatography (silica, 0-100% DCM in hexane) to give diethyl 2-(2-(2-chlorophenyl)-2-methylpropanoyl)malonate (3.25 g). MS m/e=341 $(M+H)^+$.

Step E: Preparation of Ethyl 8-chloro-4-hydroxy-1,1-dimethyl-2-oxo-naphthalene-3-carboxylate $P_2O_5$ (19.0 g, 134 mmol) was treated with concentrated $H_2SO_4$ (17.1 mL, 308 mmol) at 0° C., and the resulting mixture was stirred for 30 minutes. Diethyl 2-(2-(2-chlorophenyl)-2-methylpropanoyl)malonate (1.500 g, 3.83 mmol) was added, and the mixture was stirred at 25° C. for 1 hour. The solution was quenched with ice, and, on melting, was extracted with EtOAc (3×100 mL). The combined organic layers were washed with brine (100 mL), dried over $MgSO_4$, and concentrated and dried in vacuo to give ethyl 8-chloro-4-hydroxy-1,1-dimethyl-2-oxo-naphthalene-3-carboxylate (0.320 g). MS m/e 295 $(M+H)^+$.

Step F: Preparation of 1,1-Dimethylethyl N-((8-chloro-4-hydroxy-1,1-dimethyl-2-oxo-naphthalen-3-yl)carbonyl)glycinate A mixture of ethyl 8-chloro-4-hydroxy-1,1-dimethyl-2-oxo-naphthalene-3-carboxylate (0.320 g, 0.803 mmol), glycine tert-butyl ester hydrochloride (0.175 g, 1.04 mmol), DIEA (0.280 mL, 1.61 mmol), and 1,4-dioxane (12 mL) were heated at 120° C. for 2 hours in a sealed vessel. The mixture was diluted with water (50 mL) and extracted with DCM (2×50 mL). The combined organic layers were washed with water (30 mL) and then with brine (50 mL), dried over $MgSO_4$, and concentrated and dried in vacuo. The residue was purified by flash column chromatography (silica, 0-50% DCM in hexane) to give 1,1-dimethylethyl N-((8-chloro-4-hydroxy-1,1-dimethyl-2-oxo-naphthalen-3-yl)carbonyl)glycinate (0.214 g). MS m/e=378 $(M-H)^-$.

Step G: Preparation of N-((8-Chloro-4-hydroxy-1,1-dimethyl-2-oxo-naphthalen-3-yl)carbonyl)glycine A solution of 1,1-dimethylethyl N-((8-chloro-4-hydroxy-1,1-dimethyl-2-oxo-naphthalen-3-yl)carbonyl)glycinate (0.162 g, 0.427 mmol) in TFA (5.00 mL, 67.3 mmol) was stirred at 25° C. for 10 minutes. The solution was concentrated, azeotroped using DCM (2×100 mL), and dried in vacuo to give the title compound (0.138 g). MS m/e=324 $(M+H)^+$. Calculated for $C_{15}H_{14}ClNO_5$ 323.06.

Example 90

N-((7-Chloro-8-fluoro-4-hydroxy-1,1-dimethyl-2-oxo-naphthalen-3-yl)carbonyl)glycine

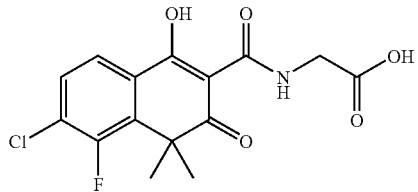

Step A: Preparation of Ethyl 2-(3-chloro-2-fluorophenyl)acetate

A solution of 2-(3-chloro-2-fluorophenyl)acetic acid (2.56 g, 13.6 mmol) and thionyl chloride (100 mL, 1371 mmol) was stirred at 95° C. for 2 hours in a 250 mL round bottom flask. The solution was concentrated, azeotroped in toluene, and dried in vacuo to give the crude acid chloride, which was then stirred in EtOH (150 mL, 2576 mmol) at 25° C. for 16 hours. The solution was concentrated in vacuo, diluted with saturated $NaHCO_3$ (aq) (100 mL), and extracted with EtOAc (2×100 mL). The combined organic layers were washed with saturated $NaHCO_3$ (aq) (100 mL), with water (100 mL), and then with brine (75 mL). The organic layer was dried over $MgSO_4$, concentrated, and purified by silica flash column chromatography (0-10% EtOAc in hexane) to give ethyl 2-(3-chloro-2-fluorophenyl)acetate (2.335 g, 79.4% yield). MS m/e=217 $(M+H)^+$.

Step B: Preparation of 2-(3-Chloro-2-fluorophenyl)-2-methylpropanoic acid

A suspension of NaH (60% dispersion in mineral oil (1.28 g, 32.0 mmol)) in DMF (50 mL) in a 500 mL round bottom flask was cooled to 0° C. A solution of ethyl 2-(3-chloro-2-fluorophenyl)acetate (2.308 g, 10.7 mmol) in DMF (20 mL) was added dropwise, and the reaction was stirred for 5 minutes. A solution of MeI (1.66 mL, 26.6 mmol) in DMF (20 mL) was added, and the mixture was stirred at 25° C. for 2 hours. The reaction was quenched with 10% HCl(aq) (200 mL), extracted with EtOAc (3×100 mL), washed with water (100 mL), and then washed with brine (100 mL). The organic layer was dried over MgSO$_4$, concentrated, and purified by flash column chromatography (silica, 0-50% DCM in hexane) to give an 11:1 mixture of ethyl 2-(3-chloro-2-fluorophenyl)-2-methylpropanoate and methyl 2-(3-chloro-2-fluorophenyl)-2-methylpropanoate. MS m/e=245, 231 (M+H)$^+$.

The above mixture was treated with KOH (5.98 g, 107 mmol) in EtOH/water (2:1, 90 mL) and heated at 150° C. in a sealed vessel for 3 hours. The solution was concentrated, diluted with diethyl ether (100 mL) and washed with 1N NaOH(aq) (2×100 mL). The aqueous solution was acidified with concentrated HCl and extracted with EtOAc (3×100 mL). The combined organic layers were washed with water (100 mL) and then with brine (75 mL). The organic layer was dried over MgSO$_4$, concentrated, and dried in vacuo to give 2-(3-chloro-2-fluorophenyl)-2-methylpropanoic acid (1.907 g). MS m/e=217 (M+H)$^+$.

Step C: Preparation of Diethyl 2-(2-(3-chloro-2-fluorophenyl)-2-methylpropanoyl)malonate A mixture of 2-(3-chloro-2-fluorophenyl)-2-methylpropanoic acid (1.386 g, 6.40 mmol) and thionyl chloride (60.0 mL, 823 mmol) was stirred at 95° C. for 2 hours. The reaction was concentrated in vacuo, azeotroped using DCM (2×100 mL), and dried in vacuo to give the crude acid chloride. A solution of diethyl malonate (0.967 mL, 6.40 mmol) and MgCl$_2$ (0.263 mL, 6.40 mmol) in ACN (40 mL) at 0° C., was treated dropwise with TEA (1.87 mL, 13.4 mmol), and the mixture was stirred at 25° C. for 3 hours. A solution of the acid chloride in ACN (35 mL) was added, and the mixture was stirred at 50° C. for 18 hours. The solution was concentrated in vacuo, diluted with 10% HCl(aq) (100 mL), and extracted with EtOAc (3×100 mL). The combined organic layers were washed with brine (75 mL), dried over MgSO$_4$, concentrated, and dried in vacuo. The residue was purified by flash column chromatography (silica, 0-100% DCM in hexane) to give 1.56 g of the title compound. MS m/e=325 (M+H)$^+$.

Step D: Preparation of 1,1-Dimethylethyl N-((6N-((7-chloro-8-fluoro-4-hydroxy-1,1-dimethyl-2-oxo-naphthalen-3-yl)carbonyl)glycinate P$_2$O$_5$ (12.5 g, 88.1 mmol) was mixed with concentrated H$_2$SO$_4$ (11.2 mL, 81.3 mmol) at 0° C., and the resulting mixture was stirred for 30 minutes. Diethyl 2-(2-(3-chloro-2-fluorophenyl)-2-methylpropanoyl)malonate (1.00 g, 2.48 mmol) was added to the reaction, and the resulting mixture was stirred at 25° C. for 1 hour. The resulting mixture was quenched with ice, and, on melting, was extracted with EtOAc (3×100 mL). The combined organic layers were washed with brine (100 mL), dried over MgSO$_4$, concentrated, and dried in vacuo to give crude ethyl 7-chloro-8-fluoro-4-hydroxy-1,1-dimethyl-2-oxo-naphthalene-3-carboxylate (0.470 g). MS m/e=313 (M+H)$^+$.

A portion of the above material (0.250 g) was treated with glycine tert-butyl ester hydrochloride (0.175 g, 1.04 mmol) and Hunig's base (0.277 mL, 1.59 mmol) in 1,4-dioxane (10 mL), and the mixture was heated at 120° C. in a sealed vessel for 2 hours. The resulting mixture was diluted with water (50 mL) and extracted with DCM (2×50 mL). The combined organic layers were washed with water (30 mL) and brine (30 mL), dried over MgSO$_4$, and concentrated. The residue was purified by flash column chromatography (silica, 0-50% DCM/hexane) to give the title compound (0.154 g). MS m/e=396.5 (M−H)−.

Step E: Preparation of N-((7-Chloro-8-fluoro-4-hydroxy-1,1-dimethyl-2-oxo-naphthalen-3-yl)carbonyl)glycine A solution of 1,1-dimethylethyl N-((6N-((7-chloro-8-fluoro-4-hydroxy-1,1-dimethyl-2-oxo-naphthalen-3-yl)carbonyl)glycinate (0.148 g, 0.372 mmol) in TFA (5.00 mL, 64.9 mmol) was stirred at 25° C. for 15 minutes. The solution was concentrated, azeotroped using DCM (2×100 mL), and dried in vacuo to give the title compound (0.128 g). MS m/e=342.4 (M+H)$^+$. Calculated for C$_{15}$H$_{13}$ClFNO$_5$ 341.05.

Example 91

N-((6-Chloro-4-hydroxy-2-oxo-1'-(phenylcarbonyl)-spiro[naphthalene-1,4'-piperidin]-3-yl)carbonyl)glycine

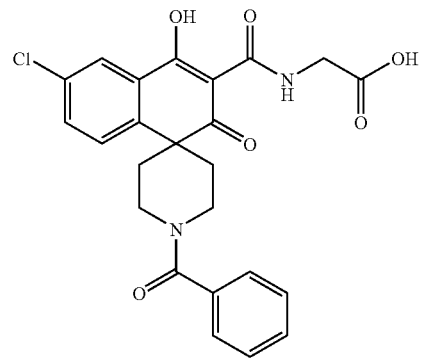

Step A: Preparation of 2-Bromo-5-chlorobenzenamine

A solution of 1-bromo-4-chloro-2-nitrobenzene (13.92 g, 58.87 mmol) in MeOH (300 mL) was treated with water (50 mL), ammonium chloride (22.99 g, 429.8 mmol), and iron powder (325 mesh, 16.44 g, 294.4 mmol). The suspension was stirred at 23° C. for 18 hours. The resulting suspension was filtered through celite. The filter cake was washed with MeOH (500 mL). The combined filtrate and washings were concentrated, and partitioned in EtOAc/water (500 mL/200 mL). The organic layer was separated. The aqueous layer was washed with EtOAc (2×200 mL). The organic layers were combined, washed with brine (200 mL), dried (MgSO$_4$), and concentrated in vacuo affording 11.51 g of 2-bromo-5-chlorobenzenamine.

Step B: Preparation of 1-Bromo-4-chloro-2-iodobenzene

A suspension of 2-bromo-5-chlorobenzenamine (11.348 g, 54.963 mmol) in concentrated HCl (100 mL) was cooled to 0°

C. and then treated in a dropwise fashion over 20 minutes using an addition funnel with a solution of sodium nitrite (4.5506 g, 65.955 mmol) in water (20 mL). The reaction was stirred at 0° C. for 75 minutes. A solution of potassium iodide (27.372 g, 164.89 mmol) in water (50 mL) was added, and the reaction was stirred at 23° C. After 1 hour, the reaction was heated to 70° C. After 18 hours, the reaction was diluted with EtOAc (500 mL) and washed with water (300 mL), 2N NaOH solution (300 mL), saturated sodium thiosulfate solution (300 mL), and brine (250 mL). The organic layer was dried over $MgSO_4$, concentrated in vacuo, and purified by silica gel chromatography (eluant: hexane) affording 11.11 g of 1-bromo-4-chloro-2-iodobenzene.

Step C: Preparation of 3,3,3-Triethoxyprop-1-yne

A solution of trimethylsilylacetylene (29.4 mL, 20.8 mmol) in diethyl ether (100 mL, anhydrous) was cooled to 0° C. in an oven-dried round bottomed flask under nitrogen. Butyllithium (2.5 M solution in hexanes (83.2 mL, 208.0 mmol)) was then added dropwise to the reaction. After 1 hour, the reaction mixture was cooled to −78° C.

A solution of tetraethyl orthocarbonate (21.8 mL, 104.0 mmol) in diethyl ether (50 mL) in a separate oven-dried round bottomed flask was cooled to 0° C. under nitrogen. The cooled mixture was treated dropwise with a solution of boron trifluoride diethyletherate (17.6 mL, 140.4 mmol) in diethyl ether (25 mL) over 20 minutes using an addition funnel. The white mixture was stirred at 0° C. for 5 minutes, and then cooled to −78° C. The TMS-acetylide solution prepared in the previous paragraph was then added to the mixture at −78° C. via cannula. After 1 hour, the reaction was removed from the dry ice-acetone bath and stirred at 23° C. for 15 minutes. The mixture was then quenched with saturated aqueous $K_2CO_3$ solution (300 mL) and extracted with diethyl ether (2×300 mL). The combined organic layers were dried over $MgSO_4$, and concentrated in vacuo affording trimethyl(3,3,3-triethoxyprop-1-ynyl)silane.

A solution of trimethyl(3,3,3-triethoxyprop-1-ynyl)silane (25 g, 102 mmol) in MeOH (400 mL) was treated with $K_2CO_3$ (14 g, 102 mmol). The reaction was stirred at 23° C. After 15 hours, the reaction was diluted with pentane (500 mL). The pentane layer was separated, and the MeOH layer was extracted with pentane (2×250 mL). The combined pentane layers were washed with water (200 mL), dried over $MgSO_4$, and concentrated (at 220 torr on rotary evaporator). The crude product was filtered through a silica gel plug, using 10% diethyl ether/pentane as the eluant, and concentrated (at 220 torr on rotary evaporator) affording 13.25 g of 3,3,3-triethoxyprop-1-yne.

Step D: Preparation of 1-Bromo-4-chloro-2-(3,3,3-triethoxyprop-1-ynyl)benzene

A suspension of 1-bromo-4-chloro-2-iodobenzene (2.5 g, 7.9 mmol), 3,3,3-triethoxyprop-1-yne (2.4 g, 13.9 mmol), copper(I) iodide, (455 mg, 2.3 mmol), and trans-dichlorobis (triphenylphosphine)palladium(II) (559 mg, 0.79 mmol) was treated with ACN (30 mL). The reaction was capped, evacuated under vacuum, backfilled with argon, and treated with TEA (9.9 mL, 71.6 mmol). The reaction was stirred at 23° C. After 2 hours, the reaction mixture was concentrated in vacuo to remove all solvents, diluted with EtOAc (250 mL), and washed with brine (150 mL). The organic layer was dried over $MgSO_4$, concentrated in vacuo, and purified by silica gel chromatography (eluant: 4% EtOAc/hexane+1% TEA) affording 2.6 g of 1-bromo-4-chloro-2-(3,3,3-triethoxyprop-1-ynyl)benzene.

Step E: Preparation of 1-tert-Butyl ethyl 4-(4-chloro-2-(3-ethoxy-3-oxoprop-1-ynyl)phenyl)piperidine-1,4-dicarboxylate A solution of dicyclohexylamine (376 µL, 1.8 mmol) in toluene (4 mL) was cooled to 0° C. under nitrogen and then treated with n-butyllithium (2.5M in hexanes (754 µL, 1.8 mmol)). After 20 minutes, 1-tert-butyl ethyl piperidine-1,4-dicarboxylate (398 µL, 1.6 mmol) was added, and the reaction was warmed to 23° C.

In a separate round-bottomed flask, 1-bromo-4-chloro-2-(3,3,3-triethoxyprop-1-ynyl)benzene (487 mg, 1.3 µmol) and $[Pd(PtBu_3)Br]_2$ (105 mg, 135 µmol) were mixed. The reaction vessel was evacuated under vacuum and backfilled with argon. Toluene (5 mL) was added, and the mixture was heated to 50° C. for 5 minutes and then transferred by syringe to the enolate solution. The aryl bromide-Pd flask was rinsed with toluene (1 mL) and added to the reaction mixture. The resulting mixture was heated at 50° C. under nitrogen. After 90 minutes, the reaction was cooled to 23° C., diluted with EtOAc (100 mL), and washed with water (50 mL) and brine (50 mL). The organic layer was dried over $MgSO_4$, concentrated in vacuo, and purified by silica gel chromatography (eluant: 4-6% EtOAc/hexane+1% TEA) affording the desired coupled product 1-tert-butyl ethyl 4-(4-chloro-2-(3,3,3-triethoxyprop-1-ynyl)phenyl)piperidine-1,4-dicarboxylate. A solution of the 1-tert-butyl ethyl 4-(4-chloro-2-(3,3,3-triethoxyprop-1-ynyl)phenyl)piperidine-1,4-dicarboxylate in EtOH (10 mL) and water (2 mL) was treated with p-toluenesulfonic acid monohydrate (69.3 mg, 364 µmol). The reaction was stirred at 23° C. for 30 minutes, and then diluted with EtOAc (100 mL) and washed with saturated $NaHCO_3$ solution (2×50 mL) and brine (50 mL), dried over $MgSO_4$, concentrated in vacuo and purified by silica gel chromatography (eluant: 12-16% EtOAc/hexane), affording 155 mg of 1-tert-butyl ethyl 4-(4-chloro-2-(3-ethoxy-3-oxoprop-1-ynyl)phenyl)piperidine-1,4-dicarboxylate. MS m/e=486.1 $(M+Na)^+$.

Step F: Preparation of Methyl N-((6-chloro-4-hydroxy-2-oxo-1'-(tert-butoxycarbonyl)-spiro[naphthalene-1,4'-piperidin]-3-yl)carbonyl)glycinate A suspension of NaH (60% dispersion in mineral oil (17 mg, 423 µmol)) in dioxane (2.5 mL) was treated with a solution of (E)-benzaldehyde oxime (51 mg, 423 µmol) in DMF (1.5 mL). The reaction was stirred at 23° C. under nitrogen. After 30 minutes, the reaction was cooled to 0° C. and then a solution of 1-tert-butyl ethyl 4-(4-chloro-2-(3-ethoxy-3-oxoprop-1-ynyl)phenyl)piperidine-1,4-dicarboxylate (157 mg, 338 µmol) in DMF (3.5 mL) was added in a dropwise fashion over 10 minutes. After 1 hour, the reaction mixture was diluted with EtOAc (100 mL) and washed with saturated $NaHCO_3$ solution (75 mL), water (75 mL) and brine (75 mL), dried over $MgSO_4$, concentrated in vacuo, and purified by silica gel chromatography (eluant: 1-8% MeOH/DCM), affording the cyclized product. The cyclized product was mixed with glycine methyl ester hydrochloride (28 mg, 220 µmol) and DIPEA (48 µL, 275 µmol) in 1,4-dioxane (4 mL) and heated to 95° C. in a sealed vessel. After 18 hours, the reaction was cooled to 23° C., diluted with EtOAc (75 mL) and washed with saturated $NaHCO_3$ solution (50 mL) and brine (50 mL), dried over $MgSO_4$, concentrated in vacuo, and purified by silica gel chromatography (eluant: 28-100% EtOAc/hexane) affording the title compound in 40 mg. MS m/e=501.2 (M+Na)+.

Step G: Preparation of Methyl N-((6-chloro-4-hydroxy-2-oxo-spiro[naphthalene-1,4'-piperidin]-3-yl) carbonyl)glycinate A solution of methyl N-((6-chloro-4-hydroxy-2-oxo-1'-(tert-butoxycarbonyl)-spiro[naphthalene-1,4'-piperidin]-3-yl)carbonyl)glycinate (333 mg, 695 µmol) in dioxane (10 mL) was treated with HCl (4.0M in 1,4-dioxane (1738 µL, 6953 µmol)). The reaction was stirred at 23° C. After 20 hours, the reaction was concentrated in vacuo affording 231 mg of the title compound as the hydrochloride salt. MS m/e=379.2 (M+H)+.

Step H: Preparation of N-((6-Chloro-4-hydroxy-2-oxo-1'-(phenylcarbonyl)-spiro[naphthalene-1,4'-piperidin]-3-yl)carbonyl)glycine A solution of the hydrochloride salt of methyl N-((6-chloro-4-hydroxy-2-oxo-spiro[naphthalene-1,4'-piperidin]-3-yl)carbonyl)glycinate (0.050 g, 0.12 mmol) and Hunig's base (0.024 mL, 0.14 mmol) in DMF/DMSO (2:1, 1.5 mL) was stirred at 25° C. for 5 minutes. A mixture of benzoic acid (0.067 g, 0.54 mmol) and N-(3-dimethylaminopropyl)-n'-ethylcarbodiimide hydrochloride (0.13 g, 0.65 mmol) in DMF (1 mL) was added. The mixture was stirred at 60° C. for 8 hours. The solution was diluted with EtOAc (20 mL), and washed with brine (2×25 mL). The organic layer was dried over MgSO4, concentrated, and purified by flash column chromatography (silica, 0-1% MeOH in DCM) to give methyl N-((6-chloro-4-hydroxy-2-oxo-1'-(phenylcarbonyl)-spiro[naphthalene-1,4'-piperidin]-3-yl)carbonyl)glycinate. MS m/e=483.5 (M+H)+.

The ester was treated with lithium hydroxide hydrate (0.025 g, 0.60 mmol) in THF (1.4 mL) and water (0.6 mL) and stirred at 25° C. for 30 minutes. The reaction was quenched with Dowex 50 (W×8) acidic resin (prewashed with MeOH) to pH<4.0 and filtered. The filtrate was concentrated and azeotroped with toluene (2×5 mL), to give the title compound (0.017 g). MS m/e=469.5 (M+H)+. Calculated for $C_{24}H_{21}ClN_2O_6$ 468.11.

Example 92

N-((6-Chloro-7-fluoro-4-hydroxy-1,1-dimethyl-2-oxo-naphthalen-3-yl)carbonyl)glycine

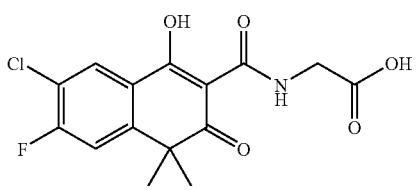

Step A: Preparation of Methyl 2-(4-chloro-3-fluorophenyl)acetate

A solution of 2-(4-chloro-3-fluorophenyl)acetic acid (10.07 g, 53.4 mmol) and concentrated $H_2SO_4$ (0.297 mL, 5.34 mmol) in MeOH (200 mL, 4940 mmol) was stirred at 95° C. for 17 hours in a 350 mL sealed vessel. The solution was concentrated in vacuo and then made basic with 1N NaOH (aq) (100 mL). The resulting mixture was extracted with EtOAc (2×100 mL), washed with water (100 mL), and then washed with brine (75 mL). The combined organic layers were dried over MgSO4, concentrated, and dried in vacuo to give methyl 2-(4-chloro-3-fluorophenyl)acetate (10.80 g). MS m/e=203.2 (M+H)+.

Step B: Preparation of Methyl 2-(4-chloro-3-fluorophenyl)-2-methylpropanoate

A mixture of NaH (60% in mineral oil (1.78 g, 44.4 mmol)) in DMF (40 mL) in an oven dried 250 mL round bottom flask was cooled to 0° C., and a solution of methyl 2-(4-chloro-3-fluorophenyl)acetate (3.00 g, 14.8 mmol) in DMF (20) was added. After stirring for 10 minutes, a solution of MeI (3.69 mL, 59.2 mmol) in DMF (40 mL) was added dropwise. The mixture was stirred at 25° C. for 4 hours. The reaction was quenched 10% HCl(aq) (150 mL) and extracted with EtOAc (3×100 mL). The combined organic layers were washed with water (200 mL) and with brine (100 mL), dried over MgSO4, concentrated, and dried in vacuo. The residue was purified by flash column chromatography (silica, 0-30% DCM in hexane) to give methyl 2-(4-chloro-3-fluorophenyl)-2-methylpropanoate (3.007 g). MS m/e=231.3 (M+H)+.

Step C: Preparation of 2-(4-Chloro-3-fluorophenyl)-2-methylpropanoic acid

A solution of methyl 2-(4-chloro-3-fluorophenyl)-2-methylpropanoate (2.94 g, 12.7 mmol) and KOH (7.15 g, 127 mmol) in EtOH (90 mL) and water (30 mL) was stirred at 150° C. in a sealed vessel for 3 hours. The solution was concentrated in vacuo, diluted with 10% HCl (aq) (150 mL), and extracted with EtOAc (2×100 mL). The combined organic layers were washed with water (2×100 mL) and then with brine (75 mL). The organic layer was dried over MgSO4, concentrated, and dried in vacuo to give 2-(4-chloro-3-fluorophenyl)-2-methylpropanoic acid (2.63 g). MS m/e=217.3 (M+H)+.

Step D: Preparation of Diethyl 2-(2-(4-chloro-3-fluorophenyl)-2-methylpropanoyl)malonate A solution of 2-(4-chloro-3-fluorophenyl)-2-methylpropanoic acid (2.05 g, 9.46 mmol) in thionyl chloride (40.0 mL, 548 mmol) in a 500 mL round bottom flask was stirred at 95° C. for 2 hours. The reaction was concentrated in vacuo and azeotroped in toluene (50 mL) to give the crude acid chloride. A solution of diethyl malonate (1.43 mL, 9.46 mmol) in ACN (20 mL) was cooled to 0° C. $MgCl_2$ (0.901 g, 9.46 mmol) and then TEA (2.76 mL, 19.9 mmol) were added, and the mixture was stirred at 25° C. for 2 hours. A solution of the acid chloride in ACN (30 mL) was added, and the mixture was stirred at 50° C. for 16 hours. The reaction was cooled, diluted with water (75 mL), and extracted with EtOAc (2×100 mL). The combined organic layers were washed with water (75 mL) and brine (75 mL). The organic layer was dried over MgSO4, concentrated, and dried in vacuo to give diethyl 2-(2-(4-chloro-3-fluorophenyl)-2-methylpropanoyl)malonate (2.95 g). MS m/e=359.4 (M+H)+.

Step E: Preparation of Ethyl 6-chloro-7-fluoro-4-hydroxy-1,1-dimethyl-2-oxo-naphthalene-3-carboxylate A suspension of $P_2O_5$ (33.0 g, 232 mmol) in concentrated $H_2SO_4$ (29.5 mL, 531 mmol) was cooled 0° C. At 0° C., the suspension was added to diethyl 2-(2-(4-chloro-3-fluorophenyl)-2-methylpropanoyl)malonate (2.90 g, 8.20 mmol), and the mixture was stirred at 25° C. for 1 hour. The reaction was quenched with ice. On melting, it was extracted with EtOAc (3×100 mL), washed with water (150 mL), and then with brine (100 mL). The organic layer was dried over MgSO$_4$ and concentrated in vacuo to give the title compound (1.349 g, 52.6% yield) as a tan solid. MS m/e=313.3 (M+H)$^+$.

Step F: Preparation of 1,1-Dimethylethyl N-((6-chloro-7-fluoro-4-hydroxy-1,1-dimethyl-2-oxo-naphthalen-3-yl)carbonyl)glycinate A solution of ethyl 6-chloro-7-fluoro-4-hydroxy-1,1-dimethyl-2-oxo-naphthalene-3-carboxylate (0.350 g, 1.12 mmol), glycine tert-butyl ester hydrochloride (0.244 g, 1.45 mmol), and Hunig's base (0.390 mL, 2.24 mmol) in 1,4-dioxane (15 mL) was heated at 120° C. for 2 hours in a sealed vessel. The solution was diluted with water (50 mL), extracted with EtOAc (2×50 mL), washed with water (50 mL), and then washed with brine (50 mL). The organic layer was dried over MgSO$_4$ and concentrated in vacuo. The residue was purified by flash column chromatography (silica, 0-75% DCM in hexane) to give the title compound (0.305 g). MS m/e=396.5 (M–H)$^-$.

Step G: Preparation of N-((6-Chloro-7-fluoro-4-hydroxy-1,1-dimethyl-2-oxo-naphthalen-3-yl)carbonyl)glycine A solution of 1,1-dimethylethyl N-((6-chloro-7-fluoro-4-hydroxy-1,1-dimethyl-2-oxo-naphthalen-3-yl)carbonyl)glycinate (0.255 g, 0.641 mmol) in TFA (5.00 mL, 67.3 mmol) was stirred at 25° C. for 10 minutes. The mixture was concentrated, azeotroped in DCM (2×50 mL), and dried in vacuo to give the title compound (0.220 g). MS m/e=342.4 (M+H)$^+$. Calculated for $C_{15}H_{13}ClFNO_5$ 341.05.

Example 93

N-((6'-Chloro-4'-hydroxy-2'-oxo-spiro[cyclobutane-1,1'-naphthalen]-3'-yl)carbonyl)glycine

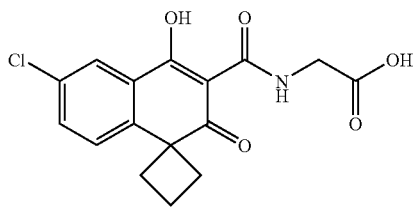

Step A: Preparation of Ethyl 2-(4-chloro-2-iodophenyl)acetate

A catalytic amount of DMF (approximately 3 drops) was added to a stirred mixture of 4-chloro-2-iodobenzoic acid (24.47 g, 86.63 mmol) and oxalyl chloride (11.34 mL, 129.9 mmol) in DCM (100 mL) under a nitrogen atmosphere. The reaction mixture was stirred for 2 hours and then concentrated in vacuo to give 4-chloro-2-iodobenzoyl chloride as a yellow oil that solidified upon standing (26.07 g).

4-Chloro-2-iodobenzoyl chloride (23.05 g, 77 mmol) was dissolved in ether (100 mL). (Trimethylsilyl)diazomethane (2.0M in diethyl ether (115 mL, 230 mmol)) was added, and the reaction mixture was stirred at room temperature for 3 hours. The reaction mixture was quenched with AcOH until nitrogen evolution stopped. The mixture was then partitioned between EtOAc and saturated NaHCO$_3$. The organic layer was separated and washed with saturated NaHCO$_3$ (2×), water (1×), and brine (1×), dried (MgSO$_4$), and concentrated in vacuo to give a yellow solid (26.93 g).

The yellow solid (26.93 g, 87.9 mmol) prepared in the previous step was dissolved in EtOH (350 mL), and silver oxide (0.564 mL, 17.6 mmol) was added. The mixture was stirred at 80° C. for 1 hour. The reaction mixture was then cooled to room temperature and filtered through celite. The filtrate was concentrated in vacuo to give a brown oil. The crude product was purified by silica flash chromatography (0-10% EtOAc/hexane) to give the desired compound as a yellow oil (20.79 g). MS (m/e)=325.0 (M+H)$^+$.

Step B: Preparation of Ethyl 1-(4-chloro-2-iodophenyl)-cyclobutanecarboxylate

Ethyl 2-(4-chloro-2-iodophenyl)acetate (3.95 g, 12 mmol) was mixed in DMF (80 mL) in a round bottom flask. NaH (60% dispersion in mineral oil (0.54 g, 13 mmol)) was added, and the reaction mixture was stirred for 15 minutes under a nitrogen atmosphere. 1,3-dibromopropane (1.4 mL, 13 mmol, 1.1 eq) was added via syringe, and the reaction mixture was stirred for 2 hours. An additional 1.10 eq NaH (60% dispersion in mineral oil (0.54 g, 13 mmol)) was added, and the reaction was stirred for 3 hours. The reaction mixture was quenched with water and diluted with EtOAc. The organic layer was separated, washed with water and brine, dried (MgSO$_4$), and concentrated in vacuo to give an orange oil. The crude product was purified by silica flash chromatography (0-30% DCM/hexane) to give the desired compound as a light yellow oil (2.01 g). MS (m/e)=365.1 (M+H)$^+$.

Step C: Preparation of Ethyl 1-(4-chloro-2-(3-ethoxy-3-oxoprop-1-ynyl)phenyl)cyclobutanecarboxylate Ethyl 1-(4-chloro-2-iodophenyl)cyclobutanecarboxylate (2.01 g, 5.51 mmol), copper(I) iodide (0.0560 mL, 1.65 mmol), and trans-dichlorobis(triphenylphosphine)palladium (II) (0.387 g, 0.551 mmol) were mixed in ACN (10 mL) and TEA (5 mL) in a round bottom flask. The flask was placed under a nitrogen atmosphere. 3,3,3-Triethoxyprop-1-yne (1.90 g, 11.0 mmol) was added via syringe, and the reaction was stirred for 16 hours. The reaction mixture was filtered through celite, and the filtrate was concentrated in vacuo to give a black oil.

The black oil prepared in the previous step was suspended in EtOH (20 mL) and water (2 mL). The mixture was treated with p-toluenesulfonic acid monohydrate (50 mg, 0.26 mmol) and stirred for 30 minutes. The reaction mixture was quenched with saturated NaHCO$_3$ and extracted with EtOAc (2×). The combined organic layers were dried (MgSO$_4$) and concentrated in vacuo to give a black oil. The crude material was purified by silica flash chromatography (0-100% DCM/hexane) to give the desired compound as a brown oil (0.80 g). MS (m/e)=335.2 (M+H)$^+$.

Step D: Preparation of Ethyl 6'-chloro-4'-hydroxy-2'-oxo-spiro[cyclobutane-1,1'-naphthalen]-3'-carboxylate Benzaldehyde oxime (174 mg, 1434 μmol) in DMF (7 mL) was added to a stirred suspension of NaH (60% dispersion in mineral oil (57 mg, 1434 µmol)) in dioxane (7 mL) under a N₂ atmosphere. The mixture was stirred for approximately 30 minutes before being cooled to 0° C. Ethyl 1-(4-chloro-2-(3-ethoxy-3-oxoprop-1-ynyl)phenyl)cyclobutanecarboxylate (400 mg, 1195 µmol) in DMF (7 mL) was added via syringe, and the reaction was stirred at 0° C. for 1 hour. The reaction was quenched with water, and extracted with EtOAc. The aqueous layer was separated and brought to a pH of about 4 with 10% HCl and extracted again with EtOAc (2×). The combined organic layers were dried (MgSO₄) and concentrated in vacuo to give an orange oil. The crude oil was purified by silica flash chromatography (0-20% EtOAc/hexane) to give the desired compound as a white solid (155 mg). MS (m/e)=307.1 (M+H)⁺.

Step E: Preparation of 1,1-Dimethylethyl N-((6'-chloro-4'-hydroxy-2'-oxo-spiro[cyclobutane-1,1'-naphthalen]-3'-yl)carbonyl)glycinate A mixture of ethyl 6'-chloro-4'-hydroxy-2'-oxo-spiro[cyclobutane-1,1'-naphthalen]-3'-carboxylate (155 mg, 505 µmol) and glycine tert-butyl ester hydrochloride (102 mg, 606 µmol) were mixed in dioxane (4 mL). DIPEA (106 µL, 606 µmol) was added, and the reaction mixture was stirred at 75° C. for 3.5 hours. The reaction mixture was cooled to room temperature and concentrated in vacuo. The resulting yellow solid was purified by silica flash chromatography (0-50% DCM/hexane) to give the desired compound as a white solid (151 mg). MS (m/e)=336.1 (M+H-tBu)⁺.

Step F: Preparation of N-((6'-Chloro-4'-hydroxy-2'-oxo-spiro[cyclobutane-1,1'-naphthalen]-3'-yl)carbonyl)glycine 1,1-Dimethylethyl N-((6'-chloro-4'-hydroxy-2'-oxo-spiro[cyclobutane-1,1'-naphthalen]-3'-yl)carbonyl)glycinate (151 mg, 385 µmol) was stirred in TFA (1 mL, 13462 µmol) for 20 minutes. Water was added. The resulting precipitate was filtered and washed with water to give the desired product as a white solid (87 mg). MS (m/e)=336.1 (M+H)⁺. Calculated for C₁₆H₁₅ClO₄ 335.06.

Example 94

N-((4-hydroxy-2-oxo-2',3',5',6'-tetrahydro-spiro[naphthalene-1,4'-pyran]-3-yl)carbonyl)glycine

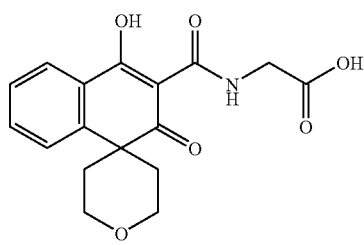

Step A: Preparation of Methyl 4-phenyl-tetrahydro-2H-pyran-4-carboxylate

To NaH (60% dispersion in mineral oil (14.2 g, 355 mmol)) was added NMP (142 mL), and the mixture was cooled to 0° C. A solution of 1-bromo-2-(2-bromoethoxy)ethane (17.8 mL, 142 mmol) and methyl phenylacetate (20.00 mL, 142 mmol) in NMP was added dropwise, and the resulting reaction mixture was stirred at 0° C. for 2 hours. The reaction was quenched with water, acidified to pH=2 with concentrated HCl, extracted with 200 mL of diethyl ether, washed 2 times with 100 mL of water, separated, dried over Na₂SO₄, and concentrated in vacuo to give the title compound after flash chromatography (15.40 g) as a white solid. MS m/e=221 (M+H)⁺.

Step B: Preparation of 4-Phenyl-tetrahydro-2H-pyran-4-carboxylic acid

Methyl 4-phenyl-tetrahydro-2H-pyran-4-carboxylate (15.4 g, 69.9 mmol) was dissolved in EtOH (100 mL). KOH (39.2 g, 699 mmol) was then added. The reaction mixture was then heated at reflux for 2 hours and then cooled to ambient temperature, diluted with 150 mL of diethyl ether, added to a separatory funnel, partitioned with water, washed 2 times with 50 mL of water, and separated. The aqueous layer was acidified to a pH of 2 with concentrated HCl and extracted with CHCl₃ (3×100 mL), dried over Na₂SO₄, and concentrated in vacuo to give the title compound (11.58 g) as a light yellow solid. MS m/e=229 (M+Na)⁺.

Step C: Preparation of Diethyl 2-(4-phenyl-tetrahydro-2H-pyran-4-carbonyl)malonate To a solution of diethyl malonate (3.96 mL, 26.2 mmol) in ACN (52.4 mL) at 0° C. was added MgCl₂ (2.74 g, 28.8 mmol) in one portion. TEA (7.30 mL, 52.4 mmol) was added dropwise, and the reaction mixture was allowed to warm to ambient temperature and stirred for 3 hours. 4-Phenyl-tetrahydro-2H-pyran-4-carboxylic acid (5.13 g, 24.9 mmol) was converted to the acid chloride by addition of thionyl chloride and reaction at 65° C. for 1 hour. The resulting acid chloride solution was then concentrated in vacuo, dissolved in ACN, and added to the initial reaction mixture. The resulting mixture was stirred at ambient temperature for 2 hours and then diluted with 200 mL of EtOAc, added to a separatory funnel, partitioned with water, washed 2 times with 75 mL of water, separated, dried over Na₂SO₄, and concentrated in vacuo to give the title compound without further purification. MS m/e=349 (M+H)⁺.

Step D: Preparation of Ethyl 4-hydroxy-2-oxo-2',3',5',6'-tetrahydro-spiro[naphthalene-1,4'-pyran]-3-carboxylate Diethyl 2-(4-phenyl-tetrahydro-2H-pyran-4-carbonyl)malonate (418 mg, 1200 µmol) was dissolved in a minimal amount of EtOAc and then cooled to 0° C. A slurry of P₂O₅ (681 mg) and H₂SO₄ (640 µL, 11998 µmol) (also at 0° C.) was added to the mixture via spatula, and the reaction mixture was stirred for 3 hours. The reaction mixture was then poured into a beaker of ice, diluted with 100 mL of EtOAc, added to a separatory funnel, partitioned with water, washed with water (2×50 mL), separated, dried over Na₂SO₄, and concentrated in vacuo to give the title compound which was used without further purification. MS m/e=303 (M+H)⁺.

Step E: Preparation of 1,1-Dimethylethyl N-((4-hydroxy-2-oxo-2',3',5',6'-tetrahydro-spiro[naphthalene-1,4'-pyran]-3-yl)carbonyl)glycinate Ethyl 4-hydroxy-2-oxo-2',3',5',6'-tetrahydro-spiro[naphthalene-1,4'-pyran]-3-carboxylate (450 mg, 1488 µmol) was dissolved in 1,4-dioxane (1488 µL) and N-ethyl-N-isopropylpropan-2-amine (778 mL, 4465 μmol). tert-Butyl 2-aminoacetate hydrochloride (374 mg, 2233 μmol) was added, and the mixture was heated at 80° C. for 3 hours. The resulting mixture was then cooled to ambient temperature, diluted with 100 mL of EtOAc, added to a separatory funnel, partitioned with NaHCO$_3$ (saturated, aqueous), washed with NaHCO$_3$ (saturated, aqueous) (2×75 mL), separated, dried over Na$_2$SO$_4$, and concentrated in vacuo to give the title compound (270 mg) as a white solid. MS m/e=388 (M+H)$^+$.

Step F: Preparation of N-((4-Hydroxy-2-oxo-2',3',5',6'-tetrahydro-spiro[naphthalene-1,4'-pyran]-3-yl)carbonyl)glycine 1,1-Dimethylethyl N-((4-hydroxy-2-oxo-2',3',5',6'-tetrahydro-spiro[naphthalene-1,4'-pyran]-3-yl)carbonyl)glycinate (270 mg, 697 mmol) was reacted with TFA (2 mL) for 30 minutes and then concentrated, precipitated with hexanes, filtered, washed with hexanes, and dried in a vacuum oven to give the title compound (193 mg) as a white solid. MS m/e=332 (M+H)$^+$. Calculated for C$_{17}$H$_{17}$NO$_6$ 331.11.

Example 95

N-((6-Chloro-4-hydroxy-2-oxo-2',3',5',6'-tetrahydro-spiro[naphthalene-1,4'-pyran]-3-yl)carbonyl)-L-serine

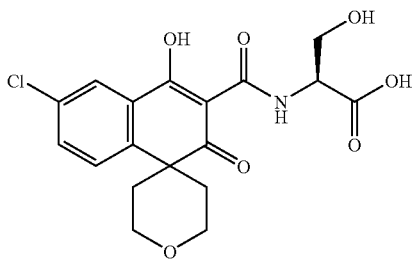

Step A: Preparation of Methyl N-((6-chloro-4-hydroxy-2-oxo-2',3',5',6'-tetrahydro-spiro[naphthalene-1,4'-pyran]-3-yl)carbonyl)-L-serinate Ethyl 6-chloro-4-hydroxy-2-oxo-2',3',5',6'-tetrahydro-spiro[naphthalene-1,4'-pyran]-3-carboxylate (287 mg, 852 μmol, Example 1 A-C) was dissolved in 1,4-dioxane (852 μL) and N-ethyl-N-isopropylpropan-2-amine (445 μL, 2557 μmol). L-Serine methyl ester hydrochloride (199 mg, 1278 μmol) was added, and the mixture was stirred at 80° C. for 3 hours. The reaction mixture was then diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the 180 mg of the title compound as a white solid after flash chromatography. MS m/e=410 (M+H)$^+$.

Step B: Preparation of N-((6-Chloro-4-hydroxy-2-oxo-2',3',5',6'-tetrahydro-spiro[naphthalene-1,4'-pyran]-3-yl)carbonyl)-L-serine Methyl N-((6-chloro-4-hydroxy-2-oxo-2',3',5',6'-tetrahydro-spiro[naphthalene-1,4'-pyran]-3-yl)carbonyl)-L-serinate (180 mg, 439 μmol) was dissolved in THF (4392 μL). NaOH in water (4392 μL, 21961 μmol) was added, and the reaction was stirred at ambient temperature for 3 hours. The pH was adjusted to about 3, and the resulting mixture was diluted with 100 mL of EtOAc, added to a separatory funnel, partitioned with water, washed 2 times with 20 mL of water, separated, dried over Na$_2$SO$_4$, and concentrated in vacuo to give the title compound (95 mg) after it was precipitated with hexanes, filtered, washed with hexanes, and dried in a vacuum oven. MS m/e=396 (M+H)$^+$. Calculated for C$_{18}$H$_{18}$NO$_7$ 395.08.

Example 96

N-((7-Chloro-6-fluoro-4-hydroxy-1,1-dimethyl-2-oxo-naphthalen-3-yl)carbonyl)glycine

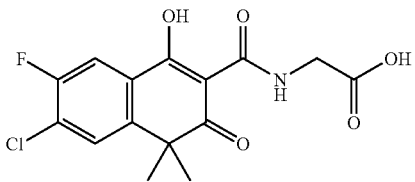

Step A: Preparation of 2-(3-Chloro-4-fluorophenyl)-2-methylpropanenitrile

NaH (60% dispersion in mineral oil, 13.3 g, 333 mmol) was suspended in DMF (151 mL, 151 mmol), cooled to 0° C., and then a solution of 3-chloro-4-fluorophenylacetonitrile (25.65 g, 151 mmol) and MeI (23.6 mL, 378 mmol) in DMF was added dropwise via addition funnel. The reaction mixture was slowly warmed to ambient temperature and stirred for 3 hours. The reaction mixture was quenched with water, diluted with 200 mL of diethyl ether, added to a separatory funnel, partitioned with water, washed with water (2×100 mL), separated, dried over Na$_2$SO$_4$, and concentrated in vacuo to give the title compound (21.01 g) as a colorless oil after flash chromatography.

Step B: Preparation of 2-(3-Chloro-4-fluorophenyl)-2-methylpropanoic acid

6M H$_2$SO$_4$ (45 mL) was added to 2-(3-chloro-4-fluorophenyl)-2-methylpropanenitrile (8.03 g, 40.6 mmol) in a sealed vial which was heated at 165° C. for 2 hours. The reaction mixture was diluted with 100 mL of diethyl ether, added to a separatory funnel, partitioned with water, washed 2 times with 100 mL of 5N NaOH (aqueous), and separated. The aqueous layer was acidified to pH=3 with 3N HCl and extracted with diethyl ether 3×75 mL). The combined organic layers were dried over Na$_2$SO$_4$, and concentrated in vacuo to give the title compound (7.73 g). MS m/e=217 (M+H)$^+$.

Step C: Preparation of Diethyl 2-(2-(3-chloro-4-fluorophenyl)-2-methylpropanoyl)malonate Diethyl malonate (5.68 mL, 37.6 mmol) was dissolved in ACN (75 mL) at 0° C. MgCl$_2$ (3.93 g, 41.3 mmol) was added to the reaction mixture in one portion and TEA (10.5 mL, 75.1 mmol) was added dropwise. 2-(3-chloro-4-fluorophenyl)-2-methylpropanoic acid (7.73 g, 35.7 mmol) was converted to the acid chloride by reaction with thionyl chloride at 65° C. for 1 hour, and the resulting acid chloride was concentrated under reduced pressure. The acid chloride was then dissolved in ACN and added dropwise via addition funnel to the initial reaction mixture. The resulting mixture was stirred at ambient temperature for 2 hours and then quenched with water, acidified with 5N HCl, diluted with 100 mL of diethyl ether, added to a separatory funnel, partitioned with water, washed with water (2×50 mL), separated, dried over Na$_2$SO$_4$, and concentrated in vacuo to give the title compound (7.17 g) as a light yellow oil after flash chromatography. MS m/e=359 (M+H)$^+$.

Step D: Preparation of Ethyl 7-chloro-6-fluoro-4-hydroxy-1,1-dimethyl-2-oxo-naphthalene-3-carboxylate P$_2$O$_5$ (1.43 g, 10.1 mmol) was suspended in H$_2$SO$_4$ (5.38 mL) and cooled to 0° C. Diethyl 2-(2-(3-chloro-4-fluorophenyl)-2-methylpropanoyl)malonate (3.62 g, 10.1 mmol) was added, and the reaction was stirred at 0° C. for 1 hour. The reaction mixture was poured into ice, diluted with 150 mL of diethyl ether, added to a separatory funnel, partitioned with water, washed with water (2×75 mL), separated, dried over Na$_2$SO$_4$, and concentrated in vacuo to the title compound (1.46 g) as a white amorphous solid after flash chromatography. MS m/e=313 (M+H)$^+$.

Step E: Preparation of 1,1-Dimethylethyl N-((7-chloro-6-fluoro-4-hydroxy-1,1-dimethyl-2-oxo-naphthalen-3-yl)carbonyl)glycinate Ethyl 7-chloro-6-fluoro-4-hydroxy-1,1-dimethyl-2-oxo-naphthalene-3-carboxylate (820 mg, 2622 µmol) was dissolved in 1,4-dioxane (5244 µL) and N-ethyl-N-isopropyl-propan-2-amine (1370 µL, 7866 µmol). tert-Butyl 2-aminoacetate hydrochloride (659 mg, 3933 µmol) was added, and the reaction was stirred at 80° C. for 3 hours. The reaction mixture was then diluted with 100 mL of EtOAc, added to a separatory funnel, partitioned with NaHCO$_3$ (saturated, aqueous), washed 2 times with 50 mL of NaHCO$_3$ (saturated, aqueous), separated, dried over Na$_2$SO$_4$, and concentrated in vacuo to give the title compound (200 mg) as a white solid after flash chromatography. MS m/e 420 (M+Na)$^+$.

Step F: Preparation of N-((7-Chloro-6-fluoro-4-hydroxy-1,1-dimethyl-2-oxo-naphthalen-3-yl)carbonyl)glycine 1,1-Dimethylethyl N-((7-chloro-6-fluoro-4-hydroxy-1,1-dimethyl-2-oxo-naphthalen-3-yl)carbonyl)glycinate (200 mg, 503 µmol) was reacted with TFA (2 mL) at ambient temperature for 30 minutes. The mixture was concentrated, precipitated with hexanes, filtered, washed with hexanes, and dried in a vacuum oven to give the title compound (139 mg) as a white solid. MS m/e=342 (M+H)$^+$. Calculated for C$_{15}$H$_{13}$NO$_5$ 341.05.

Example 97

N-((7-Chloro-6-fluoro-4-hydroxy-2-oxo-2',3',5',6'-tetrahydro-spiro[naphthalene-1,4'-pyran]-3-yl)carbonyl)glycine

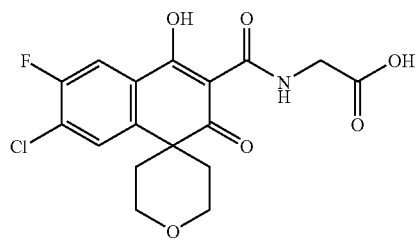

Step A: Preparation of 4-(3-Chloro-4-fluorophenyl)-tetrahydro-pyran-4-carbonitrile NaH (60% in mineral oil, 14.3 g, 357 mmol) was suspended in NMP (143 mL) and cooled to 0° C. A solution of 1-chloro-2-(2-chloroethoxy)ethane (20.4 g, 143 mmol) and 3-chloro-4-fluorophenylacetonitrile (24.23 g, 143 mmol) in ether was then added dropwise via addition funnel. The resulting reaction mixture was stirred at 0° C. for 3 hours and then quenched with water, acidified with 5N HCl, diluted with 400 mL of diethyl ether, added to a separatory funnel, partitioned with water, washed 3 times with 100 mL of water, separated, dried over Na$_2$SO$_4$, and concentrated in vacuo to give the title (16.99 g) after flash chromatography. MS m/e=240 (M+H)$^+$.

Step B: Preparation of 4-(3-Chloro-4-fluorophenyl)-tetrahydro-pyran-4-carboxylic acid 6M H$_2$SO$_4$ (43.6 mL) was added to 4-(3-chloro-4-fluorophenyl)-tetrahydro-pyran-4-carbonitrile (9.40 g, 39.2 mmol) in a sealed vial which was then heated at 165° C. for 4 hours. The reaction mixture was subsequently cooled to ambient temperature, diluted with 100 mL of diethyl ether, added to a separatory funnel, partitioned with water, washed 2 times with 100 mL of 5N NaOH (aqueous), and separated. The aqueous layer was acidified to pH=3 with 3N HCl and extracted 2 times with 75 mL of diethyl ether. The combined organic layers were dried over Na$_2$SO$_4$, and concentrated in vacuo to give the title compound (5.61 g). MS m/e=259 (M+H)$^+$.

Step C: Preparation of Diethyl 2-(4-(3-chloro-4-fluorophenyl)-tetrahydro-pyran-4-carbonyl)malonate MgCl$_2$ (2.39 g, 25.1 mmol) was added to diethyl malonate (3.45 mL, 22.8 mmol) in ACN (45.7 mL) after cooling the reaction mixture to 0° C. TEA (6.36 mL, 45.7 mmol) was then added dropwise, and the reaction mixture was warmed to ambient temperature and stirred for 2 hours. 4-(3-Chloro-4-fluorophenyl)-tetrahydro-pyran-4-carboxylic acid (5.61 g, 21.7 mmol) was converted to the acid chloride by reaction with thionyl chloride at 70° C. for 1 hour. The acid chloride reaction mixture was concentrated, dissolved in ACN, and added dropwise to the initial reaction mixture. The resulting mixture was stirred at ambient temperature for 2 hours and then quenched with water, acidified with 5N HCl, diluted with 100 mL of diethyl ether, added to a separatory funnel, partitioned with water, washed 2 times with 50 mL of water, separated, dried over Na$_2$SO$_4$, and concentrated in vacuo to give the title (3.87 g) after flash chromatography. MS m/e=401 (M+H)$^+$.

Step D: Preparation of Ethyl 7-chloro-6-fluoro-4-hydroxy-2-oxo-2',3',5',6'-tetrahydro-spiro[naphthalene-1,4'-pyran]-3-carboxylate P$_2$O$_5$ (1.4 g) was suspended in H$_2$SO$_4$ (3.34 mL), and the mixture was cooled to 0° C. Diethyl 2-(4-(3-chloro-4-fluorophenyl)-tetrahydro-pyran-4-carbonyl)malonate (1.43 g, 3.57 mmol) was then added dropwise, and the resulting mixture was stirred for 1.5 hours. The reaction mixture was allowed to warm to ambient temperature and stirred for 5 hours. The reaction mixture was then poured into a beaker of ice, diluted with 200 mL of diethyl ether, added to a separatory funnel, partitioned with water, washed with water (2×75 mL), separated, dried over Na$_2$SO$_4$, and concentrated in vacuo to give the title compound (0.96 g) as a colorless oil after flash chromatography. MS m/e=355 (M+H)+.

Step E: Preparation of 1,1-Dimethylethyl N-((7-chloro-6-fluoro-4-hydroxy-2-oxo-2',3',5',6'-tetrahydro-spiro[naphthalene-1,4'-pyran]-3-yl)carbonyl) glycinate Ethyl 7-chloro-6-fluoro-4-hydroxy-2-oxo-2',3',5',6'-tetrahydro-spiro[naphthalene-1,4'-pyran]-3-carboxylate (580 mg, 1635 μmol) was dissolved in 1,4-dioxane (3270 μL) and N-ethyl-N-isopropylpropan-2-amine (854 μL, 4905 μmol). tert-Butyl 2-aminoacetate hydrochloride (411 mg, 2452 μmol) was added, and the reaction was stirred at 80° C. for 2 hours. The reaction was then diluted with 100 mL of EtOAc, added to a separatory funnel, partitioned with NaHCO₃ (saturated, aqueous), washed 2 times with 75 mL of NaHCO₃ (saturated, aqueous), separated, dried over Na₂SO₄, and concentrated in vacuo to give the title (30 mg) compound as a white solid after flash chromatography. MS m/e=440 (M+H)+.

Step F: Preparation of N-((7-Chloro-6-fluoro-4-hydroxy-2-oxo-2',3',5',6'-tetrahydro-spiro[naphthalene-1,4'-pyran]-3-yl)carbonyl)glycine 1,1-Dimethylethyl N-((7-chloro-6-fluoro-4-hydroxy-2-oxo-2',3',5',6'-tetrahydro-spiro[naphthalene-1,4'-pyran]-3-yl)carbonyl)glycinate (79 mg, 180 μmol) was reacted with TFA (2 mL) at ambient temperature for 30 minutes. The resulting mixture was concentrated, precipitated with hexanes, filtered, washed with hexanes, and dried in a vacuum oven to give the title compound (49 mg) as an off-white solid. MS m/e=384 (M+H)+. Calculated for C₁₇H₁₅NO₆ 383.06.

Example 98

N-((4-Hydroxy-1,1-dimethyl-7-((1E)-3-(methyloxy)-1-propen-1-yl)-2-oxo-naphthalen-3-yl)carbonyl) glycine

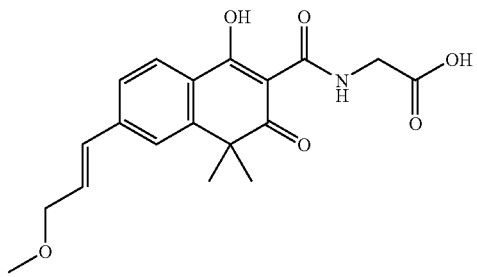

Step A: Preparation of 1,1-Dimethylethyl N-((4-hydroxy-1,1-dimethyl-7-((1E)-3-(methyloxy)-1-propen-1-yl)-2-oxo-naphthalen-3-yl)carbonyl)glycinate 1,1-Dimethylethyl N-((7-bromo-4-hydroxy-1,1-dimethyl-2-oxo-naphthalen-3-yl)carbonyl)glycinate (500 mg, 1178 μmol, see Example 53) was dissolved in 1,4-dioxane (11785 μL). 2M K₂CO₃ in water (2357 μL, 4714 μmol), Pd(Ph₃P)₄ (136 mg, 118 μmol), and (E)-2-(3-methoxyprop-1-enyl)-4,4,5,5-tetramethyl-1,3,2-dioxaborolane (300 μL, 1414 μmol) were added, and the reaction was stirred at 80° C. for 2 hours.

The reaction mixture was cooled to ambient temperature, diluted with 100 mL of EtOAc, added to a separatory funnel, partitioned with NaHCO₃ (saturated, aqueous), washed 2 times with 50 mL of NaHCO₃ (saturated, aqueous), separated, dried over Na₂SO₄, and concentrated in vacuo to give the title compound (385 mg) after flash chromatography. MS m/e=438 (M+Na)+.

Step B: Preparation of N-((4-Hydroxy-1,1-dimethyl-7-((1E)-3-(methyloxy)-1-propen-1-yl)-2-oxo-naphthalen-3-yl)carbonyl)glycine 1,1-Dimethylethyl N-((4-hydroxy-1,1-dimethyl-7-((1E)-3-(methyloxy)-1-propen-1-yl)-2-oxo-naphthalen-3-yl)carbonyl)glycinate (75 mg, 181 μmol) was dissolved in TFA (2 mL) at ambient temperature for 30 minutes before it was concentrated, precipitated with hexanes, filtered, washed with hexanes, and dried in a vacuum oven to give the title compound (15 mg) as a yellow solid. MS m/e=360 (M+H)+. Calculated for C₁₉H₂₁NO₆ 359.14.

Example 99

N-((4-Hydroxy-1,1-dimethyl-7-(3-(methyloxy)propyl)-2-oxo-naphthalen-3-yl)carbonyl)glycine

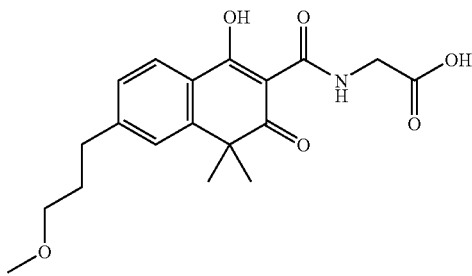

Step A: Preparation of 1,1-Dimethylethyl N-((4-hydroxy-1,1-dimethyl-7-(3-(methyloxy)propyl)-2-oxo-naphthalen-3-yl)carbonyl)glycinate To a mixture of 1,1-dimethylethyl N-((4-hydroxy-1,1-dimethyl-7-((1E)-3-(methyloxy)-1-propen-1-yl)-2-oxo-naphthalen-3-yl)carbonyl)glycinate (245 mg, 590 μmol, Example 98A) in EtOH (5897 μL), was added palladium (10 wt. % on activated carbon (62.8 mg, 590 μmol)) at ambient temperature. The mixture was placed under hydrogen gas using a balloon, and the reaction mixture was stirred for 1.5 hours before it was filtered through a pad of Celite, washed with DCM, and concentrated to give the title compound (284 mg) as a light yellow oil. MS m/e=440 (M+Na)+.

Step B: Preparation of N-((4-Hydroxy-1,1-dimethyl-7-(3-(methyloxy)propyl)-2-oxo-naphthalen-3-yl) carbonyl)glycine TFA (2 mL) was added to 1,1-dimethylethyl N-((4-hydroxy-1,1-dimethyl-7-(3-(methyloxy)propyl)-2-oxo-naphthalen-3-yl)carbonyl)glycinate (284 mg, 680 μmol) at ambient temperature, and the reaction was stirred for 30 minutes. The resulting mixture was concentrated to give the title compound (108 mg) as a light yellow amorphous solid after purification via preparatory LC. MS m/e=362 (M+H)⁺. Calculated for $C_{19}H_{23}NO_6$ 361.15.

Example 100

6-Chloro-4-hydroxy-N,1,1-trimethyl-2-oxo-naphthalene-3-carboxamide

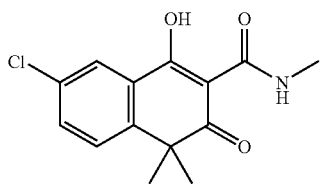

Step A: Preparation of 6-Chloro-4-hydroxy-N,1,1-trimethyl-2-oxo-naphthalene-3-carboxamide Ethyl 6-chloro-4-hydroxy-1,1-dimethyl-2-oxo-naphthalene-3-carboxylate (1.10 g, 3732 μmol, see Example 2) was dissolved in 2M methanamine in THF (9331 μL, 18661 μmol). The resulting mixture was stirred at 60° C. for 16 hours and then diluted with 100 mL of EtOAc. The resulting mixture was added to a separatory funnel, partitioned with NaHCO₃ (saturated, aqueous), washed 2 times with 20 mL of NaHCO₃ (saturated, aqueous), separated, dried over Na₂SO₄ and concentrated in vacuo to give the title compound (131 mg) as a white solid after purification via preparatory LC. MS m/e=280 (M+H)⁺. Calculated for $C_{14}H_{14}ClNO_3$ 279.07.

Example 101

6-Chloro-4-hydroxy-1,1-dimethyl-2-oxo-naphthalene-3-carboxamide

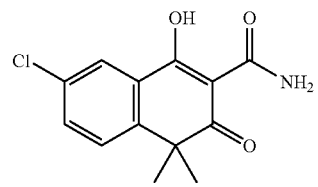

Step A: Preparation of 6-Chloro-4-hydroxy-1,1-dimethyl-2-oxo-naphthalene-3-carboxamide Ethyl 6-chloro-4-hydroxy-1,1-dimethyl-2-oxo-naphthalene-3-carboxylate (1.19 g, 4038 μmol, see Example 2) was dissolved in ammonia (0.5M in 1,4-dioxane (40376 μL, 20188 μmol)), and the resulting mixture was heated at 70° C. for 16 hours. The reaction mixture was then concentrated, dissolved in MeOH and ammonium hydroxide, and stirred at ambient temperature for 16 hours. The reaction mixture was then heated at 80° C. for 16 hours. The reaction mixture was concentrated, suspended in DCM, filtered, and washed with DCM. The mother liquor was purified via preparatory LC to give the title compound (31 mg) as an off-white solid. MS m/e=266 (M+H)⁺. Calculated for $C_{13}H_{12}ClNO_3$ 265.09.

Example 102

N-((6-chloro-4-hydroxy-1,1-dimethyl-2-oxo-naphthalen-3-yl)carbonyl)-D-alanine

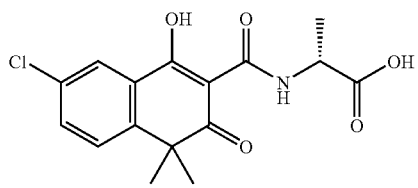

Step A: Preparation of Methyl N-((6-chloro-4-hydroxy-1,1-dimethyl-2-oxo-naphthalen-3-yl)carbonyl)-D-alaninate To ethyl 6-chloro-4-hydroxy-1,1-dimethyl-2-oxo-naphthalene-3-carboxylate (100 mg, 339 μmol, see Example 2) and D-alanine methyl ester hydrochloride (71 mg, 509 mmol) was added 1,4-dioxane (339 μL) and N-ethyl-N-isopropylpropan-2-amine (177 μL, 1018 μmol). The reaction was then heated at 80° C. for 16 hours. The resulting reaction mixture was evaporated to give the title compound (78 mg) as an amorphous solid after purification via preparatory LC. MS m/e=352 (M+1)⁺.

Step B: Preparation of N-((6-Chloro-4-hydroxy-1,1-dimethyl-2-oxo-naphthalen-3-yl)carbonyl)-D-alanine Methyl N-((6-chloro-4-hydroxy-1,1-dimethyl-2-oxo-naphthalen-3-yl)carbonyl)-D-alaninate (75 mg, 213 μmol) was dissolved in THF (2132 μL). 5N NaOH in water (2132 μL, 10660 μmol) was added at ambient temperature, and the reaction was stirred for 3 hours. The reaction mixture was acidified with 3N HCl, diluted with 50 mL of EtOAc, added to a separatory funnel, washed 2 times with 20 mL of brine (saturated, aqueous), separated, dried over Na₂SO₄, and concentrated to give the title compound as a white amorphous solid. MS m/e 338 (M+H)⁺. Calculated for $C_{16}H_{16}ClNO_5$ 337.07.

Example 103

2-(5-Hydroxy-8,8-dimethyl-7-oxo-7,8-dihydroquinoline-6-carboxamido)acetic acid

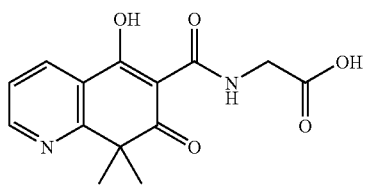

Step A: Preparation of 2-(3-Iodopyridin-2-yl)acetonitrile

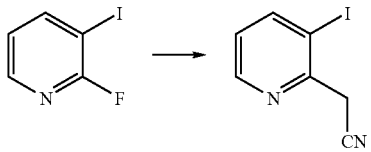

To a solution of n-butyllithium (11 mL, 27 mmol) in dry THF (150 mL) at −78° C., was added dry ACN (2 mL, 29 mmol). The resulting mixture was stirred at −78° C. for 45 minutes to generate a suspension of lithionitrile. 2-Fluoro-3-iodopyridine (5 g, 22 mmol) was added as a solution in 10 mL of THF, and the yellow mixture was allowed to warm slowly to room temperature. By the time that the temperature reached −19° C., the reaction had turned dark green. After 35 minutes (reaction temperature=−7° C.), TLC (0-30% EtOAc/hexane) showed a new lower spot and a trace of starting material. LCMS showed the desired mass ((M+H)$^+$=245). The reaction was quenched with saturated NH$_4$Cl and extracted with EtOAc. The combined organic layers were washed 3 times with saturated NH$_4$Cl and brine, and then dried over MgSO$_4$ and concentrated in vacuo to give a dark solid. The resulting product was purified by silica flash chromatography (0-50% EtOAc/hexane and then 10% MeOH/DCM) to give the title compound as a dark yellow solid (1.8 g, 33%). MS (m/z)=245 (M+H)$^+$. Calculated for C$_7$H$_5$IN$_2$ 244.0.

Step B: Preparation of 2-(3-Iodopyridin-2-yl)-2-methylpropanenitrile

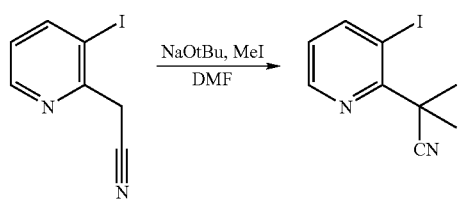

To a solution of 2-(3-iodopyridin-2-yl)acetonitrile (1.8 g, 7.4 mmol) and DMF (20 mL), was added sodium tert-butoxide (1.8 g, 18 mmol) and then MeI (1.0 mL, 16 mmol) at 0° C. The mixture was allowed to warm to room temperature. After 1.5 hours, LCMS showed complete reaction and the desired mass. The reaction was filtered through Celite and then concentrated in vacuo. The resulting product was extracted with EtOAc and washed with water and brine (3× each) and then dried over MgSO$_4$ and concentrated in vacuo to give the crude product as a brown oil. The crude product was purified by silica flash chromatography (0-50% EtOAc/hexane) to give the title compound as a light-orange oil (1.8 g, 90%). MS (m/z)=273 (M+H)$^+$. Calculated for C$_9$H$_9$IN$_2$ 272.1.

Step C: Preparation of 2-Methyl-2-(3-(2-(trimethylsilyl)ethynyl)pyridin-2-yl)propanenitrile

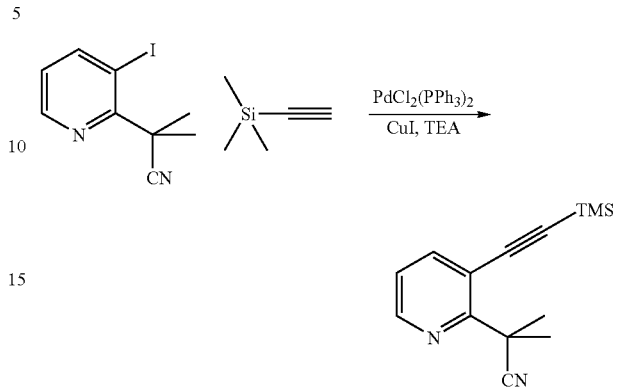

2-(3-Iodopyridin-2-yl)-2-methylpropanenitrile (1.8 g, 6.6 mmol), cuprous iodide (0.045 mL, 1.3 mmol) and dichlorobis(triphenylphosphine)palladium (II) (0.46 g, 0.66 mmol) were dissolved in TEA (20 mL, 143 mmol). Ethynyltrimethylsilane (4.7 mL, 33 mmol) was added to the reaction mixture, and the reaction mixture was placed under an argon atmosphere. The reaction mixture was stirred and heated at 80° C. After 45 minutes, the reaction was >95% complete as determined by LCMS. The reaction was cooled to room temperature and then filtered through Celite to remove a dark solid. The filtrate was concentrated in vacuo and purified by silica flash chromatography (0-50% EtOAc/hexane) to give the title compound as a light-orange oil (1.6 g, 100%). MS (m/z)=243 (M+H)$^+$. Calculated for C$_{14}$H$_{18}$N$_2$Si 242.4.

Step D: Preparation of 2-(3-Ethynylpyridin-2-yl)-2-methylpropanenitrile

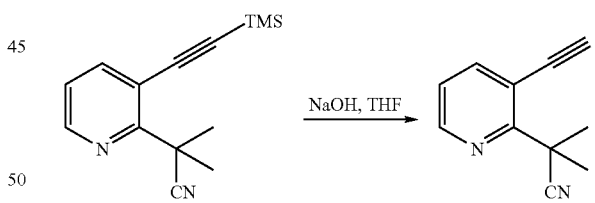

To a solution of 2-methyl-2-(3-(2-(trimethylsilyl)ethynyl)pyridin-2-yl)propanenitrile (1.6 g, 6.6 mmol) and THF (20 mL, 244 mmol), was added NaOH (13 mL, 66 mmol). After 1.5 hours, TLC (30% EtOAc/hexane) showed complete reaction to provide a product with a lower spot. The reaction was acidified with 5N HCl (pH=2) and then was extracted with EtOAc. The organic layer was washed with water and brine (3× each) and then dried over MgSO$_4$ and concentrated in vacuo to give a yellow oil. The crude product was purified by silica flash chromatography (0-75% EtOAc/hexane) to give the desired product as a light-orange crystalline solid (0.93 g, 83%). MS (m/z)=171 (M+H)$^+$. Calculated for C$_{11}$H$_{10}$N$_2$ 170.2.

Step E: Preparation of Ethyl 3-(2-(2-cyanopropan-2-yl)pyridin-3-yl)propiolate

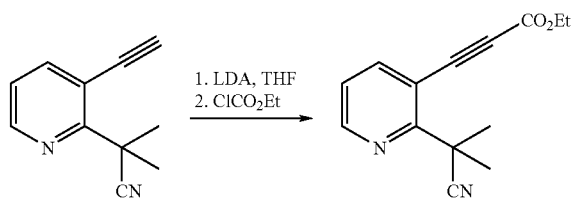

2.5M n-butyllithium (6.6 mL, 16 mmol) was added to a stirred solution of diisopropylamine (2.4 mL, 17 mmol) in THF (20 mL) at −78° C. The reaction mixture was then allowed to warm to ambient temperature for 5 minutes before being cooled back down to −78° C. 2-(3-Ethynylpyridin-2-yl)-2-methylpropanenitrile (0.93 g, 5.5 mmol) was then added dropwise as a solution in THF (20 mL). After 15 minutes, ethyl chloroformate (1.7 mL, 17 mmol) in 5 mL of THF was added to the reaction. The resulting solution was allowed to warm to ambient temperature, and was then stirred for 15 minutes. TLC (30% EtOAc/hexane) showed complete reaction and a slightly lower spot than the starting material. 3 mL of MeOH was added at 8° C. and then 3 mL of $H_2O$ was added. The mixture was extracted with EtOAc, and the combined organic layers were washed with water (3×), saturated $NH_4Cl$ (3×) and brine (3×). The organic layer was then dried over $MgSO_4$ and concentrated in vacuo. The crude product was purified by silica flash chromatography (0-75% EtOAc/hexane) to give the title compound as a white crystalline solid (0.98 g, 74%). MS (m/z)=243 (M+H)$^+$. Calculated for $C_{14}H_{14}N_2O_2$ 242.3.

Step F: Preparation of Ethyl 5-hydroxy-7-imino-8,8-dimethyl-7,8-dihydroquinoline-6-carboxylate

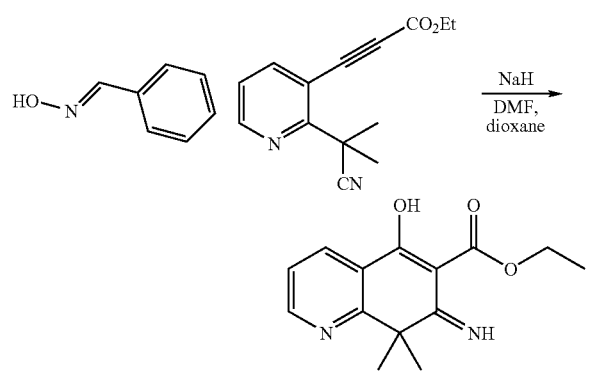

A solution of benzaldehyde oxime (0.6 g, 5 mmol) in dry DMF (10 mL, 129 mmol) was added to a stirred suspension of 60% NaH (0.2 g, 5 mmol) in dry 1,4-dioxane (10 mL, 117 mmol) under a nitrogen atmosphere at room temperature. After 0.5 hours, a solution of the ethyl 3-(2-(2-cyanopropan-2-yl)pyridin-3-yl)propiolate (0.98 g, 4 mmol) in dry DMF (10 mL, 129 mmol) was added, and the solution was stirred for 30 minutes. The solvent was removed under vacuum, and water was added to the residue. The product was extracted with EtOAc. The organic layer was washed with water (3×) and then with saturated $NH_4Cl$ and brine (3× each) and dried over $MgSO_4$. The resulting mixture was concentrated in vacuo to give a light-yellow crystalline solid/yellow oil. The yellow residue was washed with hexane providing the product as a yellow solid which was filtered off (0.65 g, 62%). MS (m/z)= 261 (M+H)$^+$. Calculated for $C_{14}H_{16}N_2O_3$ 260.3.

Step G: Preparation of Ethyl 5-hydroxy-8,8-dimethyl-7-oxo-7,8-dihydroquinoline-6-carboxylate

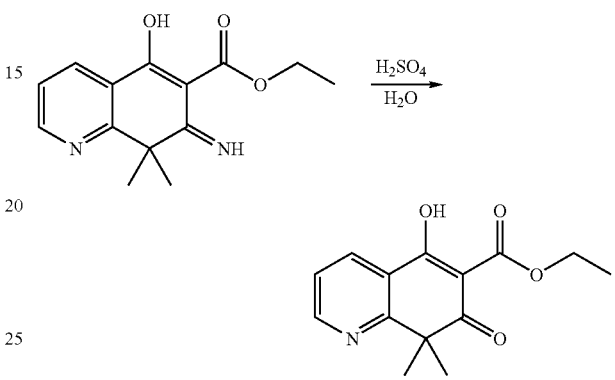

To a mixture of ethyl 5-hydroxy-7-imino-8,8-dimethyl-7,8-dihydroquinoline-6-carboxylate (100 mg, 384 μmol) and water (3 mL, 166525 μmol), was added $H_2SO_4$ (0.02 mL, 384 μmol). The resulting mixture was then heated to 80° C. After 30 minutes, 0.1 mL of $H_2SO_4$ was added. After 90 minutes, the reaction was cooled to room temperature and extracted with EtOAc. The organic phase was washed with water and then with saturated $NaHCO_3$ and brine. The organic layer was dried over $MgSO_4$ and concentrated in vacuo to give a light-yellow solid. The aqueous layer was concentrated in vacuo to give a white solid/yellow liquid. The solid was washed with EtOH and a white solid was filtered away. The filtrate was concentrated in vacuo to give a yellow solid. The solid was washed with DCM and the supernatant was decanted off. The solid was dissolved in MeOH and concentrated in vacuo to give a light-yellow solid which was washed once more with DCM and the supernatant was decanted away. The solid was placed under high-vacuum to leave a light-yellow solid which was purified by silica flash chromatography (0-10% MeOH/DCM) to give the title compound as a white crystalline solid (24 mg, 24%). MS (m/z)=262 (M+H)$^+$. Calculated for $C_{14}H_{15}NO_4$ 261.3.

Step H: Preparation of tert-Butyl 2-(5-hydroxy-8,8-dimethyl-7-oxo-7,8-dihydroquinoline-6-carboxamido)acetate

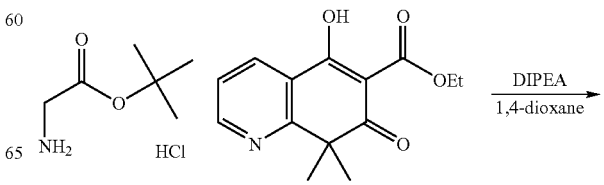

-continued

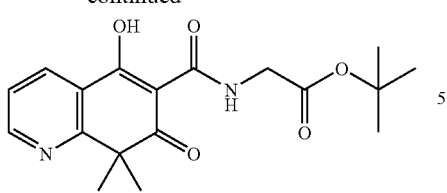

DIPEA (0.05 mL, 276 μmol) was added to a stirred mixture of ethyl 5-hydroxy-8,8-dimethyl-7-oxo-7,8-dihydroquinoline-6-carboxylate (24 mg, 92 μmol) and glycine tert-butyl ester hydrochloride (38 mg, 230 μmol) in 1,4-dioxane (3 mL). The reaction mixture was then stirred at 75° C. for 1.5 hours. The reaction mixture was concentrated, and the residue was purified by silica flash chromatography (0-75% EtOAc/hexane) to give the title compound as a crystalline white solid (15 mg, 47%). MS (m/z)=347 (M+H)$^+$. Calculated for $C_{18}H_{22}N_2O_5$ 346.4.

Step I: Preparation of 2-(5-Hydroxy-8,8-dimethyl-7-oxo-7,8-dihydroquinoline-6-carboxamido)acetic acid

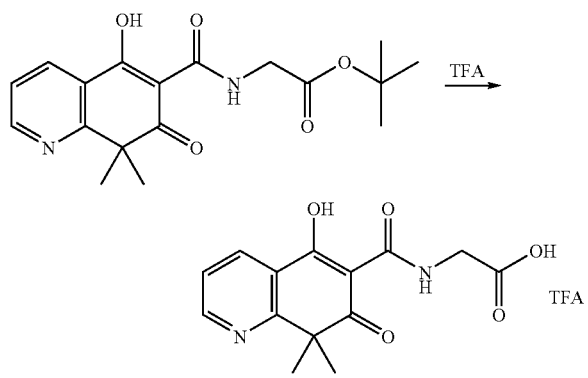

A solution of tert-butyl 2-(5-hydroxy-8,8-dimethyl-7-oxo-7,8-dihydroquinoline-6-carboxamido)acetate (15 mg) and TFA (1 mL) was stirred at room temperature. After 20 minutes, LCMS showed that the reaction was complete. The reaction was concentrated in vacuo to give a yellow oil. The sample was lyophilized to give a white solid (10 mg, 60%). MS (m/z)=291 (M+H)$^+$. Calculated for $C_{14}H_{14}N_2O_5$ 290.3.

Example 104

4-(7-Bromo-1-hydroxy-4,4-dimethyl-3-oxo-3,4-dihydronaphthalen-2-yl)-4-oxobutanoic acid

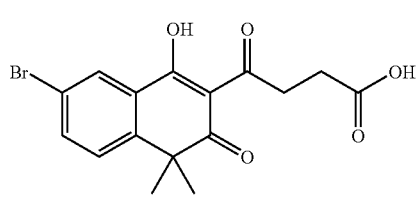

Step A: Preparation of 6-Bromo-4-hydroxy-1,1-dimethylnaphthalen-2(1H)-one

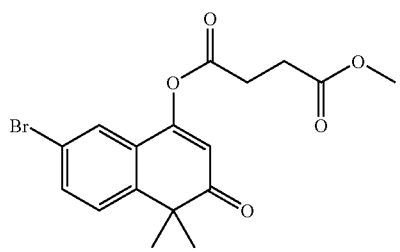

Concentrated aqueous HCl (36.5-37.5%, 10 mL) was added to a solution of ethyl 7-bromo-1-hydroxy-4,4-dimethyl-3-oxo-3,4-dihydronaphthalene-2-carboxylate (1.40 g, 4 mmol) in TFA (10 mL). The mixture was heated to 80° C. for 18 hours. The solvent was then removed under reduced pressure, and the residue was rinsed with water and diethyl ether. The remaining solids were dried in vacuo at 50° C. to afford the title compound in 70% yield. $^1$H-NMR (300 MHz, DMSO-d$_6$) δ ppm 7.98 (1H, d, J=1.9 Hz), 7.75 (1H, dd, J=2.0, 8.5 Hz), 7.67 (1H, br. d, J~8.0 Hz), 5.64 (1H, s), 2.51 (6H, m). MS (m/z not observed).

Step B: Preparation of 7-Bromo-4,4-dimethyl-3-oxo-3,4-dihydronaphthalen-1-yl methyl succinate

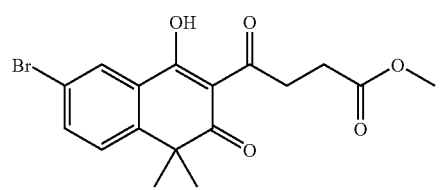

Methyl 4-chloro-4-oxobutyrate (0.107 mL, 0.873 mmol) was added to a solution of 6-bromo-4-hydroxy-1,1-dimethylnaphthalen-2(1H)-one (0.212 g, 0.794 mmol), TEA (0.121 mL, 0.873 mmol) in 1,2-dichloroethane (3 mL). The mixture was diluted with DCM, washed with water, washed with NaHCO$_3$, and dried over MgSO$_4$. The crude product was purified by flash chromatography using EtOAc/hexane to afford 7-bromo-4,4-dimethyl-3-oxo-3,4-dihydronaphthalen-1-yl methyl succinate in 85% yield. $^1$H-NMR (300 MHz, CDCl$_3$) δ ppm 7.74 (1H, d, J=2.0 Hz), 7.59 (1H, dd, J=8.4, 2.1 Hz), 7.36 (1H, d, J=8.5 Hz), 6.20 (1H, s), 3.73 (3H, s), 3.01 (2H, t, J=6.0 Hz), 2.80 (2H, t, J=6.0 Hz), 1.48 (6H, s). MS m/z: 381.

Step C: Preparation of Methyl 4-(7-bromo-1-hydroxy-4,4-dimethyl-3-oxo-3,4-dihydronaphthalen-2-yl)-4-oxobutanoate A mixture of 7-bromo-4,4-dimethyl-3-oxo-3,4-dihydronaphthalen-1-yl methyl succinate (0.112 g, 0.29 mmol)

and sodium acetate (0.024 g, 0.29 mmol) was heated at 160° C. for 15 minutes. The mixture was cooled to room temperature, diluted with DCM, and washed with water. The organic phase was dried over MgSO$_4$ and concentrated. The crude product was purified by flash chromatography using EtOAc/hexane to afford the title compound in 23% yield. $^1$H-NMR (300 MHz, CDCl$_3$) δ ppm 8.36-8.31 (1H, m), 7.73-7.68 (1H, m), 7.39-7.35 (1H, m), 3.72, 3.71 (3H, 2 s), 3.62, 3.49 (2H, 2 t, J~6.4 Hz), 2.74-2.68 (2H, m), 1.64, 1.50 (6H, 2 s). MS m/z: 383 (M$^+$).

Step D: Preparation of 4-(7-Bromo-1-hydroxy-4,4-dimethyl-3-oxo-3,4-dihydronaphthalen-2-yl)-4-oxobutanoic acid

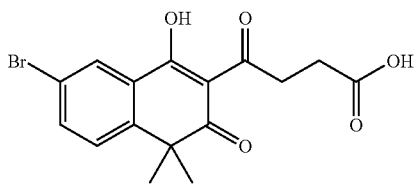

A solution of aqueous NaOH (5M, 2.0 mL) was added to a solution of methyl 4-(7-bromo-1-hydroxy-4,4-dimethyl-3-oxo-3,4-dihydronaphthalen-2-yl)-4-oxobutanoate (0.061 g, 0.16 mmol) in THF (1.5 mL). The mixture was stirred for 15 minutes at room temperature, diluted with DCM, and extracted with water. The water phase was acidified to pH=1 using aqueous HCl (5M) and extracted with EtOAc. The combined organic layers were dried over MgSO$_4$ and evaporated. The product was rinsed with diethyl ether and dried to afford the title compound in 31% yield. $^1$H-NMR (300 MHz, DMSO-d$_6$) δ ppm 12.19 (1H, br. s.), 8.17, 8.16 (1H, 2 s), 7.91-7.88 (1H, m), 7.75-7.72 (1H, m), 3.45-3.35 (2H, m, partially covered by HDO signal), 2.60-2.56 (2H, m), 1.54 (6H, br. s.). MS m/z: 368 (M$^+$).

Example 105

2-(5-Hydroxy-8,8-dimethyl-7-oxo-7,8-dihydroisoquinoline-6-carboxamido)acetic acid

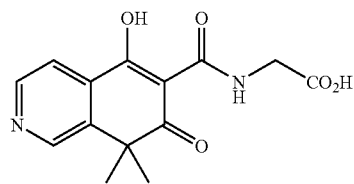

Step A: Preparation of ethyl 2-(3-fluoroisonicotinoyl)-4-methyl-3-oxopentanoate

A mixture of ethyl isobutyrylacetate (2 mL, 10 mmol) in 20 mL ACN stirred at room temperature was treated with magnesium chloride (0.9 g, 10 mmol) in one portion and TEA (2 g, 22 mmol) drop wise. The mixture was stirred at room temperature for 2.5 hours.
A mixture of 3-fluoroisonicotinic acid (1.4 g, 10 mmol) in sulfuryl dichloride (12 g, 99 mmol) was refluxed for 2 hours until all solid was dissolved. The mixture was concentrated in vacuo. The residue was diluted with 30 mL ACN, and added to the above mixture drop wise. The mixture turned cloudy and was stirred at room temperature for 3.5 hours, M+1=282. The mixture was diluted with 200 mL ether, neutralized with 5N HCl to pH=5, washed with H$_2$O (2×50 mL), brine 20 mL, dried over anhydrous Na$_2$SO$_4$, and concentrated in vacuo. The crude product was purified by column eluting with 10-20% EtOAc/hexane to give 2.1 g of the intermediate as a pale orange yellow oil. MS m/e: (M+H)$^+$ 282.

Step B: Preparation of ethyl 5-hydroxy-8,8-dimethyl-7-oxo-7,8-dihydroisoquinoline-6-carboxylate A mixture of potassium t-butoxide (0.34 g, 3.0 mmol) in 8 mL NMP stirred at room temperature was treated with a solution of ethyl 2-(3-fluoroisonicotinoyl)-4-methyl-3-oxopentanoate (0.28 g, 1.00 mmol) in 1 mL NMP drop wise. The dark red solution was stirred at room temperature for 15 hours, M+1=262. There were two spots that had the MS=262. The mixture was poured into 200 mL water. The mixture was extracted with DCM (3×50 mL). The combined organic layers were washed with brine (20 mL), dried, and concentrated. The crude product was purified by column eluting with 10-50% EtOAc/hexane to give 0.2 g oil. MS m/e: (M+H)$^+$ 262.

Step C: Preparation of tert-butyl 2-(5-hydroxy-8,8-dimethyl-7-oxo-7,8-dihydroisoquinoline-6-carboxamido)acetate A mixture of ethyl 5-hydroxy-8,8-dimethyl-7-oxo-7,8-dihydroisoquinoline-6-carboxylate (0.2 g, 0.8 mmol) and tert-butyl 2-aminoacetate hydrochloride (0.2 g, 0.9 mmol) in 1 mL dioxane was treated with N-ethyl-N-isopropylpropan-2-amine (0.4 mL, 2 mmol). The mixture was warmed to 100° C. and stirred for 2.5 hours, M+1=347. The mixture was cooled to room temperature, diluted with 20 mL H$_2$O, and 100 mL EtOAc. The organic layer was concentrated. The crude product was purified by column eluting with 10-20% EtOAc/hexane to give 0.02 g of the product as an off-white solid. MS m/e: (M+H)$^+$ 347.

Step D: Preparation of 2-(5-hydroxy-8,8-dimethyl-7-oxo-7,8-dihydroisoquinoline-6-carboxamido)acetic acid A mixture of tert-butyl 2-(5-hydroxy-8,8-dimethyl-7-oxo-7,8-dihydroisoquinoline-6-carboxamido)acetate (0.02 g, 0.06 mmol) in 2 mL TFA was stirred at room temperature for 1 hour, M+1=291. The mixture was diluted with 10 mL water. The solution was concentrated and dried to give 0.018 g of the product as a pale yellow solid. MS m/e: (M+H)$^+$ 291.

Example 106

6-((Carboxymethyl)carbamoyl)-7-hydroxy-8,8-dimethyl-5-oxo-5,8-dihydronaphthalene-2-carboxylic acid

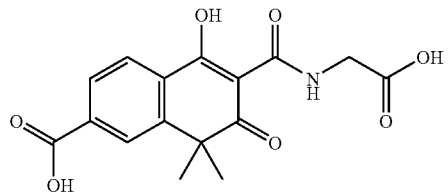

Tert-butyl 2-(7-bromo-2-hydroxy-1,1-dimethyl-4-oxo-1,4-dihydronaphthalene-3-carboxamido)acetate (253 mg, 596 μmol, Example 53A-E), trans-dichlorobis(triphenylphosphine)palladium (II) (21 mg, 30 μmol), and triphenylphosphine (16 mg, 60 μmol) were added to a vial, followed by water (32 μL, 1789 μmol) and n-tributylamine (1491 μL). The reaction mixture was placed under 4 atm of carbon monoxide at 90° C. for 18 hours. The reaction mixture was diluted with 50 mL of EtOAc, washed 3 times with 50 mL of 5 N NaOH (aqueous), and separated. The aqueous layer was acidified to pH 2 with concentrated HCl and extracted 2 times with 50 mL of EtOAc, dried over sodium sulfate, and concentrated via rotovap to give the title compound. MS (ESI) m/z: Calculated; 333.3: Observed; 334.0.

Example 107

2-(2-Hydroxy-1,1-dimethyl-7-(2-morpholinoethylamino)-4-oxo-1,4-dihydronaphthalene-3-carboxamido)acetic acid

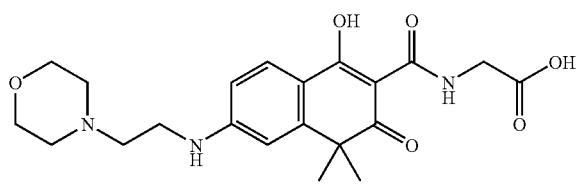

Step A: Preparation of tert-butyl 2-(2-hydroxy-1,1-dimethyl-7-(2-morpholinoethylamino)-4-oxo-1,4-dihydronaphthalene-3-carboxamido)acetate Tert-butyl 2-(7-bromo-2-hydroxy-1,1-dimethyl-4-oxo-1,4-dihydronaphthalene-3-carboxamido)acetate (125 mg, 295 μmol, Example 53A-E), palladium acetate (7 mg, 29 μmol), racemic-2,2-bis(diphenylphosphino)-1,1-binaphthyl (18 mg, 29 μmol), and sodium tert-butoxide (42 mg, 442 μmol) were added to toluene (5892 μL) followed by 2-morpholinoethylamine (77 μL, 589 μmol). The reaction was then stirred at 110° C. for 3 hours. The reaction mixture was diluted with 100 mL of EtOAc, washed 2 times with 50 mL of 3 N HCl (aqueous), and separated. The organic layer was dried over sodium sulfate and concentrated to give crude product which was purified via HPLC to give the title compound.

Step B: Preparation of 2-(2-hydroxy-1,1-dimethyl-7-(2-morpholinoethylamino)-4-oxo-1,4-dihydronaphthalene-3-carboxamido)acetic acid Tert-butyl 2-(2-hydroxy-1,1-dimethyl-7-(2-morpholinoethylamino)-4-oxo-1,4-dihydronaphthalene-3-carboxamido)acetate (25 mg, 53 μmol) was dissolved in TFA (2 mL) at room temperature for 30 minutes and concentrated to give crude product. The crude product was purified via preparatory TLC to give the title compound. MS (ESI) m/z: Calculated; 417.5: Observed; 418.1.

Example 108

(E)-2-(2-Hydroxy-1,1-dimethyl-4-oxo-7-styryl-1,4-dihydronaphthalene-3-carboxamido)acetic acid

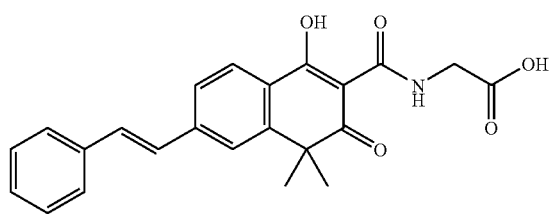

Step A: Preparation of (E)-tert-butyl 2-(2-hydroxy-1,1-dimethyl-4-oxo-7-styryl-1,4-dihydronaphthalene-3-carboxamido)acetate Tert-butyl 2-(7-bromo-2-hydroxy-1,1-dimethyl-4-oxo-1,4-dihydronaphthalene-3-carboxamido)acetate (360 mg, 848 μmol, Example 53A-E) was dissolved in 1,4-dioxane (8485 μL) and then beta-styrylboronic acid pinacol ester (293 mg, 1273 mmol), potassium carbonate (2 M in water, 2121 μL, 4242 μmol) and tetrakis(triphenylphosphine)palladium (98.0 mg, 84.8 μmol) were added. The reaction was stirred at 80° C. for 4 hours. The reaction mixture was diluted with 100 mL of EtOAc, washed 2 times with 50 mL of sodium bicarbonate (saturated, aqueous), separated, dried over sodium sulfate, and concentrated to give crude product. The title compound was obtained by flash chromatography.

Step B: Preparation of (E)-2-(2-hydroxy-1,1-dimethyl-4-oxo-7-styryl-1,4-dihydronaphthalene-3-carboxamido)acetic acid (E)-tert-butyl 2-(2-hydroxy-1,1-dimethyl-4-oxo-7-styryl-1,4-dihydronaphthalene-3-carboxamido)acetate (120 mg, 268 μmol) was dissolved in TFA (2 mL) and stirred at room temperature for 30 minutes. The reaction mixture was concentrated, suspended in hexanes, filtered, washed with hexanes, and dried in a vacuum oven to give the title compound. MS (ESI) m/z: Calculated; 391.4: Observed; 392.0.

Example 109

2-(2-Hydroxy-1,1-dimethyl-4-oxo-7-phenethyl-1,4-dihydronaphthalene-3-carboxamido)acetic acid

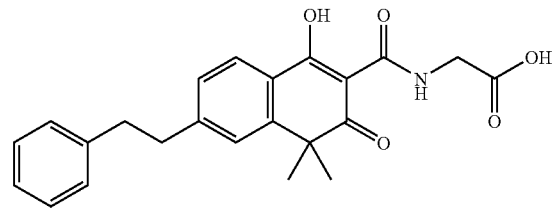

Step A: Preparation of tert-butyl 2-(2-hydroxy-1,1-dimethyl-4-oxo-7-phenethyl-1,4-dihydronaphthalene-3-carboxamido)acetate (E)-tert-butyl 2-(2-hydroxy-1,1-dimethyl-4-oxo-7-styryl-1,4-dihydronaphthalene-3-carboxamido)acetate (150 mg, 335 μmol, Example 108) was dissolved in EtOH (3352 μL). Palladium (10% on carbon, 35.7 mg, 335 μmol) was added, and the reaction mixture was placed under one atmosphere of hydrogen with a balloon for 2 hours. The reaction mixture was filtered through a pad of Celite, washed with DCM, and concentrated to give the title compound.

Step B: Preparation of 2-(2-hydroxy-1,1-dimethyl-4-oxo-7-phenethyl-1,4-dihydronaphthalene-3-carboxamido)acetic acid Tert-butyl 2-(2-hydroxy-1,1-dimethyl-4-oxo-7-phenethyl-1,4-dihydronaphthalene-3-carboxamido)acetate (130 mg, 289 μmol) was dissolved and stirred in TFA (2 mL) at ambient temperature for 30 minutes. The mixture was then concentrated to give the title compound. MS (ESI) m/z: Calculated; 393.4: Observed; 394.0

Example 110

2-(2-Hydroxy-1,1-dimethyl-4-oxo-7-(2-phenylethynyl)-1,4-dihydronaphthalene-3-carboxamido)acetic acid

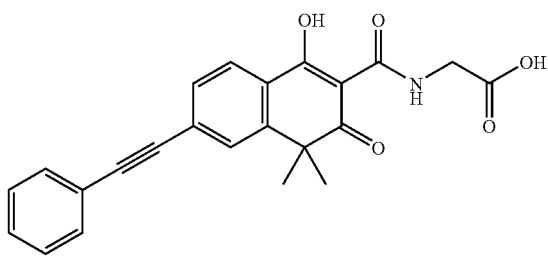

Step A: Preparation of tert-butyl 2-(2-hydroxy-1,1-dimethyl-4-oxo-7-(2-phenylethynyl)-1,4-dihydronaphthalene-3-carboxamido)acetate To a mixture of tert-butyl 2-(7-bromo-2-hydroxy-1,1-dimethyl-4-oxo-1,4-dihydronaphthalene-3-carboxamido)acetate (120 mg, 283 µmol, Example 53A-E), palladium dichloride bistriphenylphosphine (20 mg, 28 µmol), and copper(I) iodide (11 mg, 57 µmol) was added THF (1414 µL), N-ethyl-N-isopropylpropan-2-amine (148 µL, 848 µmol), and phenylacetylene (62 µL, 566 µmol). The reaction was heated at 80° C. for 2 hours. The reaction mixture was diluted with 100 mL of EtOAc, washed 2 times with 75 mL of sodium bicarbonate (saturated, aqueous), separated, dried over sodium sulfate, and concentrated to give crude product which was purified via flash chromatography to give the title compound.

Step B: Preparation of 2-(2-hydroxy-1,1-dimethyl-4-oxo-7-(2-phenylethynyl)-1,4-dihydronaphthalene-3-carboxamido)acetic acid Tert-butyl 2-(2-hydroxy-1,1-dimethyl-4-oxo-7-(2-phenylethynyl)-1,4-dihydronaphthalene-3-carboxamido)acetate (68 mg, 153 µmol) was dissolved and stirred in TFA (2 mL) at room temperature for 30 minutes. The reaction was concentrated, suspended in hexanes, filtered, washed with hexanes, and dried in a vacuum oven to give the title compound. MS (ESI) m/z: Calculated; 389.4: Observed; 390.0.

Example 111

N-((8-Chloro-2-hydroxy-4-oxo-2',3',5',6'-tetrahydro-4H-spiro[naphthalene-1,4'-pyran]-3-yl)carbonyl)glycine

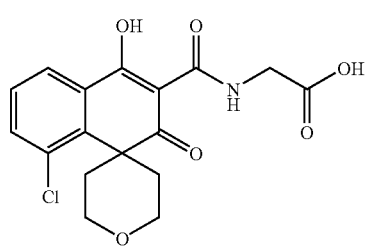

Step A: Preparation of 2-(bromomethyl)-1-chloro-3-iodobenzene

A mixture of 1-chloro-3-iodo-2-methylbenzene (11 g, 44 mmol) in 60 mL $CCl_4$ was stirred at 70° C. and treated with 1-bromopyrrolidine-2,5-dione (12 g, 65 mmol) and dibenzoyl peroxide (1.1 g, 4.4 mmol) slowly. The resulting mixture was refluxed for 15 hours. The mixture was cooled to room temperature, filtered through a plug of Celite, and washed with 10% EtOAc/hexane. The organic was concentrated and purified by column chromatography (0-10% EtOAc/hexane) to give 14 g pink solid.

Step B: Preparation of 2-(2-chloro-6-iodophenyl)acetonitrile

A mixture of 2-(bromomethyl)-1-chloro-3-iodobenzene (14 g, 42 mmol) in 100 mL EtOH was treated with a solution of potassium cyanide (3.6 mL, 84 mmol) in 40 mL water. The mixture was refluxed for 2.5 hours. The mixture was cooled to room temperature and then concentrated. The residue was diluted with 200 mL EtOAc, washed with water (2×50 mL), saturated NaCl (50 mL), dried over sodium sulfate and concentrated. The crude product was purified by column chromatography (20% EtOAc/hexane) to give 10.18 g pale yellow solid. MS m/e: (M−1)⁻ 276.

Step C: Preparation of 2-(2-chloro-6-iodophenyl)acetic acid

A mixture of 2-(2-chloro-6-iodophenyl)acetonitrile (10 g, 36 mmol) in 20 mL dioxane was treated with 25 mL 9M $H_2SO_4$. The mixture was stirred at 115° C. for 2 hours. The mixture was transferred into a sealed tube and heated to 150° C. and stirred for 2 hours. The mixture was then cooled to room temperature and diluted with 100 mL water. The mixture was extracted with EtOAc (3×50 mL). The combined organic layers were washed with saturated NaCl (20 mL), dried over sodium sulfate, and concentrated to give crude product 10.3 g as pale yellow solid. MS m/e: (M+H)⁺ 297.

Step D: Preparation of ethyl 2-(2-chloro-6-iodophenyl)acetate

A mixture of 2-(2-chloro-6-iodophenyl)acetic acid (10 g, 34 mmol) in 100 mL EtOH was treated with 2 mL concentrated $H_2SO_4$, and refluxed for 15 hours. The resulting mixture was cooled to room temperature and concentrated. The residue was diluted with 200 mL EtOAc, washed with water (3×50 mL), saturated NaCl (20 mL), dried over sodium sulfate and concentrated. The crude mixture was purified by column chromatography (10-20% EtOAc/hexane) to give 9.5 g of pale yellow oil. MS m/e: (M+H)⁺ 324.

Step E: Preparation of ethyl 4-(2-bromoethoxy)-2-(2-chloro-6-iodophenyl)butanoate A mixture of ethyl 2-(2-chloro-6-iodophenyl)acetate (4.5 g, 14 mmol) in 12 mL DMF was stirred at room temperature and treated with sodium hydride (0.80 g, 35 mmol). The mixture turned to orange and was stirred for 10 minutes. The mixture was treated dropwise with 1-bromo-2-(2-bromoethoxy)ethane (4.2 g, 18 mmol) in 12 mL DMF. The resulting mixture was stirred at room temperature for 2.5 hours. The reaction mixture was then warmed to 60° C. and stirred for 2 hours. The mixture was cooled to room temperature and quenched carefully with 20 mL $H_2O$, extracted with ether (3×100 mL). The combined organic layers were washed with water (3×50 mL), 20 mL saturated NaCl, dried over anhydrous Na$_2$SO$_4$, and concentrated to give 5.8 g of the crude product as a yellow oil. MS m/e: (M+H)$^+$ 475/477.

Step F: Preparation of ethyl 4-(2-chloro-6-(3,3,3-triethoxyprop-1-ynyl)phenyl)-tetrahydro-2H-pyran-4-carboxylate A mixture of ethyl 4-(2-bromoethoxy)-2-(2-chloro-6-iodophenyl)butanoate (5.8 g, 12 mmol) and TEA (15 mL, 110 mmol) in 24 mL ACN was degassed by vacuum and back filled with nitrogen 3 times. The mixture was treated with 3,3,3-triethoxyprop-1-yne (2.7 g, 16 mmol), dichlorobis(triphenylphosphine)palladium(ii) (0.17 g, 0.24 mmol) and copper(I) iodide (0.12 g, 0.61 mmol). The mixture was stirred at 55° C. for 2 hours. The mixture was cooled to room temperature, diluted with 100 mL EtOAc, and washed with water (3×20 mL) and then with 20 mL saturated NaCl. The organic layers were dried and concentrated. The crude product was evaporated from 50 mL toluene and dissolved in 50 mL DMF. The mixture was treated with 0.7 g NaH. The mixture was stirred at room temperature for 15 hours. The mixture was quenched with 50 mL water and neutralized with 10% HCl to pH=5. The mixture was then extracted with ether (3×100 mL). The combined organic layers were washed with water (3×20 mL) and saturated NaCl (20 mL), and then dried over anhydrous sodium sulfate and concentrated. The crude product was purified by column chromatography (10% EtOAc/hexane) to give 2.42 g yellow oil. MS m/e: (M+H)$^+$ 487.

Step G: Preparation of ethyl 4-(2-chloro-6-(3-ethoxy-3-oxoprop-1-ynyl)phenyl)-tetrahydro-2H-pyran-4-carboxylate A mixture of ethyl 4-(2-chloro-6-(3,3,3-triethoxyprop-1-ynyl)phenyl)-tetrahydro-2H-pyran-4-carboxylate (2.42 g, 5.51 mmol) in 50 mL EtOH and 10 mL water was treated with 4-methylbenzenesulfonic acid hydrate (0.105 g, 0.551 mmol). The mixture was stirred at room temperature for 2 hours. The mixture was diluted with 100 mL EtOAc, washed with 20 mL saturated NaHCO$_3$, dried over anhydrous Na$_2$SO$_4$ and concentrated. The concentrate was purified by column chromatography (20% EtOAc/hexane) to give 1.19 g pale yellow solid. MS m/e: (M+H)$^+$ 365.

Step H: Preparation of (Z)-ethyl 4-(2-chloro-6-(3-ethoxy-1-hydroxy-3-oxoprop-1-enyl)phenyl)-tetrahydro-2H-pyran-4-carboxylate A mixture of lithium acetate (0.21 g, 3.2 mmol) in 5 mL TFA at room temperature was treated with ethyl 4-(2-chloro-6-(3-ethoxy-3-oxoprop-1-ynyl)phenyl)-tetrahydro-2H-pyran-4-carboxylate (1.18 g, 3.2 mmol), and palladium(II) acetate (0.036 g, 0.16 mmol). The reaction was stirred at room temperature for 2 hours. The residue was diluted with 100 mL EtOAc, washed with water (3×20 mL), saturated NaCl (20 mL), dried over anhydrous sodium sulfate, and concentrated. The concentrate was purified by column chromatography (10-20% EtOAc/hexane) to give 0.38 g yellow oil. MS m/e: (M+H)$^+$ 383.

Step I: Preparation of ethyl 8-chloro-4-hydroxy-2-oxo-2',3',5',6'-tetrahydro-4H-spiro[naphthalene-1,4'-pyran]-3-carboxylate A mixture of (Z)-ethyl 4-(2-chloro-6-(3-ethoxy-1-hydroxy-3-oxoprop-1-enyl)phenyl)-tetrahydro-2H-pyran-4-carboxylate (0.38 g, 0.99 mmol) in 5 mL EtOH was treated with NaOEt (freshly made from 0.1 g Na and 5 mL EtOH), and stirred at 60° C. for 2 hours. The mixture was cooled to room temperature and diluted with 100 mL EtOAc, neutralized with 5N HCl to pH 5, washed with water (20 mL), saturated NaCl (20 mL), dried over anhydrous sodium sulfate and concentrated. The concentrate was purified by column chromatography (10-40% EtOAc/hexane) to give 0.27 g yellow solid. MS m/e: (M+H)$^+$ 337.

Step J: Preparation of t-butyl-N-((8-chloro-2-hydroxy-4-oxo-2',3',5',6'-tetrahydro-4H-spiro[naphthalene-1,4'-pyran]-3-yl)carbonyl)glycinate A mixture of ethyl 8-chloro-4-hydroxy-2-oxo-2',3',5',6'-tetrahydro-4H-spiro[naphthalene-1,4'-pyran]-3-carboxylate (0.27 g, 0.80 mmol), and tert-butyl 2-aminoacetate hydrochloride (0.20 g, 1.2 mmol) in 1 mL dioxane was treated with N-ethyl-N-isopropylpropan-2-amine (0.26 g, 2.0 mmol). The mixture was warmed to 100° C. and stirred for 2.5 hours. The mixture was then cooled to room temperature, diluted with 20 mL H$_2$O and 100 mL EtOAc. The organic layer was separated, dried over anhydrous sodium sulfate and concentrated. The concentrate was purified by column chromatography (10-20% EtOAc/hexane) to give 0.13 g off-white solid. MS m/e: (M+H)$^+$ 422.

Step K: Preparation of N-((8-chloro-2-hydroxy-4-oxo-2',3',5',6'-tetrahydro-4H-spiro[naphthalene-1,4'-pyran]-3-yl)carbonyl)glycine A mixture of t-butyl-N-((8-chloro-2-hydroxy-4-oxo-2',3',5',6'-tetrahydro-4H-spiro[naphthalene-1,4'-pyran]-3-yl)carbonyl)glycinate (0.13 g, 0.31 mmol) in 1.5 mL TFA was stirred at room temperature for 30 minutes. The mixture was diluted with 20 mL water, and a white solid precipitate formed. The solid was collected by filtration and washed with 20 mL water. The solid was dried under high vacuum to give 0.11 g off-white solid. MS m/e: (M+H)$^+$ 366.

Example 112

7 N-((5-Chloro-2-hydroxy-4-oxo-2',3',5',6'-tetrahydro-4H-spiro[naphthalene-1,4'-pyran]-3-yl)carbonyl)glycine

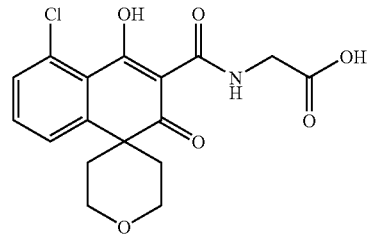

Step A: Preparation of 1-(bromomethyl)-3-chloro-2-iodobenzene

A mixture of 1-chloro-2-iodo-3-methylbenzene (7.5 g, 30 mmol) in 60 mL CCl$_4$ stirred at 70° C. was treated with 1-bromopyrrolidine-2,5-dione (7.9 g, 45 mmol) and dibenzoyl peroxide (0.72 g, 3.0 mmol) slowly. The mixture was refluxed under a sunlight lamp for 15 hours. The mixture was cooled to room temperature, filtered through a plug of Celite, and rinsed with 10% EtOAc/hexane. The filtrate was concentrated and purified by column chromatography (0-10% EtOAc/hexane) to give 7.1 g pink oil.

Step B: Preparation of 2-(3-chloro-2-iodophenyl)acetonitrile

A mixture of 1-(bromomethyl)-3-chloro-2-iodobenzene (7 g, 21 mmol) in 100 mL EtOH was treated with a solution of potassium cyanide (2 mL, 42 mmol) in 20 mL water. The mixture was refluxed for 2.5 hours. The mixture was cooled to room temperature and concentrated. The residue was diluted with 200 mL EtOAc, washed with water (2×50 mL), saturated NaCl (50 mL), dried over anhydrous sodium sulfate and concentrated. The crude product was purified by column chromatography (20% EtOAc/hexane) to give 3.2 g pale yellow solid. MS m/e: $(M+H)^+$ 278.

Step C: Preparation of 2-(3-chloro-2-iodophenyl)acetic acid

A mixture of 2-(3-chloro-2-iodophenyl)acetonitrile (3.2 g, 12 mmol) in 20 mL dioxane was treated with 25 mL 9M $H_2SO_4$. The mixture was stirred at 115° C. for 2 hours, cooled to room temperature, and diluted with 100 mL water. The mixture was extracted with EtOAc (3×50 mL). The combined organic layers were washed with saturated NaCl (20 mL), dried over anhydrous sodium sulfate, and concentrated to give crude product in 4 g as pale yellow solid. MS m/e: $(M+H)^+$ 297.

Step D: Preparation of ethyl 2-(3-chloro-2-iodophenyl)acetate

A mixture of 2-(3-chloro-2-iodophenyl)acetic acid (3.2 g, 11 mmol) in 50 mL EtOH was treated with 2 mL con. $H_2SO_4$, and refluxed for 2 hours. The mixture was cooled to room temperature, diluted with 200 mL EtOAc, washed with water (3×50 mL), saturated NaCl (20 mL), dried over anhydrous sodium sulfate and concentrated. The concentrate was purified by column chromatography (10-20% EtOAc/hexane) to give 3.62 g pale yellow oil. MS m/e: $(M+H)^+$ 325.

Step E: Preparation of ethyl 4-(3-chloro-2-iodophenyl)-tetrahydro-2H-pyran-4-carboxylate A mixture of ethyl 2-(3-chloro-2-iodophenyl)acetate (1.3 g, 4.0 mmol) in 6 mL DMF was stirred at room temperature and treated with sodium hydride (0.23 g, 10 mmol). The mixture turned orange, was stirred for 10 minutes, and was treated with 1-bromo-2-(2-bromoethoxy)ethane (1.2 g, 5.2 mmol) in 6 mL DMF dropwise. The mixture was then stirred at room temperature for 2.5 hours. The mixture was carefully quenched with 20 mL $H_2O$ and extracted with ether (3×100 mL). The combined organic layers were washed with water (3×50 mL), 20 mL saturated NaCl, dried over anhydrous $Na_2SO_4$, and concentrated. The crude product was purified by column eluting with (10-20% EtOAc/hexane) to give the title compound in 0.57 g. MS m/e: $(M+H)^+$ 395.

Step F: Preparation of ethyl 4-(3-chloro-2-(3-ethoxy-3-oxoprop-1-ynyl)phenyl)-tetrahydro-2H-pyran-4-carboxylate A mixture of ethyl 4-(3-chloro-2-iodophenyl)-tetrahydro-2H-pyran-4-carboxylate (0.57 g, 1.4 mmol) and TEA (1.8 mL, 13 mmol) in 10 mL ACN was degassed by vacuum and back filled with nitrogen 3 times. The mixture was treated with 3,3,3-triethoxyprop-1-yne (0.37 g, 2.2 mmol), dichlorobis(triphenylphosphine)palladium(II) (0.051 g, 0.072 mmol) and copper(I) iodide (0.028 g, 0.14 mmol) and stirred at 55° C. for 2 hours. The mixture was cooled to room temperature and concentrated. The residue was diluted with 50 mL EtOH and 10 mL water. The mixture was treated with 4-methylbenzenesulfonic acid hydrate (0.105 g, 0.551 mmol) and stirred at room temperature for 2 hours. The mixture was diluted with 100 mL EtOAc, washed with 20 mL saturated $NaHCO_3$, dried over anhydrous $Na_2SO_4$ and concentrated. The crude product was purified by column chromatography (10-25% EtOAc/hexane) to give 0.5 g yellow oil. MS m/e: $(M+H)^+$ 365.

Step G: Preparation of (Z)-ethyl 4-(3-chloro-2-(3-ethoxy-1-hydroxy-3-oxoprop-1-enyl)phenyl)-tetrahydro-2H-pyran-4-carboxylate A mixture of ethyl 4-(3-chloro-2-(3-ethoxy-3-oxoprop-1-ynyl)phenyl)-tetrahydro-2H-pyran-4-carboxylate (0.5 g, 1 mmol) in 1.5 mL TFA was stirred at room temperature and treated with lithium acetate (0.09 g, 1 mmol) and palladium (II) acetate (0.02 g, 0.07 mmol). The resulting solution was stirred at room temperature for 2 hours and concentrated. The residue was diluted with 100 mL EtOAc, washed with water (3×20 mL), 20 mL saturated NaCl, dried over anhydrous sodium sulfate, and concentrated. The concentrate was purified by column chromatography (10-20% EtOAc/hexane) to give 0.15 g of the product as a yellow oil. MS m/e: $(M+H)^+$ 383.

Step H: Preparation of ethyl 5-chloro-4-hydroxy-2-oxo-2',3',5',6'-tetrahydro-4H-spiro[naphthalene-1,4'-pyran]-3-carboxylate A mixture of (Z)-ethyl 4-(3-chloro-2-(3-ethoxy-1-hydroxy-3-oxoprop-1-enyl)phenyl)-tetrahydro-2H-pyran-4-carboxylate (0.14 g, 0.37 mmol) in 5 mL EtOH was treated with NaOEt (from 0.1 g Na reacted with 5 mL EtOH). The mixture was stirred at room temperature for 2 hours, quenched with 20 mL water, and neutralized with 5N HCl to pH=5. The mixture was extracted with EtOAc 3×50 mL. The combined organic layers were washed with saturated NaCl (20 mL), dried over anhydrous sodium sulfate, and concentrated. The concentrate was purified by column chromatography (10-40% EtOAc/hexane) to give 67 mg white solid. MS m/e: $(M+H)^+$ 337.

Step I: Preparation of t-butyl-N-((5-chloro-2-hydroxy-4-oxo-2',3',5',6'-tetrahydro-4H-spiro[naphthalene-1,4'-pyran]-3-yl)carbonyl)glycinate A mixture of ethyl 5-chloro-4-hydroxy-2-oxo-2',3',5',6'-tetrahydro-4H-spiro[naphthalene-1,4'-pyran]-3-carboxylate (70 mg, 208 µmol) and tert-butyl 2-aminoacetate hydrochloride (52 mg, 312 µmol) in 1 mL dioxane was treated with N-ethyl-N-isopropylpropan-2-amine (81 mg, 624 µmol). The mixture was warmed to 95° C. and stirred for 2.5 hours, cooled to room temperature, and then diluted with 20 mL $H_2O$ and 100 mL EtOAc. The organic layers were separated, washed with 20 mL 1N HCl×2, water 20 mL, saturated NaCl 20 mL, dried over anhydrous sodium sulfate, and concentrated. The concentrate was purified by column chromatography (10-20% EtOAc/hexane) to give 51 mg pale yellow solid. MS m/e: $(M+H)^+$ 366.

Step J: Preparation of N-((5-chloro-2-hydroxy-4-oxo-2',3',5',6'-tetrahydro-4H-spiro[naphthalene-1,4'-pyran]-3-yl)carbonyl)glycine A mixture of t-butyl-N-((5-chloro-2-hydroxy-4-oxo-2',3',5',6'-tetrahydro-4H-spiro[naphthalene-1,4'-pyran]-3-yl)carbonyl)glycinate (51 mg, 121 μmol) in 1 mL TFA was stirred at room temperature for 30 minutes and diluted with 20 mL water. The solid was collected by filtration and washed with 20 mL water. The solid was then dried under high vacuum to give, 39 mg pale yellow solid. MS m/e: (M+H)$^+$ 366.

Example 113

N-((7,8-Difluoro-2-hydroxy-4-oxo-2',3',5',6'-tetrahydro-4H-spiro[naphthalene-1,4'-pyran]-3-yl)carbonyl)glycine

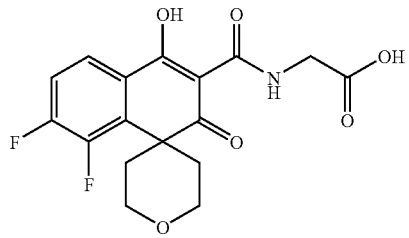

Step A: Preparation of 4-(2,3-difluorophenyl)-tetrahydro-2H-pyran-4-carbonitrile A mixture of sodium hydride (2 mL, 88 mmol) in 120 mL NMP was stirred at 0° C. and treated with a mixture of bis(2-bromoethyl)ether (9 mL, 40 mmol) and 2-(2,3-difluorophenyl)acetonitrile (6.12 g, 40 mmol) in 20 mL ether. The reaction was stirred at room temperature for 4 hours, carefully quenched with 20 mL H$_2$O, and neutralized to pH=5 with concentrated HCl. The mixture was further diluted with 200 mL water, and the precipitate was collected by filtration. The solid was redissolved in 200 mL ether, washed with 20 mL saturated NaCl, dried over anhydrous Na$_2$SO$_4$, and concentrated to give 6.55 g of the title compound as a white solid. MS m/e: (M+H)$^+$ 224.

Step B: Preparation of 4-(2,3-difluorophenyl)-tetrahydro-2H-pyran-4-carboxylic acid A mixture of 4-(2,3-difluorophenyl)-tetrahydro-2H-pyran-4-carbonitrile (7.8 g, 35 mmol) in 100 mL dioxane was treated with concentrated sulfuric acid (6.9 g, 70 mmol) 13 mL H$_2$O, and stirred at 160° C. in a sealed tube for 2 hours. The mixture was treated with 20 mL water and stirred at 110° C. for 15 hours. The mixture was then stirred at 160° C. for another 5 hours. The resulting mixture was cooled to room temperature. The reaction was then diluted with water and extracted with EtOAc. The organic layer was extracted with 1M NaOH. Upon acidifying the aqueous phase with concentrated HCl, a precipitate formed. The precipitate was collected by filtration to give 6.2 g of the title compound as pale yellow solid. MS m/e: (M+H)$^+$ 243.

Step C: Preparation of diethyl 2-(4-(2,3-difluorophenyl)-tetrahydro-2H-pyran-4-carbonyl)malonate A mixture of diethyl malonate (4.2 g, 26 mmol) in 50 mL ACN was stirred at 0° C. and treated with magnesium chloride (2.5 g, 26 mmol) in one portion and TEA (5.9 g, 58 mmol) dropwise. The mixture was stirred at room temperature for 2.5 hours. In a separate flask, a mixture of 4-(2,3-difluorophenyl)-tetrahydro-2H-pyran-4-carboxylic acid (6.4 g, 26 mmol) in sulfuryl dichloride (31 g, 264 mmol) was refluxed for 2 hours, then concentrated in vacuo. This residue was diluted with 30 mL ACN, and added to the malonate/magnesium chloride mixture dropwise. The resulting reaction was stirred at 50° C. for 1.5 hours. The mixture was cooled to room temperature, diluted with 200 mL EtOAc, neutralized to pH=5 with concentrated HCl, washed with H$_2$O (2×50 mL), saturated NaCl (20 mL), dried over anhydrous Na$_2$SO$_4$ and concentrated in vacuo. The crude product was purified by column chromatography (10-20% EtOAc/hexane) to give the intermediate 3.3 g as pale yellow oil. MS m/e: (M+H)$^+$ 385.

Step D: Preparation of ethyl 7,8-difluoro-4-hydroxy-2-oxo-2',3',5',6'-tetrahydro-4H-spiro[naphthalene-1,4'-pyran]-3-carboxylate To 10 mL concentrated H$_2$SO$_4$ stirred at 0° C. was added diethyl 2-(4-(2,3-difluorophenyl)-tetrahydro-2H-pyran-4-carbonyl)malonate (3.3 g, 8.6 mmol) dropwise. The mixture was stirred at 0° C. and allowed to warm to room temperature over 2 hours. The mixture was poured into 100 g crushed ice and extracted with EtOAc (3×100 mL). The combined organic layers were washed with saturated NaCl (20 mL), dried over anhydrous Na$_2$SO$_4$, concentrated in vacuo, and purified by column chromatography (20% EtOAc/hexane) to give the title compound 0.23 g as a pale yellow solid. MS m/e: (M+H)$^+$ 339.

Step E: Preparation of t-butyl N-((7,8-difluoro-2-hydroxy-4-oxo-2',3',5',6'-tetrahydro-4H-spiro[naphthalene-1,4'-pyran]-3-yl)carbonyl)glycinate A mixture of ethyl 7,8-difluoro-4-hydroxy-2-oxo-2',3',5',6'-tetrahydro-4H-spiro[naphthalene-1,4'-pyran]-3-carboxylate (0.23 g, 0.68 mmol), tert-butyl 2-aminoacetate hydrochloride (0.14 g, 0.82 mmol) in 3 mL dioxane was treated with N-ethyl-N-isopropylpropan-2-amine (0.26 g, 2.0 mmol). The mixture was warmed to 120° C. and stirred for 1.5 hours. The mixture was cooled to room temperature, diluted with 20 mL H$_2$O, and 100 mL EtOAc. The organic layer was separated, washed with 20 mL 1N HCl, saturated NH$_4$Cl, dried over anhydrous sodium sulfate and concentrated. The crude product was purified by column chromatography (10-20% EtOAc/hexane) to give 0.13 g white solid. MS m/e: (M+H)$^+$ 424.

Step F: Preparation of (f) N-((7,8-difluoro-2-hydroxy-4-oxo-2',3',5',6'-tetrahydro-4H-spiro[naphthalene-1,4'-pyran]-3-yl)carbonyl)glycine A mixture of t-butyl N-((7,8-difluoro-2-hydroxy-4-oxo-2',3',5',6'-tetrahydro-4H-spiro[naphthalene-1,4'-pyran]-3-yl)

carbonyl)glycinate (0.13 g, 0.3 mmol) in 3 mL TFA was stirred at room temperature for 1 hour. The mixture was diluted with 100 mL water and a white precipitate was formed to form a suspension. The suspension was stirred for 30 minutes at room temperature, filtered, and washed with 20 mL water. The solid was dried under vacuum at 45° C. for 15 hours to give 0.09 g of the title compound as a white solid. MS m/e: (M+H)+ 368.

Example 114

N-(((4S)-3-Hydroxy-4-methyl-1-oxo-4-phenyl-1,4-dihydro-2-naphthalenyl)carbonyl)glycine or N-(((4R)-3-Hydroxy-4-methyl-1-oxo-4-phenyl-1,4-dihydro-2-naphthalenyl)carbonyl)glycine

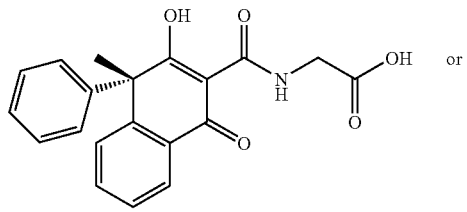

or

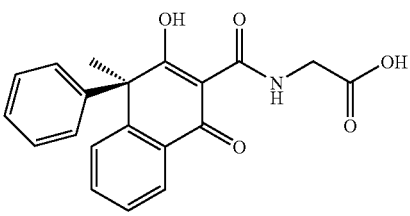

A mixture of one of the enantiomers of 2-(6-chloro-1-(4-chlorophenyl)-2-hydroxy-1-methyl-4-oxo-1,4-dihydronaphthalene-3-carboxamido)acetic acid (50 mg, 119 μmol, Example 29) and 50 mg 10% Pd—C in 10 mL MeOH was treated with sodium acetate (29 mg, 357 μmol). The mixture was stirred at room temperature under hydrogen for 4 hours, M+1=352. The mixture was filtered through a short plug of silica gel and washed with 20 mL EtOAc. The organic layer was concentrated and purified by column eluting with 1:50:100=AcOH/EtOAc/hexane to give 20 mg white solid. MS m/e: (M+H)+ 352.

TABLE 1

The following table lists compounds which were prepared by the methods described in the referenced Examples.

| Ex. | Structure | Name | MS H+ | Synthetic Method |
|---|---|---|---|---|
| 115 | 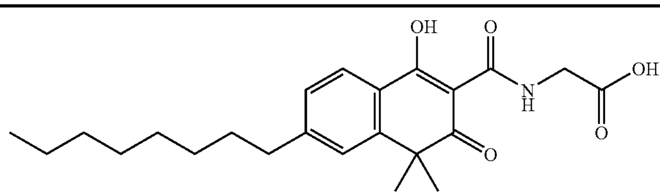 | 2-(2-hydroxy-1,1-dimethyl-7-octyl-4-oxo-1,4-dihydronaphthalene-3-carboxamido) acetic acid | 402.3 | Examples 108 and 109 |
| 116 | 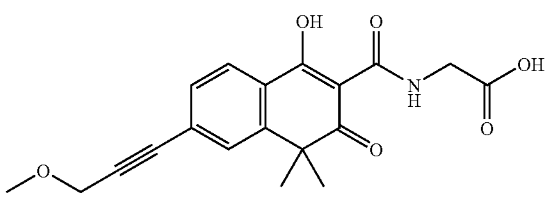 | 2-(2-hydroxy-7-(3-methoxyprop-1-ynyl)-1,1-dimethyl-4-oxo-1,4-dihydronaphthalene-3-carboxamido) acetic acid | 358.0 | Example 110 |
| 117 | 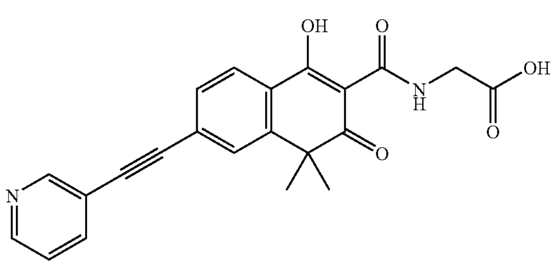 | 2-(2-hydroxy-1,1-dimethyl-4-oxo-7-(2-(pyridin-3-yl)ethynyl)-1,4-dihydronaphthalene-3-carboxamido) acetic acid | 391.1 | Example 110 |

Scheme 5.
General method for the preparation of the 4-Oxobutanoic acid side chain.

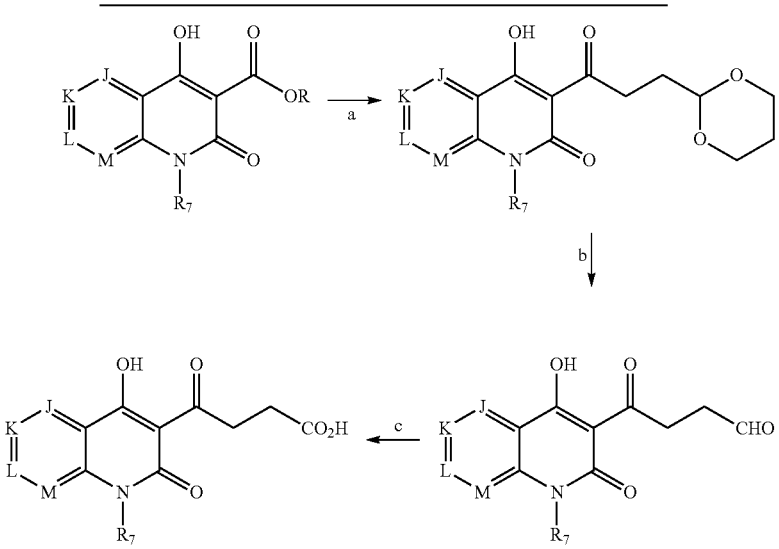

Example 118

4-(6,7-Dichloro-3-hydroxy-4,4-dimethyl-1-oxo-1,4-dihydro-2-naphthalenyl)-4-oxobutanoic acid

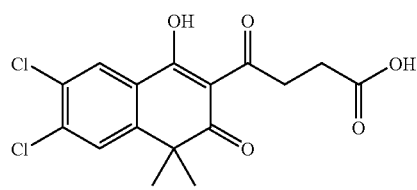

Step A: Preparation of 3-(3-(1,3-dioxan-2-yl)propanoyl)-6,7-dichloro-4-hydroxy-1,1-dimethylnaphthalen-2(1H)-one A mixture of ethyl 6,7-dichloro-1-hydroxy-4,4-dimethyl-3-oxo-3,4-dihydronaphthalene-2-carboxylate (0.5 g, 2 mmol, Example 4A-E) in 20 mL THF was stirred at room temperature and treated with sodium hydride (0.2 mL, 8 mmol). The resulting mixture was then stirred for 30 minutes. The mixture was then treated with 2-[2-(1,3-dioxanyl)]ethyl-magnesium bromide (3 mL, 2 mmol) dropwise and stirred at room temperature for 2 hours. The mixture was quenched with water 10 mL at 0° C., and neutralized with 2N HCl to pH=5. The mixture was extracted with EtOAc 3×50 mL. The combined organic layers were washed with brine 20 mL, dried over anhydrous $Na_2SO_4$, and concentrated. The crude product was purified by column chromatography eluting with 20% EtOAc/hexane to give 0.26 g pure product as white solid. MS m/e: 399 $(M+H)^+$.

Step B: Preparation of 4-(6,7-dichloro-1-hydroxy-4,4-dimethyl-3-oxo-3,4-dihydronaphthalen-2-yl)-4-oxobutanal A mixture of 3-(3-(1,3-dioxan-2-yl)propanoyl)-6,7-dichloro-4-hydroxy-1,1-dimethylnaphthalen-2(1H)-one (0.26 g, 0.65 mmol) in 25 mL acetic acid/water (4:1) was warmed to 95° C. and stirred for 1 hour. The mixture was treated with 10 mL water and stirred at 95° C. for another 30 minutes. The reaction mixture was diluted with 20 mL water and cooled to room temperature. The resulting mixture was then diluted with 200 mL additional water. The precipitate that formed was filtered and washed with 20 mL $H_2O$. The crude precipitate was dissolved in 100 mL DCM, washed with 20 mL saturated $NH_4Cl$, dried over anhydrous $Na_2SO_4$, and concentrated to give 0.22 g of the product as a pale yellow solid. MS m/e: 341 $(M+H)^+$.

Step C: Preparation of 4-(6,7-dichloro-3-hydroxy-4,4-dimethyl-1-oxo-1,4-dihydro-2-naphthalenyl)-4-oxobutanoic acid A mixture of 4-(6,7-dichloro-1-hydroxy-4,4-dimethyl-3-oxo-3,4-dihydronaphthalen-2-yl)-4-oxobutanal (0.22 g, 0.64 mmol) in 6 mL DMF was stirred at room temperature and treated with oxone (0.36 mL, 0.64 mmol). The mixture was stirred at room temperature for 2 hours. The mixture was quenched with 50 mL $H_2O$ and adjusted to pH=5 with concentrated HCl. The solid was collected by filtration and washed with 20 mL $H_2O$. The crude was dried under high vacuum to give 0.23 g white solid. MS m/e: 357 $(M+H)^+$. Calculated for $C_{16}H_{14}Cl_2O_5$: 356.

Scheme 6.
General method for the preparation of the 4-Oxobutanoic acid side chain.

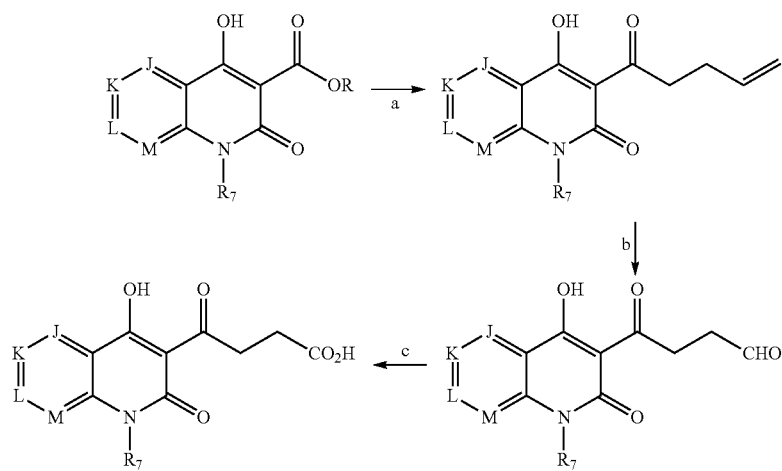

Example 119

4-(6-Chloro-2-hydroxy-4-oxo-2',3',5',6'-tetrahydro-4H-spiro[naphthalene-1,4'-pyran]-3-yl)-4-oxobutanoic acid

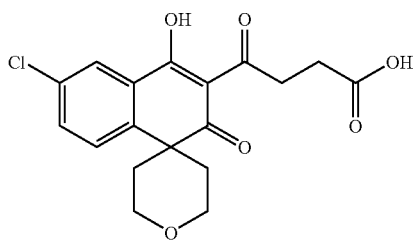

Step A: Preparation of 6-chloro-2-hydroxy-3-(4-pentenoyl)-2',3',5',6'-tetrahydro-4H-spiro[naphthalene-1,4'-pyran]-4-one A mixture of ethyl 6-chloro-2-hydroxy-4-oxo-2',3',5',6'-tetrahydro-spiro[naphthalene-1,4'-pyran]-3-carboxylate (2.53 g, 8 mmol, Example 1 A-C) in 20 mL THF was stirred at room temperature and treated with sodium hydride (0.6 g, 15 mmol, 60% in oil). The resulting mixture was stirred for 10 minutes. The mixture was then treated with 3-butenylmagnesium bromide (15 mL, 8 mmol). After 5 minutes, the mixture was warmed to 60° C., and the reaction was stirred for another 0.5 hours. The mixture was cooled to 0° C., quenched with 20 mL saturated NH$_4$Cl, and 100 mL EtOAc was added. The organic layer was separated, dried over anhydrous Na$_2$SO$_4$, and concentrated in vacuo. The crude product was purified by column chromatography eluting with 10-20% EtOAc/hexane to give 2.17 g white solid. MS m/e: 347 (M+H)$^+$.

Step B: Preparation of 4-(6-chloro-2-hydroxy-4-oxo-2',3',5',6'-tetrahydro-4H-spiro[naphthalene-1,4'-pyran]-3-yl)-4-oxobutanal A mixture of 6-chloro-2-hydroxy-3-(4-pentenoyl)-2',3',5',6'-tetrahydro-4H-spiro[naphthalene-1,4'-pyran]-4-one (0.65 g, 1.9 mmol) in 50 mL DCM was stirred at −78° C. and treated with O$_3$ until the solution remained blue. The mixture was stirred at −78° C. for 30 minutes and then treated with 1 mL dimethyl sulfide and stirred from −78° C. to 0° C. for 2 hours. The mixture was concentrated in vacuo and purified by column eluting with 40:100=EtOAc/hexane to give the desired product. MS m/e: 349 (M+H)$^+$.

Step C: Preparation of 4-(6-chloro-2-hydroxy-4-oxo-2',3',5',6'-tetrahydro-4H-spiro[naphthalene-1,4'-pyran]-3-yl)-4-oxobutanoic acid A mixture of 4-(6-chloro-2-hydroxy-4-oxo-2',3',5',6'-tetrahydro-4H-spiro[naphthalene-1,4'-pyran]-3-yl)-4-oxobutanal (0.2 g, 0.6 mmol) in 3 mL DMF was stirred at room temperature and treated with oxone (0.3 mL, 0.6 mmol). The mixture was stirred at room temperature for 2 hours. The mixture was quenched with 10 mL H$_2$O and adjusted to pH=5 with concentrated HCl. The solid was collected by filtration and washed with 10 mL H$_2$O. The crude product was dissolved in 50 mL EtOAc and washed with 20 mL H$_2$O and then with 20 mL brine. The organic layer was dried over anhydrous Na$_2$SO$_4$, and concentrated in vacuo to give 0.20 g white solid. MS m/e: 365 (M+H)$^+$. Calculated for C$_{18}$H$_{17}$ClO$_6$: 364.

Example 120

Resolution of 4-(7-chloro-4-cyano-1-hydroxy-4-methyl-3-oxo-3,4-dihydronaphthalen-2-yl)-4-oxobutanoic acid

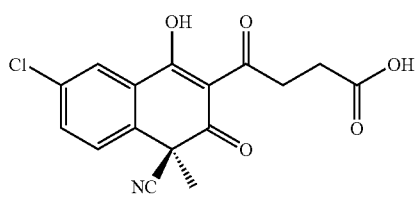

-continued

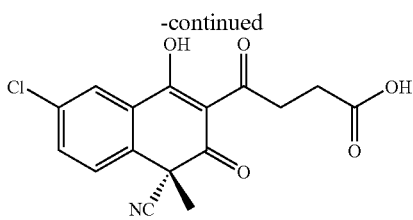

4-(7-Chloro-4-cyano-1-hydroxy-4-methyl-3-oxo-3,4-dihydronaphthalen-2-yl)-4-oxobutanoic acid (0.1 g, prepared according to Example 123) was dissolved in dimethyoxy ethylenegycol (10 mL) and separated on a chiralpack ADH (21×250 mm, 5 μm) column in ten 1 mL injections (flow: 60 mL/min, eluent: 50% MeOH in supercritical fluid and carbon dioxide). The first peak was concentrated and dried in vacuo to give the first enantiomer (35 mg). MS m/z 334 (M+H)+. Calculated for $Cl_6H_{12}ClNO_5$: 333. The second peak was concentrated and dried in vacuo to give the other enantiomer (36 mg). MS m/z 334 (M+H)+. Calculated for $Cl_6H_{12}ClNO_5$: 333.

Example 121

4-(6-Chloro-2-hydroxy-4-oxo-2',3',5',6'-tetrahydro-4H-spiro[naphthalene-1,4'-pyran]-3-yl)-3-methyl-4-oxobutanoic acid

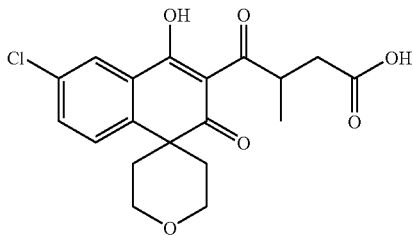

Step A: Preparation of 3-(3-(1,3-dioxan-2-yl)propanoyl)-2-methyl-(6-chloro-2-hydroxy-4-oxo-2',3',5',6'-tetrahydro-4H-spiro[naphthalene-1,4'-pyran]-3-yl)-one A mixture of 6-chloro-2-hydroxy-3-(4-pentenoyl)-2',3',5',6'-tetrahydro-4H-spiro[naphthalene-1,4'-pyran]-4-one (0.3 g, 0.7 mmol, see Example 119) in 20 mL THF stirred at 0° C. was treated with lithium bis(trimethylsilyl)amide (1.0M solution in THF, 2 mL, 2 mmol). The mixture was stirred at 0° C. for 1 hour and was then treated with methyl iodide (0.09 mL, 1 mmol). The resulting mixture was stirred at 0° C. and allowed to warm to room temperature over 5 hours. The mixture was treated with another 1.0 mL LHMDS and 0.1 mL iodomethane and stirred at room temperature for 15 hours. The mixture was treated with another 1 mL LHMDS and stirred at room temperature for 2 additional hours. The mixture was quenched with 20 mL water, adjusted pH=5 with concentrated HCl, and extracted with EtOAc 3×50 mL. The combined organic layers were washed with brine (20 mL), dried, and concentrated. The crude product was purified by column chromatography eluting with 20-40% EtOAc/hexane to give 0.13 g of the product as a pale yellow solid. MS m/z 421 (M+H)+.

Step B: Preparation of 4-(6-chloro-2-hydroxy-4-oxo-2',3',5',6'-tetrahydro-4H-spiro[naphthalene-1,4'-pyran]-3-yl)-3-methyl-4-oxobutanal A mixture of 3-(3-(1,3-dioxan-2-yl)propanoyl)-2-methyl-(6-chloro-2-hydroxy-4-oxo-2',3',5',6'-tetrahydro-4H-spiro[naphthalene-1,4'-pyran]-3-yl)-one (0.13 g, 0.3 mmol) in 20 mL 50% acetic acid/water was stirred at 95° C. for 1 h. The mixture was cooled to room temperature and diluted with 100 mL water. The mixture was extracted with EtOAc 3×50 mL. The combined organic layers were washed with saturated $NaHCO_3$ 3×50 mL, brine 30 mL, dried over anhydrous $Na_2SO_4$, and concentrated to give 0.1 g of the product as a yellow solid. MS m/z 363 (M+H)+.

Step C: Preparation of 4-(6-chloro-2-hydroxy-4-oxo-2',3',5',6'-tetrahydro-4H-spiro[naphthalene-1,4'-pyran]-3-yl)-3-methyl-4-oxobutanoic acid A mixture of 4-(6-chloro-2-hydroxy-4-oxo-2',3',5',6'-tetrahydro-4H-spiro[naphthalene-1,4'-pyran]-3-yl)-3-methyl-4-oxobutanal (0.1 g, 0.3 mmol) in 2 mL DMF was stirred at room temperature and treated with oxone (0.2 mL, 0.3 mmol). The mixture was stirred at room temperature for 2 hours. The mixture was quenched with 20 mL $H_2O$, and the pH was adjusted to pH=5 with concentrated HCl. The precipitate that formed was collected by filtration and washed with 20 mL water. The product was dried under high vacuum to give 0.1 g of the product as an off-white solid. MS m/z 379 (M+H)+. Calculated for $C_{19}H_{19}ClO_6$: 378.

TABLE 2

The following table lists compounds which were prepared by the methods set forth in the Examples described above.

| Ex. | Structure | Name | MS (MH+) | Synthetic Method |
|---|---|---|---|---|
| 122 | (structure shown) | 4-(6,7-dichloro-1-hydroxy-4,4-dimethyl-3-oxo-3,4-dihydronaphthalen-2-yl)-4-oxobutanoic acid | 357 | Example 118 |

TABLE 2-continued

The following table lists compounds which were prepared by the
methods set forth in the Examples described above.

| Ex. | Structure | Name | MS (MH+) | Synthetic Method |
|---|---|---|---|---|
| 123 | 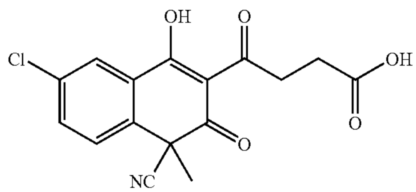 | 4-(7-chloro-4-cyano-3-hydroxy-4-methyl-1-oxo-1,4-dihydro-2-naphthalenyl)-4-oxobutanoic acid | 334 | Example 118 |
| 124 | | (R)-4-(7-chloro-4-cyano-1-hydroxy-4-methyl-3-oxo-3,4-dihydronaphthalen-2-yl)-4-oxobutanoic acid or (S)-4-(7-chloro-4-cyano-1-hydroxy-4-methyl-3-oxo-3,4-dihydronaphthalen-2-yl)-4-oxobutanoic acid | 334 | Example 120 |
| 125 | Enantiomer of Example 124 | Enantiomer of Example 124 | 334 | Example 120 |
| 126 | 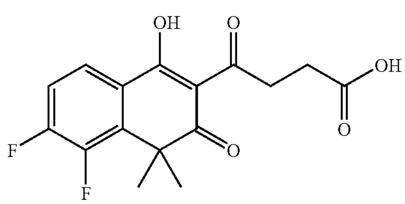 | 4-(5,6-difluoro-1-hydroxy-4,4-dimethyl-3-oxo-3,4-dihydronaphthalen-2-yl)-4-oxobutanoic acid | 325 | Example 118 |
| 127 | 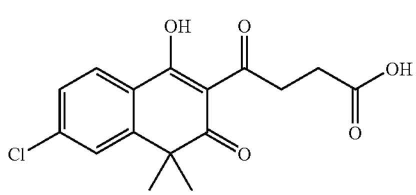 | 4-(6-chloro-1-hydroxy-4,4-dimethyl-3-oxo-3,4-dihydronaphthalen-2-yl)-4-oxobutanoic acid | 323 | Example 118 |
| 128 | 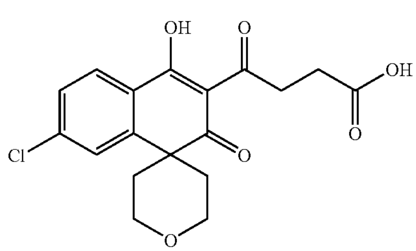 | 4-(7-chloro-2-hydroxy-4-oxo-2',3',5',6'-tetrahydro-4H-spiro[naphthalene-1,4'-pyran]-3-yl)-4-oxobutanoic acid | 365 | Example 118 |

TABLE 3

The following table lists compounds which were prepared by the methods set forth in the Examples described above.

| Ex. | Structure | Name | MS (MH+) | Synthetic Method |
|---|---|---|---|---|
| 129 | 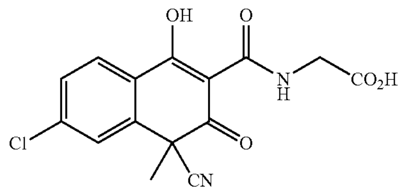 | 2-(7-chloro-1-cyano-4-hydroxy-1-methyl-2-oxo-1,2-dihydronaphthalene-3-carboxamido)acetic acid | 335.7 | Example 84 |
| 130 | 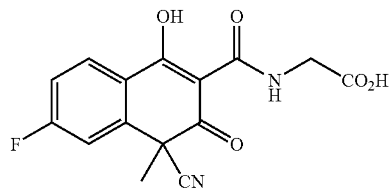 | 2-(1-cyano-7-fluoro-4-hydroxy-1-methyl-2-oxo-1,2-dihydronaphthalene-3-carboxamido)acetic acid | 319.2 | Example 84 |
| 131 | 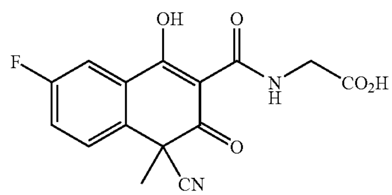 | 2-(1-cyano-6-fluoro-4-hydroxy-1-methyl-2-oxo-1,2-dihydronaphthalene-3-carboxamido)acetic acid | 319.2 | Example 84 |
| 132 | 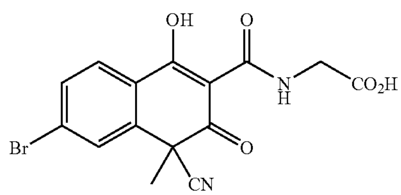 | 2-(7-bromo-1-cyano-4-hydroxy-1-methyl-2-oxo-1,2-dihydronaphthalene-3-carboxamido)acetic acid | 380.1 | Example 84 |
| 133 | 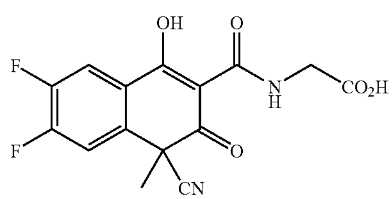 | 2-(1-cyano-6,7-difluoro-4-hydroxy-1-methyl-2-oxo-1,2-dihydronaphthalene-3-carboxamido)acetic acid | 337.2 | Example 84 |
| 134 | | (R)-2-(7-bromo-1-cyano-4-hydroxy-1-methyl-2-oxo-1,2-dihydronaphthalene-3-carboxamido)acetic acid or (S)-2-(7-bromo-1-cyano-4-hydroxy-1-methyl-2-oxo-1,2-dihydronaphthalene-3-carboxamido)acetic acid | 380.1 | Example 85 |

TABLE 3-continued

The following table lists compounds which were prepared by the methods set forth in the Examples described above.

| Ex. | Structure | Name | MS (MH+) | Synthetic Method |
|---|---|---|---|---|
| 135 | 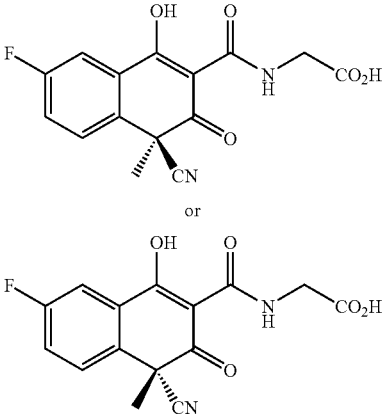 | (R)-2-(1-cyano-6-fluoro-4-hydroxy-1-methyl-2-oxo-1,2-dihydronaphthalene-3-carboxamido) acetic acid or (S)-2-(1-cyano-6-fluoro-4-hydroxy-1-methyl-2-oxo-1,2-dihydronaphthalene-3-carboxamido) acetic acid | 319.2 | Example 85 |
| 136 | 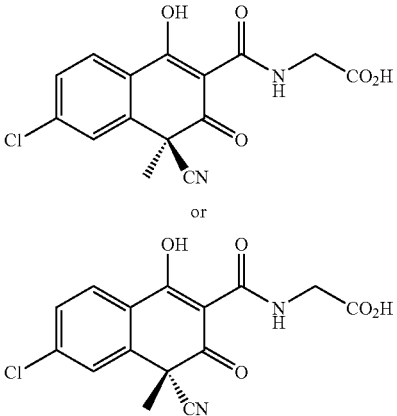 | (R)-2-(7-chloro-1-cyano-4-hydroxy-1-methyl-2-oxo-1,2-dihydronaphthalene-3-carboxamido) acetic acid or (S)-2-(7-chloro-1-cyano-4-hydroxy-1-methyl-2-oxo-1,2-dihydronaphthalene-3-carboxamido) acetic acid | 335.7 | Example 85 |
| 137 | 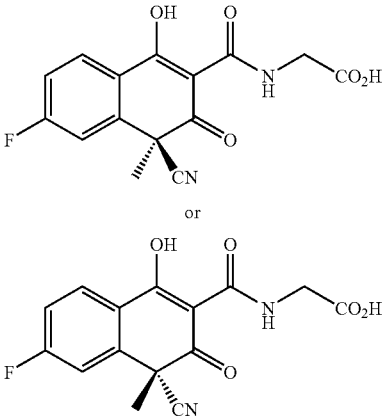 | (R)-2-(1-cyano-7-fluoro-4-hydroxy-1-methyl-2-oxo-1,2-dihydronaphthalene-3-carboxamido) acetic acid or (S)-2-(1-cyano-7-fluoro-4-hydroxy-1-methyl-2-oxo-1,2-dihydronaphthalene-3-carboxamido) acetic acid | 319.2 | Example 85 |
| 138 | Enantiomer of Example 135 | Enantiomer of Example 135 | 319.2 | Example 86 |
| 139 | Enantiomer of Example 134 | Enantiomer of Example 134 | 380.1 | Example 86 |
| 140 | Enantiomer of Example 137 | Enantiomer of Example 137 | 319.2 | Example 86 |
| 141 | Enantiomer of Example 136 | Enantiomer of Example 136 | 335.7 | Example 86 |

TABLE 3-continued

The following table lists compounds which were
prepared by the methods set forth in the Examples described above.

| Ex. | Structure | Name | MS (MH+) | Synthetic Method |
|---|---|---|---|---|
| 142 | 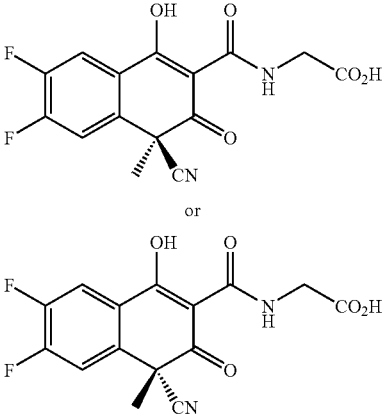 | (R)-2-(1-cyano-6,7-difluoro-4-hydroxy-1-methyl-2-oxo-1,2-dihydronaphthalene-3-carboxamido) acetic acid or (S)-2-(1-cyano-6,7-difluoro-4-hydroxy-1-methyl-2-oxo-1,2-dihydronaphthalene-3-carboxamido) acetic acid | 337.2 | Example 85 |
| 143 | Enantiomer of Example 142 | Enantiomer of Example 142 | 337.2 | Example 86 |

The following are examples of methods that may be used to quantitate HIF PHD activity and the inhibition of HIF PHD activity by compounds of the present invention.

Expression, Purification and Europium Labeling of VCB and Design of an Eu-VCB Based TR-FRET Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in E. coli and purified from the soluble fraction. The amino acid sequences of the three protein components are as follows:

```
VHL (Amino Acids 54-213)
                                        (SEQ ID NO: 1)
MHHHHHHEAGRPRPVLRSVNSREPSQVIFCNRSPRVVLPVWLNFDGEPQ

PYPTLPPGTGRRIHSYRGHLWLFRDAGTHDGLLVNQTELFVPSLNVDGQ

PIFANITLPVYTLKERCLQVVRSLVKPENYRRLDIVRSLYEDLEDHPNVQ

KDLERLTQERIAHQRMGD

ElonginB
                                        (SEQ ID NO: 2)
MDVFLMIRRHKTTIFTDAKESSTVFELKRIVEGILKRPPDEQRLYKDDQL

LDDGKTLGECGFTSQTARPQAPATVGLAFRADDTFEALCIEPFSSPPELP

DVMKPQDSGSSANEQAVQ*

ElonginC (Amino Acids 17-112)
                                        (SEQ ID NO: 3)
MYVKLISSDGHEFIVKREHALTSGTIKAMLSGPGQFAENETNEVNFREIP

SHVLSKVCMYFTYKVRYTNSSTEIPEFPIAPEIALELLMAANFLDC
```

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in E. coli, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any E. coli strain to serve as host.

ElonginB was cloned into pTA2 (pACYC184.1 based vector) under the control of a Lac promoter. Competent E. coli cells were transformed with the pAMG21-VHL-ElonginC construct. These E. coli cells were rendered competent again prior to transformation with the pTA2-elonginB construct to produce the final E. coli strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble E. coli fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

```
                                            (SEQ ID NO: 4)
(unmodified)  Biotin-DLDLEALAPYIPADDDFQLR-CONH2

(SEQ ID NO: 5)
(modified)    Biotin-DLDLEALA[hyP]YIPADDDFQLR-CONH2
```

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted Hydroxyprolyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% $NaN_3$. The optimal signal over background and the linear range of detection was determined by titrating the hydroxylated or unhydroxylated peptide at varied concentrations between 0 and 1 μM with a titration of VCB-Eu at varying concentrations between 0 and 50 nM with 50 nM of streptavidin APC. The binding reagents were allowed to reach equilibrium by shaking for 1 hour before it was read on the Discovery Instriment (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 μM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 μM $FeCl_2$ in a final volume of 100 μL. The time-course was determined by periodically transferring 2.5 μL of the reaction into 250 μL of 10×TR-FRET buffer containing 500 mM HEPES (pH 7.5), 1M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 μL in 10×TR-FRET buffer. The TR-FRET reagents were placed on a shaker for 1 hour before detection on the Discovery platform.

Figure 2A:
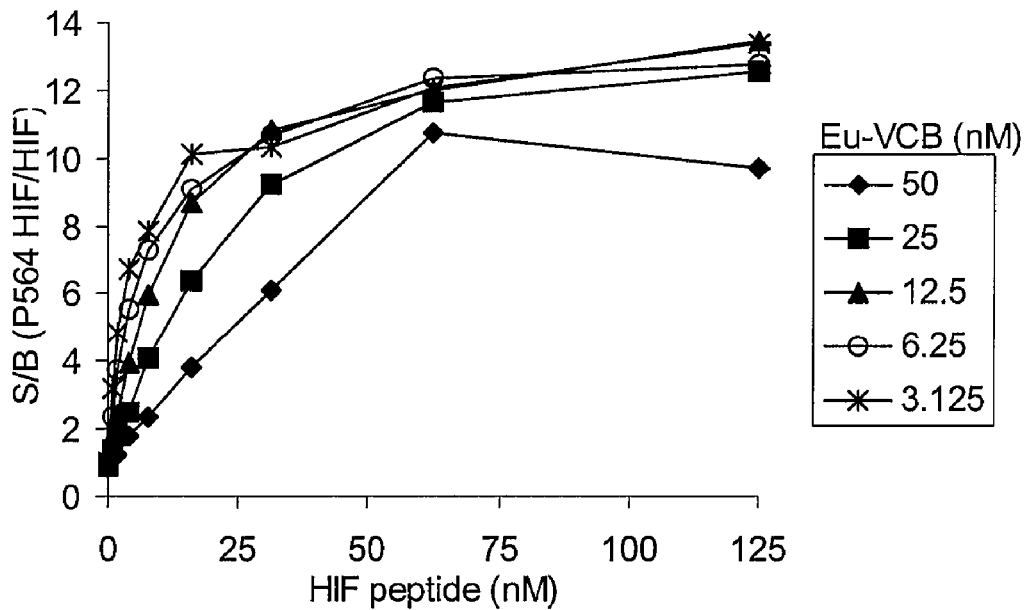
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).
Figure 2B:
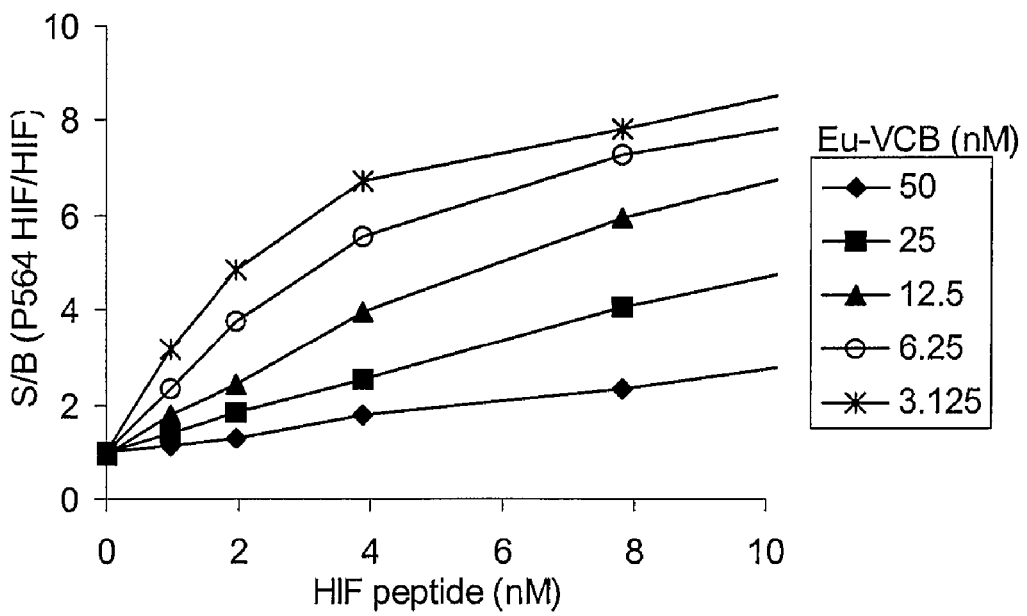

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
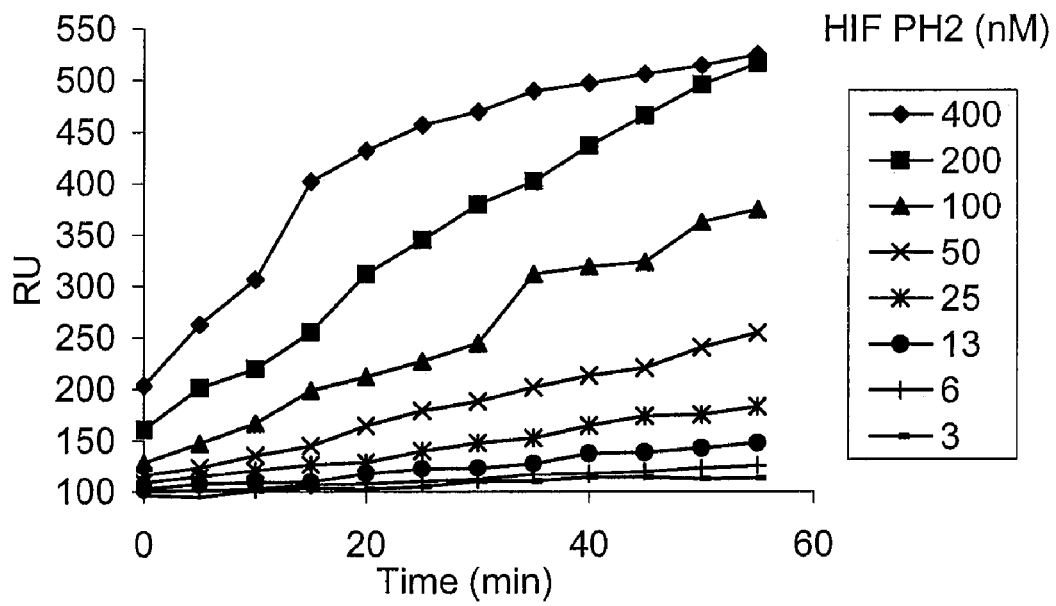
FIGS. 3A and 3B are graphs illustrating VCB binding and TR-FRET detection for determining HIF PHD2 hydroxylation of a HIF1α peptide.
Figure 3B:
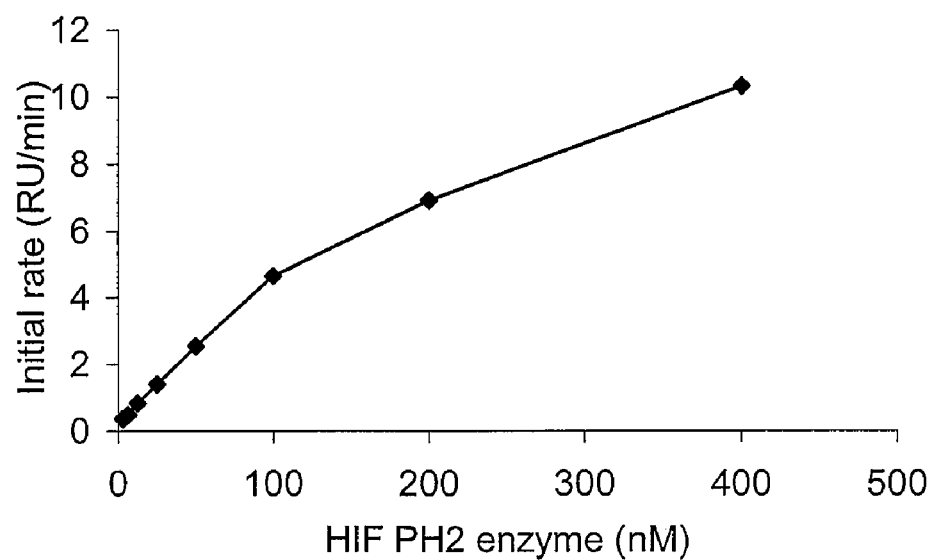

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 μM (100 μM final concentration) in PHD2 Reaction Buffer containing 30 mM MES, pH 6, 10 mM NaCl, 0.25% Brij-35, 0.01% BSA, and 1% DMSO. 28 μL of the iron solution and 2 μL of inhibitor compounds serially diluted in 100% DMSO (5% DMSO final) were added to black polypropylene 96-well microtiter plates. To that, 10 μL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 μL of a solution containing 500 nM P564-HIF1α peptide (100 nM final), 10 mM ascorbic acid (2 mM final), and 1.25 μM 2-oxoglutarate (α-ketoglutarate; 0.25 μM final) in PHD2 Reaction Buffer was added to all wells of the plate and allowed to incubate on the shaker at room temperature for one hour.

The reaction was terminated by addition of 25 μL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in μM) was fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 μM or less. In additional embodiments, compounds of the present invention exhibit a HIF PHD inhibitory activity $IC_{50}$ value of 10 μM or less and in further embodiments, compounds of the present invention exhibit a HIP PHD inhibitory activity $IC_{50}$ value of 5 μM or less.

The following table includes PHD2 $IC_{50}$ values obtained using the procedures set forth herein for various Examples compounds described herein.

TABLE 4

| Example | $^a$PHD2 $IC_{50}$ (nM) |
|---|---|
| 1 | +++++ |
| 2 | +++++ |
| 3 | +++++ |
| 4 | +++++ |
| 5 | +++++ |
| 6 | ++++ |
| 7 | ++++ |
| 8 | ++++ |
| 9 | ++ |
| 10 | +++++ |
| 11 | +++++ |
| 12 | +++++ |
| 13 | +++++ |
| 14 | +++++ |
| 15 | ++++ |

TABLE 4-continued

| Example | $^a$PHD2 $IC_{50}$ (nM) |
|---|---|
| 16 | +++++ |
| 17 | +++++ |
| 18 | +++++ |
| 19 | +++++ |
| 20 | ++++ |
| 21 | ++++ |
| 22 | ++++ |
| 23 | +++++ |
| 24 | +++++ |
| 25 | ++++ |
| 26 | ++++ |
| 27 | +++++ |
| 28 | +++++ |
| 29 | ++++ |
| 30 | +++ |
| 31 | +++++ |
| 32 | ++++ |
| 33 | +++++ |
| 34 | ++++ |
| 35 | ++++ |
| 36 | ++++ |
| 37 | +++ |
| 38 | +++ |
| 39 | ++++ |
| 40 | +++++ |
| 41 | +++++ |
| 42 | +++++ |
| 43 | ++++ |
| 44 | +++++ |
| 45 | +++++ |
| 46 | +++++ |
| 47 | +++++ |
| 48 | +++++ |
| 49 | +++++ |
| 50 | ++++ |
| 51 | +++++ |
| 52 | ++++ |
| 53 | +++++ |
| 54 | + |
| 55 | ++++ |
| 56 | + |
| 57 | +++++ |
| 58 | +++++ |
| 59 | +++++ |
| 60 | ++++ |
| 61 | +++++ |
| 62 | +++++ |
| 63 | +++++ |
| 64 | +++++ |
| 65 | +++ |
| 66 | ++++ |
| 67 | ++ |
| 68 | +++ |
| 69 | +++++ |
| 70 | ++++ |
| 71 | +++++ |
| 72 | +++++ |
| 73 | +++++ |
| 74 | ++++ |
| 75 | +++++ |
| 76 | ++++ |
| 77 | +++++ |
| 78 | ++++ |
| 79 | ++++ |
| 80 | +++++ |
| 81 | +++++ |
| 82 | +++++ |
| 83 | +++++ |
| 84 | +++++ |
| 85 | +++++ |
| 86 | +++++ |
| 87 | +++++ |
| 88 | +++++ |
| 89 | +++++ |
| 90 | +++++ |
| 91 | +++++ |
| 92 | +++++ |
| 93 | +++++ |

TABLE 4-continued

| Example | $^{a}$PHD2 IC$_{50}$ (nM) |
|---|---|
| 94 | +++++ |
| 95 | ++++ |
| 96 | +++++ |
| 97 | +++++ |
| 98 | +++++ |
| 99 | +++++ |
| 100 | + |
| 101 | + |
| 102 | + |
| 103 | +++++ |
| 104 | +++++ |
| 105 | +++++ |
| 106 | +++++ |
| 107 | ++++ |
| 108 | +++++ |
| 109 | +++++ |
| 110 | ++++ |
| 111 | +++++ |
| 112 | +++++ |
| 113 | +++++ |
| 114 | ++++ |
| 115 | ++ |
| 116 | +++++ |
| 117 | +++++ |
| 118 | ++++ |
| 119 | +++++ |
| 120 | ++ |
| 121 | ++ |
| 122 | ++++ |
| 123 | ++ |
| 124 | ++ |
| 125 | +++ |
| 126 | ++++ |
| 127 | ++++ |
| 128 | +++++ |
| 129 | +++++ |
| 130 | +++++ |
| 131 | +++++ |
| 132 | +++++ |
| 133 | +++++ |
| 134 | +++++ |
| 135 | +++++ |
| 136 | +++++ |
| 137 | +++++ |
| 138 | +++++ |
| 139 | +++++ |
| 140 | +++++ |
| 141 | +++++ |
| 142 | +++++ |
| 143 | +++++ |

$^{a}$IC$_{50}$ value ranges
+ IC$_{50}$ >10,000 nM
++ 1000 nM ≤ IC$_{50}$ ≤ 10,000 nM
+++ 500 nM ≤ IC$_{50}$ ≤ 1,000 nM
++++ 100 nM ≤ IC$_{50}$ ≤ 500 nM
+++++ IC$_{50}$ <100 nM All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of treating ischemia or anemia in a subject, the method comprising administering to the subject an effective amount of a compound of Formula I:

![Formula I structure]

a pharmaceutically acceptable salt thereof, a tautomer thereof, or a pharmaceutically acceptable salt of the tautomer; or a mixture of any of the foregoing, wherein:

m is 0 to 4;
n is 1 to 6;
$R_1$ and $R_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents;
X is selected from —$NR_a$—, —O—, —S—, or —($CR_b R_c$)— wherein $R_a$ is selected from H or lower alkyl;
$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;
$R_5$ is selected from OH, SH, $NH_2$, lower alkyl, substituted lower alkyl, lower alkoxy, substituted lower alkoxy, or sulfanyl;
$R_6$ is chosen from H, OH, SH $NH_2$, $NHSO_2R_8$, or sulfonyl;
each $R_7$, if present, is independently selected from alkyl, substituted alkyl, alkenyl, substituted alkenyl, alkynyl, substituted alkynyl, $NR_dR_e$, C(O)$OR_8$, $OR_8$, $SR_8$, $SO_2R_8$, CN, $NO_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or —Y—$R_9$, wherein:
Y is selected from —N($R_{10}$)—Z— or —Z—N($R_{10}$)—;
Z is selected from C(O), $SO_2$, alkylene, substituted alkylene, alkenylene, substituted alkenylene, alkynylene, or substituted alkynylene;
$R_8$ is selected from H, alkyl, substituted alkyl, alkenyl, substituted alkenyl, alkynyl, or substituted alkynyl;
$R_9$ is selected from H, heterocyclyl, substituted heterocyclyl, aryl, substituted aryl, heteroaryl, or substituted heteroaryl;
$R_{10}$ is selected from H, lower alkyl, or substituted lower alkyl;
$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

2. The method according to claim 1, wherein $R_5$ is OH.

3. The method according to claim 1, wherein $R_6$ is OH.

4. The method according to claim 1, wherein m is 1 to 4 and at least one instance of $R_7$ is a substituted or unsubstituted aryl, substituted or unsubstituted heteroaryl, substituted or unsubstituted cycloalkyl, or a substituted or unsubstituted heterocyclyl group.

5. The method according to claim 1, wherein m is 1 to 4 and at least one instance of $R_7$ is independently selected from halo or a moiety substituted with at least one halo.

6. The method according to claim 1, wherein n is 1.

7. The method according to claim 1, wherein $R_1$ and $R_2$ are independently selected from CN, lower alkyl, aryl, or substituted aryl.

8. The method according to claim 1, wherein $R_1$ and $R_2$ join to form a spirocyclic ring system.

9. The method according to claim 1, wherein $R_1$ and $R_2$ join to form a heterocyclic spirocyclic ring system.

10. The method according to claim 1, wherein $R_1$ and $R_2$ join to form the group —$CH_2$—$CH_2$—O—$CH_2$—$CH_2$—.

11. The method according to claim 1, wherein $R_1$ is CN.

12. The method according to claim 1, wherein X is NH, n is 1, $R_3$ and $R_4$ are independently selected from H, lower alkyl or substituted lower alkyl, and $R_6$ is OH.

13. The method according to claim 1, wherein X is —$CH_2$—.

14. The method according to claim 1, wherein X is —NH—.

15. The method according to claim 1, wherein, the compound is selected from

![Three chemical structures]

209
-continued
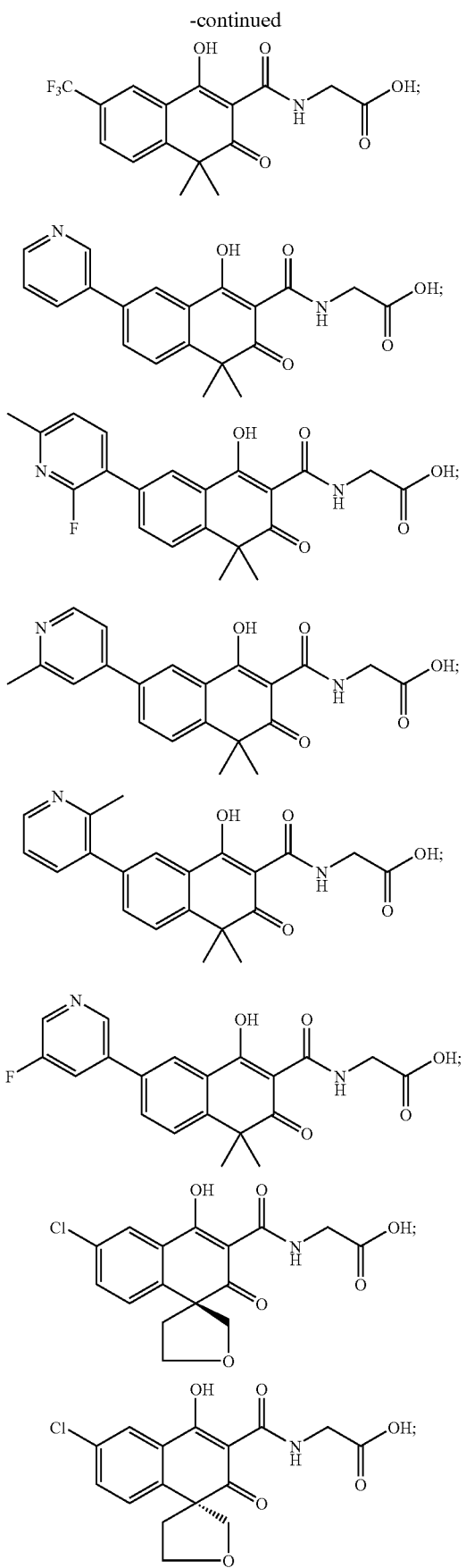
210
-continued
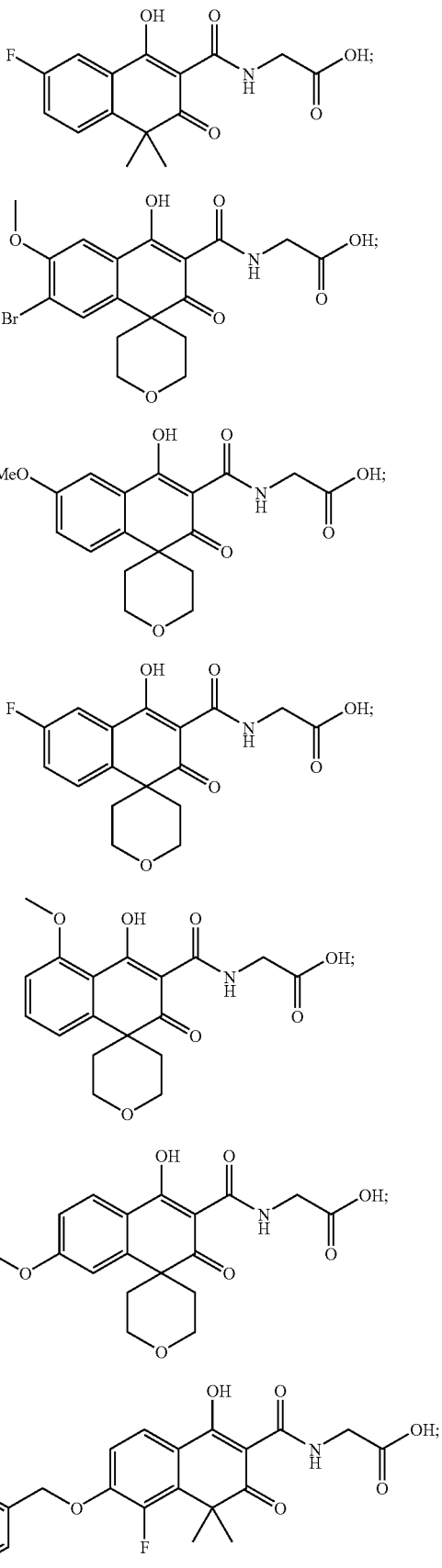

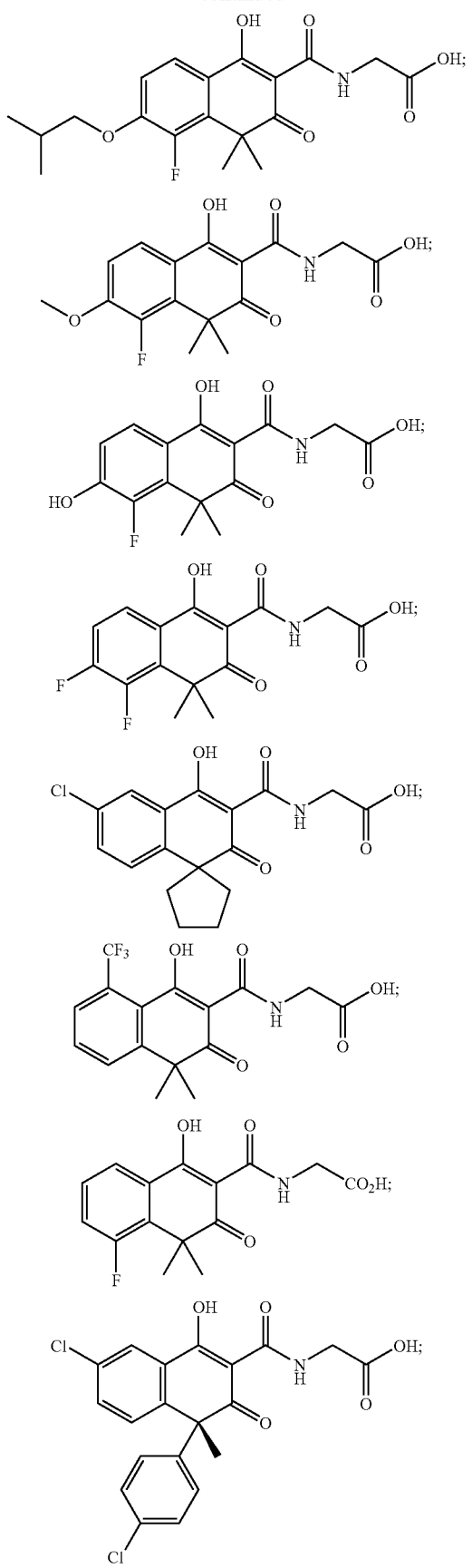
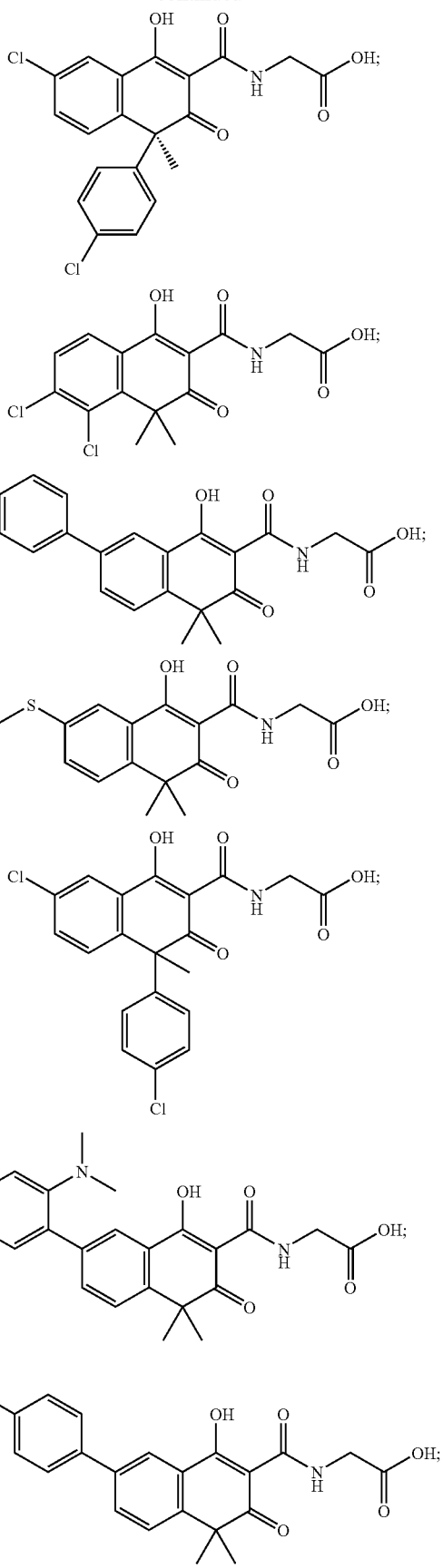

213
-continued
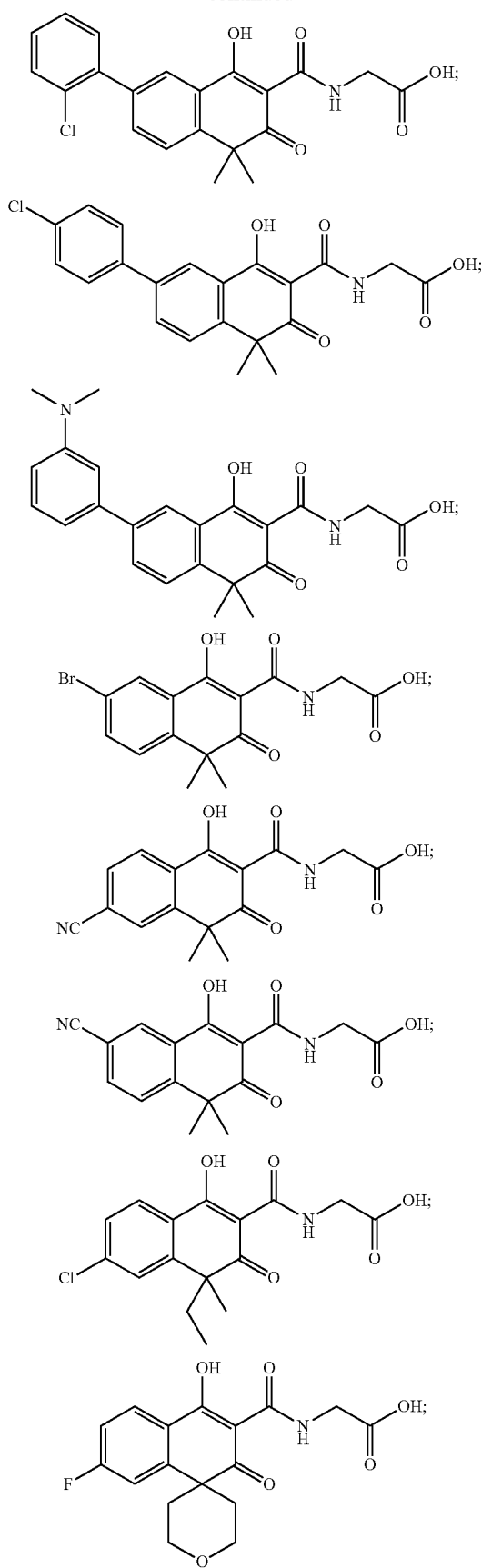
214
-continued
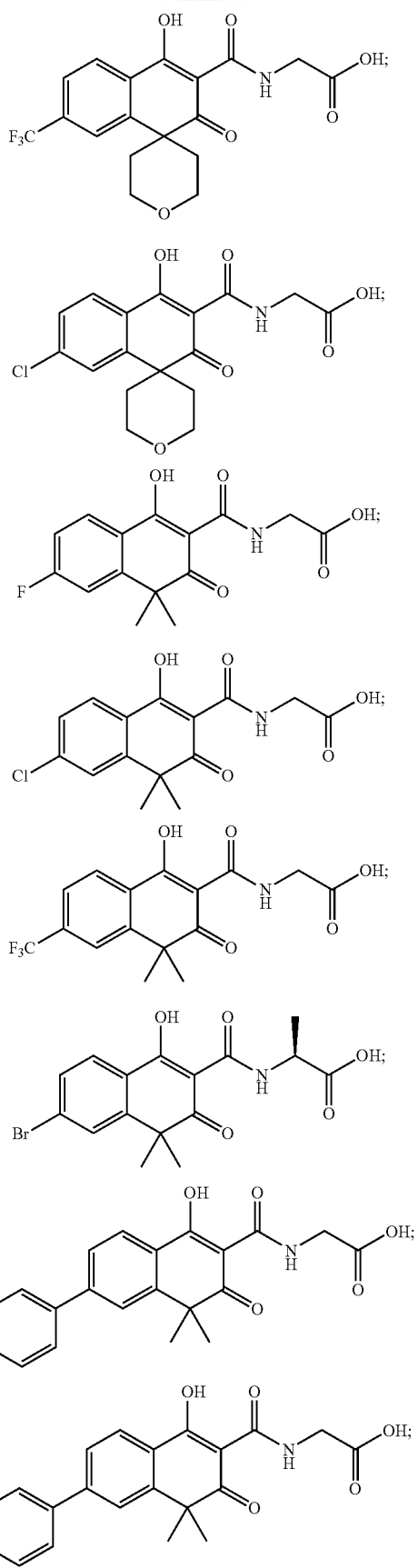

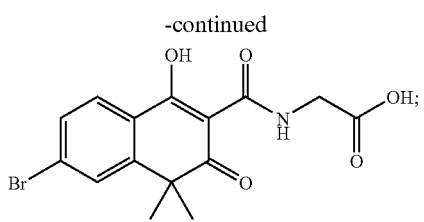
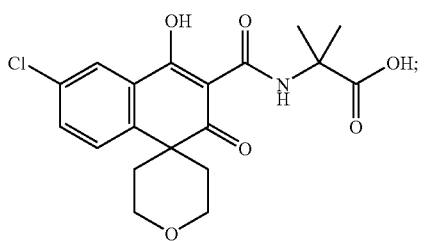
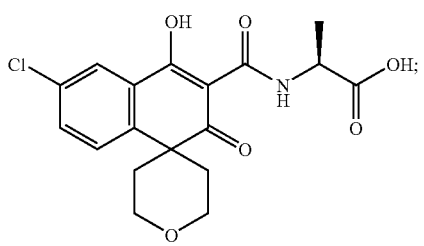
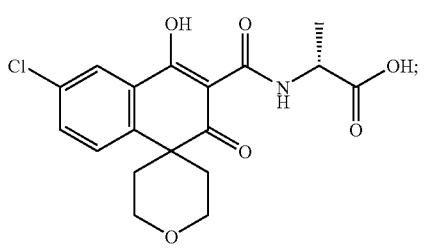
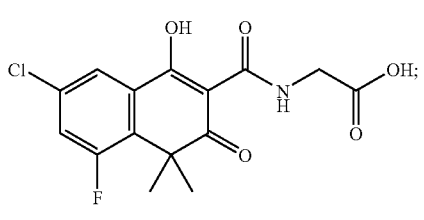
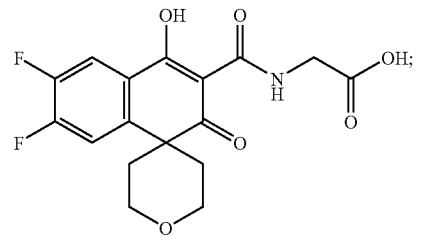
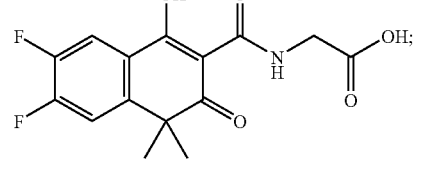
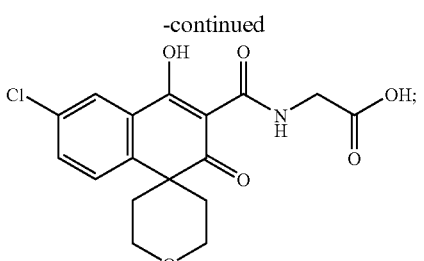
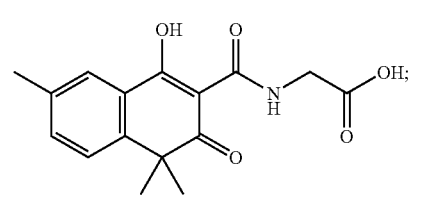
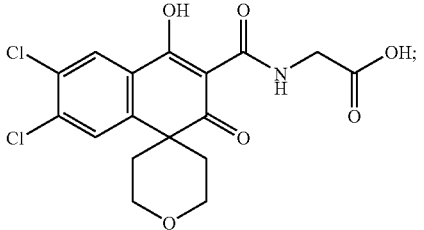
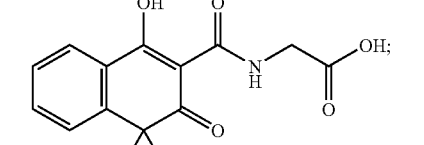
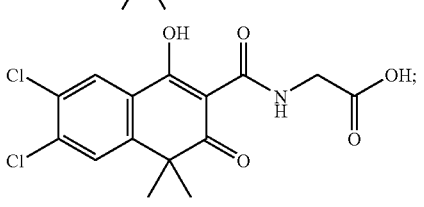
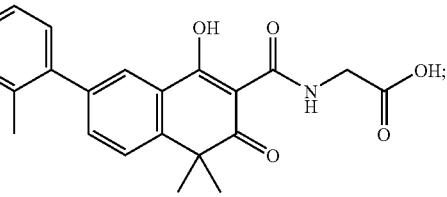
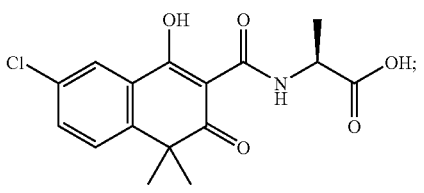
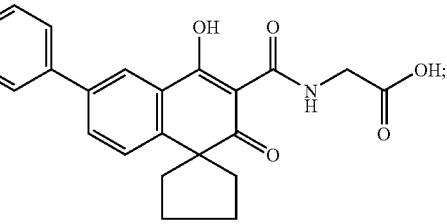

217
-continued
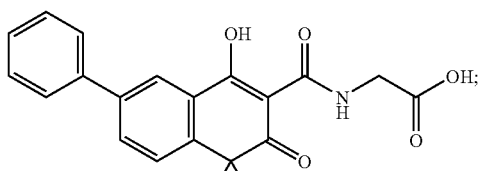
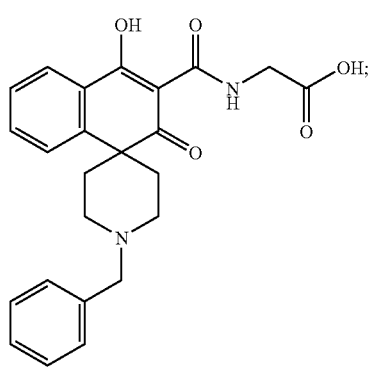
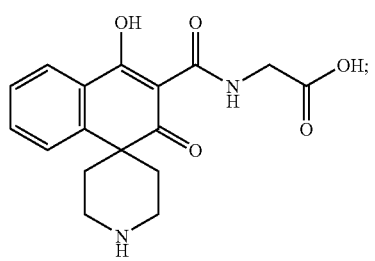
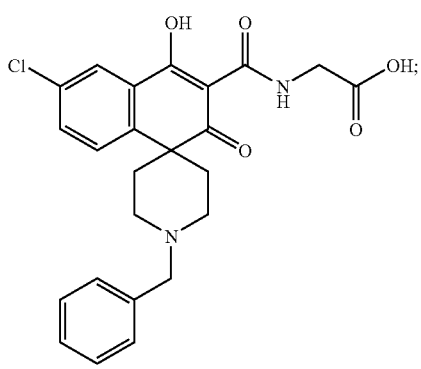
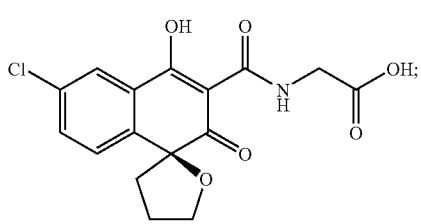
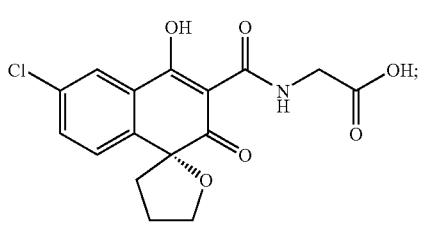
218
-continued
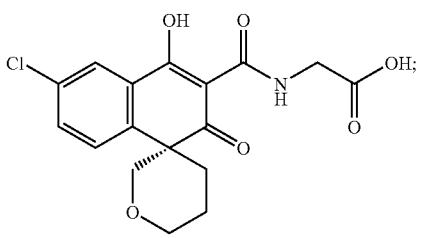
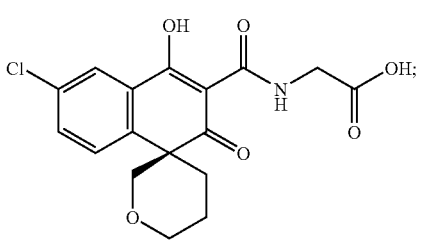
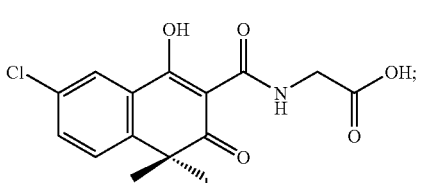
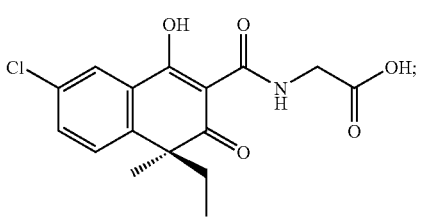
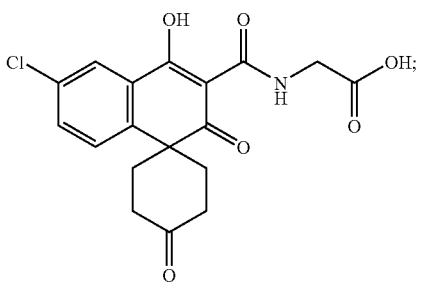
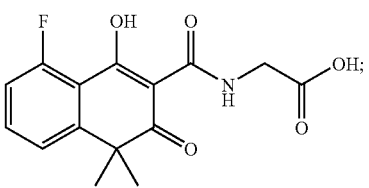
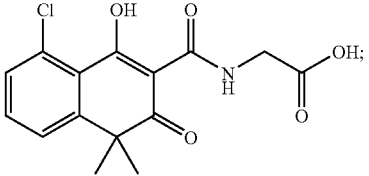

219
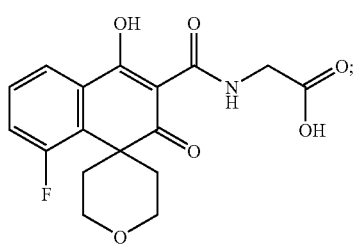
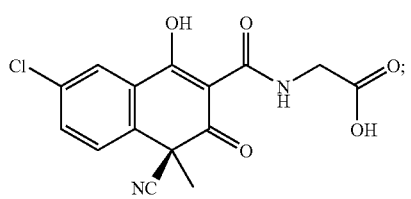
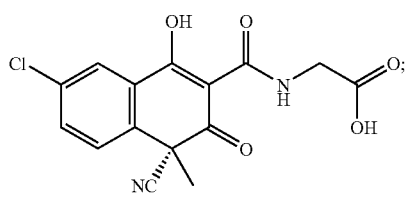
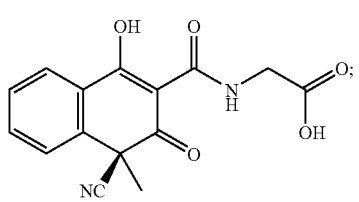
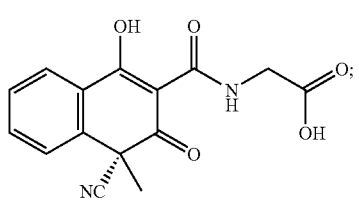
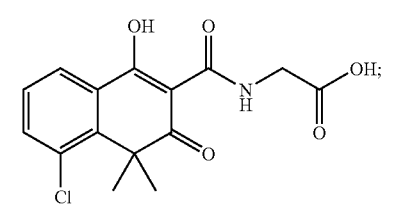
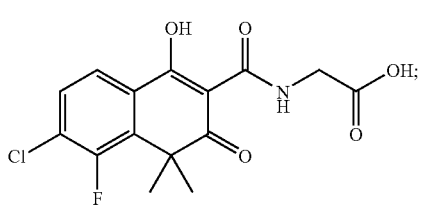
220
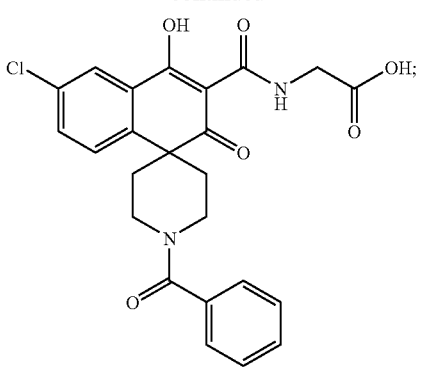
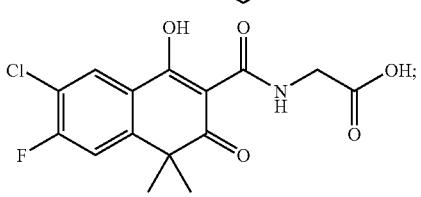
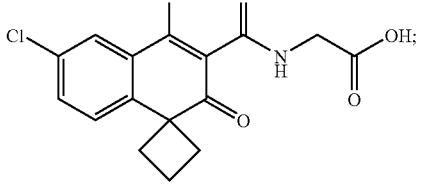
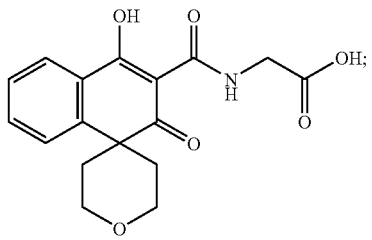
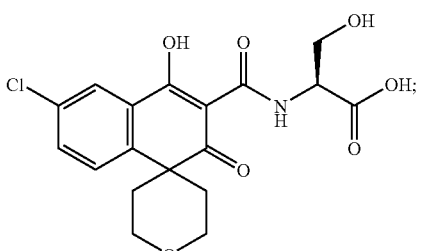
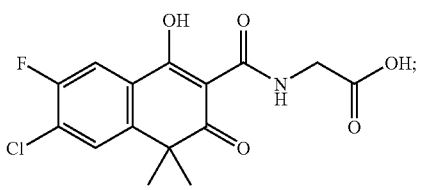
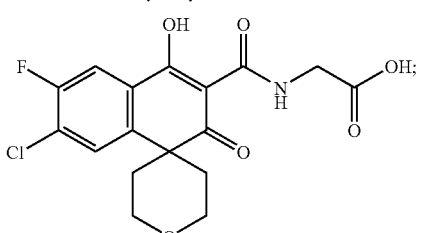

221
-continued
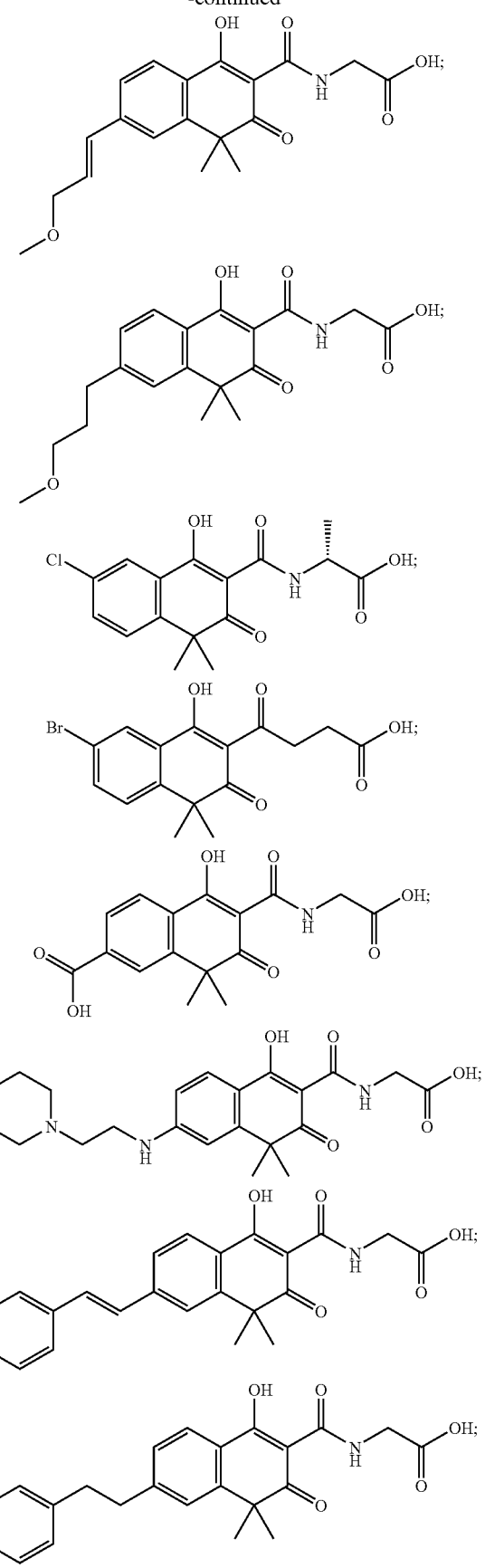
222
-continued
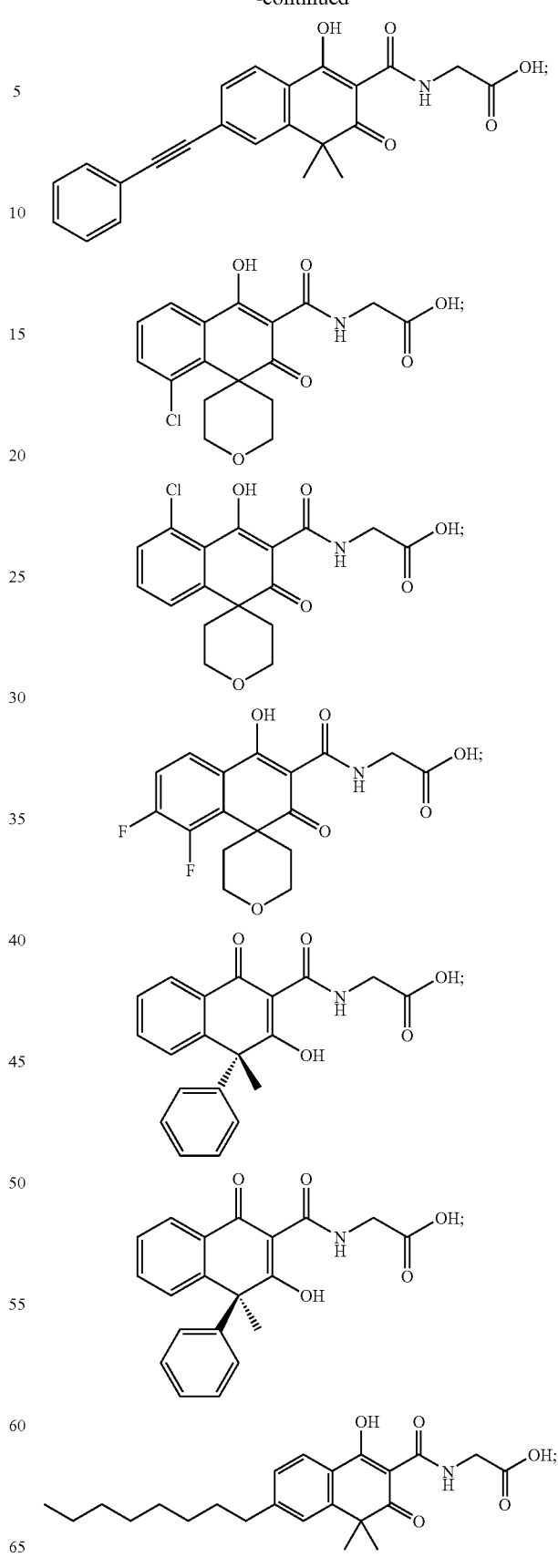

223
-continued
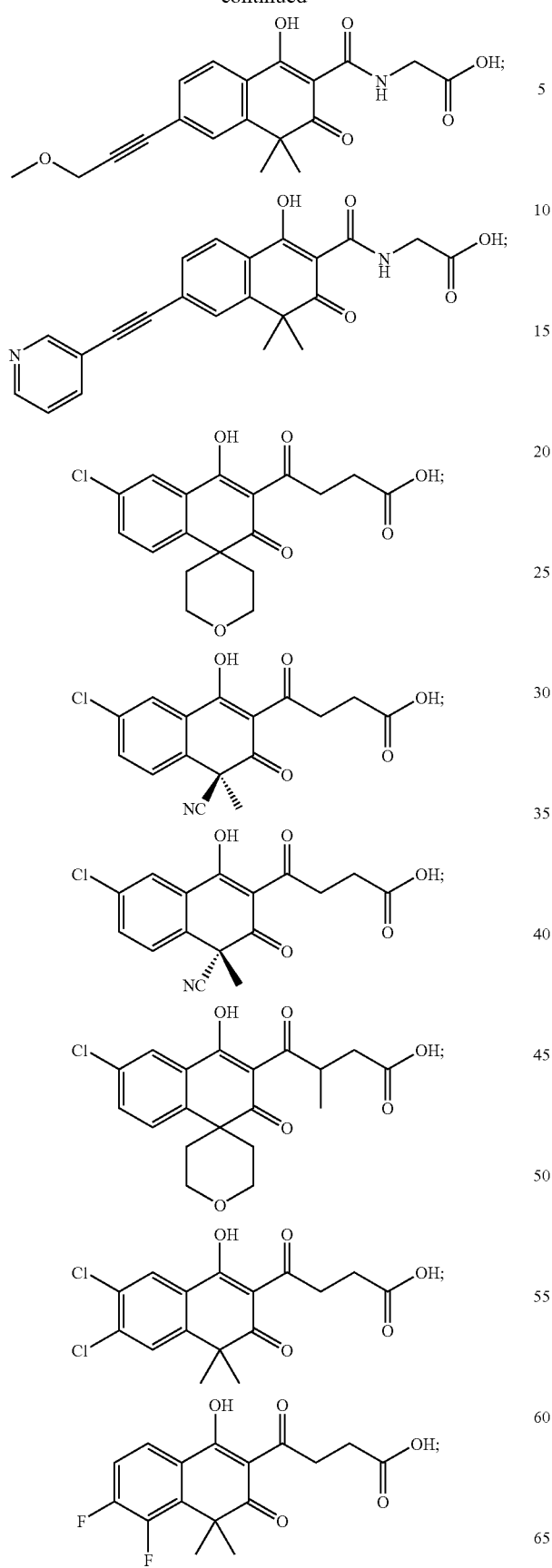
224
-continued
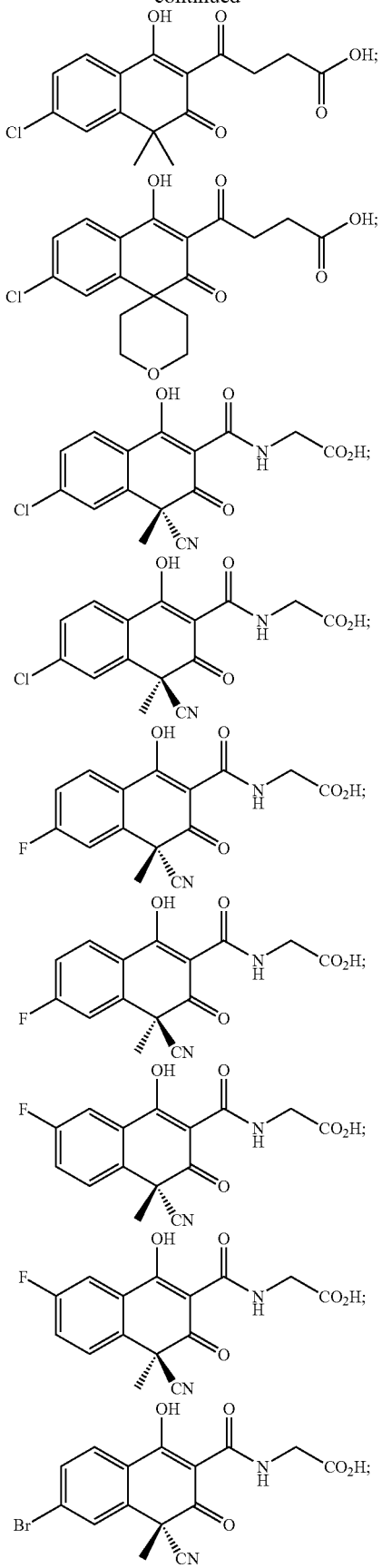

-continued

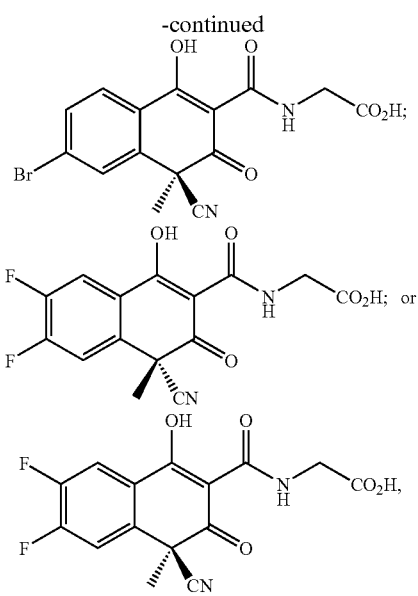

or a pharmaceutically acceptable salt thereof, a tautomer thereof, or a pharmaceutically acceptable salt of the tautomer; or a mixture thereof.

16. A method of treating ischemia or anemia in a subject, the method comprising administering to the subject an effective amount of a compound of Formula II:

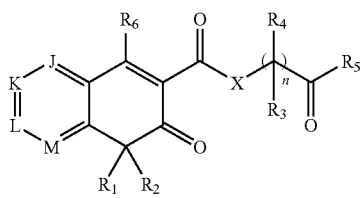

a pharmaceutically acceptable salt thereof, a tautomer thereof, or a pharmaceutically acceptable salt of the tautomer; or a mixture of any of the foregoing, wherein:

J, K, L, and M are independently selected from $CR_7$ or N, wherein 0, 1, or 2 of J, K, L, and M are N;

n is 1 to 6;

$R_1$ and $R_2$ are independently selected from halogen, CN, alkyl, substituted alkyl, alkenyl, substituted alkenyl, alkynyl, substituted alkynyl, cycloalkyl, substituted cycloalkyl, aryl, substituted aryl, aralkyl, substituted aralkyl, heterocyclyl, substituted heterocyclyl, heterocyclylalkyl, substituted heterocyclylalkyl, heteroaryl, substituted heteroaryl, heteroarylalkyl, or substituted heteroarylalkyl, or $R_1$ and $R_2$ can join to form a spirocyclic ring system that may be substituted with one or more substituents;

X is selected from $-NR_a-$, $-O-$, $-S-$, or $-(CR_b R_c)-$, wherein $R_a$ is selected from H or lower alkyl;

$R_3$ and $R_4$ are independently selected from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, or sulfanyl;

$R_6$ is selected from H, OH, SH $NH_2$, $NHSO_2R_8$, or sulfonyl;

each $R_7$ is independently selected from H, alkyl, substituted alkyl, alkenyl, substituted alkenyl, alkynyl, substituted alkynyl, $NR_dR_e$, $C(O)R_8$, $C(O)OR_9$, $OR_9$, $SR_9$, $SO_2R_9$, CN, $NO_2$, halo, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, haloalkyl, perhaloalkyl, or $-Y-R_{10}$, wherein:

Y is selected from $-N(R_{11})-Z-$ or $-Z-N(R_{11})-$;

Z is selected from C(O), $SO_2$, alkylene, substituted alkylene, alkenylene, substituted alkenylene, alkynylene, or substituted alkynylene;

$R_8$ is selected from H, alkyl, substituted alkyl, alkenyl, substituted alkenyl, alkynyl, substituted alkynyl, heterocyclyl, substituted heterocyclyl, aryl, substituted aryl, heteroaryl, or substituted heteroaryl;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl;

$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

17. The method according to claim 16, wherein each of J, K, L, and M is $CR_7$.

18. The method according to claim 16, wherein one of J, K, L, and M is N, and the other three of J, K, L, and M are $CR_7$.

19. The method according to claim 16, wherein $R_5$ is OH.

20. The method according to claim 16, wherein $R_6$ is OH.

21. The method according to claim 16, wherein at least one instance of $R_7$ is a substituted or unsubstituted aryl, a substituted or unsubstituted heteroaryl, a substituted or unsubstituted cycloalkyl, or a substituted or unsubstituted heterocyclyl group.

22. The method according to claim 16, wherein at least one instance of $R_7$ is chosen from a halo or a moiety substituted with at least one halo.

23. The method according to claim 16, wherein n is 1.

24. The method according to claim 16, wherein $R_1$ and $R_2$ are independently chosen from CN, lower alkyl, aryl, or substituted aryl.

25. The method according to claim 16, wherein $R_1$ and $R_2$ join to form a spirocyclic ring system.

26. The method according to claim 16, wherein $R_1$ and $R_2$ join to form a heterocyclic spirocyclic ring system.

27. The method according to claim 16, wherein $R_1$ and $R_2$ join to form the group $-CH_2-CH_2-O-CH_2-CH_2-$.

28. The method according to claim 16, wherein X is $-CH_2-$.

29. The method according to claim 16, wherein X is $-NH-$.

30. The method according to claim 16, wherein $R_3$ and $R_4$ are independently selected from H and lower alkyl.

* * * * *

SEQUENCE LISTING

```
<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Met His His His His His His Glu Ala Gly Arg Pro Arg Pro Val Leu
1               5                   10                  15

Arg Ser Val Asn Ser Arg Glu Pro Ser Gln Val Ile Phe Cys Asn Arg
            20                  25                  30

Ser Pro Arg Val Val Leu Pro Val Trp Leu Asn Phe Asp Gly Glu Pro
        35                  40                  45

Gln Pro Tyr Pro Thr Leu Pro Pro Gly Thr Gly Arg Arg Ile His Ser
    50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
                85                  90                  95

Gly Gln Pro Ile Phe Ala Asn Ile Thr Leu Pro Val Tyr Thr Leu Lys
            100                 105                 110

Glu Arg Cys Leu Gln Val Val Arg Ser Leu Val Lys Pro Glu Asn Tyr
        115                 120                 125

Arg Arg Leu Asp Ile Val Arg Ser Leu Tyr Glu Asp Leu Glu Asp His
```

```
                130                 135                 140
Pro Asn Val Gln Lys Asp Leu Glu Arg Leu Thr Gln Glu Arg Ile Ala
145                 150                 155                 160

His Gln Arg Met Gly Asp
                165
```

<210> SEQ ID NO 2
<211> LENGTH: 118
<212> TYPE: PRT
<213> ORGANISM: Homo sapiens

<400> SEQUENCE: 2

```
Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Pro Gln Asp Ser Gly Ser Ser Ala
                100                 105                 110

Asn Glu Gln Ala Val Gln
            115
```

<210> SEQ ID NO 3
<211> LENGTH: 96
<212> TYPE: PRT
<213> ORGANISM: Homo sapiens

<400> SEQUENCE: 3

```
Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
                20                  25                  30

Pro Gly Gln Phe Ala Glu Asn Glu Thr Asn Glu Val Asn Phe Arg Glu
            35                  40                  45

Ile Pro Ser His Val Leu Ser Lys Val Cys Met Tyr Phe Thr Tyr Lys
50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
                85                  90                  95
```

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (20)..(20)

```
<223> OTHER INFORMATION: Carboxyamidated

<400> SEQUENCE: 4

Asp Leu Asp Leu Glu Ala Leu Ala Pro Tyr Ile Pro Ala Asp Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated

<400> SEQUENCE: 5

Asp Leu Asp Leu Glu Ala Leu Ala Xaa Tyr Ile Pro Ala Asp Asp Asp
1               5                   10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Asp Leu Glu Met Leu Ala Pro Tyr Ile Pro Met Asp Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation

<400> SEQUENCE: 7

Asp Leu Glu Met Leu Ala Pro Tyr Ile Pro Met Asp Asp Asp Phe Gln
1               5                   10                  15

Leu
```